US011027000B2

(12) United States Patent
Kotin et al.

(10) Patent No.: US 11,027,000 B2

(45) **Date of Patent: *Jun. 8, 2021**

(54) AADC POLYNUCLEOTIDES FOR THE TREATMENT OF PARKINSON'S DISEASE

(71) Applicant: VOYAGER THERAPEUTICS, INC., Cambridge, MA (US)

(72) Inventors: Robert Kotin, Bethesda, MD (US); Adrian Philip Kells, Cambridge, MA (US); Bernard Ravina, Newton, MA (US)

(73) Assignee: Voyager Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/540,375

(22) Filed: Aug. 14, 2019

(65) Prior Publication Data

US 2019/0358306 A1 Nov. 28, 2019

Related U.S. Application Data

(63) Continuation of application No. 16/136,926, filed on Sep. 20, 2018, now abandoned, which is a continuation of application No. 15/524,986, filed as application No. PCT/US2015/059201 on Nov. 5, 2015, now Pat. No. 10,335,466.

(60) Provisional application No. 62/243,537, filed on Oct. 19, 2015, provisional application No. 62/199,578, filed on Jul. 31, 2015, provisional application No. 62/155,692, filed on May 1, 2015, provisional application No. 62/075,298, filed on Nov. 5, 2014.

(51) Int. Cl.

| | |
|---|---|
| ***A61K 35/76*** | (2015.01) |
| ***A61K 38/51*** | (2006.01) |
| ***A61K 48/00*** | (2006.01) |
| ***C12N 15/86*** | (2006.01) |
| ***C12N 9/88*** | (2006.01) |
| ***A61P 25/14*** | (2006.01) |
| ***C12N 7/00*** | (2006.01) |

(52) U.S. Cl.

CPC .............. *A61K 38/51* (2013.01); *A61K 35/76* (2013.01); *A61K 48/005* (2013.01); *A61P 25/14* (2018.01); *C12N 7/00* (2013.01); *C12N 9/88* (2013.01); *C12N 15/86* (2013.01); *C12Y 401/01028* (2013.01); *C12N 2750/14121* (2013.01); *C12N 2750/14143* (2013.01); *C12N 2800/22* (2013.01); *C12N 2830/42* (2013.01); *C12N 2830/50* (2013.01)

(58) Field of Classification Search

None

See application file for complete search history.

(56) References Cited

U.S. PATENT DOCUMENTS

| | | | |
|---|---|---|---|
| 5,064,764 | A | 11/1991 | Besnainon |
| 5,474,935 | A | 12/1995 | Chatterjee |
| 5,538,885 | A | 7/1996 | Hollis et al. |
| 5,587,308 | A | 12/1996 | Carter |
| 5,652,224 | A | 7/1997 | Wilson |
| 5,658,785 | A | 8/1997 | Johnson |
| 5,688,676 | A | 11/1997 | Zhou |
| 5,691,176 | A | 11/1997 | Lebkowski |
| 5,693,531 | A | 12/1997 | Chiorini |
| 5,741,683 | A | 4/1998 | Zhou |
| 5,756,283 | A | 5/1998 | Wilson |
| 5,856,152 | A | 1/1999 | Wilson |
| 5,858,351 | A | 1/1999 | Podsakoff |
| 5,858,775 | A | 1/1999 | Johnson |
| 5,866,552 | A | 2/1999 | Wilson |
| 5,866,696 | A | 2/1999 | Carter |
| 5,871,982 | A | 2/1999 | Wilson |
| 5,952,221 | A | 9/1999 | Kurtzman |
| 5,962,313 | A | 10/1999 | Podsakoff |
| 5,989,540 | A | 11/1999 | Carter |
| 6,083,716 | A | 7/2000 | Wilson |
| 6,143,548 | A | 11/2000 | O'Riordan |
| 6,143,567 | A | 11/2000 | Van Agthoven |
| 6,146,874 | A | 11/2000 | Zolotukhin |
| 6,156,303 | A | 12/2000 | Russell |
| 6,174,527 | B1 | 1/2001 | Wilson |
| 6,180,613 | B1 | 1/2001 | Kaplitt |
| 6,194,191 | B1 | 2/2001 | Zhang |
| 6,200,560 | B1 | 3/2001 | Couto |
| 6,204,059 | B1 | 3/2001 | Samulski |
| 6,211,163 | B1 | 4/2001 | Podsakoff |
| 6,251,677 | B1 | 6/2001 | Wilson |
| 6,258,595 | B1 | 7/2001 | Gao |

(Continued)

FOREIGN PATENT DOCUMENTS

| | | |
|---|---|---|
| EP | 1015619 A1 | 7/2000 |
| EP | 1078096 A1 | 2/2001 |

(Continued)

OTHER PUBLICATIONS

Andersson C et al., Striatal volume changes in the rat following long-term administration of typical and atypical antipsychotic drugs. Neuropsychopharmacology. vol. 27, No. 2, 2002.

Blesa J et al., Classic and New Animal Models of Parkinson's Disease. J Biomed Biotechnol. 2012;2012:845618.

Coleman RR et al., Validity and Efficacy of Screening Algorithms for Assessing Deep Brain Stimulation Candidacy in Parkinson Disease. Mov Disord Clin Pract. Dec. 1, 2014;1(4):342-347.

Nagatsu T et al., Biochemistry of postmortem brains in Parkinson's disease: historical overview and future prospects. J Neural Transm Suppl. 2007;(72):113-20.

(Continued)

*Primary Examiner* — Michael D Burkhart

(74) *Attorney, Agent, or Firm* — McCarter & English, LLP; Maria Laccotripe Zacharakis; Yu Lu

(57) ABSTRACT

The disclosure relates to compositions and methods for the preparation, manufacture and therapeutic use of polynucleotides encoding AADC for the treatment of Parkinson's Disease.

26 Claims, No Drawings

Specification includes a Sequence Listing.

(56) References Cited

U.S. PATENT DOCUMENTS

| | | | |
|---|---|---|---|
| 6,261,551 | B1 | 7/2001 | Wilson |
| 6,265,389 | B1 | 7/2001 | Burke |
| 6,270,996 | B1 | 8/2001 | Wilson |
| 6,274,354 | B1 | 8/2001 | Wilson |
| 6,281,010 | B1 | 8/2001 | Gao |
| 6,309,634 | B1 | 10/2001 | Bankiewicz |
| 6,325,998 | B1 | 12/2001 | Podsakoff |
| 6,335,011 | B1 | 1/2002 | Podsakoff |
| 6,365,394 | B1 | 4/2002 | Gao |
| 6,387,368 | B1 | 5/2002 | Wilson |
| 6,399,385 | B1 | 6/2002 | Croyle |
| 6,410,300 | B1 | 6/2002 | Samulski |
| 6,416,992 | B1 | 7/2002 | Mejza |
| 6,428,988 | B1 | 8/2002 | Wilson |
| 6,436,392 | B1 | 8/2002 | Engelhardt |
| 6,436,394 | B1 | 8/2002 | Henderson |
| 6,468,524 | B1 | 10/2002 | Chiorini |
| 6,468,771 | B1 | 10/2002 | Einerhand |
| 6,475,769 | B1 | 11/2002 | Wilson |
| 6,482,634 | B1 | 11/2002 | Wilson |
| 6,485,966 | B2 | 11/2002 | Gao |
| 6,503,888 | B1 | 1/2003 | Kaplitt |
| 6,509,150 | B1 | 1/2003 | Salvetti |
| 6,521,426 | B1 | 2/2003 | Ciliberto |
| 6,555,525 | B2 | 4/2003 | Burke |
| 6,566,118 | B1 | 5/2003 | Atkinson |
| 6,582,692 | B1 | 6/2003 | Podsakoff |
| 6,593,123 | B1 | 7/2003 | Wright |
| 6,610,290 | B2 | 8/2003 | Podsakoff |
| 6,642,051 | B1 | 11/2003 | Lynch |
| 6,660,514 | B1 | 12/2003 | Zolotukhin |
| 6,660,521 | B2 | 12/2003 | Brough |
| 6,670,176 | B1 | 12/2003 | Samulski |
| 6,676,935 | B2 | 1/2004 | Henderson |
| 6,699,706 | B1 | 3/2004 | Brooks |
| 6,710,036 | B2 | 3/2004 | Kurtzman |
| 6,723,551 | B2 | 4/2004 | Kotin |
| 6,726,907 | B1 | 4/2004 | Zhang |
| 6,753,419 | B1 | 6/2004 | Toniatti |
| 6,759,237 | B1 | 7/2004 | Wilson |
| 6,841,357 | B1 | 1/2005 | Vaillancourt |
| 6,846,665 | B1 | 1/2005 | Horer |
| 6,855,314 | B1 | 2/2005 | Chiorini |
| 6,887,463 | B2 | 5/2005 | Wilson |
| 6,897,045 | B2 | 5/2005 | Engelhardt |
| 6,943,019 | B2 | 9/2005 | Wilson |
| 6,953,575 | B2 | 10/2005 | Bankiewicz |
| 6,953,690 | B1 | 10/2005 | Gao |
| 6,984,517 | B1 | 1/2006 | Chiorini |
| 6,995,006 | B2 | 2/2006 | Atkinson |
| 7,015,026 | B2 | 3/2006 | O'Riordan |
| 7,022,519 | B2 | 4/2006 | Gao |
| 7,048,920 | B2 | 5/2006 | Yu |
| 7,056,502 | B2 | 6/2006 | Hildinger |
| 7,070,998 | B2 | 7/2006 | Johnson |
| 7,091,030 | B2 | 8/2006 | Setiawan |
| 7,094,604 | B2 | 8/2006 | Snyder |
| 7,105,345 | B2 | 9/2006 | Wilson |
| 7,112,321 | B2 | 9/2006 | Wang |
| 7,125,705 | B2 | 10/2006 | Colosi |
| 7,125,706 | B2 | 10/2006 | Zhang |
| 7,169,612 | B2 | 1/2007 | Kostenis |
| 7,182,944 | B2 | 2/2007 | Bankiewicz |
| 7,186,552 | B2 | 3/2007 | Wilson |
| 7,198,951 | B2 | 4/2007 | Gao |
| 7,223,585 | B2 | 5/2007 | Coffey |
| 7,235,393 | B2 | 6/2007 | Gao |
| 7,238,526 | B2 | 7/2007 | Wilson |
| 7,241,447 | B1 | 7/2007 | Engelhardt |
| 7,247,472 | B2 | 7/2007 | Wilson |
| 7,259,015 | B2 | 8/2007 | Kingsman et al. |
| 7,271,002 | B2 | 9/2007 | Kotin |
| 7,282,199 | B2 | 10/2007 | Gao |
| 7,291,498 | B2 | 11/2007 | Roy |
| 7,300,797 | B2 | 11/2007 | Van Agthoven |
| 7,306,794 | B2 | 12/2007 | Wilson |
| 7,319,002 | B2 | 1/2008 | Wilson |
| 7,326,555 | B2 | 2/2008 | Konz |
| 7,344,872 | B2 | 3/2008 | Gao |
| 7,419,817 | B2 | 9/2008 | Chiorini |
| 7,419,956 | B2 | 9/2008 | Ohtaki |
| 7,445,930 | B2 | 11/2008 | Zhang |
| 7,479,554 | B2 | 1/2009 | Chiorini |
| 7,491,508 | B2 | 2/2009 | Roy |
| 7,510,872 | B2 | 3/2009 | Clark |
| 7,510,875 | B2 | 3/2009 | Zhang |
| 7,534,613 | B2 | 5/2009 | Bankiewicz |
| 7,579,181 | B2 | 8/2009 | O'Riordan |
| 7,588,757 | B2 | 9/2009 | Ozawa |
| 7,588,772 | B2 | 9/2009 | Kay et al. |
| 7,625,570 | B1 | 12/2009 | Schaffer |
| 7,638,120 | B2 | 12/2009 | Liu |
| 7,662,627 | B2 | 2/2010 | Johnson |
| 7,704,492 | B2 | 4/2010 | Podsakoff |
| 7,704,721 | B2 | 4/2010 | Wright |
| 7,732,129 | B1 | 6/2010 | Zhang |
| 7,790,449 | B2 | 9/2010 | Gao |
| 7,803,622 | B2 | 9/2010 | Engelhardt |
| 7,838,277 | B2 | 11/2010 | Gao |
| 7,888,096 | B2 | 2/2011 | Wu |
| 7,901,921 | B2 | 3/2011 | Coffey |
| 7,906,111 | B2 | 3/2011 | Wilson et al. |
| 7,968,333 | B2 | 6/2011 | Yu |
| 8,105,574 | B2 | 1/2012 | Wilson |
| 8,110,351 | B2 | 2/2012 | Bosnes |
| 8,137,948 | B2 | 3/2012 | Qu |
| 8,163,543 | B2 | 4/2012 | Urabe |
| 8,231,880 | B2 | 7/2012 | Roy |
| 8,236,495 | B2 | 8/2012 | Nochumson |
| 8,241,622 | B2 | 8/2012 | Englehardt |
| 8,273,344 | B2 | 9/2012 | Wang |
| 8,283,151 | B2 | 10/2012 | Schmidt |
| 8,309,355 | B2 | 11/2012 | Bankiewicz |
| 8,318,480 | B2 | 11/2012 | Gao |
| 8,318,687 | B2 | 11/2012 | Tabira |
| 8,394,386 | B2 | 3/2013 | Wilson |
| 8,409,842 | B2 | 4/2013 | Clark |
| 8,470,310 | B2 | 6/2013 | Roy |
| 8,476,418 | B2 | 7/2013 | Mueller |
| 8,512,981 | B2 | 8/2013 | Hermens et al. |
| 8,524,219 | B2 | 9/2013 | Roy |
| 8,524,446 | B2 | 9/2013 | Gao |
| 8,603,459 | B2 | 12/2013 | Wilson |
| 8,614,101 | B2 | 12/2013 | VanDine |
| 8,637,255 | B2 | 1/2014 | Wilson |
| 8,642,314 | B2 | 2/2014 | Bakker |
| 8,685,734 | B2 | 4/2014 | Coffey |
| 8,697,417 | B2 | 4/2014 | Bakker |
| 8,697,665 | B2 | 4/2014 | Fontanellas |
| 8,834,863 | B2 | 9/2014 | Roy |
| 8,846,389 | B2 | 9/2014 | Chiorini |
| 8,906,387 | B2 | 12/2014 | Kay |
| 8,906,675 | B2 | 12/2014 | Gao |
| 8,927,514 | B2 | 1/2015 | Chatterjee |
| 8,962,330 | B2 | 2/2015 | Gao |
| 8,962,332 | B2 | 2/2015 | Gao |
| 8,999,678 | B2 | 4/2015 | Vandenberghe |
| 9,034,836 | B2 | 5/2015 | Dodge |
| 9,050,299 | B2 | 6/2015 | Bankiewicz |
| 9,051,542 | B2 | 6/2015 | Wright |
| 9,056,892 | B2 | 6/2015 | Pun |
| 9,066,966 | B2 | 6/2015 | Puccio |
| 9,080,183 | B2 | 7/2015 | Klein |
| 9,089,667 | B2 | 7/2015 | Bankiewicz |
| 9,102,943 | B2 | 8/2015 | Shinmura |
| 9,102,949 | B2 | 8/2015 | Gao |
| 9,107,884 | B2 | 8/2015 | Chedotal |
| 9,115,373 | B2 | 8/2015 | Hermens et al. |
| 9,116,157 | B2 | 8/2015 | Ringe |
| 9,163,260 | B2 | 10/2015 | Wilson |
| 9,217,155 | B2 | 12/2015 | Gao |
| 9,217,159 | B2 | 12/2015 | Roy |
| 9,228,174 | B2 | 1/2016 | Noordman |
| 9,233,174 | B2 | 1/2016 | Chen |

(56) References Cited

U.S. PATENT DOCUMENTS

| | | | |
|---|---|---|---|
| 9,238,800 | B2 | 1/2016 | Bossis |
| 9,260,724 | B2 | 2/2016 | Bakker |
| 9,283,357 | B2 | 3/2016 | Stedman |
| 9,415,119 | B2 | 8/2016 | Passini |
| 9,415,121 | B2 | 8/2016 | Kaspar |
| 9,434,776 | B2 | 9/2016 | Ando |
| 9,434,928 | B2 | 9/2016 | Mendell |
| 9,439,979 | B2 | 9/2016 | Chiorini |
| 9,441,206 | B2 | 9/2016 | Grieger |
| 9,441,244 | B2 | 9/2016 | Schaffer |
| 9,447,433 | B2 | 9/2016 | Hirsch |
| 9,457,103 | B2 | 10/2016 | Schaffer |
| 9,458,517 | B2 | 10/2016 | Schaffer |
| 9,464,119 | B2 | 10/2016 | Sonntag |
| 9,475,845 | B2 | 10/2016 | Asokan |
| 9,486,541 | B2 | 11/2016 | Hutton |
| 9,492,415 | B2 | 11/2016 | Bankiewicz |
| 9,493,788 | B2 | 11/2016 | Gao |
| 9,504,762 | B2 | 11/2016 | Colosi |
| 9,506,052 | B2 | 11/2016 | Samulski |
| 9,506,083 | B2 | 11/2016 | Arbetman |
| 9,528,126 | B2 | 12/2016 | Qu |
| 9,540,659 | B2 | 1/2017 | Davidson |
| 9,546,112 | B2 | 1/2017 | Voit |
| 9,546,369 | B2 | 1/2017 | Gao |
| 9,567,376 | B2 | 2/2017 | Cronin |
| 9,567,607 | B2 | 2/2017 | Wilson |
| 9,580,691 | B2 | 2/2017 | Bakker |
| 9,719,070 | B2 | 2/2017 | Vandenberghe |
| 9,585,971 | B2 | 3/2017 | Deverman |
| 9,587,250 | B2 | 3/2017 | Gao |
| 9,587,282 | B2 | 3/2017 | Schaffer |
| 9,593,346 | B2 | 3/2017 | Roy |
| 9,596,835 | B2 | 3/2017 | Gao |
| 9,597,363 | B2 | 3/2017 | Roy |
| 9,598,468 | B2 | 3/2017 | Weigel-Van Aken |
| 9,598,703 | B2 | 3/2017 | Garcia |
| 9,803,218 | B2 | 3/2017 | Chatterjee |
| 9,611,302 | B2 | 4/2017 | Srivastava |
| 9,616,090 | B2 | 4/2017 | Conway |
| 9,617,561 | B2 | 4/2017 | Roy |
| 9,623,120 | B2 | 4/2017 | Chatterjee |
| 9,624,274 | B2 | 4/2017 | Lux |
| 9,629,930 | B2 | 4/2017 | Gregory |
| 9,636,370 | B2 | 5/2017 | McCown |
| 9,670,507 | B2 | 6/2017 | Xiao |
| 9,677,088 | B2 | 6/2017 | Nakai |
| 9,677,089 | B2 | 6/2017 | Gao |
| 9,682,193 | B2 | 6/2017 | Anand |
| 9,695,220 | B2 | 7/2017 | Vandenberghe |
| 9,701,984 | B2 | 7/2017 | Gao |
| 9,708,627 | B2 | 7/2017 | Hermens et al. |
| 9,777,291 | B2 | 7/2017 | Chatterjee |
| 9,783,825 | B2 | 7/2017 | Chatterjee |
| 9,719,106 | B2 | 8/2017 | Wilson |
| 9,725,485 | B2 | 8/2017 | Srivastava |
| 9,732,345 | B2 | 8/2017 | Martin |
| 9,737,618 | B2 | 8/2017 | Wilson |
| 9,745,590 | B2 | 8/2017 | Kay |
| 9,775,918 | B2 | 10/2017 | Zhong |
| 9,783,824 | B2 | 10/2017 | Kay |
| 9,790,472 | B2 | 10/2017 | Gao |
| 10,041,090 | B2 | 8/2018 | Gao |
| 2001/0006955 | A1 | 7/2001 | Wilson |
| 2001/0049144 | A1 | 12/2001 | Rivera |
| 2002/0019050 | A1 | 2/2002 | Gao |
| 2002/0037867 | A1 | 3/2002 | Wilson |
| 2002/0081721 | A1 | 6/2002 | Allen |
| 2002/0090717 | A1 | 7/2002 | Gao |
| 2002/0102714 | A1 | 8/2002 | Wilson |
| 2002/0131961 | A1 | 9/2002 | Wilson |
| 2003/0013189 | A1 | 1/2003 | Wilson |
| 2003/0032613 | A1 | 2/2003 | Gao |
| 2003/0092161 | A1 | 5/2003 | Gao |
| 2003/0096264 | A1 | 5/2003 | Altar et al. |
| 2003/0100115 | A1 | 5/2003 | Raj |
| 2003/0119191 | A1 | 6/2003 | Gao |
| 2003/0138772 | A1 | 7/2003 | Gao |
| 2004/0043490 | A1 | 3/2004 | Shimada |
| 2004/0057931 | A1 | 3/2004 | Wilson |
| 2004/0136963 | A1 | 7/2004 | Wilson |
| 2004/0171807 | A1 | 9/2004 | Gao |
| 2005/0261218 | A1 | 11/2005 | Esau |
| 2006/0003451 | A1 | 1/2006 | Gao |
| 2006/0204479 | A1 | 9/2006 | Wilson |
| 2007/0004042 | A1 | 1/2007 | Gao et al. |
| 2008/0008684 | A1 | 1/2008 | Wilson |
| 2008/0050343 | A1 | 2/2008 | Wilson |
| 2008/0050345 | A1 | 2/2008 | Wilson |
| 2008/0075737 | A1 | 3/2008 | Gao |
| 2009/0215871 | A1 | 8/2009 | Wilson |
| 2009/0275107 | A1 | 11/2009 | Lock |
| 2009/0317417 | A1 | 12/2009 | Vandenberghe |
| 2010/0247490 | A1 | 9/2010 | Roy |
| 2010/0278791 | A1 | 11/2010 | Wilson |
| 2011/0136227 | A1 | 6/2011 | Bakker |
| 2011/0171262 | A1 | 7/2011 | Bakker |
| 2011/0206616 | A1 | 8/2011 | Ichtchenko |
| 2011/0223135 | A1 | 9/2011 | Roy |
| 2011/0229971 | A1 | 9/2011 | Knop |
| 2011/0263001 | A1 | 10/2011 | Lakshmipathy |
| 2012/0046349 | A1 | 2/2012 | Bell |
| 2012/0058102 | A1 | 3/2012 | Wilson |
| 2012/0064115 | A1 | 3/2012 | John |
| 2012/0093853 | A1 | 4/2012 | Wilson |
| 2012/0137379 | A1 | 5/2012 | Gao |
| 2012/0220648 | A1 | 8/2012 | Hwu et al. |
| 2012/0258046 | A1 | 10/2012 | Mutzke |
| 2012/0295960 | A1 | 11/2012 | Palfi et al. |
| 2013/0023033 | A1 | 1/2013 | Wilson |
| 2013/0045186 | A1 | 2/2013 | Gao |
| 2013/0101558 | A1 | 4/2013 | Gao |
| 2013/0195801 | A1 | 8/2013 | Gao et al. |
| 2013/0296532 | A1 | 11/2013 | Hermens et al. |
| 2013/0323226 | A1 | 12/2013 | Wilson |
| 2013/0323302 | A1 | 12/2013 | Constable |
| 2014/0031418 | A1 | 1/2014 | Wilson |
| 2014/0044680 | A1 | 2/2014 | Roy |
| 2014/0065105 | A1 | 3/2014 | Wilson |
| 2014/0087361 | A1 | 3/2014 | Dobbelaer |
| 2014/0099666 | A1 | 4/2014 | Rossomando |
| 2014/0107186 | A1 | 4/2014 | Garcia |
| 2014/0336245 | A1 | 11/2014 | Mingozzi |
| 2014/0341852 | A1 | 11/2014 | Srivastava |
| 2014/0342434 | A1 | 11/2014 | Hermens et al. |
| 2015/0005369 | A1 | 1/2015 | Muzyczka |
| 2015/0023924 | A1 | 1/2015 | High |
| 2015/0065562 | A1 | 3/2015 | Yazicioglu |
| 2015/0118287 | A1 | 4/2015 | Hammond |
| 2015/0139952 | A1 | 5/2015 | Webster |
| 2015/0151007 | A1 | 6/2015 | Dodge |
| 2015/0152127 | A1 | 6/2015 | Selnick |
| 2015/0159173 | A1 | 6/2015 | Vandenberghe |
| 2015/0184197 | A1 | 7/2015 | Davidson |
| 2015/0196671 | A1 | 7/2015 | Byrne |
| 2015/0203553 | A1 | 7/2015 | Chiorini |
| 2015/0238610 | A1 | 8/2015 | Sista |
| 2015/0307898 | A2 | 10/2015 | Hermens et al. |
| 2015/0315610 | A1 | 11/2015 | Nishie |
| 2015/0374803 | A1 | 12/2015 | Wolfe |
| 2016/0032319 | A1 | 2/2016 | Wright |
| 2016/0108373 | A1 | 4/2016 | Bennett |
| 2016/0153992 | A1 | 6/2016 | Buening |
| 2016/0166709 | A1 | 6/2016 | Davidson |
| 2016/0256534 | A1 | 9/2016 | Bankiewicz |
| 2016/0271192 | A1 | 9/2016 | Roy |
| 2016/0273058 | A1 | 9/2016 | Akashika |
| 2016/0289275 | A1 | 10/2016 | Chiorini |
| 2016/0296694 | A1 | 10/2016 | Bankiewicz |
| 2016/0319278 | A1 | 11/2016 | Khvorova |
| 2016/0331897 | A1 | 11/2016 | Anand |
| 2016/0333372 | A1 | 11/2016 | Srivastava |
| 2016/0333373 | A1 | 11/2016 | Farley |
| 2016/0333375 | A1 | 11/2016 | Chen |

(56) References Cited

U.S. PATENT DOCUMENTS

| | | | |
|---|---|---|---|
| 2016/0334417 | A1 | 11/2016 | Rouillon |
| 2016/0340393 | A1 | 11/2016 | Schaffer |
| 2016/0340692 | A1 | 11/2016 | Wang |
| 2016/0346359 | A1 | 12/2016 | Buchlis |
| 2016/0347822 | A1 | 12/2016 | Crystal |
| 2016/0354487 | A1 | 12/2016 | Zhang |
| 2016/0355577 | A1 | 12/2016 | Kelley |
| 2016/0355796 | A1 | 12/2016 | Davidson |
| 2016/0361439 | A1 | 12/2016 | Agbandje-McKenna |
| 2016/0367661 | A1 | 12/2016 | Flavell |
| 2016/0369297 | A1 | 12/2016 | Byrne |
| 2016/0369298 | A1 | 12/2016 | Marsic |
| 2016/0369299 | A1 | 12/2016 | Boye |
| 2016/0375110 | A1 | 12/2016 | High |
| 2016/0375151 | A1 | 12/2016 | Schaffer |
| 2016/0376323 | A1 | 12/2016 | Schaffer |
| 2016/0376608 | A1 | 12/2016 | Chou |
| 2017/0000904 | A1 | 1/2017 | Wilson |
| 2017/0007645 | A1 | 1/2017 | Handa |
| 2017/0007669 | A1 | 1/2017 | Sarkar |
| 2017/0007720 | A1 | 1/2017 | Boye |
| 2017/0008939 | A1 | 1/2017 | Khanna |
| 2017/0021037 | A1 | 1/2017 | Wang |
| 2017/0022507 | A1 | 1/2017 | Reyon |
| 2017/0028082 | A1 | 2/2017 | Wilson |
| 2017/0043037 | A1 | 2/2017 | Kariko |
| 2017/0044504 | A1 | 2/2017 | Schaffer |
| 2017/0051259 | A1 | 2/2017 | Wang |
| 2017/0067028 | A1 | 3/2017 | Ballon |
| 2017/0071972 | A1 | 3/2017 | Buj Bello |
| 2017/0073703 | A1 | 3/2017 | Chatterjee |
| 2017/0087219 | A1 | 3/2017 | Bunting |
| 2017/0088819 | A1 | 3/2017 | Vandendriessche |
| 2017/0088858 | A1 | 3/2017 | Gao |
| 2017/0095538 | A1 | 4/2017 | Colosi |
| 2017/0096646 | A1 | 4/2017 | Roy |
| 2017/0105927 | A1 | 4/2017 | Thorne |
| 2017/0107536 | A1 | 4/2017 | Zhang |
| 2017/0112946 | A1 | 4/2017 | Ikeda |
| 2017/0121734 | A1 | 5/2017 | Cairns |
| 2017/0128581 | A1 | 5/2017 | Freskgard |
| 2017/0128594 | A1 | 5/2017 | Wright |
| 2017/0130208 | A1 | 5/2017 | Potter |
| 2017/0130245 | A1 | 5/2017 | Kotin |
| 2017/0145440 | A1 | 5/2017 | Hermens et al. |
| 2017/0151348 | A1 | 6/2017 | Kaspar |
| 2017/0151416 | A1 | 6/2017 | Kutikov |
| 2017/0152525 | A1 | 6/2017 | Hermens et al. |
| 2017/0157213 | A1 | 6/2017 | Dickson |
| 2017/0157267 | A1 | 6/2017 | Kay |
| 2017/0159026 | A1 | 6/2017 | Kay |
| 2017/0159027 | A1 | 6/2017 | Wilson |
| 2017/0159072 | A9 | 6/2017 | Arbeit |
| 2017/0165377 | A1 | 6/2017 | Gao |
| 2017/0166871 | A1 | 6/2017 | Nishie |
| 2017/0166925 | A1 | 6/2017 | Gao |
| 2017/0166926 | A1 | 6/2017 | Deverman |
| 2017/0166927 | A1 | 6/2017 | Gao |
| 2017/0183636 | A1 | 6/2017 | Roy |
| 2017/0191039 | A1 | 7/2017 | Gao |
| 2017/0191079 | A1 | 7/2017 | Vandenberghe |
| 2017/0198304 | A1 | 7/2017 | Wilson |
| 2017/0204144 | A1 | 7/2017 | Deverman |
| 2017/0211092 | A1 | 7/2017 | Chatterjee |
| 2017/0211093 | A1 | 7/2017 | Chatterjee |
| 2017/0211094 | A1 | 7/2017 | Chatterjee |
| 2017/0211095 | A1 | 7/2017 | Chatterjee |
| 2017/0216458 | A1 | 8/2017 | Kaspar |
| 2017/0218395 | A1 | 8/2017 | Byrne |
| 2017/0226160 | A1 | 8/2017 | Sonntag |
| 2017/0232072 | A1 | 8/2017 | Ikeda |
| 2017/0232117 | A1 | 8/2017 | Arbetman |
| 2017/0240885 | A1 | 8/2017 | Deverman |
| 2017/0240921 | A1 | 8/2017 | Gao |
| 2017/0246322 | A1 | 8/2017 | Mendell |
| 2017/0247664 | A1 | 8/2017 | Wright |
| 2017/0258996 | A1 | 9/2017 | Anand |
| 2017/0260545 | A1 | 9/2017 | Qu |
| 2017/0274024 | A1 | 9/2017 | McCown |
| 2017/0275337 | A1 | 9/2017 | Srivastava |
| 2017/0298323 | A1 | 10/2017 | Vandenberghe |
| 2017/0304464 | A1 | 10/2017 | Kügler |
| 2017/0306354 | A1 | 10/2017 | Gao |
| 2017/0306355 | A1 | 10/2017 | Davidson |
| 2017/0321290 | A1 | 11/2017 | Lubelski |
| 2017/0333538 | A1 * | 11/2017 | Kotin .................... A61K 38/51 |
| 2018/0339065 | A1 | 11/2018 | Wilson |
| 2019/0000940 | A1 | 1/2019 | Kotin |
| 2019/0000991 | A1 | 1/2019 | Pykett |
| 2019/0008933 | A1 | 1/2019 | Kotin |

FOREIGN PATENT DOCUMENTS

| | | | |
|---|---|---|---|
| EP | 1183380 | A1 | 3/2002 |
| EP | 1218035 | A2 | 7/2002 |
| EP | 1240345 | A2 | 9/2002 |
| EP | 1279740 | A1 | 1/2003 |
| EP | 1621625 | | 2/2006 |
| EP | 1621625 | A2 | 2/2006 |
| EP | 1046711 | B1 | 12/2006 |
| EP | 1847614 | A1 | 10/2007 |
| EP | 1849872 | A1 | 10/2007 |
| EP | 1857552 | A1 | 11/2007 |
| EP | 1944043 | A1 | 7/2008 |
| EP | 1696036 | B1 | 4/2010 |
| EP | 2186283 | | 5/2010 |
| EP | 1164195 | B1 | 10/2010 |
| EP | 2250256 | B1 | 11/2010 |
| EP | 2292780 | B1 | 3/2011 |
| EP | 2301582 | B1 | 3/2011 |
| EP | 2311967 | B1 | 4/2011 |
| EP | 2524037 | A1 | 11/2012 |
| EP | 2359866 | B1 | 7/2013 |
| EP | 2660325 | A3 | 2/2014 |
| EP | 2699270 | B1 | 2/2014 |
| EP | 2383346 | B1 | 10/2014 |
| EP | 2814958 | A1 | 12/2014 |
| EP | 2198016 | B1 | 5/2015 |
| EP | 2871239 | A9 | 6/2015 |
| EP | 2879719 | A1 | 6/2015 |
| EP | 2212348 | B1 | 7/2015 |
| EP | 1578253 | B1 | 8/2015 |
| EP | 2943567 | B1 | 11/2015 |
| EP | 3058959 | A1 | 8/2016 |
| EP | 1453547 | B1 | 9/2016 |
| EP | 2220241 | B1 | 9/2016 |
| EP | 2325298 | B1 | 10/2016 |
| EP | 2007795 | B1 | 11/2016 |
| EP | 2176283 | | 11/2016 |
| EP | 2292779 | B1 | 11/2016 |
| EP | 3067417 | A3 | 11/2016 |
| EP | 2220242 | B1 | 12/2016 |
| EP | 3108000 | | 12/2016 |
| EP | 3117005 | A1 | 1/2017 |
| EP | 2737071 | B1 | 3/2017 |
| EP | 2933336 | B1 | 3/2017 |
| EP | 3134431 | A1 | 3/2017 |
| EP | 2348119 | B1 | 4/2017 |
| EP | 2531604 | B1 | 4/2017 |
| EP | 2771471 | B1 | 5/2017 |
| EP | 3168298 | A1 | 5/2017 |
| EP | 3209311 | A1 | 8/2017 |
| EP | 3215191 | A2 | 9/2017 |
| EP | 3215602 | A1 | 9/2017 |
| EP | 3219801 | A1 | 9/2017 |
| EP | 3221349 | A1 | 9/2017 |
| EP | 3221453 | A1 | 9/2017 |
| EP | 3221456 | A2 | 9/2017 |
| EP | 3224376 | A1 | 10/2017 |
| EP | 3230441 | A1 | 10/2017 |
| EP | 3235827 | A2 | 10/2017 |
| JP | 2002516295 | A | 6/2002 |
| JP | 2007524386 | A | 8/2007 |
| JP | 2014511180 | A | 5/2014 |

(56) References Cited

FOREIGN PATENT DOCUMENTS

| | | | |
|---|---|---|---|
| WO | 1993009239 | | 5/1993 |
| WO | 1995034670 | | 12/1995 |
| WO | 1996023810 | | 8/1996 |
| WO | 1996023810 | A1 | 8/1996 |
| WO | 1996030540 | A2 | 10/1996 |
| WO | 1998010088 | | 3/1998 |
| WO | 1999027110 | A1 | 6/1999 |
| WO | 1999043360 | A1 | 9/1999 |
| WO | 1999058700 | A1 | 11/1999 |
| WO | 1999061066 | A2 | 12/1999 |
| WO | 1999061595 | A2 | 12/1999 |
| WO | 200023116 | | 4/2000 |
| WO | 2000023116 | A1 | 4/2000 |
| WO | 1999060146 | | 5/2000 |
| WO | 2000024916 | | 5/2000 |
| WO | 2000066780 | A2 | 11/2000 |
| WO | 2000075353 | A1 | 12/2000 |
| WO | 2001014539 | A2 | 3/2001 |
| WO | 2001023001 | | 4/2001 |
| WO | 2001025465 | A1 | 4/2001 |
| WO | 2001036623 | A2 | 5/2001 |
| WO | 2001068888 | A2 | 9/2001 |
| WO | 2001089583 | A2 | 11/2001 |
| WO | 2001096587 | A2 | 12/2001 |
| WO | 2001032711 | B1 | 1/2002 |
| WO | 2001042444 | A3 | 1/2002 |
| WO | 2002012525 | A2 | 2/2002 |
| WO | 2002014487 | A2 | 2/2002 |
| WO | 2002020748 | A2 | 3/2002 |
| WO | 2002070719 | A2 | 9/2002 |
| WO | 2002071843 | A1 | 9/2002 |
| WO | 2003010320 | A2 | 2/2003 |
| WO | 2003024502 | | 3/2003 |
| WO | 2003042397 | A2 | 5/2003 |
| WO | 2003087382 | A1 | 10/2003 |
| WO | 2003087383 | A1 | 10/2003 |
| WO | 2004044003 | | 5/2004 |
| WO | 2004083441 | A2 | 9/2004 |
| WO | 2004108922 | A2 | 12/2004 |
| WO | 2004111248 | A2 | 12/2004 |
| WO | 2004112727 | A2 | 12/2004 |
| WO | 2005005610 | | 1/2005 |
| WO | 2005012537 | | 2/2005 |
| WO | 2005111220 | A2 | 11/2005 |
| WO | 2006063247 | | 6/2006 |
| WO | 2006102072 | | 9/2006 |
| WO | 2007130519 | | 11/2007 |
| WO | 2007148971 | | 7/2009 |
| WO | 2009134681 | | 11/2009 |
| WO | 2011038187 | | 3/2011 |
| WO | 2011054976 | A2 | 5/2011 |
| WO | 2011122950 | | 10/2011 |
| WO | 2010109053 | | 11/2011 |
| WO | 2012007458 | | 1/2012 |
| WO | 2012007458 | A1 | 1/2012 |
| WO | 2012057363 | | 5/2012 |
| WO | 2012109570 | | 8/2012 |
| WO | 2012109570 | A1 | 8/2012 |
| WO | 2012114090 | | 8/2012 |
| WO | 2012144446 | | 10/2012 |
| WO | 2013078199 | | 5/2013 |
| WO | 2013164793 | | 11/2013 |
| WO | 2013170078 | A1 | 11/2013 |
| WO | 2014160092 | | 10/2014 |
| WO | 2014168953 | | 10/2014 |
| WO | 2014170470 | | 10/2014 |
| WO | 2014170480 | | 10/2014 |
| WO | 2014172669 | | 10/2014 |
| WO | 2014186579 | | 11/2014 |
| WO | 2014194132 | | 12/2014 |
| WO | 2014201252 | | 12/2014 |
| WO | 2015012924 | | 1/2015 |
| WO | 2015013148 | A2 | 1/2015 |
| WO | 2015018503 | | 2/2015 |
| WO | 2014186746 | | 3/2015 |
| WO | 2015038625 | A1 | 3/2015 |
| WO | 2015031686 | | 4/2015 |
| WO | 2015044292 | | 4/2015 |
| WO | 2015060722 | | 4/2015 |
| WO | 2015106273 | A2 | 7/2015 |
| WO | 2015108610 | | 7/2015 |
| WO | 2015114365 | | 8/2015 |
| WO | 2015121501 | | 8/2015 |
| WO | 2015124546 | | 8/2015 |
| WO | 2015137802 | | 9/2015 |
| WO | 2015127128 | | 11/2015 |
| WO | 2015196179 | | 12/2015 |
| WO | 2016019364 | | 2/2016 |
| WO | 2016054554 | | 4/2016 |
| WO | 2016054557 | | 4/2016 |
| WO | 2016065001 | | 4/2016 |
| WO | 2016073693 | | 5/2016 |
| WO | 2016081811 | | 5/2016 |
| WO | 2016081927 | | 5/2016 |
| WO | 2016115382 | | 7/2016 |
| WO | 2016122791 | | 8/2016 |
| WO | 2016126857 | | 8/2016 |
| WO | 2016130591 | | 8/2016 |
| WO | 2016145217 | A1 | 9/2016 |
| WO | 2016154055 | | 9/2016 |
| WO | 2016154344 | | 9/2016 |
| WO | 2016137949 | A1 | 10/2016 |
| WO | 2016164609 | | 10/2016 |
| WO | 2016168728 | | 10/2016 |
| WO | 2016172008 | | 10/2016 |
| WO | 2016172155 | | 10/2016 |
| WO | 2016179496 | | 11/2016 |
| WO | 2016183297 | A1 | 11/2016 |
| WO | 2016191418 | | 12/2016 |
| WO | 2016196328 | A1 | 12/2016 |
| WO | 2016196507 | | 12/2016 |
| WO | 2017004514 | | 1/2017 |
| WO | 2017005806 | | 1/2017 |
| WO | 2017015102 | | 1/2017 |
| WO | 2017019876 | | 2/2017 |
| WO | 2017019994 | | 2/2017 |
| WO | 2017023724 | A1 | 2/2017 |
| WO | 2017024198 | A1 | 2/2017 |
| WO | 2017058892 | | 4/2017 |
| WO | 2017070476 | | 4/2017 |
| WO | 2017070516 | | 4/2017 |
| WO | 2017070525 | | 4/2017 |
| WO | 2017070678 | | 4/2017 |
| WO | 2017075335 | | 5/2017 |
| WO | 2017079768 | A1 | 5/2017 |
| WO | 2017083423 | | 5/2017 |
| WO | 2017093330 | | 6/2017 |
| WO | 2017096039 | | 6/2017 |
| WO | 2017100671 | | 6/2017 |
| WO | 2017100674 | | 6/2017 |
| WO | 2017100676 | | 6/2017 |
| WO | 2017100704 | | 6/2017 |
| WO | 2017106236 | A1 | 6/2017 |
| WO | 2017112948 | A1 | 6/2017 |
| WO | 2017122789 | A1 | 7/2017 |
| WO | 2017123934 | A1 | 7/2017 |
| WO | 2017136202 | A1 | 8/2017 |
| WO | 2017136536 | A1 | 8/2017 |
| WO | 2017139381 | A1 | 8/2017 |
| WO | 2017143100 | A1 | 8/2017 |
| WO | 2017147477 | A1 | 8/2017 |
| WO | 2017151884 | A1 | 9/2017 |
| WO | 2017152149 | A1 | 9/2017 |
| WO | 2017155973 | A1 | 9/2017 |
| WO | 2017160360 | A2 | 9/2017 |
| WO | 2017165167 | A1 | 9/2017 |
| WO | 2017165859 | A1 | 9/2017 |
| WO | 2017172733 | A1 | 10/2017 |
| WO | 2017172772 | A1 | 10/2017 |
| WO | 2017173043 | A1 | 10/2017 |
| WO | 2017173283 | A1 | 10/2017 |
| WO | 2017180854 | A1 | 10/2017 |
| WO | 2017181162 | A1 | 10/2017 |
| WO | 2017184879 | A1 | 10/2017 |

(56) References Cited

FOREIGN PATENT DOCUMENTS

| | | | |
|---|---|---|---|
| WO | 2017190031 | A1 | 11/2017 |
| WO | 2017192699 | A1 | 11/2017 |
| WO | 2017192750 | A1 | 11/2017 |
| WO | 2018191450 | | 10/2018 |

OTHER PUBLICATIONS

Olanowa et al., Risk of dyskinesia in Parkinson's disease patients who already have developed wearing-off: A secondary analysis of STRIDE-PD study. J Neurol Sci. 2013;333:e65-e66.

Porras et al., Modeling Parkinson's Disease in Primates: The MPTP Model. Cold Spring Harb Perspect Med Mar. 2 (3), 2012.

Richardson RM et al., Interventional MRI-guided putaminal delivery of AAV2-GDNF for a planned clinical trial in Parkinson's disease. Mol Ther. Jun. 2011;19(6):1048-57.

Rolston JD et al., An unexpectedly high rate of revisions and removals of deep brain stiulation surgery: Analysis of multiple databases. Parkinsonism and Related Disorders (33) 72-77, 2016.

SuX et al., Safety evaluation of AAV2-GDNF gene transfer into the dopaminergic higrostriatal pathway in aged and parkinsonian rhesus monkeys. Hum Gene Ther. Dec. 2009;20(12):1627-40.

Wächter et al., A tool to improve pre-selection for deep brain stimulation in patients with Parkinson's disease. J Neurol. Apr. 2011; 258(4): 641-646.

Xu et al., Quantitative comparison of expression with adeno-associated virus (AAV-2) brain-specific gene cassettes. Gene Ther. Sep. 2001;8(17):1323-32.

Dickson, Neuropathology of Parkinson disease. Parkinsonism Relat Disord. Jan. 2018;46 Suppl 1:S30-S33. Epub Aug. 1, 2017.

Examination Report No. 1 received in corresponding Australian Patent Application No. 2015343037 dated Jan. 25, 2018.

Japanese Office Action received in corresponding Japanese Patent Application No. 2017-544285 dated Apr. 24, 2018.

Examiner's Report received in corresponding Canadian Patent Application No. 2,966,620 dated Feb. 28, 2018.

Douglas, M.R., Expert Rev Neurother, 13, pp. 695-705, 2013.

Adachi K, et al. Drawing a high-resolution functional map of adeno-associated virus capsid by massively parallel sequencing. Nat Commun. 2014;5:3075. doi: 10.1038/ncomms4075.

Ahmed SS, et al. rAAV gene therapy in a Canavan's disease mouse model reveals immune impairments and an extended pathology beyond the central nervous system. Mol Ther. Jun. 2016;24(6):1030-41.

Al J, et al. Adeno-associated virus serotype rh.10 displays strong muscle tropism following intraperitoneal delivery. Sci Rep. Jan. 2017;7:40336.

Altschul SF, et al. Basic local alignment search tool. J Mol Biol. Oct. 5, 1990;215(3):403-10.

Aoyama Y, et al. Wnt11 gene therapy with adeno-associated virus 9 improves the survival of mice with myocarditis induced by coxsackievirus B3 through the suppression of the inflammatory reaction. J Mol Cell Cardiol. Jul. 2015;84:45-51.

Aubourg P. Gene therapy for rare central nervous system diseases comes to age. Endocr Dev. 2016;30:141-6.

Aydemir F, et al. Mutants at the 2-fold interface of AAV2 structural proteins suggest a role in viral transcription for AAV capsids. J Virol. Jul. 2016;90(16):7196-204.

Bankiewicz KS et al. AAV Viral Vector Delivery to the Brain by Shape-conforming MR-guided Infusions. J Control Release. Oct. 28, 2016;240:434-442.

Bantel-Schaal U, et al. Human adeno-associated virus type 5 is only distantly related to other known primate helper-dependent parvoviruses. J Virol. Feb. 1999;73(2):939-47.

Baum BJ, et al. Advances in salivary gland gene therapy—oral and systemic implications. Expert Opinion on Biological Therapy. 2015;15(10):1443-54.

Bell P, et al. Effects of self-complementarity, codon optimization, transgene, and dose on liver transduction with AAV8. Hum Gene Ther Methods. Dec. 2016;27(6):228-237.

Berge SM Pharmaceutical salts. J Pharm Sci. Jan. 1977;66(1):1-19.

Berry GE, et al. Cellular transduction mechanisms of adeno-associated viral vectors. Curr Opin Virol. Dec. 2016;21:54-60.

Chiorini JA, et al. Adeno-associated virus (AAV) type 5 Rep protein cleaves a unique terminal resolution site compared with other AAV serotypes. J Virol. May 1999;73(5):4293-8.

Bey K, et al. Efficient CNS targeting in adult mice by intrathecal infusion of single-stranded AAV9-GFP for gene therapy of neurological disorders. Gene Ther. Apr. 20, 2017. Epub ahead of print.

Brulet R, et al. NEUROD1 Instructs Neuronal Conversion in Non-Reactive Astrocytes. Stem Cell Reports. May 11, 2017. Epub ahead of print.

Cabral-Miranda F, et al. rAAV8-733-Mediated Gene Transfer of CHIP/Stub-1 Prevents Hippocampal Neuronal Death in Experimental Brain Ischemia. Mol Ther. Feb. 2017;25(2):392-400.

Carillo H, et al. The Multiple Sequence Alignment Problem in Biology. SIAM J. Appl. Math. 48-5 (1988), pp. 1073-1082.

Carter BJ. Adeno-associated virus and the development of adeno-associated virus vectors: a historical perspective. Mol Ther. Dec. 2004;10(6):981-9.

Chandler RJ, et al. Systemic AAV9 gene therapy improves the lifespan of mice with Niemann-Pick disease, type C1. Hum Mol Genet. Jan. 2017;26(1):52-64.

Chiorini JA, et al. Adeno-associated virus (AAV) type 5 Rep protein cleaves a unique terminal resolution site compared with other AAV serotypes. J Virol. May 1999;73(5):4293-8.

Chiorini JA, et al. Cloning and characterization of adeno-associated virus type 5. J Virol. Feb. 1999;73(2):1309-19.

Chiorini JA, et al. Cloning of adeno-associated virus type 4 (AAV4) and generation of recombinant AAV4 particles. J Virol. Sep. 1997;71(9):6823-33.

Dang CH, et al. In vivo dynamics of AAV-mediated gene delivery to sensory neurons of the trigeminal ganglia. Sci Rep. Apr. 19, 2017;7(1):927.

Dashkoff J, et al. Tailored transgene expression to specific cell types in the central nervous system after peripheral injection with AAV9. Mol Ther Methods Clin Dev. Dec. 2016;3:16081.

Devereux J A Comprehensive set of sequence analysis programs for the VAX. Nucleic Acids Res. Jan. 11, 1984;12(1 Pt 1):387-95.

Dimidschstein J, et al. A viral strategy for targeting and manipulating interneurons across vertebrate species. Nat Neurosci. Dec. 2016;19(12):1743-1749.

Ding C, et al., Biochemical Characterization of Junonia Coenia Densovirus Nonstructural Protein NS-1. J. Virol., 76(1):338-345 2002.

Donsante A et al. Intracerebroventricular delivery of self-complementary adeno-associated virus serotype 9 to the adult rat brain. Gene Ther. May 2016;23(5):401-7.

Earley LF, et al. Adeno-Associated Virus Assembly-Activating Protein Is Not an Essential Requirement for Capsid Assembly of AAV Serotypes 4, 5 and 11. J Virol. Jan. 2017;91(3):pii:e0198-16.

El-Shamayleh Y, et al. Strategies for targeting primate neural circuits with viral vectors. J Neurophysiol. Jul. 2016;116(1):122-34.

Fargnoli AS, et al. Liquid jet delivery method featuring S100A1 gene therapy in the rodent model following acute myocardial infarction. Gene Ther. Feb. 2016;23(2):151-7.

Foust KD, et al. Intravascular AAV9 preferentially targets neonatal neurons and adult astrocytes. Nat Biotechnol. Jan. 2009;27(1):59-65. doi: 10.1038/nbt.1515. Epub Dec. 21, 2008.

Gessler DJ et al. Gene Therapy for the Treatment of Neurological Disorders: Metabolic Disorders. Methods Mol Biol. 2016;1382:429-65.

Gilkes JA et al. Preferred Transduction with AAV8 and AAV9 Via Thalamic Administration in the MPS IIIB Model: A Comparison of Four rAAV Serotypes. Mol Genet Metab Rep. Dec. 7, 2015;6:48-54.

Gombash SE, et al. Systemic Gene Therapy for Targeting the CNS. Methods Mol Biol. 2016;1382:231-7.

Greig JA, et al. Impact of intravenous infusion time on AAV8 vector pharmacokinetics, safety, and liver transduction in cynomolgus macaGRUNTMAN AM, et al. Delivery of Adeno-associated virus gene therapy by intravascular limb infusion methods. Hum Gene Ther Clin Dev Sep. 2015;26(3):159-64. ques. Mol Ther Methods Clin Dev. Dec. 2016;3:16079.

(56) References Cited

OTHER PUBLICATIONS

Greig JA, et al. Intramuscular administration of AAV overcomes pre-existing neutralizing antibodies in rhesus macaques. Vaccine. Dec. 2016;34(50):6323-6329.
Gribskov M, et al. Sequence Analysis Primer. M Stockton Press, New York, 1991.
Grimm D, et al. Progress in adeno-associated virus type 2 vector production: promises and prospects for clinical use. Hum Gene Ther. Oct. 10, 1999;10(15):2445-50.
Grimson A, et al. MicroRNA targeting specificity in mammals: determinants beyond seed pairing. Mol Cell. Jul. 6, 2007;27(1):91-105.
Gruntman AM, et al. Delivery of Adeno-associated virus gene therapy by intravascular limb infusion methods. Hum Gene Ther Clin Dev Sep. 2015;26(3):159-64.
Gruntman AM, et al. Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230.
Gurda BL, et al. Evaluation of AAV-mediated gene therapy for central nervous system disease in canine mucopolysaccharidosis VII. Mol Ther. Feb. 2016;24(2):206-16.
Hagg A, et al. Using AAV vectors expressing the beta 2-adrenoceptor or associated G alpha proteins to modulate skeletal muscle mass and muscle fiber size. Sci Rep. Mar. 2016;6:23042.
Hai B, et al. Long-term transduction of miniature pig parotid glands using serotype 2 adeno-associated viral vectors. J Gene Med. Jun. 2009;11(6):506-14.
Hastie E, et al. Adeno-Associated Virus at 50: A Golden Anniversary of Discovery, Research, and Gene Therapy Success—A Personal Perspective. Hum Gene Ther. May 2015, 26(5):257-65.
Hastie E, et al. Recombinant adeno-associated virus vectors in the treatment of rare diseases. Expert Opin Orphan Drugs. 2015;3(6):675-689.
Heim et al., Wavelength mutations and posttranslational autoxidation of green fluorescent protein. Proc. Natl. Acad. Sci. USA (1994).
Bosch ME et al. Self-Complementary AAV9 Gene Delivery Partially Corrects Pathology Associated with Juvenile Neuronal Ceroid Lipofuscinosis (CLN3). J Neurosci. Sep. 14, 2016;36(37):9669-82.
Hocquemiller M et al. Adeno-Associated Virus-Based Gene Therapy for CNS Diseases. Hum Gene Ther. Jul. 2016;27(7):478-96.
Chali F, et al. Inhibiting cholesterol degradation induces neuronal sclerosis and epileptic activity in mouse hippocampus. Eur J Neurosci. May 2015, 41(10):1345-55.
Bassil F, et al. Viral-mediated oligodendroglial alpha-synuclein expression models multiple system atrophy. Mov Disord. May 29, 2017. Epub ahead of print Movement Disorders Aug. 2017 32(8)1230-1239.
Kao JH, et al. Effect of naltrexone on neuropathic pain in mice locally transfected with the mutant mu-opioid receptor gene in spinal cord. Br J Pharmacol. Jan. 2015, 172(2):630-41.
Blits B, et al. Perspective on the Road toward Gene Therapy for Parkinson's Disease. Front Neuroanat. Jan. 2017;10:128.
Daher JPL, et al. Leucine-rich Repeat Kinase 2 (LRRK2) Pharmacological Inhibition Abates alpha-Synuclein Gene-induced Neurodegeneration. J Biol Chem. Aug. 2015, 290(32):19433-44.
Kirik D et al. Gene Therapy for Parkinson's Disease: Disease Modification by GDNF Family of Ligands. Neurobiol Dis. Jan. 2017 97(Part B)179-188.
Singh A et al. Therapeutic Value of Adeno Associated Virus as a Gene Therapy Vector for Parkinson's Disease—A Focused Review. Curr Gene Ther. Jul. 29, 2016 16(4)278-286.
Van Rompuy AS, et al. Nigral overexpression of alpha-synuclein in the absence of parkin enhances alpha-synuclein phosphorylation but does not modulate dopaminergic neurodegeneration. Mol Neurodegener. Jun. 2015, 10:23.
Sehara Y, et al. Persistent Expression of Dopamine-Synthesizing Enzymes 15 years after Gene Transfer in a Primate Model of Parkinson's Disease. Hum Gene Ther Clin Dev. Mar. 9, 2017 Epub ahead of print. Jun. 28, 2017(2):74-79.
Ciesielska A, et al. Carbidopa-Based Modulation of the Functional Effect of the AAV2-hAADC Gene Therapy in 6-OHDA Lesioned Rats. PLoS One. Apr. 2015, 10(4):e0122708.
Hadaczek P, et al. GDNF signaling implemented by GM1 ganglioside; failure in Parkinson's disease and GM1-deficient murine model. Exp Neurol. Jan. 2015, 263:177-89.
Rocha EM, et al. Glucocerebrosidase gene therapy prevents alpha-synucleinopathy of midbrain dopamine neurons. Neurobiol Dis. Oct. 2015;82:495-503.
Thome AD et al. Fractalkine Signaling Regulates the Inflammatory Response in an α-Synuclein Model of Parkinson Disease. PLoS One. Oct. 15, 2015;10(10):e0140566.
Marks WJ et al. Long-Term Safety of Patients with Parkinson's Disease Receiving rAAV2-Neurturin (CERE-120) Gene Transfer. Hum Gene Ther. Jul. 2016;27(7):522-7.
Olanow CW, et al. Gene delivery of neurturin to putamen and substantia nigra in Parkinson disease: A double-blind randomized controlled trial. Ann Neurol.Aug. 2015, 78(2):248-57.
Paul G, et al. Safety and tolerability of intracerebroventricular PDGF-BB in Parkinson's disease patients. J Clin Invest. Mar. 2, 2015;125(3):1339-46.
Kim YC, et al. RNA Interference of Human α-Synuclein in Mouse. Front Neurol. Jan. 2017;8:13.
Marongiu R et al. Gene Therapy Blockade of Dorsal Striatal p11 Improves Motor Function and Dyskinesia in Parkinsonian Mice. Proc Natl Acad Sci USA. Feb. 2, 2016;113(5):1423-8.
Stavarache MA, et al. The tumor suppressor PTEN regulates motor responses to striatal dopamine in normal and Parkinsonian animals. Neurobiol Dis. Oct. 2015;82:487-94.
Zharikov AD, et al. shRNA targeting α-synuclein prevents neurodegeneration in a Parkinson's disease model. J Clin Invest. Jul. 1, 2015;125(7):2721-35.
Lee NC, et al. Mutation-adapted U1 snRNA corrects a splicing error of the dopa decarboxylase gene. Hum Mol Genet. Dec. 2016;25(23):5142-5147.
Lee NC, et al. Benefits of Neuronal Preferential Systemic Gene Therapy for Neurotransmitter Deficiency. Mol Ther. Oct. 2015;23(10):1572-81.
Bradbury AM, et al. Biomarkers for disease progression and AAV therapeutic efficacy in feline Sandhoff disease. Exp Neurol. Jan. 2015, 263:102-12.
Hemphill DD, et al. Adeno-associated virus gene therapy vector scAAVIGF-1 for transduction of equine articular chondrocytes and RNA-seq analysis. Osteoarthritis Cartilage. May 2016;24(5):902-11.
Ito H, et al. HMGB1 facilitates repair of mitochondrial DNA damage and extends the lifespan of mutant ataxin-1 knock-in mice. EMBO Mol Med. Dec. 2015;7(1):78-101.
Ito H, et al. In utero gene therapy rescues microcephaly caused by Pqbp1-hypofunction in neural stem progenitor cells. Mol Psychiatry. Apr. 2015, 20(4):459-71.
Ko AR, et al. AAV8-mediated expression of N-acetylglucosamine-1-phosphate transferase attenuates bone loss in a mouse model of mucolipidosis II. Mol Genet Metab. Apr. 2016;117(4):447-55.
Lai Z, et al. Aquaporin gene therapy corrects Sjogren's syndrome phenotype in mice. PNAS. May 2016;113(20):5694-9.
Meadows AS, et al. A GLP-compliant toxicology and biodistribution study: systemic delivery of an rAAV9 vector for the treatment of mucopolysaccharidosis IIIB. Hum Gene Ther Clin Dev. Dec. 2015;26(4):228-42.
Osmon KJ, et al. Systemic Gene Transfer of a Hexosaminidase Variant Using a scAAV9.47 Vector Corrects GM2 Gangliosidosis in Sandhoff Mice. Hum Gene Ther. Jul. 2016;27(7):497-508.
Ramos J, et al. Gene therapy for Duchenne muscular dystrophy. Exp Opin Orphan Drugs. 2015;3(11):1255-1266.
Rockwell HE, et al. AAV-Mediated Gene Delivery in a Feline Model of Sandhoff Disease Corrects Lysosomal Storage in the Central Nervous System. ASN Neuro. Apr. 2015, 7(2).
Rosenberg JB et al. Gene Therapy for Metachromatic Leukodystrophy. J Neurosci Res. Nov. 2016:94(11):1169-79.
Sun BD, et al. Preclinical Development of New Therapy for Glycogen Storage Diseases. Curr Gene Ther. Jan. 2015, 15(4):338-47.

(56) References Cited

OTHER PUBLICATIONS

Talla V, et al. Complex I Subunit Gene Therapy with NDUFA6 Ameliorates Neurodegeneration in EAE. Invest Ophthalmol Vis Sci. Jan. 2015, 22;56(2):1129-40.
Wang L, et al. AAV gene therapy corrects OTC deficiency and prevents liver fibrosis in aged OTC-knock out heterozygous mice. Mol Genet Metab. Apr. 2017;120(4):299-305.
Wilson JM, et al. Adeno-associated virus vector-mediated gene therapy can effectively treat CNS and cardiac lesions and induce immune tolerance to the therapeutic enzyme in large animal models of mucopolysaccharidosis type. Feb. 2015 ,114(2): 126-127.
Yi H, et al. Systemic correction of murine glycogen storage disease type IV by an AAV-mediated gene therapy. Hum Gene Ther. Mar. 2017;28(3):286-294.
Zolotukhim I, et al. Potential for cellular stress response to hepatic factor VIII expression from AAV vector. Mol Ther Methods Clin Dev. Sep. 2016;3:16063.
Arruda VR, et al. Obstacles and future of gene therapy for hemophilia. Expert Opin Orphan Drugs. 2015;3(9):997-1010.
George LA, et al. Gene therapy for hemophilia: past, present and future. Semin Hematol. Jan. 2016;53(1):46-54.
Francis JS et al. N-Acetylaspartate supports the Energetic Demands of Developmental Myelination via Oligodendroglial Asparloacyclase. Neurobiol Dis. Oct. 4, 2016;96:323-334.
Loring HS, et al. Development of rAAV2-CFTR: History of the First rAAV Vector Product to be Used in Humans. Hum Gene Ther Methods. Apr. 2016;27(2):49-58.
Doerfler PA, et al. Copackaged AAV9 Vectors Promote Simultaneous Immune Tolerance and Phenotypic Correction of Pompe Disease. Hum Gene Ther. Jan. 2016;27(1):43-59.
Fu H, et al. Functional correction of neurological and somatic disorders at later stages of disease in MPS IIIA mice by systemic scAAV9-hSGSH gene delivery. Mol Ther Methods Clin Dev. Jun. 2016;3:16036.
Gessler DJ, et al. Redirecting N-acetylaspartate metabolism in the central nervous system normalizes myelination and rescues Canavan disease. JCI Insight. Feb. 2017;2(3):e90807.
Gilkes JA, et al. Mucopolysaccharidosis IIIB confers enhanced neonatal intracranial transduction by AAV8 but not by 5, 9 or rh10. Gene Ther. Mar. 2016;23(3):263-71.
Golebiowski D, et al. Direct intracranial injection of AAVrh8 encoding monkey β-N-acetylhexosaminidase causes neurotoxicity in primate brain. Hum Gene Ther. Jan. 26, 2017 Epub ahead of print.
Iwayamah, et al. Adeno associated virus 9-based gene therapy delivers a functional monocarboxylate transporter 8 which improves thyroid hormone availability to the brain of Mct8 deficient mice. Thyroid. Sep. 2016;26(9):1311-9.
Meyer K, et al. Improving Single Injection CSF Delivery of AAV9-mediated Gene Therapy for SMA: A Dose-response Study in Mice and Nonhuman Primates. Mol Ther. Mar. 2015,23(3):477-87.
Zerah M, et al. Intracerebral Gene therapy using AAV rh.10-hARSA recombinant vector to treat patients with early-onset forms of metachromatic leukodystrophy: preclinical feasibility and safety assessments in NHP. Hum Gene Ther Clin Dev. Jun. 2015;26(2):113-24.
Gadalla KKE, et al. Development of a Novel AAV Gene Therapy Cassette with Improved Safety Features and Efficacy in a Mouse Model of Rett Syndrome. Mol Ther Methods Clin Dev. Apr. 22, 2017;5:180-190.
Sinnett SE, et al. Improved MECP2 Gene Therapy Extends the Survival of MeCP2-Null Mice without Apparent Toxicity after Intracisternal Delivery. Mol Ther Methods Clin Dev. Apr. 19, 2017;5:106-115.
Armbruster N, et al. Efficacy and biodistribution analysis of intracerebroventricular administration of an optimized scAAV9-SMN1 vector in a mouse model of spinal muscular atrophy. Mol Ther Methods Clin Dev. Sep. 2016;3:16060.
Pan B, et al. Gene therapy restores auditory and vestibular function in a mouse model of Usher syndrome type 1c. Nat. Biotechnol. Mar. 2017;35(3):264-272.
Dinculescu A, et al. AAV-mediated clarin-1 expression in the mouse retina: Implications for USH3A gene therapy. PLoS One. Feb. 2016;11(2):e0148874.
Conlon TJ, et al. Transfer of Therapeutic Genes into Fetal Rhesus Monkeys using Recombinant Adeno-Associated Type I Viral Vectors. Hum Gene Ther Clin Dev. Dec. 2016;27(4):152-159.
Marcos-Contreras OA, et al. Sustained correction of FVII deficiency in dogs using AAV-mediated expression of zymogen FVII. Blood. Feb. 2016;127(5):565-71.
Chiuchiolo MJ, et al. Gene therapy for alpha-1 antitrypsin deficiency lung disease. Ann Am Thorac Soc. Aug. 2016;13 Suppl 4:S352-69.
Griesenbach, UTA et al. Cystic Fibrosis Gene Therapy in the UK and Elsewhere. Hum Gene Ther. May 1, 2015; 26(5): 266-275.
Corti M, et al. Evaluation of Readministration of a Recombinant Adeno-Associated Virus Vector Expressing Acid Alpha-Glucosidase in Pompe Disease: Preclinical to Clinical Planning. Human Gene Therapy Clin Dev Sep. 2015;26(3):185-193.
Mack DL, et al. Minimally Effective Dose of Systemic AAV8-MTM1 Needed to Prolong Survival and Correct Severe Muscle Pathology in a Canine Model of X-Linked Myotubular Myopathy. Molecular Therapy, vol. 23, Supplement 1, p. S201, May 2015.
Mack DL, et al. Systemic AAV8-Mediated Gene Therapy Drives Whole-Body Correction of Myotubular Myopathy in Dogs. Mol Ther. Apr. 2017;25(4):839-854.
Pozsgai ER, et al. β-sarcoglycan gene transfer decreases fibrosis and restores force in LGMD2E mice. Gene Ther. Jan. 2016;23(1):57-66.
Todd A.G., et al. Correcting Neuromuscular Deficits With Gene Therapy in Pompe Disease. Ann Neurol. Aug. 2015, 78(2):222-34.
Han So, et al. Enhanced Efficacy from Gene Therapy in Pompe Disease Using Coreceptor Blockade. Hum Gene Ther.Jan. 2015, 26(1):26-35.
Pierce EA, et al. The status of RPE65 Gene Therapy Trials: Safety and Efficacy. Cold Spring Harb Perspect Med. Sep. 2015;5(9):a017285.
Landau DJ, et al. In vivo zinc finger nuclease mediated targeted integration of a glucose-6-phosphatase transgene promotes survival in mice with glycogen storage disease type 1a. Mol Ther. Apr. 2016;24(4):697-706.
Valdmanis P, et al. Future of rAAV gene therapy: Platform for RNAi, Gene Editing and Beyond. Hum Gene Ther. Apr. 2017;28(4):361-372.
Ronzitti G, et al. A translationally optimized AAV-UGT1A1 vector drives safe and long-lasting correction of Crigler-Najjar syndrome. Mol Ther Methods Clin Dev. Jul. 2016;3:16049.
Sun J, et al. Gene delivery of activated Factor VII Using Alternative AAV Serotype Improves Hemostasis in Hemophiliac Mice with FVIII Inhibitors and AAV Neutralizing antibodies. Hum Gene Ther. May 6, 2017. Epub ahead of print.
Tse LV, et al. Structure-guided evolution of antigenically distinct adeno-associated virus variants for immune evasion. Proc Natl Acad Sci U S A. May 30, 2017. Epub ahead of print.
Vandamme C, et al. Unraveling the complex story of immune responses to AAV vectors trial after trial. Hum Gene Ther. Aug. 23, 2017.
Fu H, et al. Differential prevalence of antibodies against adeno-associated virus in healthy children and patients with mucopolysaccharidosis III: perspective for AAV-mediated gene therapy. Human Gene Ther Clin Dev Sep. 19, 2017 Epub ahead of print.
Mingozzi F, et al. Overcoming the Host Immune Response to Adeno-Associated Virus Gene Delivery Vectors: The Race Between Clearance, Tolerance, Neutralization, and Escape. Annu Rev Virol Sep. 29, 2017;4(1):511-534.
Majowicz A, et al. Successful Repeated Hepatic Gene Delivery in Mice and Non-human Primates Achieved by Sequential Administration of AAV5ch and AAV1. Mol Ther. Jun. 5, 2017. Epub ahead of print.
Kim Y, et al. Mutagenic Analysis of an Adeno-Associated Virus Variant Capable of Simultaneously Promoting Immune Resistance and Robust Gene Delivery. Hum Gene Ther. Jun. 24, 2017. Epub ahead of print.
Gil-Farina I, et al. Recombinant AAV Integration Is Not Associated With Hepatic Genotoxicity in Nonhuman Primates and Patients. Mol Ther. Jun. 2016;24(6):1100-5.

(56) References Cited

OTHER PUBLICATIONS

Logan GJ, et al. Identification of liver-specific enhancer-promoter activity in the 3' untranslated region of the wild-type AAV2 genome. Nat Genet. Jun. 19, 2017. Epub ahead of print.
Pillay S, et al. AAV serotypes have distinctive interactions with domains of the cellular receptor AAVR. J Virol. Jul. 5, 2017. Epub ahead of print.
Wang M, Sun J, Crosby A, Woodard K, Hirsch ML, Samulski RJ, Li C. Direct interaction of human serum proteins with AAV virions to enhance AAV transduction: immediate impact on clinical applications. Gene Ther. Jan. 2017;24(1):49-59. doi: 10.1038/gt.2016.75. Epub Nov. 11, 2016.
Lu J, et al. A 5' Noncoding Exon Containing Engineered Intron Enhances Transgene Expression from Recombinant AAV Vectors in vivo. Hum Gene Ther. Jan. 2017;28(1):125-134.
Bennett A, et al. Thermal Stability as a Determinant of AAV Serotype Identity. Mol Ther Methods Clin Dev. Jul. 24, 2017;6:171-182. doi: 10.1016/j.omtm.2017.07.003.
Gray-Edwards H, et al. AAV gene therapy in a sheep model of Tay-Sachs disease. Human Gene Therapy. Sep. 19, 2017 Epub ahead of print.
Guggino W, et al. A Preclinical Study in Rhesus Macaques for Cystic Fibrosis to Assess Gene Transfer and Transduction by AAV1 and AAV5 With a Dual-Luciferase Reporter System. Hum Gene Ther Clin Dev. Jul. 20, 2017.
Eichler F, et al. Hematopoietic Stem-Cell Gene Therapy for Cerebral Adrenoleukodystrophy. N Engl J Med Oct. 4, 2017 Epub ahead of print.
Bennett A, et al. Understanding capsid assembly and genome packaging for adeno-associated viruses. Future Virology Jun. 2017; 12(6): 283-297.
Grimm D, et al. Small but increasingly mightly—latest advances in AAV vector research, design and evolution. Hum Gene Ther. Aug. 23 Epub ahead of print.
Pillay S. et al. Host determinants of adeno-associated viral vector entry. Curr Opin Virol. Jun. 30, 2017;24:124-131. Epub ahead of print.
Smith LJ, et al. Gene transfer properties and structural modeling of human stem cell-derived AAV. Molecular Therapy. Sep. 2014;22(9):1625-1634.
Wooley DP, et al. A directed evolution approach to select for novel Adeno-associated virus capsids on an HIV-1 producer T cell line. J Virol. Methods. Sep. 13, 2017 Epub ahead of print.
Eichler K, et al. The complete connectome of a learning and memory centre in an insect brain. Nature. Aug. 9, 2017;548(7666):175-182.
Le Pichon CE, et al. Loss of dual leucine zipper kinase signaling is protective in animal models of neurodegenerative disease. Sci Transl Med. Aug. 16, 2017;9(403).
Durost P, et al. Gene therapy with an AAV vector expressing human IL-2 alters immune system homeostasis in humanized mice. Hum Gene Ther. Aug. 21, 2017 Epub ahead of print.
Ahmad M, et al. Engineered Expression of Broadly Neutralizing Antibodies Against Human Immunodeficiency Virus. Annu Rev Virol. Jun. 23, 2017. Epub ahead of print.
Brady JM, et al. Antibody gene transfer with adeno-associated viral vectors as a method for HIV prevention. Immunol Rev. Jan. 2017;275(1):324-333. dol: 10.1111/imr.12478.
Magnani DM et al., Dengue virus evades AAV-mediated neutralizing antibody prophylaxis in rhesus monkeys. Mol Ther Jul. 24, 2017 Epub ahead of print.
Zhu Z, et al. Zika virus has oncolytic activity against glioblastoma stem cells. J Exp Med. Sep. 5, 2017 Epub ahead of print.
Liu Z et al. Single cell transcriptomics reconstructs fate conversion from fibroblast to cardiomyocyte. Nature. Oct. 25, 2017 Epub ahead of print.
Kurosaki F, et al. Optimization of adeno-associated virus vector-mediated gene transfer to the respiratory tract. Gene Ther. May 2017;24(5):290-297.
Tadokoro T, et al. Subpial Adeno-associated Virus 9 (AAV9) Vector Delivery in Adult Mice. J Vis Exp. Jul. 13, 2017;(125). doi: 10.3791/55770.
Merkel SF, et al. Trafficking of adeno-associated virus vectors across a model of the blood-brain barrier; a comparative study of transcytosis and transduction using primary human brain endothelial cells. J Neurochem. Jan. 2017;140(2):216-230. doi: 10.1111/jnc.13861.
Hinderer C, et al. Delivery of an Adeno-Associated Virus Vector into Cerebrospinal Fluid Attenuates Central Nervous System Disease in Mucopolysaccharidosis Type II Mice. Hum Gene Ther. Nov. 2016;27(11):906-915. Epub Aug. 10, 2016.
Gombash SE, et al. Systemic gene delivery transduces the enteric nervous system of guinea pigs and cynomolgus macaques. Gene Ther. Aug. 3, 2017. doi: 10.1038/gt.2017.72.
Hinderer C, et al. Evaluation of intrathecal routes of administration for adeno-associated virus vectors in large animals. Hum Gene Ther . Aug. 15, 2017. doi: 10.1089/hum.2017.026.
Hordeaux J, et al. Long-term neurologic and cardiac correction by intrathecal gene therapy in Pompe disease. Acta Neuropathol Commun Sep. 6, 2017(5):66.
Tardieu M, et al. Intrace/2 clinical trial. Lancet Neurol. Sep. 2017;16(9):712-720.
Yazdan-Shahmorad A, et al. Widespread Optogenetic Expression in Macaque Cortex Obtained with MR-Guided, Convection Enhanced Delivery (CED) of AAV vector to the Thalamus. J Neurosci Methods. Oct. 14, 2017 Epub ahead of print.
Lee NC, et al. A neuron-specific gene therapy relieves motor deficits in pompe disease mice. Mol Neurobiol. Sep. 11, 2017 Epub ahead of print.
Carvalho LS, et al. Evaluating efficiencies of dual AAV approaches for retinal targeting. Front Neursci. Sep. 8, 2017, 2017;11:503.
Reichel FF, et al. AAV8 can induce innate and adaptive immune response in the primate eye. Mol Ther. Aug. 31, 2017 Epub ahead of print.
De Silva SR, Charbel Issa P, Singh MS, Lipinski DM, Barnea-Cramer AO, Walker NJ, Barnard AR, Hankins MW, MacLaren RE. Single residue AAV capsid mutation improves transduction of photoreceptors in the Abca4<sup>-/-</sup> mouse and bipolar cells in the rd1 mouse and human retina ex vivo. Gene Ther. Nov. 2016;23(11):767-774. doi: 10.1038/gt.2016.54. Epub Jul. 14, 2016.
Katz MG, et al. Use of Adeno-Associated Virus Vector for Cardiac Gene Delivery in Large Animal Surgical Models of Heart Failure. Hum Gene Ther Clin Dev. Jul. 20, 2017.
Watanabe S, et al. Protein Phosphatase Inhibitor-1 Gene Therapy in a Swine Model of Nonischemic Heart Failure. Journal of the American College of Cardiology 2017.
Mandel RJ, et al. Novel oligodendroglial alpha synuclein viral vector models of multiple system atrophy: studies in rodents and nonhuman primates. Acta Neuropathol Commun. Jun. 16, 2017;5(1):47.
Landeck N, et al. Toxic effects of human and rodent variants of alpha-synuclein in vivo. Eur J Neurosci. Feb. 2017;45(4):536-547.
Arrigo A, et al. Visual System Involvement in Patients with Newly Diagnosed Parkinson Disease. Radiology. Jul. 11, 2017:161732.
Athauda D, et al. Exenatide once weekly versus placebo in Parkinson's disease: a randomised, double-blind, placebo-controlled trial. The Lancet. Aug. 3, 2017.
Mittal S, et al. $\beta$2-Adrenoreceptor is a regulator of the $\alpha$-synuclein gene driving risk of Parkinson's disease. Science Sep. 1, 2017.
Burbulla LF, et al. Dopamine oxidation mediates mitochondrial and lysosomal dysfunction in Parkinson's disease. Science. Sep. 22;357(6357):1255-1261.
Latourelle JC, et al. Large-scale identification of clinical and genetic predictors of motor progression in patients with newly diagnosed Parkinson's disease: a longitudinal cohort study and validation. Lancet Neurology. Sep. 25, 2017.
Deyaert E, et al. A homologue of the Parkinson's disease-associated protein LRRK2 undergoes a monomer-dimer transition during GTP turnover. Nat Commun. Oct. 18, 2017;8(1):1008.
Brown N, et al. Adeno-Associated Virus Vectors and Stem Cells: Friends or Foes? Hum Gene Ther. Jun. 2017;28(6):450-463.

(56) References Cited

OTHER PUBLICATIONS

Kikuchi T, et al. Human iPS cell-derived dopaminergic neurons function in a primate Parkinson's disease model. Nature. Aug. 30, 2017;548(7669):592-596.
Morizane A, et al. MHC matching improves engraftment of iPSC-derived neurons in non-human primates. Nat. Commun. Aug. 30, 2017;8(1):385.
Chansel-Debordeaux, et al. In utero delivery of rAAV2/9 induces neuronal expression of the transgene in the brain: towards new models of Parkinson's disease. Gene Ther. Aug. 30, 2017. doi: 10.1038/gt.2017.84.
Delenclos M, et al. Neonatal AAV delivery of alpha-synuclein induces pathology in the adult mouse brain. Acta Neuropathol Commun. Jun. 23, 2017;5(1):51.
Morabito G, et al. Global-scale control of gene expression in the adult mouse nervous system by a single AAV-PHP.B systemic injection enables GBA1 gene therapy for complete protection from synucleinopathy Aug. 10, 2017.
Piguet F, et al. Clinical gene therapy for neurodegenerative diseases: past, present, and future. Hum Gene Ther. Nov. 2017;28(11):988-1003.
Jin X, et al. Direct LC/MS Analysis for Complete Characterization of Recombinant Adeno-Associated Virus Capsid Proteins. Hum Gene Ther Methods. Jun. 18, 2017. Epub ahead of print.
Galli A, et al. Strategies to optimize capsid protein expression and single stranded DNA formation of Adeno-associated virus in *Saccharomyces cerevisiae*. J Appl Microbiol. Jun. 13, 2017. Epub ahead of print.
Wang Z, et al. Human Bocavirus 1 Is a Novel Helper for Adeno-Associated Virus Replication. J Virol. Jun. 28, 2017. Epub ahead of print.
Grobe S, et al. Relevance of assembly-activating protein for Adeno-associated virus vector production and capsid protein stability in mammalian and insect cells. J Virol. Aug. 2, 2017. pii: JVI.01198-17. doi: 10.1128/JVI.01198-17.
Kondratov O, et al. Direct head-to-head evaluation of recombinant Adeno-associated viral (rAAV) vectors manufactured in human vs insect cells. Molecular Therapy. Aug. 10, 2017.
Jungmann A, et al. Protocol for efficient generation and characterization of adeno-associated viral (AAV) vectors. Hum Gene Ther Methods Sep. 21, 2017 Epub ahead of print.
Luo Y, et al. AAVS1-Targeted Plasmid Integration in AAV Producer Cell Lines. Hum Gene Ther Methods. Jun. 2017;28(3):124-138.
Savy A, et al. Impact of ITR integrity on rAAV8 production using baculovirus/Sf9 cells system. Hum Gene Ther Methods. Oct. 1, 2017 Epub ahead of print.
GTEx Consortium et al. Genetic effects on gene expression across human tissues. Nature. Oct. 11, 2017;550(7675):204-213.
Li X, et al. The impact of rare variation on gene expression across tissues. Nature. Oct. 11, 2017;550(7675):239-243.
Ojala DS, et al. In Vivo Selection of a Computationally Designed SCHEMA AAV Library Yields a Novel Variant for Infection of Adult Neural Stem Cells in the SVZ. Mol Ther. Sep. 8, 2017 Epub ahead of print.
Chandran JS, et al. Site Specific Modification of Adeno-Associated Virus Enables Both Fluorescent Imaging of Viral Particles and Characterization of the Capsid Interactome. Sci Rep. Nov. 7, 2017;7(1):14766.
Chai Z, et al. Application of polyploid adeno-associated virus vectors for transduction enhancement and neutralizing antibody evasion. J Control Release. Aug. 5, 2017. pii: S0168-3659(17)30772-1. doi: 10.10164/j.jconrel.2017.08.005.
Hickey DG, et al. Tropism of engineered and evolved recombinant AAV serotypes in the rd1 mouse and ex vivo primate retina. Gene Ther. Sep. 5, 2017 Epub ahead of print.
Yan Z, et al. Human Bocavirus Type-1 Capsid Facilitates the Transduction of Ferret Airways by Adeno-Associated Virus Genomes. Hum Gene Ther. May 10, 2017. Epub ahead of print.
Kanaan NM, et al. Rationally Engineered AAV Capsids Improve Transduction and Volumetric Spread in the CNS. Molecular Therapy-Nucleic Acids 8: 184-197 Sep. 15, 2017.
Powell SK, Khan N, Parker CL, Samulski RJ, Matsushima G, Gray SJ, McCown TJ. Characterization of a novel adeno-associated viral vector with preferential oligodendrocyte tropism. Gene Ther. Nov. 2016;23(11):807-814. doi: 10.1038/gt.2016.62. Epub Sep. 15, 2016.
Chan KY, et al. Engineered AAVs for efficient noninvasive gene delivery to the central and peripheral nervous systems. Nat Neurosci. Jun. 26, 2017. Epub ahead of print.
Paulk NK, et al. Bioengineered AAV Capsids with Combined High Human Liver Transduction in Vivo and Unique Humoral Seroreactivity. Mol Ther. Sep. 25, 2017 Epub ahead of print.
Hagedorn C, et al. S/MAR element facilitates episomal long-term persistence of Adeno-associated viral (AAV) vector genomes in proliferating cells. Hum Gene Ther. Jun. 30, 2017. Epub ahead of print.
Ziegler T, et al. Steerable induction of the Thymosin ß4/MRTF—A pathway via AAV-based overexpression induces therapeutic neovascularization. Hum Gene Ther. Jul. 20, 2017.
Potter RA, et al. Systemic Delivery of Dysferlin Overlap Vectors Provides Long-Term Functional Improvement for Dysferlinopathy. Hum Gene Ther. Jul. 14, 2017. Epub ahead of print.
Huang W, et al. Targeting Visceral Fat by Intraperitoneal Delivery of Novel AAV Serotype Vector Restricting Off-Target Transduction in Liver. Mol Ther Methods Clin Dev. Jun. 19, 2017;6:68-78.
Herrera-Carrillo E, et al. Improving miRNA delivery by optimizing miRNA expression cassettes in viral vectors. Hum Gene Ther Methods. Jul. 16, 2017.
Krhac Levacic A, et al. Minicircle versus plasmid DNA delivery by receptor-targeted polyplexes. Hum Gene Ther. Aug. 21, 2017 Epub ahead of print.
Moffett HF, et al. Hit-and-run programming of therapeutic cytoreagents using mRNA nanocarriers. Nat Commun. Aug. 30, 2017;8(1):389.
Bankiewicz KS, et al. Convection-enhanced delivery of AAV vector in Parkinsonian monkeys; in vivo detection of gene expression and restoration of dopaminergic function using pro-drug approach. Exp. Neurol. 2000 164;2-14.
Bankiewicz KS, et al. Long-term clinical improvement in MPTP-lesioned primates after gene therapy with AAV-hAADC. Mol Ther. Oct. 2006;14(4):564-570.
Bartus RT, et al. Parkinson's disease gene therapy: success by design meets failure by efficacy. Mol Ther. Mar. 2014;22(3):487-497.
Brodsky MA, et al. Effects fo a dopamine agonist on the pharmacodynamics of levodopa in Parkinson Disease. Arch Neurol. Jan. 2010;67(1):27-32.
Chan PLS et al. Modeling the short- and long-duration responses to exogenous levodopa and to endogenous levodopa production in Parkinson's Disease. J Pharmacokinetics and Pharmacodynamics. Jun. 2004;31(3):243-268.
Chan PLS, et al. Pharmacokinetic and pharmacodynamic changes during the first four years of levodopa treatment in Parkinson's Disease. J Pharmacokinetics and Pharmacodynamics. Aug. 2005;32(3-4):459.
Christine CW, et al. Safety and tolerability of putaminal AADC gene therapy for Parkinson disease. Neurology 2009;73:1662-1669.
Ciesielska A, et al. Depletion of AADC activity in caudate nucleus and putamen of Parkinson's disease patients; Implications for ongoing AAV2-AADC gene therapy trial. PLoS One 12(2):e0169965, Feb. 6, 2017, pp. 1-13.
Dhawan V, et al. Comparative analysis of striatal FDOPA uptake in Parkinson's disease: ratio method versus graphical approach. J Nucl Med 2002;43:1324-1330.
Espay AJ, et al. Optimizing extended-release carbidopa/levodopa in Parkinson disease. Neurol Clin Pract 2017;7:86-93.
Fahn S, et al. Levodopa and the progression of Parkinson's disease. N Engl J Med. Dec. 9, 2004;351(24):2498-508.
Forsayeth J, et al. A Dose-Ranging Study of AAV-hAADC Therapy in Parkinsonian Monkeys. Mol Ther. Oct. 2006;14(4):571-577.
Forsayeth J and Bankiewicz KS. Transduction of antigen-presenting cells in the brain by AAV9 warrants caution in preclinical studies. Mol Ther. 2015;23(4):612.

(56) References Cited

OTHER PUBLICATIONS

PD MED Collaborative Group, et al. Long-term effectiveness of dopamine agonists and monoamine oxidase B inhibitors compared with levodopa as initial treatment for Parkinson's disease (PD MED): a large, open-label, pragmatic randomised trial. Lancet Sep. 27, 2014;384(9949):1196-205.
Hadaczek P, et al. Eight Years of Clinical Improvement in MPTP-Lesioned Primates After Gene Therapy With AAV2-hAADC. Molecular Therapy. Aug. 2010;vol. 18 No. 8, 1458-1461.
Hauser RA, et al. A home diary to assess functional status in patients with Parkinson's disease with motor fluctuations and dyskinesia. Clin Neuropharm. 2000; 23(2):75-81.
Kordower JH, et al. Disease duration and the integrity of the nigrostriatal system in Parkinson's disease. Brain 2013; 136:2419-2431.
Lidstone SC. Great expectations: the placebo effect in Parkinson's disease. Handb Exp Pharmacol. 2014;225:139-47.
Mittermeyer G, et al. Long-term evaluation of a phase I study of AADC gene therapy for Parkinson's disease. Hum Gene Ther. Apr. 23, 2012;377-381.
Muramatsu S, et al. A Phase I Study of Aromatic I—Amino Acid Decarboxylase Gene Therapy for Parkinson's Disease. Mol Ther. Sep. 2010;18(9):1731-5.
Richardson RM, et al. Novel platform for MRI-guided convection enhanced delivery of therapeutics: preclinical validation in nonhuman primate brain. Stereotact Fund Neurosurg 2011;89:141-151.
Sanchez-Pernaute R, et al. Functional Effect of Adeno-associated Virus Mediated Gene Transfer of Aromatic L-Amino Acid Decarboxylase into the Striatum of 6-OHDA-Lesioned Rats. Mol Ther Oct. 4, 2001(4):324-330.
Sehara Y, et al. Persistent Expression of Dopamine-Synthesizing Enzymes 15 years after Gene Transfer in a Primate Model of Parkinson's Disease. Hum Gene Ther Clin Dev. Mar. 9, 2017 Epub ahead of print.
Shulman LM, et al. The clinically important difference on the Unified Parkinson's Disease Rating Scale, Arch Neurol, vol. 67, No. 1, Jan. 2010, 64-70.
Su X, et al. Real-time MR imaging with gadoteridol predicts distribution of transgenes after convection-enhanced delivery of AAV2 vectors. Mol Ther Aug. 2010; 18(8):1490-1495.
Tomlinson CL, et al. Systematic review of levodopa dose equivalency reporting in Parkinson's disease. Movement Disorders. 2010;25(15):2649-2685.
Voon V, et al. Impulse control disorders and levodopa-induced dyskinesias in Parkinson's disease: an update. Lancet Neurol. Mar. 2017;16(3):238-250.
Matsuura, M et al., Human Herpesvirus 6 Major Immediate Early Promoter Has Strong Activity in T Cells and is Useful for Heterologous Gene Expression. Virology Journal. 2011, vol. 8, No. 9, p. 1-9; Figures 1-2.
Brun, L et al., Clinical and Biochemical Features of Aromatic L-amino Acid Decarboxylase Deficiency. Neurology. Jul. 6, 2010, vol. 75, No. 1, pp. 64-71; abstract; Table 1; p. 66, first column, first paragraph.
Quattrochi, JJ et al., Dose-Related Suppression of REM Sleep and PGO Waves by the Serotonin-1 Agonist Eltopraxine. Neuropsychopharmacology. 1993, vol. 8, No. 1, pp. 7-13.
International Search Report dated Apr. 21, 2016 received in corresponding PCT Application No. PCT/US2015/059201.
Merten OW, et al. Viral vectors for gene therapy and gene modification approaches. Biochem Eng J. Apr. 2016;108:98-115.
Muzyczka N, et al. AAV's Golden Jubilee. Mol Ther. May 2015;23(5):807-8.
Rutledge EA, et al. Infectious clones and vectors derived from adeno-associated virus (AAV) serotypes other than AAV type 2. J Virol. Jan. 1998;72(1):309-19.
Pillay S, et al. An essential receptor for adeno-associated virus infection. Nature. Nov. 17, 2016;539(7629):456.
Platt MP, et al. Embryonic disruption of the candidate dyslexia susceptibility gene homolog Kiaa0319-like results in neuronal migration disorders. Neuroscience. Sep. 17, 2013;248:585-93.
Poon MW, et al. Distribution of Kiaa0319-like immunoreactivity in the adult mouse brain—a novel protein encoded by the putative dyslexia susceptibility gene KIAA0319-like. Histol Histopathol. Aug. 2011;26(8):953-63.
Poon MW, et al. Dyslexia-associated kiaa0319-like protein interacts with axon guidance receptor nogo receptor 1. Cell Mol Neurobiol. Jan. 2011;31(1):27-35.
Moser, et al. Computational Molecular Biology. Oxford University Press, New York, 1988.
Kozak M. Interpreting cDNA sequences: some insights from studies on translation. Mamm Genome. Aug. 1996;7(8):563-74.
Kozak M. Point mutations define a sequence flanking the AUG initiator codon that modulates translation by eukaryotic ribosomes. Cell. Jan. 31, 1986;44(2):283-92.
Kozak M. The scanning model for translation: an update. J Cell Biol. Feb. 1989;108(2):229-41.
Heim R, et al. Engineering green fluorescent protein for improved brightness, longer wavelengths and fluorescence resonance energy transfer. Curr Biol. Feb. 1, 1996;6(2):178-82.
Heim R,et al. Improved green fluorescence Nature 373, 663-664 (Feb. 23, 1995); doi:10.1038/373663b0.
Nygaard S, et al. A universal system to select gene-modified hepatocytes in vivo. Sci Transl Med. Jun. 2016;8(342):342ra79.
Smith RH, et al. Germline viral "fossils" guide in silico reconstruction of a mid-Cenozoic era marsupial adeno-associated virus. Sci Rep. Jul. 2016;6:28965.
Li L, et al. Production and characterization of novel recombinant adeno-associated virus replicative-form genomes: a eukaryotic source of DNA for gene transfer. PLoS One. Aug. 1, 2013;8(8):e69879. doi: 10.1371/journal.pone.0069879. Print 2013.
Oliva B, et al. An automated classification of the structure of protein loops. J Mol Biol. Mar. 7, 1997;266(4):814-30.
Samaranch L, et al. MR-guided parenchymal delivery of adeno-associated viral vector serotype 5 in non-human primate brain. Gene Ther. Apr. 2017;24(4):253-261.
Petit L, et al. Rod Outer Segment Development Influences AAV-Mediated Photoreceptor Transduction After Subretinal Injection. Hum Gene Ther. May 16, 2017. Epub ahead of print.
Hinderer C et al. Delivery of an Adeno-Associated Virus Vector into CSF Attenuates Central Nervous System Disease in Mucopolysaccharidosis Type II Mice. Hum Gene Ther. Aug. 10, 2016.
Hordeaux J., et al. Efficient central nervous system AAVrh10-mediated intrathecal gene transfers in adult and neonate rats. Gene Ther.Apr. 22, 2015(4):316-24.
Merkel SF et al. Trafficking of AAV Vectors Across a Model of the Blood-Brain Barrier; a Comaparative Study of Transcytosis and Transduction Using Primary Human Brain Endothelial Cells. J Neurochem. Oct. 8, 2016.
Miyanohara A et al. Potent Spinal Parenchymal AAV9-mediated Gene Delivery by Subpial Injection in Adult Rats and Pigs. Mol Ther Methods Clin Dev. Jul. 13, 2016;3:16046.
Muralidharan G , et al. Unique glycan signatures regulate adeno-associated virus tropism in the developing brain. J Virol. Apr. 2015;89(7):3976-87.
Ponder K, et al. Intrathecal injection of lentiviral vector results in high expression in the brain of mucopolysaccharidosis VII dogs but the pattern of expression is different than for AAV9 or AAV-rh10. J Control Release. Dec. 2014, 196:71-8.
Salegio EA, et al. MRI-Guided Delivery of Viral Vectors. Methods Mol Viol. 2016;1382:217-30.
Samaranch L et al. Cerebellomedullary Cistern Delivery for AAV-Based Gene Therapy: A Technical Note for Nonhuman Primates. Hum Gene Ther Methods. Feb. 2016;27(1):13-6.
Saraiva J et al. Gene Therapy for the CNS Using AAVs: The Impact of Systemic Delivery by AAV9. J Control Release. Nov. 10, 2016;241:94-109.
Shen F, et al. Inhibition of pathological brain angiogenesis through systemic delivery of AAV vector expressing soluble FLT1. Gene Therapy. Nov. 22, 2015(11):893-900.

(56) References Cited

OTHER PUBLICATIONS

Hinderer C, et al. Neonatal Systemic AAV Induces Tolerance to CNS Gene Therapy in MPS I Dogs and Nonhuman Primates. Mol Ther. 201-307.
Ojala DS, et al. Adeno-associated virus vectors and neurological gene therapy. Neuroscientist. Feb. 2015;21(1):84-98.
Katz ML, et al. AAV gene transfer delays disease onset in a TPP1-deticient canine model of the late infantile form of Batten Disease. Sci Transl Med. Nov. 2015;7(313):313ra180.
Landegger LD, et al. A synthetic AAV vector enables safe and efficient gene transfer to the mammalian inner ear. Nat Biotechnol. Mar. 2017;35(3):280-284.
Mason JB, et al. Delivery and evaluation of recombinant adeno-associated viral vectors in the equine distal extremity for the treatment of laminitis. Equine Vet J. Jan. 2017;49(1):79-86.
Jeong D, et al. Matricellular Protein CCN5 Reverses Established Cardiac Fibrosis. J Am Coll Cardiol. Apr. 5, 2016;67(13):1556-68.
Knezevic T, et al. Adeno-associated Virus Serotype 9—Driven Expression of BAG3 Improves Left Ventricular Function in Murine Hearts with Left Ventricular Dysfunction Secondary to a Myocardial Infarction. JACC Basic Transl Sci. Dec. 2016;1(7):647-656.
Ibrahim S, et al. Stable liver specific expression of human IDOL in humanized mice raises plasma cholesterol. Cardiovasc Res. May 2016;110(1):23-9.
Li SY, et al. Efficient and targeted transduction of nonhuman primate liver with systemically delivered optimized AAV3B vectors. Mol Ther. Dec. 2015;23(12):1867-76.
Heller KN, et al. Human alpha 7 integrin gene (ITGA7) delivered by adeno-associated virus extends survival of severely affected dystrophin/utrophin deficient mice. Oct. 2015;26(1):647-56.
Mendell JR, et al. Follistatin Gene Therapy for Sporadic Inclusion Body Myositis Improves Functional Outcomes. Mol Ther. Apr. 2017;25(4):870-879.
Schnepp BC, et al. Recombinant adeno-associated virus vector genomes take the form of long-lived transcriptionally competent episomes in human muscle. Hum Gene Ther. Jan. 2016;27(1):32-42.
Murlidharan G et al. Glymphatic Fluid Transport Controls Paravascular Clearance of AAV Vectors from the Brain. JCI Insight. Sep. 8, 2016;1(14).
Neuberger EWI, et al. Establishment of two quantitative nested qPCR assays targeting the human EPO transgene. Gene Ther. Apr. 2016;23(4):330-9.
Lentz TB, et al. Insight into the Mechanism of Inhibition of Adeno-Associated Virus by the Mre11/Rad50/Nbs1 Complex. J Virol. Jan. 2015, 89(1):181-94.
Nicolson SC, et al. Identification and validation of small molecules that enhance recombinant Adeno-associated virus transduction following high throughput screen. J Virol. Jul. 2016;90(16):7019-31.
Wang M, et al. Direct interaction of human serum proteins with AAV virions to enhance AAV transduction: Immediate impact on clinical applications. Gene Ther. Jan. 2017;24(1):49-59.
Watakabe A, et al. Comparative analyses of adeno-associated viral vector serotypes 1 2 5 8 and 9 in marmoset mouse and macaque cerebral cortex. Neurosci Res.Apr. 2015, 93:144-57.
Xiao P, et al. Disruption of microtubules post virus entry enhances adeno-associated virus vector transduction. Hum Gene Ther. Apr. 2016;27(4):309-24.
Hudry EM, et al. Exosome-associated AAV vector as a robust and convenient neursocience tool. Gene Ther. Apr. 2016;23(4):380-92.
Nery FC, et al. New methods for investigation of neuronal migration in embryonic brain explants J Neurosci Methods.Jan. 2015, 239:80-4.
Su W et al. Recombinant adeno-associated viral (rAAV) vectors mediate efficient gene transduction in cultured neonatal and adult microglia. J Neurochem. Jan. 2016;136 Suppl 1:49-62.
Ren XF, et al. Adeno-associated virus-mediated BMP-7 and SOX9 in vitro co-transfection of human degenerative intervertebral disc cells. Genet Mol Res. Apr. 22, 2015;14(2):3736-44.
Alves S et al. Ultramicroscopy as a Novel Tool to Unravel the Tropism of AAV Gene Therapy Vectors in the Brain. Sci Rep. Jun. 20, 2016;6:28272.
Kothari P, et al. Radioiodinated Capsids Facilitate in Vivo Non-Invasive Tracking of Adeno-Associated Gene Transfer Vectors. Sci Rep. Jan. 2017;7:39594.
Xie Q, et al. The 2.8 Å Electron Microscopy Structure of Adeno-Associated Virus-DJ Bound by a Heparinoid Pentasaccharide. Mol Ther Methods Clin Dev. Mar. 8, 2017;5:1-12.
Srivastava A. Adeno-Associated Virus: The Naturally Occurring Virus Versus the Recombinant Vector. Hum Gene Ther. Jan. 2016;27(1):1-6.
Tratschin JD, et al. Adeno-associated virus vector for high-frequency integration, expression, and rescue of genes in mammalian cells. Mol Cell Biol. Nov. 1985;5(11):3251-60.
Srivastava A, et al. Nucleotide sequence and organization of the adeno-associated virus 2 genome. J Virol. Feb. 1983;45(2):555-64.
Summerford C, et al. AAVR: A multi-serotype receptor for AAV. Mol Ther. Apr. 2016;24(4):663-6.
Xie Q, et al. The atomic structure of adeno-associated virus (AAV-2), a vector for human gene therapy. Proc Natl Acad Sci U S A. Aug. 6, 2002;99(16):10405-10. Epub Jul. 22, 2002.
Wu P, et al. Mutational analysis of the adeno-associated virus type 2 (AAV2) capsid gene and construction of AAV2 vectors with altered tropism. J Virol. Sep. 2000;74(18):8635-47.
Yang C, et al. Sequential adeno-associated viral vector serotype 9-green fluorescent protein gene transfer causes massive inflammation and intense immune response in rat striatum. Hum Gene Ther. Jul. 2016;27(7):528-43.
Chandler RJ, et al. rAAV integration and genotoxicity: insights from animal models. Hum Gene Ther. Apr. 2017;28(4):314-322.
Ye L., et al. Adeno-Associated Virus Vector Mediated Delivery of the HBV Genome Induces Chronic Hepatitis B Virus Infection and Liver Fibrosis in Mice. PLoS One. Jun. 2015, 10(6):e0130052.
Wang S, et al. Direct brain infusion can be enhanced with focused ultrasound and microbubbles. J Cereb Blood Flow Metab. Feb. 2016;37(2):706-714.
Wang et al., Noninvasive, neuron-specific gene therapy can be facilitated by focused ultrasound and recombinant adeno-associated virus. Gene Therapy. Nov. 22, 2014, 104-110.
Weber-Adrian D, et al. Gene delivery to the spinal cord using MRI-guided focused ultrasound. Gene Ther. Jul. 2015, 22(7):568-77.
Wu D et al. Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush. Front Mol Neurosci. Jul. 5, 2016;9:49.
Zhu W, et al. Soluble FLT1 Gene Therapy Alleviates Brain Arteriovenous Malformation Severity. Stroke. May 2017;48(5):1420-1423.
Watson ZL, et al. Adeno-associated Virus Vectors Efficiently Transduce Mouse and Rabbit Sensory Neurons Coinfected with Herpes Simplex Virus 1 following Peripheral Inoculation. J Virol. Aug. 12, 2016;90(17):7894-901.
Suzuki J, et al. Cochlear gene therapy with ancestral AAV in adult mice: complete transduction of inner hair cells without cochlear dysfunction. Apr. 3, 2017;7:45524.
Woodard KT et al. Heparan Sulfate Binding Promotes Accumulation of Intravitreally Delivered Adeno-associated Viral Vectors at the Retina for Enhanced Transduction but Weakly Influences Tropism. J Virol. Oct. 14, 2016;90(21):9878-9888.
Wang LL, et al. Comparative study of liver gene transfer with AAV vectors based on endogenous and engineered AAV capsids. Mol Ther Dec. 2015;23(12):1877-87.
Sondhi D, et al. Genetic Modification of the Lung Directed Toward Treatment of Human Disease. Hum Gene Ther. Jan. 2017;28(1):3-84.
Yalvac ME, et al. AAV1.NT-3 gene therapy attenuates spontaneous autoimmune peripheral polyneuropathy. Gene Ther. Jan. 2016;23(1):95-102.
Srivastava A. In Vivo Tissue-tropism of Adeno-associated Viral Vectors. Curr Opin Virol. Sep. 2, 2016;21:75-80.

(56) References Cited

OTHER PUBLICATIONS

Adamson-Small L, et al. Sodium chloride enhances rAAV production in a serum-free suspension manufacturing platform using the Herpes Simplex Virus System. Hum Gene Ther Methods. Feb. 2017;28(1):1-14.
Al J, et al. A Scalable and Accurate Method for Quantifying Vector Genomes of Recombinant Adeno-Associated Viruses in Crude Lysate. Hum Gene Ther Methods. Apr. 13, 2013. Epub ahead of print.
Buclez PO, et al. Rapid, scalable, and low-cost purification of recombinant adeno-associated virus produced by baculovirus expression vector system. Mol Ther Methods Clin Dev. May 2016;3:16035.
Burnham B, et al. Analytical ultracentrifugation as an approach to characterize recombinant adeno-associated viral vectors. Hum Gene Ther Methods. Dec. 2015;26(6):228-42.
Clement N, et al. Manufacturing of recombinant adeno-associated viral vectors for clinical trials. Mol Ther Methods Clin Dev. Mar. 2016;3:16002.
D'Costa S, et al. Practical utilization of recombinant AAV vector reference standards: focus on vector genome titration by free ITR qPCR. Mol Ther Methods Clin Dev. Mar. 2016;5:16019.
Grieger JC, et al. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24(2):287-97.
Gruntman AM, et al. Stability and Compatibility of Recombinant Adeno-Associated Virus Under Conditions Commonly Encountered in Human Gene Therapy Trials. Hum Gene Ther Methods. Apr. 2015, 26(2):71-6.
Kajigaya S, et al. Self-assembled B19 parvovirus capsids, produced in a baculovirus system, are antigenically and immunogenically similar to native virions. Proc Natl Acad Sci U S A. Jun. 1, 1991;88(11):4646-50.
Kirnbauer R, et al. Virus-like particles of bovine papillomavirus type 4 in prophylactic and therapeutic immunization. Virology. May 1, 1996;219(1):37-44.
Kohlbrenner E, et al. Production and Characterization of Vectors Based on the Cardiotropic AAV Serotype 9. Methods Mol Biol. 2017;1521:91-107.
Kotin RM, et al. Large-scale recombinant adeno-associated virus production. Hum Mol Genet. Apr. 15, 2011;20(R1): R2-6. doi: 10.1093/hmg/ddr141. Epub Apr. 29, 2011.
Xie J, et al. Short DNA Hairpins Compromise Recombinant Adeno-Associated Virus Genome Homogeneity. Mol Ther. Apr. 24, 2017. Epub ahead of print.
Davidsson M, et al. A novel process of viral vector barcoding and library preparation enables high-diversity library generation and recombination-free paired-end sequencing. Sci Rep. Nov. 2016;6:3563.
Chamberlain K, et al. Expressing transgenes that exceed the packaging capacity of AAV capsids. Hum Gene Ther Methods. Feb. 2016;27(1):1-12.
De Leeuw CN et al. rAAV-compatible MiniPromoters for Restricted Expression in the Brain and Eye. Mol Brain. May 10, 2016;9(1):52.
Hirsch ML, et al. Delivering Transgenic DNA Exceeding the Carrying Capacity of AAV Vectors. Methods Mol Biol. 2016;1382:21-39.
Powell SK, et al. Viral expression cassette elements to enhance transgene target specificity and expression in gene therapy. Discov Med. Jan. 2015;19(102):49-57.
Rosario AM et al. Microglia-specific Targeting by Novel Capsid-modified AAV6 Vectors. Mol Ther Methods Clin Dev. Apr. 13, 2016;3:16026.
Wang L, et al. Productive life cycle of adeno-associated virus serotype 2 in the complete absence of a conventional polyadenylation signal. J Gen Virol. Sep. 2015;96(9):2780-7.
Yan ZY, et al. Optimization of recombinant adeno-associated virus mediated expression for large transgenes, using a synthetic promoter and tandem array enhancers. Hum Gene Ther. Jun. 2015;26(6):334-46.
Jackson KL, et al. Better Targeting, Better Efficiency for Wide-Scale Neuronal Transduction with the Synapsin Promoter and AAV-PHP. B. Front Mol Neurosci. Nov. 2016;6:116.
McClements ME, et al. A fragmented adeno-associated viral dual vector strategy for treatment of diseases caused by mutations in large genes leads to expression of hybrid transcripts. J Genet Syndr Gene Ther. Nov. 2016;7(5):311.
Parr MJ, et al. Tumor-selective transgene expression in vivo mediated by an E2F-responsive adenoviral vector. Nat Med. Oct. 1997;3(10):1145-9.
Reid CA, et al. miRNA mediated post-transcriptional silencing of transgenes leads to increased adeno-associated viral vector yield and targeting specificity. Gene Ther. Jun. 15, 2017. Epub ahead of print.
Sawada Y et al. Inflammation-induced Reversible Switch of the Neuron-specific Enolase Promoter from Purkinje Neurons to Bergmann Glia. Sci Rep. Jun. 13, 2016;6:27758.
Lukashcuk V et al. AAV9-mediated central nervous system-targeted gene delivery via cisterna magna route in mice. Mol Ther Methods Clin Dev. Feb. 17, 2016;3:15055.
Tarantal AF, et al. Systemic and Persistent Muscle Gene Expression in Rhesus Monkeys with a Liver De-targeted Adeno-Associated Virus (AAV) Vector. Hum Gene Ther. May 2017;28(5):385-391.
Huang LY, et al. Characterization of the Adeno-Associated Virus 1 and 6 Sialic Acid Binding Site. J Virol. May 12, 2016;90(11):5219-30.
Siu JJ, et al. Improved gene delivery to adult mouse spinal cord through the use of engineered hybrid adeno-associated viral serotypes. Gene Ther. Apr. 25, 2017. Epub ahead of print.
Deng XF, et al. Replication of an autonomous human parvovirus in non-dividing human airway epithelium is facilitated trough the DNA damage and repair pathways. PLoS Pathog. Jan. 2016;12(1):e1005399.
Kailasan S, et al. Structure of an Enteric Pathogen, Bovine Parvovirus.J Virol. Mar. 2015, 89(5):2603-14.
Alton EW, et al. Repeated nebulisation of non-viral CFTR gene therapy in patients with cystic fibrosis: a randomised, double-blind, placebo-controlled, phase 2b trial. Lancet Respir Med. Sep. 2015;3(9):684-91.
Baum BJ, et al. Early responses to adenoviral-mediated transfer of the aquaporin-1 cDNA for radiation-induced salivary hypofunction. Proc Natl Acad Sci U S A. Nov. 20, 2012;109(47)19403-7.
Shen W, et al. Analysis of the CIS and Trans Requirements for DNA Replication at the Right End Hairpin of the Human Bocavirus 1 Genome. J Virol. Aug. 2016;90(17):7761-77.
Kotin RM, et al. Manufacturing clinical grade recombinant adeno-associated virus using invertebrate cell lines. Hum Gene Ther. Mar. 28, 2017. Epub ahead of print.
Kotterman MA, et al. Enhanced cellular secretion of AAV2 by expression of foreign viral envelope proteins. Biochemical Engineering Journal, vol. 93, Jan. 15, 2015, pp. 108-114.
Methods in Molecular Biology, ed. Richard, Humana Press, NJ (1995).
Mietzsch M, et al. OneBac 2.0: Sf9 Cell Lines for Production of AAV1, AAV2 and AAV8 Vectors with Minimal Encapsidation of Foreign DNA. Hum Gene Ther Methods. Feb. 2017;28(1):15-22.
Mietzsch M, et al. OneBac 2.0: Sf9 cell lines for production of AAV5 vectors with enhanced infectivity and minimal encapsidation of foreign DNA. Hum Gene Ther. Oct. 26, 2015(10):688-97.
Nambiar B, et al. Characteristics of minimally oversized adeno-associated virus vectors encoding human Factor VIII generated using producer cell lines and triple transfection. Hum Gene Ther Methods. Feb. 2017;28(1):23-38.
Pacourets S, et al. AAV-ID: A Rapid and Robust Assay for Batch-to-Batch Consistency Evaluation of AAV Preparations. Mol Ther. Apr. 17, 2017. Epub ahead of print.
Penaud-Budloo M, et al. Accurate identification and quantification of DNA species by next-generation sequencing in adeno-associated viral vectors produced in insect cells. Hum Gene Ther Methods. May 2, 2017. Epub ahead of print.
Ruffing M, et al. Assembly of viruslike particles by recombinant structural proteins of adeno-associated virus type 2 in insect cells. J Virol. Dec. 1992;66(12):6922-30.

(56) References Cited

OTHER PUBLICATIONS

Samulski RJ, et al. Helper-free stocks of recombinant adeno-associated viruses: normal integration does not require viral gene expression. J Virol. Sep. 1989;63(9):3822-8.
Smith RH, et al. A simplified baculovirus-AAV expression vector system coupled with one-step affinity purification yields high-titer rAAV stocks from insect cells. Mol Ther. Nov. 2009;17(11):1888-96. doi: 10.1038/mt.2009.128. Epub Jun. 16, 2009.
Urabe M, et al. Scalable generation of high-titer recombinant adeno-associated virus type 5 in insect cells. J Virol. Feb. 2006;80(4):1874-85.
Van Der Loo JCM, et al. Progress and challenges in viral vector manufacturing. Hum Mol Genet. Apr. 2016;25(R1): R42-52.
Wasilko DJ, et al. The titerless infected-cells preservation and scale-up (TIPS) method for large-scale production of NO-sensitive human soluble guanylate cyclase (sGC) from insect cells infected with recombinant baculovirus. Protein Expr Purif. Jun. 2009;65(2):122-32. doi: 10.1016/j.pep.2009.01.002. Epub Jan. 11, 2009.
Zhao KN, et al. BPV1 E2 protein enhances packaging of full-length plasmid DNA in BPV1 pseudovirions. Virology. Jul. 5, 2000;272(2):382-93.
Pierson EE, et al. Resolving adeno-associated viral particle diversity with charge detection mass spectrometry. Anal Chem. Jul. 2016;88(13):6718-25.
Rashnonejad A, et al. Large-Scale Production of Adeno-Associated Viral Vector Serotype-9 Carrying the Human Survival Motor Neuron Gene. Mol Biotechnol. Jan. 2016;58(1):30-6.
Ling C, et al. Strategies to generate high-titer, high-potency recombinant AAV3 serotype vectors. Mol Ther Methods Clin Dev. May 2016;3:16029.
Afione S, et al. Identification and Mutagenesis of the Adeno-Associated Virus 5 Sialic Acid Binding Region.J Virol. Feb. 2015, 89(3):1660-72.
Drouin LM, et al. Cryo-electron microscopy reconstruction and stability studies of Wild-Type and R432A Variant of AAV2 Reveals Capsid Structural Stability is a Major Factor in Genome Packaging. J Virol. Sep. 2016;90(19):8542-51.
Halder S, et al. Structure of neurotropic adeno-associated virus AAVrh.8. J Struct Biol. Oct. 2015;192(1):21-36.
Huang LY, et al. Characterization of the adeno-associated virus 1 and 6 sialic acid binding site. J Virol. May 2016;90(11):5219-30.
Mao Y, et al. Single point mutation in adeno-associated viral vectors—DJ capsid leads to improvement for gene delivery in vivo. BMC Biotechnol. Jan. 2016;16:1.
Tu MY, et al. Role of capsid proteins in parvoviruses infection. Virol J. Aug. 4, 2015;12:114.
Zeng C, et al. Probing the Link between Genomic Cargo, Contact Mechanics and Nanoindentation in Recombinant Adeno-Associated Virus 2. J Phys Chem B. Mar. 2017;121(8):1843-1853.
Zinn E, et al. In Silico Reconstruction of the Viral Evolutionary Lineage Yields a Potent Gene Therapy Vector. Cell Rep. Aug. 2015, 12(6):1056-68.
Grimm D, et al. E Pluribus Unum: 50 years of research, millions of viruses and one goal—tailored acceleration of AAV evolution. Mol Ther. Dec. 2015;23(12):1819-1831.
Karamuthil-Melethil S, et al. Novel Vector Design and Hexosaminidase Variant Enabling Self-Complementary Adeno-Associated Virus for the Treatment of Tay-Sachs Disease. Hum Gene Ther. Jul. 2016;27(7):509-21.
Pillay S, et al. An essential receptor for adeno-associated virus infection. Nature. Feb. 2016;530(7588):108-12.
Li BZ, et al. Site directed mutagenesis of surface-exposed lysine residues leads to improved transduction by AAV2 but not AAV8 vectors in murine hepatocytes in vivo. Hum Gene Ther Methods. Dec. 2015;26(6):211-20.
Shen S, et al. Functional Analysis of the Putative Integrin Recognition Motif on Adeno-associated virus 9. J Biol Chem. Jan. 2015, 290(3):1496-504.
Steines B, et al. CFTR gene transfer with AAV improves early cystic fibrosis pig phenotypes. JCI Insight. Sep. 2016;1(14):e88728.
Bensky MJ, et al. Targeted gene delivery to the enteric nervous system using AAV: a comparison across serotypes and capsid mutants.Mol Ther. Mar. 2015;23(3):488-500.
Castle MJ, et al. Controlling AAV Tropism in the Nervous System with Natural and Engineered Capsids. Methods Mol Biol. 2016;1382:133-49.
Choudhury SR, et al. Widespread CNS gene transfer and silencing after systemic delivery of novel AAV-AS motors. Mol Ther. Apr. 2016;24(4):726-35.
Davis AS, et al. Rational design and engineering of a modified adeno-associated virus (AAV1)-based vector system for enhanced retrograde gene delivery. Neurosurgery. Feb. 2015;76(2):216-25.
Deverman BE et al. Cre-dependent selection yields AAV variants for widespread gene transfer to the adult brain. Nat Biotechnol. Feb. 2016;34(2):204-9.
Powell SK et al. Characterization of a novel adeno-associated viral vector with preferential oligodendrocyte tropism. Gene Ther. Sep. 15, 2016.
Tervo et al. A Designer AAV Variant Permits Efficient Retrograde Access to Projection Neurons. Neuron. Oct. 19, 2016;92(2):372-382.
Choudhury et al. In Vivo Selection Yields AAV-B1 Capsid for Central Nervous System and Muscle Gene Therapy. Mol Ther. Aug. 2016;24(7):1247-57.
Keravala A, et al. Evaluating AAV Hybrid Variants for Improved Tropism after Intravitreal Gene Delivery to the Retina. Molecular Therapy, vol. 23, Supplement 1, May 2015, pp. S127-S128.
Vercauteren K, et al. Superior in vivo Transduction of Human Hepatocytes Using Engineered AAV3 Capsid. Mol Ther. Jun. 2016;24(6):1042-9.
Chen M, et al. Efficient Gene Delivery and Expression in Pancreas and Pancreatic Tumors by Capsid-optimized AAV8 Vectors. Hum Gling C, et al. High-Efficiency Transduction of Primary Human Hematopoietic Stem/Progenitor Cells by AAV6 Vectors: Strategies for Overcoming Donor-Variation and Implications in Genome Editing. Sci Rep. Oct. 2016;6:35495. ene Ther Methods. Feb. 2017;28(1):49-59.
Ling C, et al. High-Efficiency Transduction of Primary Human Hematopoietic Stem/Progenitor Cells by AAV6 Vectors: Strategies for Overcoming Donor-Variation and Implications in Genome Editing. Sci Rep. Oct. 2016;6:35495.
Earley LF, et al. Identification and Characterization of Nuclear and Nucleolar Localization Signals in the Adeno-Associated Virus Serotype 2 Assembly-Activating Protein. J Virol. Mar. 2015, 89(6):3038-48.
Zou W, et al. Nonstructural protein NP1 of human bocavirus 1 plays a critical role in the expression of viral capsid proteins. J Virol. Apr. 2016;90(9):4658-69.
Mingozzi F, et al. Adeno-associated viral vectors at the frontier between tolerance and immunity. Front Immunol.Mar. 2015, 6:120.
Ling C, et al. Enhanced Transgene Expression from Recombinant Single-Stranded D-Sequence-Substituted Adeno-Associated Virus Vectors in Human Cell Lines in Vitro and in Murine Hepatocytes in Vivo. J Virol. Jan. 2015, 89(2):952-61.
Extended European Search Report received in corresponding EP Application No. 15857231.3 dated Jun. 29, 2018.
Doroudchi MM, et al. AAV Gene Transfer of AADC protects dopaminergenic and striatal neurons from toxicity of L-DOPA in a primary cultur model (Abstract). 33rd Annual Meeting of the Society of Neuroscience: New Orleans, LA, USA. Nov. 8, 2003.
Examination Report No. 2 received in corresponding AU Application No. 2015343037 dated Oct. 12, 2018.
Matsushita, T. et al. 1998 "Adeno-associated virus vectors can be efficienty produced without helper virus", Gene Ther. vol. 5, pp. 938-945.
Fluri, D. et al. 2007 "Adeno-associated viral vectors engineered for macrolide-adjustable transgene expression in mammalian cells and mice". BMC Biotechnology, vol. 7, art. 75, pp. 1-15.
Naidoo J, et al. Extensive Transduction and Enhanced Spread of a Modified AAV2 Capsid in the Non-human Primate CNS. Mol Ther. Jul. 12, 2018 Epub ahead of print.
Man JHK, et al. Cell reprogramming approaches in gene- and cell-based therapies for Parkinson's disease. J Control Release Jul. 17, 2018;286:114-124 Epub ahead of print.

(56) References Cited

OTHER PUBLICATIONS

Stoker TB, et al. Regenerative therapies for Parkinson's Disease: An Update. BioDrugs (2018) 32:357-366. Published online Jul. 19, 2018.
Chandran JS, et al. Gene therapy in the nervous system: failures and successes. Adv Exp Med Biol. 2017;1007:241-257.
Lee NC, et al. Regulation of the dopaminergic system in a murine model of aromatic L-amino acid decarboxylase deficiency. Neurobiology of Disease (2013). 52:177-190.
Hwu WL, et al. Gene Therapy for Aromatic L-Amino Acid Decarboxylase Deficiency. Science Translational Medicine (May 16, 2012). 4:134.
Australian Examination Report No. 1 issued in corresponding AU Application No. 2015343037 dated Jan. 25, 2018.
Japanese Office Action received in corresponding JP Application No. 2017-544285 dated Apr. 24, 2018.
Canadian Examiner's Report received in corresponding CA Application No. 2,966,620 dated Feb. 28, 2018.
Douglas, M.R. Gene therapy for Parkinson's disease: state-of-the-art treatments for neurodegenerative disease. Expert Rev Neurother. Jun. 2013; 13(6):695-705.
Kojima K et al., Gene therapy improves motor and mental function of aromatic I—amino acid decarboxylase deficiency. Brain. Jan. 23, 2019. [Epub ahead of print].
Dorsey ER, et al. The Emerging Evidence of the Parkinson Pandemic, .J Parkinsons Dis. 2018;8(s1):S3-S8.
Wang D, et al. Adeno-associated virus vector as a platform for gene therapy delivery. Nat Rev Drug Discov. Feb 1, 2019. doi: 10.1038/s41573-019-0012-9. [Epub ahead of print] Review.
Chen YH etl a., Viral Vectors for Gene Transfer. Curr Protoc Mouse Biol. Dec. 2018;8(4):e58.
Hudry E, Vandenberghe LH. Therapeutic AAV Gene Transfer to the Nervous System: A Clinical Reality. Neuron. Mar. 6, 2019;101(5):839-862.
Cell Biolabs. Product Data Sheet: pAAVS-MCS Expression Vector. 2010.
Yan et al., Inverted terminal repeat sequences are important for intermolecular recombination and circularization of adeno-associated virus genomes. J Virol. Jan. 2005;79(1):364-79.
San Sebastian et al., Safety and tolerability of magnetic resonance imaging-guided convection-enhanced delivery of AAV2-hAADC with a novel delivery platform in nonhuman primate striatum. Hum Gene Ther. Feb. 2012;23(2):210-7. Epub Jan. 26, 2012.
San Sebastian et al., Safety and tolerability of MRI-guided infusion of AAV2-hAADC into the mid-brain of nonhuman primate. Mol Ther Methods Clin Dev. 2014; 3: 14049. Published online Oct. 15, 2014.
Sehara et al., Persistent Expression of Dopamine-Synthesizing Enzymes 15 Years After Gene Transfer in a Primate Model of Parkinson's Disease. Hum Gene Ther Clin Dev. Jun. 2017;28(2):74-79. Epub Mar. 9, 2017.
Nutt et al., The response to levodopa in Parkinson's disease: imposing pharmacological law and order. Ann Neurol. May 1996;39(5):561-73.
De la Manza et al., Molecular Structure of Adeno-associated Virus Variant DNA. The Journal of Biological Chemistry (1980), 255, 3194-3203.
Ossig et al., Treatment of Parkinson's disease in the advanced stage. J Neural Transm. Apr. 2013; 120(4): 523-529. Published online Mar. 10, 2013.
Varanese et al., Treatment of Advanced Parkinson's Disease. Parkinsons Dis. Feb. 7, 2011;2010:480260.
Dewey RB Jr. Autonomic dysfunction in Parkinson's disease. Neurol Clin. Oct. 2004;22(3 Suppl):S127-39.
Fahn S. The medical treatment of Parkinson disease from James Parkinson to George Cotzias. Mov Disord. Jan. 2015;30(1):4-18. doi: 10.1002/mds.26102.
Tysnes OB and Storstein A., Epidemiology of Parkinson's disease. J Neural Transm (Vienna). Aug. 2017;124(8):901-905.
Ferla R, et al. Prevalence of anti-adeno-associated virus serotype 8 neutralizing antibodies and arylsulfatase B cross-reactive immunologic material in mucopolysaccharidosis VI patient candidates for a gene therapy trial. Hum Gene Ther. Mar. 2015;26(3):145-52.
Harrington EA, et al. Neutralizing Antibodies Against Adeno-Associated Viral Capsids in Patients with mut Methylmalonic Acidemia. Hum Gene Ther. May 2016;27(5):345-53.
Kotterman MA, et al. Antibody neutralization poses a barrier to intravitreal adeno-associated viral vector gene delivery to non-human primates. Gene Ther. Feb. 2015;22(2):116-26.
Hu JE, et al. Opposing effects of viral mediated brain expression of apolipoprotein E2 (apoE2) and apoE4 on apoE lipidation and A beta metabolism in apoE4-targeted replacement mice. Mol Neurodegener. Mar. 2015, 10:6.
Zhao L et al. Intracerebral adeno-associated virus gene delivery of apolipoprotein E2 markedly reduces brain amyloid pathology in Alzheimer's disease mouse models. Neurobiol Aging. Aug. 2016;44:159-72.
Fol R et al. Viral gene transfer of APPsα rescues synaptic failure in an Alzheimer's disease mouse model. Acta Neuropathol. Feb. 2016;131(2):247-66.
Gant JC, et al. Reversal of Aging-Related Neuronal Ca2+ Dysregulation and Cognitive Impairment by Delivery of a Transgene Encoding FK506-Binding Protein 12.6/1b to the Hippocampus. J Neurosci. Jul. 2015, 29;35(30):10878-87.
Ren J, et al. Noninvasive tracking of gene transcript and neuroprotection after gene therapy. Gene Ther. Jan. 2016;23(1):1-9.
Verhelle A, et al. AAV9 delivered bispecific nanobody attenuates amyloid burden in the gelsolin amyloidosis mouse model. Hum Mol Genet. Apr. 2017;26(7):1353-1364.
Fan D-S, et al. Behavioral Recovery in 6-Hydroxydopamine-Lesioned Rats by Contransduction of Striatum with Tyrosine Hydroxylase and Aromatic L-Amino Acid Decarboxylase Genes Using Two Separate Adeno-Associated Virus Vectors. Human Gene Therapy. Nov. 20, 1998; 9:2527-2535.
Herzog R, et al. Long-term correction of canine hemophilia B by gene transfer of blood coagulation factor IX mediated by adeno-associated viral vector. Nature Medicine. Jan. 1999; vol. 5 No. 1.
Jolesz F. Intraoperative Imaging in Neurosurgery: Where Will the Future Take Us?. Acta Nerochir Suppl. 2011:109:21-25.
MacLullich A, et al. Enlarged perivascular spaces are associated with cognitive function in healthy elderly men. J Neurol Neurosurg Psychiatry. 2004;75:1519-1523.
Potter G, et al. Cerebral Perivascular Spaces Visible on Magnetic Resonance Imaging: Development of a Qualitative Rating Scale and its Observer Reliability. Cerebrovascular Diseases. Mar. 19, 2015;39:224-231.
Potter G, et al. Enlarged perivascular spaces (EPVS): a visual rating scale and user guide. Guide prepared by Gillian Potter, Zoe Morris and Prof Joanna Wardlaw (University of Edinburgh).
Grimm D, et al. In Vitro and in Vivo Gene Therapy Vector Evolution via Multispecies Interbreeding and Retargeting of Adeno-Associated Viruses. Journal of Virology. Jun. 2008;5887-5911.
Kern A, et al. Identification of a Heparin-Binding Motif on Adeno-Associated Virus Type 2 Capsids. Journal of Virology. Oct. 2003;11072-11081.
Voyager Therapeutics—Investors & Media—Press Release, Voyager Therapeutics Announces Positive Interim Results from Phase 1b Trial of VY-AADC01 for Advanced Parkinson's Disease, Dec. 7, 2016, pp. 1-6.
Van Lieshout LP, et al. A Novel Triple-Mutant AAV6 Capsid Induces Rapid and Potent Transgene Expression in the Muscle and Respiratory Tract of Mice. Mol Ther Meth Clin Dev Jun. 15, 2018.
Jankovic J, et al. Safety and Tolerability of Multiple Ascending Doses of PRX002/RG7935, an Anti-α-Synuclein Monoclonal Antibody, in Patients With Parkinson Disease: A Randomized Clinical Trial. JAMA Neurol. Jun. 18, 2018 Epub ahead of print.
Hacker ML, et al. Effects of deep brain stimulation on rest tremor progression in early stage Parkinson disease. Neurology. Jun. 29, 2018 Epub ahead of print.
Kubu CS, et al. Patients' shifting goals for deep brain stimulation and informed consent. Neurology Jun. 29, 2018 Epub ahead of print.

(56) References Cited

OTHER PUBLICATIONS

Ciurleo R, et al. Assessment of Duodopa® effects on quality of life of patients with advanced Parkinson's disease and their caregivers. J Neurol. Jun. 27, 2018 Epub ahead of print.

Yun SP, et al. Block of A1 astrocyte conversion by microglia is neuroprotective in models of Parkinson's disease. Nat Med Jun. 11, 2018 Epub ahead of print.

Hudry E, et al. Efficient gene transfer to the central nervous system by single stranded Anc80L65. Mol Ther Meth Clin Dev. Jul. 15, 2018, pp. 197-209.

Di Maio R, et al. LRRK2 activation in idiopathic Parkinson's disease. Sci Transl Med. Jul. 25, 2018;10(451).

Tse LV, et al. Mapping and engineering function domains of the assembly-activating protein of adeno-associated viruses. J. Virol. Jun. 29, 2018;92(14).

Chien YH, et al. Efficacy and safety of AAV2 gene therapy in children with aromatic L-amino acid decarboxylase deficiency: an open-label, phase 1/2 trial. Lancet Chil Adolesc Health Dec. 2017;1(4):265-273.

Palfi S, et al. Long-term follow up of a phase 1/2 study of ProSavin, a lentiviral vector gene therapy for Parkinson's disease. Hum Gen Ther Clin Dev. Aug. 29, 2018 Epub ahead of print.

Lee NC, et al. Treatment of Congenital Neurotransmitter Deficiencies by Intracerebral Ventricular Injection of an Adeno-Associated Virus Serotype 9 Vector. Human Gene Therapy. Mar. 2014. 25:189-198.

Hwu WL, et al. AADC Deficiency: Occurring in Humans, Modeled in Rodents. Advances in Pharmacology (2013). 68: 273-284.

Gowanlock D, et al. A designer AAV variant permits efficient retrograde access to projection neurons. Neuron. (Oct. 19, 2016);92(2):372-382.

International Search Report issued in corresponding PCT Application No. PCT/US2018/037437 dated Oct. 26, 2018.

Rosas et al. Patterns of scAAV vector insertion associated with oncogenic events in a mouse model for genotoxicity. Mol Ther. Nov. 2012 (Epub Sep. 18, 2012); 20(11):2098-110.

Kotin et al. Organization of adeno-associated virus DNA in latently infected Detroit 6 cells. Virology. Jun. 1989;170(2):460-7.

Cuende et al., Cell, tissue and gene products with marketing authorization in 2018 worldwide.Cytotherapy. Nov. 2018;20(11):1401-1413.

Christine CW, et al. MRI-guided Phase 1 Trial of Putaminal AADC Gene Therapy for Parkinson's Disease. Ann Neurol. Feb. 25, 2019.

Büning and Srivastava. Capsid Modifications for Targeting and Improving the Efficacy of AAV Vectors. vol. 12, p. 248-265, Mar. 15, 2019.

Bartus et al., Safety/feasibility of targeting the substantia nigra with AAV2-neurturin in Parkinson patients. Neurology. Apr. 30, 2013;80(18):1698-701. Epub Apr. 10, 2013.

Jolesz, Intraoperative imaging in neurosurgery: where will the future take us?. Acta Neurochir Suppl. 2011;109:21-5.

Kells et al., Efficient gene therapy-based method for the delivery of therapeutics to primate cortex. PNAS Feb. 17, 2009 106 (7) 2407-2411.

Muramatsu et al., Behavioral Recovery in a Primate Model of Parkinson's Disease by Triple Transduction of Striatal Cells with Adeno-Associated Viral Vectors Expressing Dopamine-Synthesizing Enzymes. Human Gene Therapy (2002), 13:345-354.

Ng et al., Clinical Features and Pharmacotherapy of Childhood Monoamine Neurotransmitter Disorders. Pediatr Drugs (2014) 16:275-291.

Richardson et al., Novel platform for MRI-guided convection-enhanced delivery of therapeutics: preclinical validation in nonhuman primate brain. Stereotact Funct Neurosurg. 2011;89(3):141-51. Epub Apr. 14, 2011.

Salegio et al., Axonal transport of adeno-associated viral vectors is serotypedependent. Gene Ther. Mar. 2013; 20(3): 348-352.

Braak, Staging of brain pathology related to sporadic Parkinson's disease. Neurobiol Aging. Mar.-Apr. 2003;24(2):197-211.

Lloyd et al., The neurochemistry of Parkinson's disease: effect of L-dopa therapy. J Pharmacol Exp Ther. Dec. 1975;195(3):453-64.

Cunningham et al., Biodistribution of Adeno-associated Virus Type-2 in Nonhuman Primates after Convection-enhanced Delivery to Brain. Mol Ther. Jul. 2008;16(7):1267-75. Epub Jun. 3, 2008.

Löw et al., "Direct and Retrograde Transduction of Nigral Neurons with AAV6, 8, and 9 and Intraneuronal Persistence of Viral Particles" Human Gene Therapy, 2013, vol. 24, p. 613-629.

Racette B, et al. [18F]FDOPA PET as an Endophenotype for Parkinson's Disease Linkage Studies. Am J Med Genet B Neuropsychiatr Genet. Apr. 5, 2006;141B(3):245-249.

Yamada et al., "Parkin Gene Therapy for α-Synucleinopathy: A Rat Model of Parkinson's Disease," Human Gene Therapy, 2005, vol. 16, No. 2, p. 262-270.

Examination Report received in Taiwanese Application No. Application No. 107120835 dated Feb. 21, 2020.

Ayuso et al. High AAV vector purity results in serotype- and tissue-independent enhancement of transduction efficiency. *Gene Therapy* vol. 17, pp. 503-510 (2010).

* cited by examiner

SEQUENCE LISTING

```
<160> NUMBER OF SEQ ID NOS: 23

<210> SEQ ID NO 1
<211> LENGTH: 480
<212> TYPE: PRT
<213> ORGANISM: Homo sapiens

<400> SEQUENCE: 1

Met Asn Ala Ser Glu Phe Arg Arg Arg Gly Lys Glu Met Val Asp Tyr
1               5                   10                  15

Val Ala Asn Tyr Met Glu Gly Ile Glu Gly Arg Gln Val Tyr Pro Asp
            20                  25                  30

Val Glu Pro Gly Tyr Leu Arg Pro Leu Ile Pro Ala Ala Ala Pro Gln
        35                  40                  45

Glu Pro Asp Thr Phe Glu Asp Ile Ile Asn Asp Val Glu Lys Ile Ile
    50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95

Ala Ile Gly Cys Ile Gly Phe Ser Trp Ala Ala Ser Pro Ala Cys Thr
            100                 105                 110

Glu Leu Glu Thr Val Met Met Asp Trp Leu Gly Lys Met Leu Glu Leu
```

-continued

```
        115                 120                 125

Pro Lys Ala Phe Leu Asn Glu Lys Ala Gly Glu Gly Gly Gly Val Ile
    130                 135                 140

Gln Gly Ser Ala Ser Glu Ala Thr Leu Val Ala Leu Leu Ala Ala Arg
145                 150                 155                 160

Thr Lys Val Ile His Arg Leu Gln Ala Ala Ser Pro Glu Leu Thr Gln
                165                 170                 175

Ala Ala Ile Met Glu Lys Leu Val Ala Tyr Ser Ser Asp Gln Ala His
            180                 185                 190

Ser Ser Val Glu Arg Ala Gly Leu Ile Gly Gly Val Lys Leu Lys Ala
        195                 200                 205

Ile Pro Ser Asp Gly Asn Phe Ala Met Arg Ala Ser Ala Leu Gln Glu
    210                 215                 220

Ala Leu Glu Arg Asp Lys Ala Ala Gly Leu Ile Pro Phe Phe Met Val
225                 230                 235                 240

Ala Thr Leu Gly Thr Thr Thr Cys Cys Ser Phe Asp Asn Leu Leu Glu
                245                 250                 255

Val Gly Pro Ile Cys Asn Lys Glu Asp Ile Trp Leu His Val Asp Ala
            260                 265                 270

Ala Tyr Ala Gly Ser Ala Phe Ile Cys Pro Glu Phe Arg His Leu Leu
        275                 280                 285

Asn Gly Val Glu Phe Ala Asp Ser Phe Asn Phe Asn Pro His Lys Trp
    290                 295                 300

Leu Leu Val Asn Phe Asp Cys Ser Ala Met Trp Val Lys Lys Arg Thr
305                 310                 315                 320

Asp Leu Thr Gly Ala Phe Arg Leu Asp Pro Thr Tyr Leu Lys His Ser
                325                 330                 335

His Gln Asp Ser Gly Leu Ile Thr Asp Tyr Arg His Trp Gln Ile Pro
            340                 345                 350

Leu Gly Arg Arg Phe Arg Ser Leu Lys Met Trp Phe Val Phe Arg Met
        355                 360                 365

Tyr Gly Val Lys Gly Leu Gln Ala Tyr Ile Arg Lys His Val Gln Leu
    370                 375                 380

Ser His Glu Phe Glu Ser Leu Val Arg Gln Asp Pro Arg Phe Glu Ile
385                 390                 395                 400

Cys Val Glu Val Ile Leu Gly Leu Val Cys Phe Arg Leu Lys Gly Ser
                405                 410                 415

Asn Lys Val Asn Glu Ala Leu Leu Gln Arg Ile Asn Ser Ala Lys Lys
            420                 425                 430

Ile His Leu Val Pro Cys His Leu Arg Asp Lys Phe Val Leu Arg Phe
        435                 440                 445

Ala Ile Cys Ser Arg Thr Val Glu Ser Ala His Val Gln Arg Ala Trp
    450                 455                 460

Glu His Ile Lys Glu Leu Ala Ala Asp Val Leu Arg Ala Glu Arg Glu
465                 470                 475                 480


<210> SEQ ID NO 2
<211> LENGTH: 8150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
```

-continued

```
cattcgccat tcaggctgca aataagcgtt gatattcagt caattacaaa cattaataac      60
gaagagatga cagaaaaatt ttcattctgt gacagagaaa aagtagccga agatgacggt     120
ttgtcacatg gagttggcag gatgtttgat taaaaacata acaggaagaa aaatgccccg     180
ctgtgggcgg acaaaatagt tgggaactgg gaggggtgga aatggagttt ttaaggatta     240
tttagggaag agtgacaaaa tagatgggaa ctgggtgtag cgtcgtaagc taatacgaaa     300
attaaaaatg acaaaatagt ttggaactag atttcactta tctggttcgg atctcctagg     360
cgatatcagt gatcagatcc agacatgata agatacattg atgagtttgg acaaaccaca     420
actagaatgc agtgaaaaaa atgctttatt tgtgaaattt gtgatgctat tgctttattt     480
gtaaccatta taagctgcaa taaacaagtt aacaacaaca attgcattca ttttatgttt     540
caggttcagg gggaggtgtg ggaggttttt taaagcaagt aaaacctcta caaatgtggt     600
atggctgatt atgatcctct agtacttctc gacaagctta cattattgaa gcatttatca     660
gggttattgt ctcagacctg caggcagctg cgcgctcgct cgctcactga ggccgcccgg     720
gcaaagcccg ggcgtcgggc gacctttggt cgcccggcct cagtgagcga gcgagcgcgc     780
agagagggag tggccaactc catcactagg ggttccttgt agttaatgat taacccgcca     840
tgctacttat ctacgtagcc atgctctaga gcggccgcac gcgtggagct agttattaat     900
agtaatcaat tacggggtca ttagttcata gcccatatat ggagttccgc gttacataac     960
ttacggtaaa tggcccgcct ggctgaccgc ccaacgaccc ccgcccattg acgtcaataa    1020
tgacgtatgt tcccatagta acgtcaatag ggactttcca ttgacgtcaa tgggtggagt    1080
atttacggta aactgcccac ttggcagtac atcaagtgta tcatatgcca agtacgcccc    1140
ctattgacgt caatgacggt aaatggcccg cctggcatta tgcccagtac atgaccttat    1200
gggactttcc tacttggcag tacatctacg tattagtcat cgctattacc atggtgatgc    1260
ggttttggca gtacatcaat gggcgtggat agcggtttga ctcacgggga tttccaagtc    1320
tccaccccat tgacgtcaat gggagtttgt tttgcaccaa aatcaacggg actttccaaa    1380
atgtcgtaac aactccgccc cattgacgca aatgggcggt aggcgtgtac ggtgggaggt    1440
ctatataagc agagctcgtt tagtgaaccg tcagatcgcc tggagacgcc atccacgctg    1500
ttttgacctc catagaagac accgggaccg atccagcctc cgcggattcg aatcccggcc    1560
gggaacggtg cattggaacg cggattcccc gtgccaagag tgacgtaagt accgcctata    1620
gagtctatag gcccacaaaa aatgctttct tcttttaata tacttttttg tttatcttat    1680
ttctaatact ttccctaatc tctttctttc agggcaataa tgatacaatg tatcatgcct    1740
ctttgcacca ttctaaagaa taacagtgat aatttctggg ttaaggcaat agcaatattt    1800
ctgcatataa atatttctgc atataaattg taactgatgt aagaggtttc atattgctaa    1860
tagcagctac aatccagcta ccattctgct tttattttat ggttgggata aggctggatt    1920
attctgagtc caagctaggc ccttttgcta atcatgttca tacctcttat cttcctccca    1980
cagctcctgg gcaacgtgct ggtctgtgtg ctggcccatc actttggcaa agaattggga    2040
ttcgaacatc ggccgccacc atgaacgcaa gtgaattccg aaggagaggg aaggagatgg    2100
tggattacgt ggccaactac atggaaggca ttgagggacg ccaggtctac cctgacgtgg    2160
agcccgggta cctgcggccg ctgatccctg ccgctgcccc tcaggagcca gacacgtttg    2220
aggacatcat caacgacgtt gagaagataa tcatgcctgg ggtgacgcac tggcacagcc    2280
cctacttctt cgcctacttc cccactgcca gctcgtaccc ggccatgctt gcggacatgc    2340
tgtgcggggc cattggctgc atcggcttct cctgggcggc aagcccagca tgcacagagc    2400
```

-continued

```
tggagactgt gatgatggac tggctcggga agatgctgga actaccaaag gcatttttga   2460
atgagaaagc tggagaaggg ggaggagtga tccagggaag tgccagtgaa gccaccctgg   2520
tggccctgct ggccgctcgg accaaagtga tccatcggct gcaggcagcg tccccagagc   2580
tcacacaggc cgctatcatg gagaagctgg tggcttactc atccgatcag gcacactcct   2640
cagtggaaag agctgggtta attggtggag tgaaattaaa agccatcccc tcagatggca   2700
acttcgccat gcgtgcgtct gccctgcagg aagccctgga gagagacaaa gcggctggcc   2760
tgattccttt ctttatggtt gccaccctgg ggaccacaac atgctgctcc tttgacaatc   2820
tcttagaagt cggtcctatc tgcaacaagg aagacatatg gctgcacgtt gatgcagcct   2880
acgcaggcag tgcattcatc tgccctgagt tccggcacct tctgaatgga gtggagtttg   2940
cagattcatt caactttaat ccccacaaat ggctattggt gaattttgac tgttctgcca   3000
tgtgggtgaa aaagagaaca gacttaacgg gagcctttag actggacccc acttacctga   3060
agcacagcca tcaggattca gggcttatca ctgactaccg gcattggcag ataccactgg   3120
gcagaagatt tcgctctttg aaaatgtggt ttgtatttag gatgtatgga gtcaaaggac   3180
tgcaggctta tatccgcaag catgtccagc tgtcccatga gtttgagtca ctggtgcgcc   3240
aggatccccg ctttgaaatc tgtgtggaag tcattctggg gcttgtctgc tttcggctaa   3300
agggttccaa caaagtgaat gaagctcttc tgcaaagaat aaacagtgcc aaaaaaatcc   3360
acttggttcc atgtcacctc agggacaagt ttgtcctgcg ctttgccatc tgttctcgca   3420
cggtggaatc tgcccatgtg cagcgggcct gggaacacat caaagagctg gcggccgacg   3480
tgctgcgagc agagagggag taggagtgag ctgctcgaga gatctacggg tggcatccct   3540
gtgacccctc cccagtgcct ctcctggccc tggaagttgc cactccagtg cccaccagcc   3600
ttgtcctaat aaaattaagt tgcatcattt tgtctgacta ggtgtccttc tataatatta   3660
tggggtggag gggggtggta tggagcaagg ggcaagttgg gaagacaacc tgtagggcct   3720
gcggggtcta ttgggaacca agctggagtg cagtggcaca atcttggctc actgcaatct   3780
ccgcctcctg ggttcaagcg attctcctgc ctcagcctcc cgagttgttg ggattccagg   3840
catgcatgac caggctcagc taatttttgt ttttttggta gagacggggt ttcaccatat   3900
tggccaggct ggtctccaac tcctaatctc aggtgatcta cccaccttgg cctcccaaat   3960
tgctgggatt acaggcgtga accactgctc ccttccctgt ccttctgatt ttgtaggtaa   4020
ccccggacca cgtgcggacc gagcggccgc tctagagcat ggctacgtag ataagtagca   4080
tggcgggtta atcattaact acaaggaacc cctagtgatg gagttggcca ctccctctct   4140
gcgcgctcgc tcgctcactg aggccgggcg accaaaggtc gcccgacgcc cgggcggcct   4200
cagtgagcga gcgagcgcgc agctgcctgc aggtctgaga caataaccct gataaatgct   4260
tcaataatgt agccaaccac tagaactata gctagagtcc tgggcgaaca aacgatgctc   4320
gccttccaga aaaccgagga tgcgaaccac ttcatccggg gtcagcacca ccggcaagcg   4380
ccgcgacggc cgaggtcttc cgatctcctg aagccagggc agatccgtgc acagcacctt   4440
gccgtagaag aacagcaagg ccgccaatgc ctgacgatgc gtggagaccg aaaccttgcg   4500
ctcgttcgcc agccaggaca gaaatgcctc gacttcgctg ctgcccaagg ttgccgggtg   4560
acgcacaccg tggaaacgga tgaaggcacg aacccagttg acataagcct gttcggttcg   4620
taaactgtaa tgcaagtagc gtatgcgctc acgcaactgg tccagaacct tgaccgaacg   4680
cagcggtggt aacggcgcag tggcggtttt catggcttgt tatgactgtt tttttgtaca   4740
```

-continued

```
gtctatgcct cgggcatcca agcagcaagc gcgttacgcc gtgggtcgat gtttgatgtt   4800
atggagcagc aacgatgtta cgcagcagca acgatgttac gcagcagggc agtcgcccta   4860
aaacaaagtt aggtggctca agtatgggca tcattcgcac atgtaggctc ggccctgacc   4920
aagtcaaatc catgcgggct gctcttgatc ttttcggtcg tgagttcgga gacgtagcca   4980
cctactccca acatcagccg gactccgatt acctcgggaa cttgctccgt agtaagacat   5040
tcatcgcgct tgctgccttc gaccaagaag cggttgttgg cgctctcgcg gcttacgttc   5100
tgcccaagtt tgagcagccg cgtagtgaga tctatatcta tgatctcgca gtctccggcg   5160
agcaccggag gcagggcatt gccaccgcgc tcatcaatct cctcaagcat gaggccaacg   5220
cgcttggtgc ttatgtgatc tacgtgcaag cagattacgg tgacgatccc gcagtggctc   5280
tctatacaaa gttgggcata cgggaagaag tgatgcactt tgatatcgac ccaagtaccg   5340
ccacctaaca attcgttcaa gccgagatcg gcttcccggc cgcggagttg ttcggtaaat   5400
tgtcacaacg ccgcgaatat agtctttacc atgcccttgg ccacgcccct ctttaatacg   5460
acgggcaatt tgcacttcag aaaatgaaga gtttgcttta gccataacaa aagtccagta   5520
tgctttttca cagcataact ggactgattt cagtttacaa ctattctgtc tagtttaaga   5580
ctttattgtc atagtttaga tctattttgt tcagtttaag actttattgt ccgcccacac   5640
ccgcttacgc agggcatcca tttattactc aaccgtaacc gattttgcca ggttacgcgg   5700
ctggtctatg cggtgtgaaa taccgcacag atgcgtaagg agaaaatacc gcatcaggcg   5760
ctcttccgct tcctcgctca ctgactcgct gcgctcggtc gttcggctgc ggcgagcggt   5820
atcagctcac tcaaaggcgg taatacggtt atccacagaa tcaggggata acgcaggaaa   5880
gaacatgtga gcaaaaggcc agcaaaaggc caggaaccgt aaaaaggccg cgttgctggc   5940
gtttttccat aggctccgcc cccctgacga gcatcacaaa aatcgacgct caagtcagag   6000
gtggcgaaac ccgacaggac tataaagata ccaggcgttt ccccctggaa gctccctcgt   6060
gcgctctcct gttccgaccc tgccgcttac cggatacctg tccgcctttc tcccttcggg   6120
aagcgtggcg ctttctcata gctcacgctg taggtatctc agttcggtgt aggtcgttcg   6180
ctccaagctg ggctgtgtgc acgaaccccc cgttcagccc gaccgctgcg ccttatccgg   6240
taactatcgt cttgagtcca acccggtaag acacgactta tcgccactgg cagcagccac   6300
tggtaacagg attagcagag cgaggtatgt aggcggtgct acagagttct tgaagtggtg   6360
gcctaactac ggctacacta gaagaacagt atttggtatc tgcgctctgc tgaagccagt   6420
taccttcgga aaaagagttg gtagctcttg atccggcaaa caaaccaccg ctggtagcgg   6480
tggttttttt gtttgcaagc agcagattac gcgcagaaaa aaaggatctc aagaagatcc   6540
tttgatcttt tctacggggt ctgacgctca gtggaacgaa aactcacgtt aagggatttt   6600
ggtcatgaga ttatcaaaaa ggatcttcac ctagatcctt ttaaattaaa aatgaagttt   6660
taaatcaatc taaagtatat atgagtaaac ttggtctgac agttaccaat gcttaatcag   6720
tgaggcacct atctcagcga tctgtctatt tcgttcatcc atagttgcct gactccccgt   6780
cgtgtagata actacgatac gggagggctt accatctggc cccagtgctg caatgatacc   6840
gcgagaccca cgctcaccgg ctccagattt atcagcaata aaccagccag ccggaagggc   6900
cgagcgcaga agtggtcctg caactttatc cgcctccatc cagtctatta attgttgccg   6960
ggaagctaga gtaagtagtt cgccagttaa tagtttgcgc aacgttgttg ccattgctac   7020
aggcatcgtg gtgtcacgct cgtcgtttgg tatggcttca ttcagctccg gttcccaacg   7080
atcaaggcga gttacatgat cccccatgtt gtgcaaaaaa gcggttagct ccttcggtcc   7140
```

```
tccgatcgtt gtcagaagta agttggccgc agtgttatca ctcatggtta tggcagcact   7200

gcataattct cttactgtca tgccatccgt aagatgcttt tctgtgactg gtgagtactc   7260

aaccaagtca ttctgagaat agtgtatgcg gcgaccgagt tgctcttgcc cggcgtcaat   7320

acgggataat accgcgccac atagcagaac tttaaaagtg ctcatcattg gaaaacgttc   7380

ttcggggcga aaactctcaa ggatcttacc gctgttgaga tccagttcga tgtaacccac   7440

tcgtgcaccc aactgatctt cagcatcttt tactttcacc agcgtttctg ggtgagcaaa   7500

aacaggaagg caaaatgccg caaaaaaggg aataagggcg acacggaaat gttgaatact   7560

catactcttc ctttttcaat attattgaag catttatcag ggttattgtc tcatgagcgg   7620

atacatattt gaatgtattt agaaaaataa acaaataggg gttccgcgca catttccccg   7680

aaaagtgcca cctaaattgt aagcgttaat attttgttaa aattcgcgtt aaatttttgt   7740

taaatcagct cattttttaa ccaataggcc gaaatcggca aaatccctta taaatcaaaa   7800

gaatagaccg agatagggtt gagtgttgtt ccagtttgga acaagagtcc actattaaag   7860

aacgtggact ccaacgtcaa agggcgaaaa accgtctatc agggcgatgg cccactacgt   7920

gaaccatcac cctaatcaag ttttttgggg tcgaggtgcc gtaaagcact aaatcggaac   7980

cctaaaggga gcccccgatt tagagcttga cggggaaagc cggcgaacgt ggcgagaaag   8040

gaagggaaga aagcgaaagg agcgggcgct agggcgctgg caagtgtagc ggtcacgctg   8100

cgcgtaacca ccacacccgc cgcgcttaat gcgccgctac agggcgcgtc              8150
```

<210> SEQ ID NO 3
<211> LENGTH: 8149
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
cattcgccat tcaggctgca aataagcgtt gatattcagt caattacaaa cattaataac     60

gaagagatga cagaaaaatt ttcattctgt gacagagaaa aagtagccga agatgacggt    120

ttgtcacatg gagttggcag gatgtttgat taaaaacata acaggaagaa aaatgccccg    180

ctgtgggcgg acaaaatagt tgggaactgg gaggggtgga aatggagttt ttaaggatta    240

tttagggaag agtgacaaaa tagatgggaa ctgggtgtag cgtcgtaagc taatacgaaa    300

attaaaaatg acaaaatagt ttggaactag atttcactta tctggttcgg atctcctagg    360

cgatatcagt gatcagatcc agacatgata agatacattg atgagtttgg acaaaccaca    420

actagaatgc agtgaaaaaa atgctttatt tgtgaaattt gtgatgctat tgctttattt    480

gtaaccatta taagctgcaa taaacaagtt aacaacaaca attgcattca ttttatgttt    540

caggttcagg gggaggtgtg ggaggttttt taaagcaagt aaaacctcta caaatgtggt    600

atggctgatt atgatcctct agtacttctc gacaagctta cattattgaa gcatttatca    660

gggttattgt ctcagacctg caggcagctg cgcgctcgct cgctcactga ggccgcccgg    720

gcaaagcccg ggcgtcgggc gacctttggt cgcccggcct cagtgagcga gcgagcgcgc    780

agagagggag tggccaactc catcactagg ggttccttgt agttaatgat taacccgcca    840

tgctacttat ctacgtagcc atgctctaga gcggccgcac gcgtggagct agttattaat    900

agtaatcaat tacggggtca ttagttcata gcccatatat ggagttccgc gttacataac    960

ttacggtaaa tggcccgcct ggctgaccgc ccaacgaccc ccgcccattg acgtcaataa   1020
```

-continued

```
tgacgtatgt tcccatagta acgtcaatag ggactttcca ttgacgtcaa tgggtggagt   1080

atttacggta aactgcccac ttggcagtac atcaagtgta tcatatgcca agtacgcccc   1140

ctattgacgt caatgacggt aaatggcccg cctggcatta tgcccagtac atgaccttat   1200

gggactttcc tacttggcag tacatctacg tattagtcat cgctattacc atggtgatgc   1260

ggttttggca gtacatcaat gggcgtggat agcggtttga ctcacgggga tttccaagtc   1320

tccaccccat tgacgtcaat gggagtttgt tttgcaccaa aatcaacggg actttccaaa   1380

atgtcgtaac aactccgccc cattgacgca aatgggcggt aggcgtgtac ggtgggaggt   1440

ctatataagc agagctcgtt tagtgaaccg tcagatcgcc tggagacgcc atccacgctg   1500

ttttgacctc catagaagac accgggaccg atccagcctc cgcggattcg aatcccggcc   1560

gggaacggtg cattggaacg cggattcccc gtgccaagag tgacgtaagt accgcctata   1620

gagtctatag gcccacaaaa aatgctttct tcttttaata tactttttttg tttatcttat   1680

ttctaatact ttccctaatc tctttctttc agggcaataa tgatacaatg tatcatgcct   1740

ctttgcacca ttctaaagaa taacagtgat aatttctggg ttaaggcaat agcaatattt   1800

ctgcatataa atatttctgc atataaattg taactgatgt aagaggtttc atattgctaa   1860

tagcagctac aatccagcta ccattctgct tttattttat ggttgggata aggctggatt   1920

attctgagtc caagctaggc ccttttgcta atcatgttca tacctcttat cttcctccca   1980

cagctcctgg gcaacgtgct ggtctgtgtg ctggcccatc actttggcaa agaattggga   2040

ttcgaacatc ggccgccacc atgaacgcca gcgagttcag gaggaggggc aaggagatgg   2100

tggactacgt ggccaactac atggagggca tcgagggcag gcaggtgtac cccgacgtgg   2160

agcccggcta cctgaggccc ctgatccccg ccgccgcccc ccaggagccc gacaccttcg   2220

aggacatcat caacgacgtg gagaagatca tcatgcccgg cgtgacccac tggcacagcc   2280

cctacttctt cgcctacttc cccaccgcca gcagctaccc cgccatgctg gccgacatgc   2340

tgtgcggcgc catcggctgc atcggcttca gctgggccgc cagccccgcc tgcaccgagc   2400

tggagaccgt gatgatggac tggctgggca agatgctgga gctgcccaag gccttcctga   2460

acgagaaggc cggcgagggc ggcggcgtga tccagggcag cgccagcgag gccaccctgg   2520

tggccctgct ggccgccagg accaaggtga tccacaggct gcaggccgcc agccccgagc   2580

tgacccaggc cgccatcatg gagaagctgg tggcctacag cagcgaccag gcccacagca   2640

gcgtggagag ggccggcctg atcggcggcg tgaagctgaa ggccatcccc agcgacggca   2700

acttcgccat gagggccagc gccctgcagg aggccctgga gagggacaag gccgccggcc   2760

tgatcccctt cttcatggtg gccaccctgg gcaccaccac ctgctgcagc ttcgacaacc   2820

tgctggaggt gggccccatc tgcaacaagg aggacatctg gctgcacgtg gacgccgcct   2880

acgccggcag cgccttcatc tgccccgagt tcaggcacct gctgaacggc gtggagttcg   2940

ccgacagctt caacttcaac ccccacaagt ggctgctggt gaacttcgac tgcagcgcca   3000

tgtgggtgaa gaagaggacc gacctgaccg gcgccttcag gctggacccc acctacctga   3060

agcacagcca ccaggacagc ggcctgatca ccgactacag gcactggcag atcccccctgg   3120

gcaggaggtt caggagcctg aagatgtggt tcgtgttcag gatgtacggc gtgaagggcc   3180

tgcaggccta catcaggaag cacgtgcagc tgagccacga gttcgagagc ctggtgaggc   3240

aggaccccag gttcgagatc tgcgtggagg tgatcctggg cctggtgtgc ttcaggctga   3300

agggcagcaa caaggtgaac gaggccctgc tgcagaggat caacagcgcc aagaagatcc   3360
```

-continued

```
acctggtgcc ctgccacctg agggacaagt tcgtgctgag gttcgccatc tgcagcagga   3420
ccgtggagag cgcccacgtg cagagggcct gggagcacat caaggagctg gccgccgacg   3480
tgctgagggc cgagagggag tgagctgctc gagagatcta cgggtggcat ccctgtgacc   3540
cctccccagt gcctctcctg gccctggaag ttgccactcc agtgcccacc agccttgtcc   3600
taataaaatt aagttgcatc attttgtctg actaggtgtc cttctataat attatggggt   3660
ggaggggggt ggtatggagc aaggggcaag ttgggaagac aacctgtagg gcctgcgggg   3720
tctattggga accaagctgg agtgcagtgg cacaatcttg gctcactgca atctccgcct   3780
cctgggttca agcgattctc ctgcctcagc ctcccgagtt gttgggattc caggcatgca   3840
tgaccaggct cagctaattt ttgttttttt ggtagagacg gggtttcacc atattggcca   3900
ggctggtctc caactcctaa tctcaggtga tctacccacc ttggcctccc aaattgctgg   3960
gattacaggc gtgaaccact gctcccttcc ctgtccttct gattttgtag gtaacgtaac   4020
cccggaccac gtgcggaccg agcggccgct ctagagcatg gctacgtaga taagtagcat   4080
ggcgggttaa tcattaacta caaggaaccc ctagtgatgg agttggccac tccctctctg   4140
cgcgctcgct cgctcactga ggccgggcga ccaaaggtcg cccgacgccc gggcggcctc   4200
agtgagcgag cgagcgcgca gctgcctgca ggtctgagac aataaccctg ataaatgctt   4260
caataatgta gccaaccact agaactatag ctagagtcct gggcgaacaa acgatgctcg   4320
ccttccagaa aaccgaggat gcgaaccact tcatccgggg tcagcaccac cggcaagcgc   4380
cgcgacggcc gaggtcttcc gatctcctga agccagggca gatccgtgca cagcaccttg   4440
ccgtagaaga acagcaaggc cgccaatgcc tgacgatgcg tggagaccga aaccttgcgc   4500
tcgttcgcca gccaggacag aaatgcctcg acttcgctgc tgcccaaggt tgccgggtga   4560
cgcacaccgt ggaaacggat gaaggcacga acccagttga cataagcctg ttcggttcgt   4620
aaactgtaat gcaagtagcg tatgcgctca cgcaactggt ccagaacctt gaccgaacgc   4680
agcggtggta acggcgcagt ggcggttttc atggcttgtt atgactgttt ttttgtacag   4740
tctatgcctc gggcatccaa gcagcaagcg cgttacgccg tgggtcgatg tttgatgtta   4800
tggagcagca acgatgttac gcagcagcaa cgatgttacg cagcagggca gtcgccctaa   4860
aacaaagtta ggtggctcaa gtatgggcat cattcgcaca tgtaggctcg gccctgacca   4920
agtcaaatcc atgcgggctg ctcttgatct tttcggtcgt gagttcggag acgtagccac   4980
ctactcccaa catcagccgg actccgatta cctcgggaac ttgctccgta gtaagacatt   5040
catcgcgctt gctgccttcg accaagaagc ggttgttggc gctctcgcgg cttacgttct   5100
gcccaagttt gagcagccgc gtagtgagat ctatatctat gatctcgcag tctccggcga   5160
gcaccggagg cagggcattg ccaccgcgct catcaatctc ctcaagcatg aggccaacgc   5220
gcttggtgct tatgtgatct acgtgcaagc agattacggt gacgatcccg cagtggctct   5280
ctatacaaag ttgggcatac gggaagaagt gatgcacttt gatatcgacc caagtaccgc   5340
cacctaacaa ttcgttcaag ccgagatcgg cttcccggcc gcggagttgt tcggtaaatt   5400
gtcacaacgc cgcgaatata gtctttacca tgcccttggc cacgcccctc tttaatacga   5460
cgggcaattt gcacttcaga aaatgaagag tttgctttag ccataacaaa agtccagtat   5520
gctttttcac agcataactg gactgatttc agtttacaac tattctgtct agtttaagac   5580
tttattgtca tagtttagat ctattttgtt cagtttaaga ctttattgtc cgcccacacc   5640
cgcttacgca gggcatccat ttattactca accgtaaccg attttgccag gttacgcggc   5700
tggtctatgc ggtgtgaaat accgcacaga tgcgtaagga gaaaataccg catcaggcgc   5760
```

-continued

```
tcttccgctt cctcgctcac tgactcgctg cgctcggtcg ttcggctgcg gcgagcggta   5820
tcagctcact caaaggcggt aatacggtta tccacagaat caggggataa cgcaggaaag   5880
aacatgtgag caaaaggcca gcaaaaggcc aggaaccgta aaaaggccgc gttgctggcg   5940
tttttccata ggctccgccc ccctgacgag catcacaaaa atcgacgctc aagtcagagg   6000
tggcgaaacc cgacaggact ataaagatac caggcgtttc cccctggaag ctccctcgtg   6060
cgctctcctg ttccgaccct gccgcttacc ggatacctgt ccgcctttct cccttcggga   6120
agcgtggcgc tttctcatag ctcacgctgt aggtatctca gttcggtgta ggtcgttcgc   6180
tccaagctgg gctgtgtgca cgaacccccc gttcagcccg accgctgcgc cttatccggt   6240
aactatcgtc ttgagtccaa cccggtaaga cacgacttat cgccactggc agcagccact   6300
ggtaacagga ttagcagagc gaggtatgta ggcggtgcta cagagttctt gaagtggtgg   6360
cctaactacg gctacactag aagaacagta tttggtatct gcgctctgct gaagccagtt   6420
accttcggaa aaagagttgg tagctcttga tccggcaaac aaaccaccgc tggtagcggt   6480
ggtttttttg tttgcaagca gcagattacg cgcagaaaaa aaggatctca agaagatcct   6540
ttgatctttt ctacggggtc tgacgctcag tggaacgaaa actcacgtta agggattttg   6600
gtcatgagat tatcaaaaag gatcttcacc tagatccttt taaattaaaa atgaagtttt   6660
aaatcaatct aaagtatata tgagtaaact tggtctgaca gttaccaatg cttaatcagt   6720
gaggcaccta tctcagcgat ctgtctattt cgttcatcca tagttgcctg actccccgtc   6780
gtgtagataa ctacgatacg ggagggctta ccatctggcc ccagtgctgc aatgataccg   6840
cgagacccac gctcaccggc tccagattta tcagcaataa accagccagc cggaagggcc   6900
gagcgcagaa gtggtcctgc aactttatcc gcctccatcc agtctattaa ttgttgccgg   6960
gaagctagag taagtagttc gccagttaat agtttgcgca acgttgttgc cattgctaca   7020
ggcatcgtgg tgtcacgctc gtcgtttggt atggcttcat tcagctccgg ttcccaacga   7080
tcaaggcgag ttacatgatc ccccatgttg tgcaaaaaag cggttagctc cttcggtcct   7140
ccgatcgttg tcagaagtaa gttggccgca gtgttatcac tcatggttat ggcagcactg   7200
cataattctc ttactgtcat gccatccgta agatgctttt ctgtgactgg tgagtactca   7260
accaagtcat tctgagaata gtgtatgcgg cgaccgagtt gctcttgccc ggcgtcaata   7320
cgggataata ccgcgccaca tagcagaact ttaaaagtgc tcatcattgg aaaacgttct   7380
tcggggcgaa aactctcaag gatcttaccg ctgttgagat ccagttcgat gtaacccact   7440
cgtgcaccca actgatcttc agcatctttt actttcacca gcgtttctgg gtgagcaaaa   7500
acaggaaggc aaaatgccgc aaaaaaggga ataagggcga cacggaaatg ttgaatactc   7560
atactcttcc tttttcaata ttattgaagc atttatcagg gttattgtct catgagcgga   7620
tacatatttg aatgtattta gaaaaataaa caaatagggg ttccgcgcac atttccccga   7680
aaagtgccac ctaaattgta agcgttaata ttttgttaaa attcgcgtta aatttttgtt   7740
aaatcagctc attttttaac caataggccg aaatcggcaa aatcccttat aaatcaaaag   7800
aatagaccga gatagggttg agtgttgttc cagtttggaa caagagtcca ctattaaaga   7860
acgtggactc caacgtcaaa gggcgaaaaa ccgtctatca gggcgatggc ccactacgtg   7920
aaccatcacc ctaatcaagt tttttggggt cgaggtgccg taaagcacta aatcggaacc   7980
ctaaagggag cccccgattt agagcttgac ggggaaagcc ggcgaacgtg gcgagaaagg   8040
aagggaagaa agcgaaagga gcgggcgcta gggcgctggc aagtgtagcg gtcacgctgc   8100
```

gcgtaaccac cacacccgcc gcgcttaatg cgccgctaca gggcgcgtc 8149

<210> SEQ ID NO 4
<211> LENGTH: 8555
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
cattcgccat tcaggctgca aataagcgtt gatattcagt caattacaaa cattaataac 60
gaagagatga cagaaaaatt ttcattctgt gacagagaaa aagtagccga agatgacggt 120
ttgtcacatg gagttggcag gatgtttgat taaaaacata acaggaagaa aaatgccccg 180
ctgtgggcgg acaaaatagt tgggaactgg gaggggtgga aatggagttt ttaaggatta 240
tttagggaag agtgacaaaa tagatgggaa ctgggtgtag cgtcgtaagc taatacgaaa 300
attaaaaatg acaaaatagt ttggaactag atttcactta tctggttcgg atctcctagg 360
cgatatcagt gatcagatcc agacatgata agatacattg atgagtttgg acaaaccaca 420
actagaatgc agtgaaaaaa atgctttatt tgtgaaattt gtgatgctat tgctttattt 480
gtaaccatta taagctgcaa taaacaagtt aacaacaaca attgcattca ttttatgttt 540
caggttcagg gggaggtgtg ggaggttttt taaagcaagt aaaacctcta caaatgtggt 600
atggctgatt atgatcctct agtacttctc gacaagctta cattattgaa gcatttatca 660
gggttattgt ctcagacctg caggcagctg cgcgctcgct cgctcactga ggccgcccgg 720
gcaaagcccg ggcgtcgggc gacctttggt cgcccggcct cagtgagcga gcgagcgcgc 780
agagagggag tggccaactc catcactagg ggttccttgt agttaatgat taacccgcca 840
tgctacttat ctacgtagcc atgctctaga gcggccgcac gcgtggagct agttattaat 900
agtaatcaat tacggggtca ttagttcata gcccatatat ggagttccgc gttacataac 960
ttacggtaaa tggcccgcct ggctgaccgc ccaacgaccc ccgcccattg acgtcaataa 1020
tgacgtatgt tcccatagta acgtcaatag ggactttcca ttgacgtcaa tgggtggagt 1080
atttacggta aactgcccac ttggcagtac atcaagtgta tcatatgcca agtacgcccc 1140
ctattgacgt caatgacggt aaatggcccg cctggcatta tgcccagtac atgaccttat 1200
gggactttcc tacttggcag tacatctacg tattagtcat cgctattacc atggtgatgc 1260
ggttttggca gtacatcaat gggcgtggat agcggtttga ctcacgggga tttccaagtc 1320
tccaccccat tgacgtcaat gggagtttgt tttgcaccaa aatcaacggg actttccaaa 1380
atgtcgtaac aactccgccc cattgacgca aatgggcggt aggcgtgtac ggtgggaggt 1440
ctatataagc agagctcgtt tagtgaaccg tcagatcgcc tggagacgcc atccacgctg 1500
ttttgacctc catagaagac accgggaccg atccagcctc cgcggattcg aatcccggcc 1560
gggaacggtg cattggaacg cggattcccc gtgccaagag tgacgtaagt accgcctata 1620
gagtctatag gcccacaaaa aatgctttct tcttttaata tacttttttg tttatcttat 1680
ttctaatact ttccctaatc tctttctttc agggcaataa tgatacaatg tatcatgcct 1740
ctttgcacca ttctaaagaa taacagtgat aatttctggg ttaaggcaat agcaatattt 1800
ctgcatataa atatttctgc atataaattg taactgatgt aagaggtttc atattgctaa 1860
tagcagctac aatccagcta ccattctgct tttattttat ggttgggata aggctggatt 1920
attctgagtc caagctaggc ccttttgcta atcatgttca tacctcttat cttcctccca 1980

-continued

```
cagctcctgg gcaacgtgct ggtctgtgtg ctggcccatc actttggcaa agaattggga   2040
ttcgaacatc ggccgccacc atgaacgcaa gtgaattccg aaggagaggg aaggagatgg   2100
tggattacgt ggccaactac atggaaggca ttgagggacg ccaggtctac cctgacgtgg   2160
agcccgggta cctgcggccg ctgatccctg ccgctgcccc tcaggagcca gacacgtttg   2220
aggacatcat caacgacgtt gagaagataa tcatgcctgg ggtgacgcac tggcacagcc   2280
cctacttctt cgcctacttc cccactgcca gctcgtaccc ggccatgctt gcggacatgc   2340
tgtgcggggc cattggctgc atcggcttct cctgggcggc aagcccagca tgcacagagc   2400
tggagactgt gatgatggac tggctcggga agatgctgga actaccaaag gcatttttga   2460
atgagaaagc tggagaaggg ggaggagtga tccagggaag tgccagtgaa gccaccctgg   2520
tggccctgct ggccgctcgg accaaagtga tccatcggct gcaggcagcg tccccagagc   2580
tcacacaggc cgctatcatg gagaagctgg tggcttactc atccgatcag gcacactcct   2640
cagtggaaag agctgggtta attggtggag tgaaattaaa agccatcccc tcagatggca   2700
acttcgccat gcgtgcgtct gccctgcagg aagccctgga gagagacaaa gcggctggcc   2760
tgattccttt ctttatggtt gccaccctgg ggaccacaac atgctgctcc tttgacaatc   2820
tcttagaagt cggtcctatc tgcaacaagg aagacatatg gctgcacgtt gatgcagcct   2880
acgcaggcag tgcattcatc tgccctgagt tccggcacct tctgaatgga gtggagtttg   2940
cagattcatt caactttaat ccccacaaat ggctattggt gaattttgac tgttctgcca   3000
tgtgggtgaa aaagagaaca gacttaacgg gagcctttag actggacccc acttacctga   3060
agcacagcca tcaggattca gggcttatca ctgactaccg gcattggcag ataccactgg   3120
gcagaagatt tcgctctttg aaaatgtggt ttgtatttag gatgtatgga gtcaaaggac   3180
tgcaggctta tatccgcaag catgtccagc tgtcccatga gtttgagtca ctggtgcgcc   3240
aggatccccg ctttgaaatc tgtgtggaag tcattctggg gcttgtctgc tttcggctaa   3300
agggttccaa caaagtgaat gaagctcttc tgcaaagaat aaacagtgcc aaaaaaatcc   3360
acttggttcc atgtcacctc agggacaagt ttgtcctgcg ctttgccatc tgttctcgca   3420
cggtggaatc tgcccatgtg cagcgggcct gggaacacat caaagagctg gcggccgacg   3480
tgctgcgagc agagagggag taggagtgaa gccagctgca ggaatcaaaa attgaagaga   3540
gatatatctg aaaactggaa taagaagcaa ataaatatca tcctgccttc atggaactca   3600
gctgtctgtg gcttcccatg tctttctcca aagttatcca gagggttgtg attttgtctg   3660
cttagtatct catcaacaaa gaaatattat ttgctaatta aaaagttaat cttcatggcc   3720
atagctttta ttcattagct gtgatttttg ttgattaaaa cattatagat tttcatgttc   3780
ttgcagtcat cagaagtggt aggaaagcct cactgatata ttttccaggg caatcaatgt   3840
tcacgcaact tgaaattata tctgtggtct tcaaattgtc ttttgtcatg tggctaaatg   3900
cctaataagc tgctcgagag atctacgggt ggcatccctg tgacccctcc ccagtgcctc   3960
tcctggccct ggaagttgcc actccagtgc ccaccagcct tgtcctaata aaattaagtt   4020
gcatcatttt gtctgactag gtgtccttct ataatattat ggggtggagg ggggtggtat   4080
ggagcaaggg gcaagttggg aagacaacct gtagggcctg cggggtctat tgggaaccaa   4140
gctggagtgc agtggcacaa tcttggctca ctgcaatctc cgcctcctgg gttcaagcga   4200
ttctcctgcc tcagcctccc gagttgttgg gattccaggc atgcatgacc aggctcagct   4260
aatttttgtt tttttggtag agacggggtt tcaccatatt ggccaggctg gtctccaact   4320
cctaatctca ggtgatctac ccaccttggc ctcccaaatt gctgggatta caggcgtgaa   4380
```

-continued ccactgctcc cttccctgtc cttctgattt tgtaggtaac cgtaaccccg gaccacgtgc 4440
ggaccgagcg gccgctctag agcatggcta cgtagataag tagcatggcg ggttaatcat 4500
taactacaag gaacccctag tgatggagtt ggccactccc tctctgcgcg ctcgctcgct 4560
cactgaggcc gggcgaccaa aggtcgcccg acgcccgggc ggcctcagtg agcgagcgag 4620
cgcgcagctg cctgcaggtc tgagacaata accctgataa atgcttcaat aatgtagcca 4680
accactagaa ctatagctag agtcctgggc gaacaaacga tgctcgcctt ccagaaaacc 4740
gaggatgcga accacttcat ccggggtcag caccaccggc aagcgccgcg acggccgagg 4800
tcttccgatc tcctgaagcc agggcagatc cgtgcacagc accttgccgt agaagaacag 4860
caaggccgcc aatgcctgac gatgcgtgga gaccgaaacc ttgcgctcgt tcgccagcca 4920
ggacagaaat gcctcgactt cgctgctgcc caaggttgcc gggtgacgca caccgtggaa 4980
acggatgaag gcacgaaccc agttgacata agcctgttcg gttcgtaaac tgtaatgcaa 5040
gtagcgtatg cgctcacgca actggtccag aaccttgacc gaacgcagcg gtggtaacgg 5100
cgcagtggcg gttttcatgg cttgttatga ctgttttttt gtacagtcta tgcctcgggc 5160
atccaagcag caagcgcgtt acgccgtggg tcgatgtttg atgttatgga gcagcaacga 5220
tgttacgcag cagcaacgat gttacgcagc agggcagtcg ccctaaaaca aagttaggtg 5280
gctcaagtat gggcatcatt cgcacatgta ggctcggccc tgaccaagtc aaatccatgc 5340
gggctgctct tgatcttttc ggtcgtgagt tcggagacgt agccacctac tcccaacatc 5400
agccggactc cgattacctc gggaacttgc tccgtagtaa gacattcatc gcgcttgctg 5460
ccttcgacca agaagcggtt gttggcgctc tcgcggctta cgttctgccc aagtttgagc 5520
agccgcgtag tgagatctat atctatgatc tcgcagtctc cggcgagcac cggaggcagg 5580
gcattgccac cgcgctcatc aatctcctca agcatgaggc caacgcgctt ggtgcttatg 5640
tgatctacgt gcaagcagat tacggtgacg atcccgcagt ggctctctat acaaagttgg 5700
gcatacggga agaagtgatg cactttgata tcgacccaag taccgccacc taacaattcg 5760
ttcaagccga gatcggcttc ccggccgcgg agttgttcgg taaattgtca caacgccgcg 5820
aatatagtct ttaccatgcc cttggccacg cccctcttta atacgacggg caatttgcac 5880
ttcagaaaat gaagagtttg ctttagccat aacaaaagtc cagtatgctt tttcacagca 5940
taactggact gatttcagtt tacaactatt ctgtctagtt taagacttta ttgtcatagt 6000
ttagatctat tttgttcagt ttaagacttt attgtccgcc cacacccgct tacgcagggc 6060
atccatttat tactcaaccg taaccgattt tgccaggtta cgcggctggt ctatgcggtg 6120
tgaaataccg cacagatgcg taaggagaaa ataccgcatc aggcgctctt ccgcttcctc 6180
gctcactgac tcgctgcgct cggtcgttcg gctgcggcga gcggtatcag ctcactcaaa 6240
ggcggtaata cggttatcca cagaatcagg ggataacgca ggaaagaaca tgtgagcaaa 6300
aggccagcaa aaggccagga accgtaaaaa ggccgcgttg ctggcgtttt tccataggct 6360
ccgcccccct gacgagcatc acaaaaatcg acgctcaagt cagaggtggc gaaacccgac 6420
aggactataa agataccagg cgtttccccc tggaagctcc ctcgtgcgct ctcctgttcc 6480
gaccctgccg cttaccggat acctgtccgc ctttctccct tcgggaagcg tggcgctttc 6540
tcatagctca cgctgtaggt atctcagttc ggtgtaggtc gttcgctcca agctgggctg 6600
tgtgcacgaa ccccccgttc agcccgaccg ctgcgcctta tccggtaact atcgtcttga 6660
gtccaacccg gtaagacacg acttatcgcc actggcagca gccactggta acaggattag 6720

-continued cagagcgagg tatgtaggcg gtgctacaga gttcttgaag tggtggccta actacggcta 6780
cactagaaga acagtatttg gtatctgcgc tctgctgaag ccagttacct tcggaaaaag 6840
agttggtagc tcttgatccg gcaaacaaac caccgctggt agcggtggtt tttttgtttg 6900
caagcagcag attacgcgca gaaaaaaagg atctcaagaa gatcctttga tcttttctac 6960
ggggtctgac gctcagtgga acgaaaactc acgttaaggg attttggtca tgagattatc 7020
aaaaaggatc ttcacctaga tccttttaaa ttaaaaatga agttttaaat caatctaaag 7080
tatatatgag taaacttggt ctgacagtta ccaatgctta atcagtgagg cacctatctc 7140
agcgatctgt ctatttcgtt catccatagt tgcctgactc cccgtcgtgt agataactac 7200
gatacgggag ggcttaccat ctggccccag tgctgcaatg ataccgcgag acccacgctc 7260
accggctcca gatttatcag caataaacca gccagccgga agggccgagc gcagaagtgg 7320
tcctgcaact ttatccgcct ccatccagtc tattaattgt tgccgggaag ctagagtaag 7380
tagttcgcca gttaatagtt tgcgcaacgt tgttgccatt gctacaggca tcgtggtgtc 7440
acgctcgtcg tttggtatgg cttcattcag ctccggttcc caacgatcaa ggcgagttac 7500
atgatccccc atgttgtgca aaaaagcggt tagctccttc ggtcctccga tcgttgtcag 7560
aagtaagttg gccgcagtgt tatcactcat ggttatggca gcactgcata attctcttac 7620
tgtcatgcca tccgtaagat gcttttctgt gactggtgag tactcaacca agtcattctg 7680
agaatagtgt atgcggcgac cgagttgctc ttgcccggcg tcaatacggg ataataccgc 7740
gccacatagc agaactttaa aagtgctcat cattggaaaa cgttcttcgg ggcgaaaact 7800
ctcaaggatc ttaccgctgt tgagatccag ttcgatgtaa cccactcgtg cacccaactg 7860
atcttcagca tcttttactt tcaccagcgt ttctgggtga gcaaaaacag gaaggcaaaa 7920
tgccgcaaaa aagggaataa gggcgacacg gaaatgttga atactcatac tcttcctttt 7980
tcaatattat tgaagcattt atcagggtta ttgtctcatg agcggataca tatttgaatg 8040
tatttagaaa aataaacaaa taggggttcc gcgcacattt ccccgaaaag tgccacctaa 8100
attgtaagcg ttaatatttt gttaaaattc gcgttaaatt tttgttaaat cagctcattt 8160
tttaaccaat aggccgaaat cggcaaaatc ccttataaat caaaagaata gaccgagata 8220
gggttgagtg ttgttccagt ttggaacaag agtccactat taaagaacgt ggactccaac 8280
gtcaaagggc gaaaaaccgt ctatcagggc gatggcccac tacgtgaacc atcaccctaa 8340
tcaagttttt tggggtcgag gtgccgtaaa gcactaaatc ggaaccctaa agggagcccc 8400
cgatttagag cttgacgggg aaagccggcg aacgtggcga gaaaggaagg gaagaaagcg 8460
aaaggagcgg gcgctagggc gctggcaagt gtagcggtca cgctgcgcgt aaccaccaca 8520
cccgccgcgc ttaatgcgcc gctacagggc gcgtc 8555

<210> SEQ ID NO 5
<211> LENGTH: 8694
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5
cattcgccat tcaggctgca aataagcgtt gatattcagt caattacaaa cattaataac 60
gaagagatga cagaaaaatt ttcattctgt gacagagaaa aagtagccga agatgacggt 120
ttgtcacatg gagttggcag gatgtttgat taaaaacata acaggaagaa aaatgccccg 180

-continued

```
ctgtgggcgg acaaaatagt tgggaactgg gaggggtgga aatggagttt ttaaggatta    240
tttagggaag agtgacaaaa tagatgggaa ctgggtgtag cgtcgtaagc taatacgaaa    300
attaaaaatg acaaaatagt ttggaactag atttcactta tctggttcgg atctcctagg    360
cgatatcagt gatcagatcc agacatgata agatacattg atgagtttgg acaaaccaca    420
actagaatgc agtgaaaaaa atgctttatt tgtgaaattt gtgatgctat tgctttattt    480
gtaaccatta taagctgcaa taaacaagtt aacaacaaca attgcattca ttttatgttt    540
caggttcagg gggaggtgtg ggaggttttt taaagcaagt aaaacctcta caaatgtggt    600
atggctgatt atgatcctct agtacttctc gacaagctta cattattgaa gcatttatca    660
gggttattgt ctcagacctg caggcagctg cgcgctcgct cgctcactga ggccgcccgg    720
gcaaagcccg ggcgtcgggc gacctttggt cgcccggcct cagtgagcga gcgagcgcgc    780
agagagggag tggccaactc catcactagg ggttccttgt agttaatgat taacccgcca    840
tgctacttat ctacgtagcc atgctctaga gcggccgcaa cgcgtaaact tcgtcgacga    900
tctgcggccg cacgcgtgga gctagttatt aatagtaatc aattacgggg tcattagttc    960
atagcccata tatggagttc cgcgttacat aacttacggt aaatggcccg cctggctgac   1020
cgcccaacga cccccgccca ttgacgtcaa taatgacgta tgttcccata gtaacgtcaa   1080
tagggacttt ccattgacgt caatgggtgg agtatttacg gtaaactgcc cacttggcag   1140
tacatcaagt gtatcatatg ccaagtacgc cccctattga cgtcaatgac ggtaaatggc   1200
ccgcctggca ttatgcccag tacatgacct tatgggactt tcctacttgg cagtacatct   1260
acgtattagt catcgctatt accatggtga tgcggttttg gcagtacatc aatgggcgtg   1320
gatagcggtt tgactcacgg ggatttccaa gtctccaccc cattgacgtc aatgggagtt   1380
tgttttgcac caaaatcaac gggactttcc aaaatgtcgt aacaactccg ccccattgac   1440
gcaaatgggc ggtaggcgtg tacggtggga ggtctatata agcagagctc gtttagtgaa   1500
ccgtcagatc gcctggagac gccatccacg ctgttttgac ctccatagaa gacaccggga   1560
ccgatccagc ctccgcggat tcgaatcccg gccgggaacg gtgcattgga acgcggattc   1620
cccgtgccaa gagtgacgta agtaccgcct atagagtcta taggcccaca aaaaatgctt   1680
tcttctttta atatactttt ttgtttatct tatttctaat actttcccta atctctttct   1740
ttcagggcaa taatgataca atgtatcatg cctctttgca ccattctaaa gaataacagt   1800
gataatttct gggttaaggc aatagcaata tttctgcata taaatatttc tgcatataaa   1860
ttgtaactga tgtaagaggt ttcatattgc taatagcagc tacaatccag ctaccattct   1920
gcttttattt tatggttggg ataaggctgg attattctga gtccaagcta ggcccttttg   1980
ctaatcatgt tcatacctct tatcttcctc ccacagctcc tgggcaacgt gctggtctgt   2040
gtgctggccc atcactttgg caaagaattg ggattcgaac atcgaattcg ggcacgaggg   2100
aggacagaga gcaagtcact cccggctgcc tttttcacct ctgacagagc ccagacacca   2160
tgaacgcaag tgaattccga aggagaggga aggagatggt ggattacgtg gccaactaca   2220
tggaaggcat tgagggacgc caggtctacc ctgacgtgga gcccgggtac ctgcggccgc   2280
tgatccctgc cgctgcccct caggagccag acacgtttga ggacatcatc aacgacgttg   2340
agaagataat catgcctggg gtgacgcact ggcacagccc ctacttcttc gcctacttcc   2400
ccactgccag ctcgtacccg gccatgcttg cggacatgct gtgcggggcc attggctgca   2460
tcggcttctc ctgggcggca agcccagcat gcacagagct ggagactgtg atgatggact   2520
ggctcgggaa gatgctggaa ctaccaaagg catttttgaa tgagaaagct ggagaagggg   2580
```

-continued

```
gaggagtgat ccagggaagt gccagtgaag ccaccctggt ggccctgctg gccgctcgga   2640
ccaaagtgat ccatcggctg caggcagcgt ccccagagct cacacaggcc gctatcatgg   2700
agaagctggt ggcttactca tccgatcagg cacactcctc agtggaaaga gctgggttaa   2760
ttggtggagt gaaattaaaa gccatcccct cagatggcaa cttcgccatg cgtgcgtctg   2820
ccctgcagga agccctggag agagacaaag cggctggcct gattcctttc tttatggttg   2880
ccaccctggg gaccacaaca tgctgctcct ttgacaatct cttagaagtc ggtcctatct   2940
gcaacaagga agacatatgg ctgcacgttg atgcagccta cgcaggcagt gcattcatct   3000
gccctgagtt ccggcacctt ctgaatggag tggagtttgc agattcattc aactttaatc   3060
cccacaaatg gctattggtg aattttgact gttctgccat gtgggtgaaa aagagaacag   3120
acttaacggg agcctttaga ctggacccca cttacctgaa gcacagccat caggattcag   3180
ggcttatcac tgactaccgg cattggcaga taccactggg cagaagattt cgctctttga   3240
aaatgtggtt tgtatttagg atgtatggag tcaaaggact gcaggcttat atccgcaagc   3300
atgtccagct gtcccatgag tttgagtcac tggtgcgcca ggatccccgc tttgaaatct   3360
gtgtggaagt cattctgggg cttgtctgct ttcggctaaa gggttccaac aaagtgaatg   3420
aagctcttct gcaaagaata aacagtgcca aaaaaatcca cttggttcca tgtcacctca   3480
gggacaagtt tgtcctgcgc tttgccatct gttctcgcac ggtggaatct gcccatgtgc   3540
agcgggcctg ggaacacatc aaagagctgg cggccgacgt gctgcgagca gagagggagt   3600
aggagtgaag ccagctgcag gaatcaaaaa ttgaagagag atatatctga aaactggaat   3660
aagaagcaaa taaatatcat cctgccttca tggaactcag ctgtctgtgg cttcccatgt   3720
ctttctccaa agttatccag agggttgtga ttttgtctgc ttagtatctc atcaacaaag   3780
aaatattatt tgctaattaa aaagttaatc ttcatggcca tagcttttat tcattagctg   3840
tgatttttgt tgattaaaac attatagatt ttcatgttct tgcagtcatc agaagtggta   3900
ggaaagcctc actgatatat tttccagggc aatcaatgtt cacgcaactt gaaattatat   3960
ctgtggtctt caaattgtct tttgtcatgt ggctaaatgc ctaataaaca attcaagtga   4020
aatactaaaa aaaaaaaaaa aaaaaaaagc tgctcgagag atctacgggt ggcatccctg   4080
tgacccctcc ccagtgcctc tcctggccct ggaagttgcc actccagtgc ccaccagcct   4140
tgtcctaata aaattaagtt gcatcatttt gtctgactag gtgtccttct ataatattat   4200
ggggtggagg ggggtggtat ggagcaaggg gcaagttggg aagacaacct gtagggcctg   4260
cggggtctat tgggaaccaa gctggagtgc agtggcacaa tcttggctca ctgcaatctc   4320
cgcctcctgg gttcaagcga ttctcctgcc tcagcctccc gagttgttgg gattccaggc   4380
atgcatgacc aggctcagct aatttttgtt tttttggtag agacggggtt tcaccatatt   4440
ggccaggctg gtctccaact cctaatctca ggtgatctac ccaccttggc ctcccaaatt   4500
gctgggatta caggcgtgaa ccactgctcc cttccctgtc cttctgattt tgtaggtaac   4560
gtaaccccgg accacgtgcg gaccgagcgg ccgctctaga gcatggctac gtagataagt   4620
agcatggcgg gttaatcatt aactacaagg aacccctagt gatggagttg gccactccct   4680
ctctgcgcgc tcgctcgctc actgaggccg ggcgaccaaa ggtcgcccga cgcccgggcg   4740
gcctcagtga gcgagcgagc gcgcagctgc ctgcaggtct gagacaataa ccctgataaa   4800
tgcttcaata atgtagccaa ccactagaac tatagctaga gtcctgggcg aacaaacgat   4860
gctcgccttc cagaaaaccg aggatgcgaa ccacttcatc cggggtcagc accaccggca   4920
```

-continued

```
agcgccgcga cggccgaggt cttccgatct cctgaagcca gggcagatcc gtgcacagca   4980
ccttgccgta gaagaacagc aaggccgcca atgcctgacg atgcgtggag accgaaacct   5040
tgcgctcgtt cgccagccag gacagaaatg cctcgacttc gctgctgccc aaggttgccg   5100
ggtgacgcac accgtggaaa cggatgaagg cacgaaccca gttgacataa gcctgttcgg   5160
ttcgtaaact gtaatgcaag tagcgtatgc gctcacgcaa ctggtccaga accttgaccg   5220
aacgcagcgg tggtaacggc gcagtggcgg ttttcatggc ttgttatgac tgtttttttg   5280
tacagtctat gcctcgggca tccaagcagc aagcgcgtta cgccgtgggt cgatgtttga   5340
tgttatggag cagcaacgat gttacgcagc agcaacgatg ttacgcagca gggcagtcgc   5400
cctaaaacaa agttaggtgg ctcaagtatg ggcatcattc gcacatgtag gctcggccct   5460
gaccaagtca aatccatgcg ggctgctctt gatcttttcg gtcgtgagtt cggagacgta   5520
gccacctact cccaacatca gccggactcc gattacctcg ggaacttgct ccgtagtaag   5580
acattcatcg cgcttgctgc cttcgaccaa gaagcggttg ttggcgctct cgcggcttac   5640
gttctgccca agtttgagca gccgcgtagt gagatctata tctatgatct cgcagtctcc   5700
ggcgagcacc ggaggcaggg cattgccacc gcgctcatca atctcctcaa gcatgaggcc   5760
aacgcgcttg gtgcttatgt gatctacgtg caagcagatt acggtgacga tcccgcagtg   5820
gctctctata caaagttggg catacgggaa gaagtgatgc actttgatat cgacccaagt   5880
accgccacct aacaattcgt tcaagccgag atcggcttcc cggccgcgga gttgttcggt   5940
aaattgtcac aacgccgcga atatagtctt taccatgccc ttggccacgc ccctctttaa   6000
tacgacgggc aatttgcact tcagaaaatg aagagtttgc tttagccata acaaaagtcc   6060
agtatgcttt ttcacagcat aactggactg atttcagttt acaactattc tgtctagttt   6120
aagactttat tgtcatagtt tagatctatt ttgttcagtt taagacttta ttgtccgccc   6180
acacccgctt acgcagggca tccatttatt actcaaccgt aaccgatttt gccaggttac   6240
gcggctggtc tatgcggtgt gaaataccgc acagatgcgt aaggagaaaa taccgcatca   6300
ggcgctcttc cgcttcctcg ctcactgact cgctgcgctc ggtcgttcgg ctgcggcgag   6360
cggtatcagc tcactcaaag gcggtaatac ggttatccac agaatcaggg gataacgcag   6420
gaaagaacat gtgagcaaaa ggccagcaaa aggccaggaa ccgtaaaaag gccgcgttgc   6480
tggcgttttt ccataggctc cgcccccctg acgagcatca caaaaatcga cgctcaagtc   6540
agaggtggcg aaacccgaca ggactataaa gataccaggc gtttccccct ggaagctccc   6600
tcgtgcgctc tcctgttccg accctgccgc ttaccggata cctgtccgcc tttctccctt   6660
cgggaagcgt ggcgctttct catagctcac gctgtaggta tctcagttcg gtgtaggtcg   6720
ttcgctccaa gctgggctgt gtgcacgaac cccccgttca gcccgaccgc tgcgccttat   6780
ccggtaacta tcgtcttgag tccaacccgg taagacacga cttatcgcca ctggcagcag   6840
ccactggtaa caggattagc agagcgaggt atgtaggcgg tgctacagag ttcttgaagt   6900
ggtggcctaa ctacggctac actagaagaa cagtatttgg tatctgcgct ctgctgaagc   6960
cagttacctt cggaaaaaga gttggtagct cttgatccgg caaacaaacc accgctggta   7020
gcggtggttt ttttgtttgc aagcagcaga ttacgcgcag aaaaaaagga tctcaagaag   7080
atcctttgat cttttctacg gggtctgacg ctcagtggaa cgaaaactca cgttaaggga   7140
ttttggtcat gagattatca aaaaggatct tcacctagat ccttttaaat taaaaatgaa   7200
gttttaaatc aatctaaagt atatatgagt aaacttggtc tgacagttac caatgcttaa   7260
tcagtgaggc acctatctca gcgatctgtc tatttcgttc atccatagtt gcctgactcc   7320
```

```
ccgtcgtgta gataactacg atacgggagg gcttaccatc tggccccagt gctgcaatga   7380

taccgcgaga cccacgctca ccggctccag atttatcagc aataaaccag ccagccggaa   7440

gggccgagcg cagaagtggt cctgcaactt tatccgcctc catccagtct attaattgtt   7500

gccgggaagc tagagtaagt agttcgccag ttaatagttt gcgcaacgtt gttgccattg   7560

ctacaggcat cgtggtgtca cgctcgtcgt ttggtatggc ttcattcagc tccggttccc   7620

aacgatcaag gcgagttaca tgatccccca tgttgtgcaa aaaagcggtt agctccttcg   7680

gtcctccgat cgttgtcaga agtaagttgg ccgcagtgtt atcactcatg gttatggcag   7740

cactgcataa ttctcttact gtcatgccat ccgtaagatg cttttctgtg actggtgagt   7800

actcaaccaa gtcattctga gaatagtgta tgcggcgacc gagttgctct tgcccggcgt   7860

caatacggga taataccgcg ccacatagca gaactttaaa agtgctcatc attggaaaac   7920

gttcttcggg gcgaaaactc tcaaggatct taccgctgtt gagatccagt tcgatgtaac   7980

ccactcgtgc acccaactga tcttcagcat cttttacttt caccagcgtt tctgggtgag   8040

caaaaacagg aaggcaaaat gccgcaaaaa agggaataag ggcgacacgg aaatgttgaa   8100

tactcatact cttccttttt caatattatt gaagcattta tcagggttat tgtctcatga   8160

gcggatacat atttgaatgt atttagaaaa ataaacaaat aggggttccg cgcacatttc   8220

cccgaaaagt gccacctaaa ttgtaagcgt taatattttg ttaaaattcg cgttaaattt   8280

ttgttaaatc agctcatttt ttaaccaata ggccgaaatc ggcaaaatcc cttataaatc   8340

aaaagaatag accgagatag ggttgagtgt tgttccagtt tggaacaaga gtccactatt   8400

aaagaacgtg gactccaacg tcaaagggcg aaaaaccgtc tatcagggcg atggcccact   8460

acgtgaacca tcaccctaat caagtttttt ggggtcgagg tgccgtaaag cactaaatcg   8520

gaaccctaaa gggagccccc gatttagagc ttgacgggga aagccggcga acgtggcgag   8580

aaaggaaggg aagaaagcga aaggagcggg cgctagggcg ctggcaagtg tagcggtcac   8640

gctgcgcgta accaccacac ccgccgcgct taatgcgccg ctacagggcg cgtc         8694
```

<210> SEQ ID NO 6
<211> LENGTH: 3535
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 6

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

agagcggccg cacgcgtgga gctagttatt aatagtaatc aattacgggg tcattagttc    240

atagcccata tatggagttc cgcgttacat aacttacggt aaatggcccg cctggctgac    300

cgcccaacga cccccgccca ttgacgtcaa taatgacgta tgttcccata gtaacgtcaa    360

tagggacttt ccattgacgt caatgggtgg agtatttacg gtaaactgcc cacttggcag    420

tacatcaagt gtatcatatg ccaagtacgc cccctattga cgtcaatgac ggtaaatggc    480

ccgcctggca ttatgcccag tacatgacct tatgggactt tcctacttgg cagtacatct    540

acgtattagt catcgctatt accatggtga tgcggttttg gcagtacatc aatgggcgtg    600

gatagcggtt tgactcacgg ggatttccaa gtctccaccc cattgacgtc aatgggagtt    660
```

-continued

```
tgttttgcac caaaatcaac gggactttcc aaaatgtcgt aacaactccg ccccattgac    720
gcaaatgggc ggtaggcgtg tacggtggga ggtctatata agcagagctc gtttagtgaa    780
ccgtcagatc gcctggagac gccatccacg ctgttttgac ctccatagaa gacaccggga    840
ccgatccagc ctccgcggat tcgaatcccg gccgggaacg gtgcattgga acgcggattc    900
cccgtgccaa gagtgacgta agtaccgcct atagagtcta taggcccaca aaaaatgctt    960
tcttctttta atatactttt ttgtttatct tatttctaat actttcccta atctctttct   1020
ttcagggcaa taatgataca atgtatcatg cctctttgca ccattctaaa gaataacagt   1080
gataatttct gggttaaggc aatagcaata tttctgcata taaatatttc tgcatataaa   1140
ttgtaactga tgtaagaggt ttcatattgc taatagcagc tacaatccag ctaccattct   1200
gcttttattt tatggttggg ataaggctgg attattctga gtccaagcta ggcccttttg   1260
ctaatcatgt tcatacctct tatcttcctc ccacagctcc tgggcaacgt gctggtctgt   1320
gtgctggccc atcactttgg caaagaattg ggattcgaac atcggccgcc accatgaacg   1380
caagtgaatt ccgaaggaga gggaaggaga tggtggatta cgtggccaac tacatggaag   1440
gcattgaggg acgccaggtc taccctgacg tggagcccgg gtacctgcgg ccgctgatcc   1500
ctgccgctgc ccctcaggag ccagacacgt ttgaggacat catcaacgac gttgagaaga   1560
taatcatgcc tggggtgacg cactggcaca gcccctactt cttcgcctac ttccccactg   1620
ccagctcgta cccggccatg cttgcggaca tgctgtgcgg ggccattggc tgcatcggct   1680
tctcctgggc ggcaagccca gcatgcacag agctggagac tgtgatgatg gactggctcg   1740
ggaagatgct ggaactacca aaggcatttt tgaatgagaa agctggagaa gggggaggag   1800
tgatccaggg aagtgccagt gaagccaccc tggtggccct gctggccgct cggaccaaag   1860
tgatccatcg gctgcaggca gcgtccccag agctcacaca ggccgctatc atggagaagc   1920
tggtggctta ctcatccgat caggcacact cctcagtgga aagagctggg ttaattggtg   1980
gagtgaaatt aaaagccatc ccctcagatg gcaacttcgc catgcgtgcg tctgccctgc   2040
aggaagccct ggagagagac aaagcggctg gcctgattcc tttctttatg gttgccaccc   2100
tggggaccac aacatgctgc tcctttgaca atctcttaga agtcggtcct atctgcaaca   2160
aggaagacat atggctgcac gttgatgcag cctacgcagg cagtgcattc atctgccctg   2220
agttccggca ccttctgaat ggagtggagt ttgcagattc attcaacttt aatccccaca   2280
aatggctatt ggtgaatttt gactgttctg ccatgtgggt gaaaaagaga acagacttaa   2340
cgggagcctt tagactggac cccacttacc tgaagcacag ccatcaggat tcagggctta   2400
tcactgacta ccggcattgg cagataccac tgggcagaag atttcgctct ttgaaaatgt   2460
ggtttgtatt taggatgtat ggagtcaaag gactgcaggc ttatatccgc aagcatgtcc   2520
agctgtccca tgagtttgag tcactggtgc gccaggatcc ccgctttgaa atctgtgtgg   2580
aagtcattct ggggcttgtc tgctttcggc taaagggttc caacaaagtg aatgaagctc   2640
ttctgcaaag aataaacagt gccaaaaaaa tccacttggt tccatgtcac ctcagggaca   2700
agtttgtcct gcgctttgcc atctgttctc gcacggtgga atctgcccat gtgcagcggg   2760
cctgggaaca catcaaagag ctggcggccg acgtgctgcg agcagagagg gagtaggagt   2820
gagctgctcg agagatctac gggtggcatc cctgtgaccc ctccccagtg cctctcctgg   2880
ccctggaagt tgccactcca gtgcccacca gccttgtcct aataaaatta agttgcatca   2940
ttttgtctga ctaggtgtcc ttctataata ttatggggtg gaggggggtg gtatggagca   3000
```

-continued

```
aggggcaagt tgggaagaca acctgtaggg cctgcggggt ctattgggaa ccaagctgga   3060

gtgcagtggc acaatcttgg ctcactgcaa tctccgcctc ctgggttcaa gcgattctcc   3120

tgcctcagcc tcccgagttg ttgggattcc aggcatgcat gaccaggctc agctaatttt   3180

tgtttttttg gtagagacgg ggtttcacca tattggccag gctggtctcc aactcctaat   3240

ctcaggtgat ctacccacct tggcctccca aattgctggg attacaggcg tgaaccactg   3300

ctcccttccc tgtccttctg attttgtagg taaccccgga ccacgtgcgg accgagcggc   3360

cgctctagag catggctacg tagataagta gcatggcggg ttaatcatta actacaagga   3420

acccctagtg atggagttgg ccactccctc tctgcgcgct cgctcgctca ctgaggccgg   3480

gcgaccaaag gtcgcccgac gcccgggcgg cctcagtgag cgagcgagcg cgcag        3535
```

<210> SEQ ID NO 7
<211> LENGTH: 3534
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

agagcggccg cacgcgtgga gctagttatt aatagtaatc aattacgggg tcattagttc    240

atagcccata tatggagttc cgcgttacat aacttacggt aaatggcccg cctggctgac    300

cgcccaacga cccccgccca ttgacgtcaa taatgacgta tgttcccata gtaacgtcaa    360

tagggacttt ccattgacgt caatgggtgg agtatttacg gtaaactgcc cacttggcag    420

tacatcaagt gtatcatatg ccaagtacgc cccctattga cgtcaatgac ggtaaatggc    480

ccgcctggca ttatgcccag tacatgacct tatgggactt tcctacttgg cagtacatct    540

acgtattagt catcgctatt accatggtga tgcggttttg gcagtacatc aatgggcgtg    600

gatagcggtt tgactcacgg ggatttccaa gtctccaccc cattgacgtc aatgggagtt    660

tgttttgcac caaaatcaac gggactttcc aaaatgtcgt aacaactccg ccccattgac    720

gcaaatgggc ggtaggcgtg tacggtggga ggtctatata agcagagctc gtttagtgaa    780

ccgtcagatc gcctggagac gccatccacg ctgttttgac ctccatagaa gacaccggga    840

ccgatccagc ctccgcggat tcgaatcccg gccgggaacg gtgcattgga acgcggattc    900

cccgtgccaa gagtgacgta agtaccgcct atagagtcta taggcccaca aaaaatgctt    960

tcttctttta atatactttt ttgtttatct tatttctaat actttcccta atctctttct   1020

ttcagggcaa taatgataca atgtatcatg cctctttgca ccattctaaa gaataacagt   1080

gataatttct gggttaaggc aatagcaata tttctgcata taaatatttc tgcatataaa   1140

ttgtaactga tgtaagaggt ttcatattgc taatagcagc tacaatccag ctaccattct   1200

gcttttattt tatggttggg ataaggctgg attattctga gtccaagcta ggcccttttg   1260

ctaatcatgt tcatacctct tatcttcctc ccacagctcc tgggcaacgt gctggtctgt   1320

gtgctggccc atcactttgg caaagaattg ggattcgaac atcggccgcc accatgaacg   1380

ccagcgagtt caggaggagg ggcaaggaga tggtggacta cgtggccaac tacatggagg   1440

gcatcgaggg caggcaggtg taccccgacg tggagcccgg ctacctgagg cccctgatcc   1500
```

-continued

```
ccgccgccgc cccccaggag cccgacacct tcgaggacat catcaacgac gtggagaaga   1560
tcatcatgcc cggcgtgacc cactggcaca gcccctactt cttcgcctac ttccccaccg   1620
ccagcagcta ccccgccatg ctggccgaca tgctgtgcgg cgccatcggc tgcatcggct   1680
tcagctgggc cgccagcccc gcctgcaccg agctggagac cgtgatgatg gactggctgg   1740
gcaagatgct ggagctgccc aaggccttcc tgaacgagaa ggccggcgag ggcggcggcg   1800
tgatccaggg cagcgccagc gaggccaccc tggtggccct gctggccgcc aggaccaagg   1860
tgatccacag gctgcaggcc gccagccccg agctgaccca ggccgccatc atggagaagc   1920
tggtggccta cagcagcgac caggcccaca gcagcgtgga gagggccggc ctgatcggcg   1980
gcgtgaagct gaaggccatc cccagcgacg gcaacttcgc catgagggcc agcgccctgc   2040
aggaggccct ggagagggac aaggccgccg gcctgatccc cttcttcatg gtggccaccc   2100
tgggcaccac cacctgctgc agcttcgaca acctgctgga ggtgggcccc atctgcaaca   2160
aggaggacat ctggctgcac gtggacgccg cctacgccgg cagcgccttc atctgccccg   2220
agttcaggca cctgctgaac ggcgtggagt tcgccgacag cttcaacttc aacccccaca   2280
agtggctgct ggtgaacttc gactgcagcg ccatgtgggt gaagaagagg accgacctga   2340
ccggcgcctt caggctggac cccacctacc tgaagcacag ccaccaggac agcggcctga   2400
tcaccgacta caggcactgg cagatccccc tgggcaggag gttcaggagc ctgaagatgt   2460
ggttcgtgtt caggatgtac ggcgtgaagg gcctgcaggc ctacatcagg aagcacgtgc   2520
agctgagcca cgagttcgag agcctggtga ggcaggaccc caggttcgag atctgcgtgg   2580
aggtgatcct gggcctggtg tgcttcaggc tgaagggcag caacaaggtg aacgaggccc   2640
tgctgcagag gatcaacagc gccaagaaga tccacctggt gccctgccac ctgagggaca   2700
agttcgtgct gaggttcgcc atctgcagca ggaccgtgga gagcgcccac gtgcagaggg   2760
cctgggagca catcaaggag ctggccgccg acgtgctgag ggccgagagg gagtgagctg   2820
ctcgagagat ctacgggtgg catccctgtg acccctcccc agtgcctctc ctggccctgg   2880
aagttgccac tccagtgccc accagccttg tcctaataaa attaagttgc atcattttgt   2940
ctgactaggt gtccttctat aatattatgg ggtggagggg ggtggtatgg agcaaggggc   3000
aagttgggaa gacaacctgt agggcctgcg gggtctattg ggaaccaagc tggagtgcag   3060
tggcacaatc ttggctcact gcaatctccg cctcctgggt tcaagcgatt ctcctgcctc   3120
agcctcccga gttgttggga ttccaggcat gcatgaccag gctcagctaa tttttgtttt   3180
tttggtagag acggggtttc accatattgg ccaggctggt ctccaactcc taatctcagg   3240
tgatctaccc accttggcct cccaaattgc tgggattaca ggcgtgaacc actgctccct   3300
tccctgtcct tctgattttg taggtaacgt aaccccggac cacgtgcgga ccgagcggcc   3360
gctctagagc atggctacgt agataagtag catggcgggt taatcattaa ctacaaggaa   3420
cccctagtga tggagttggc cactccctct ctgcgcgctc gctcgctcac tgaggccggg   3480
cgaccaaagg tcgcccgacg cccgggcggc ctcagtgagc gagcgagcgc gcag         3534
```

<210> SEQ ID NO 8
<211> LENGTH: 3940
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

-continued

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
agagcggccg cacgcgtgga gctagttatt aatagtaatc aattacgggg tcattagttc    240
atagcccata tatggagttc cgcgttacat aacttacggt aaatggcccg cctggctgac    300
cgcccaacga cccccgccca ttgacgtcaa taatgacgta tgttcccata gtaacgtcaa    360
tagggacttt ccattgacgt caatgggtgg agtatttacg gtaaactgcc cacttggcag    420
tacatcaagt gtatcatatg ccaagtacgc cccctattga cgtcaatgac ggtaaatggc    480
ccgcctggca ttatgcccag tacatgacct tatgggactt tcctacttgg cagtacatct    540
acgtattagt catcgctatt accatggtga tgcggttttg gcagtacatc aatgggcgtg    600
gatagcggtt tgactcacgg ggatttccaa gtctccaccc cattgacgtc aatgggagtt    660
tgttttgcac caaaatcaac gggactttcc aaaatgtcgt aacaactccg ccccattgac    720
gcaaatgggc ggtaggcgtg tacggtggga ggtctatata agcagagctc gtttagtgaa    780
ccgtcagatc gcctggagac gccatccacg ctgttttgac ctccatagaa gacaccggga    840
ccgatccagc ctccgcggat tcgaatcccg gccgggaacg gtgcattgga acgcggattc    900
cccgtgccaa gagtgacgta agtaccgcct atagagtcta taggcccaca aaaaatgctt    960
tcttctttta atatactttt ttgtttatct tatttctaat actttcccta atctctttct   1020
ttcagggcaa taatgataca atgtatcatg cctctttgca ccattctaaa gaataacagt   1080
gataatttct gggttaaggc aatagcaata tttctgcata taaatatttc tgcatataaa   1140
ttgtaactga tgtaagaggt ttcatattgc taatagcagc tacaatccag ctaccattct   1200
gcttttattt tatggttggg ataaggctgg attattctga gtccaagcta ggcccttttg   1260
ctaatcatgt tcatacctct tatcttcctc ccacagctcc tgggcaacgt gctggtctgt   1320
gtgctggccc atcactttgg caaagaattg ggattcgaac atcggccgcc accatgaacg   1380
caagtgaatt ccgaaggaga gggaaggaga tggtggatta cgtggccaac tacatggaag   1440
gcattgaggg acgccaggtc taccctgacg tggagcccgg gtacctgcgg ccgctgatcc   1500
ctgccgctgc ccctcaggag ccagacacgt ttgaggacat catcaacgac gttgagaaga   1560
taatcatgcc tggggtgacg cactggcaca gcccctactt cttcgcctac ttccccactg   1620
ccagctcgta cccggccatg cttgcggaca tgctgtgcgg ggccattggc tgcatcggct   1680
tctcctgggc ggcaagccca gcatgcacag agctggagac tgtgatgatg gactggctcg   1740
ggaagatgct ggaactacca aaggcatttt tgaatgagaa agctggagaa gggggaggag   1800
tgatccaggg aagtgccagt gaagccaccc tggtggccct gctggccgct cggaccaaag   1860
tgatccatcg gctgcaggca gcgtccccag agctcacaca ggccgctatc atggagaagc   1920
tggtggctta ctcatccgat caggcacact cctcagtgga aagagctggg ttaattggtg   1980
gagtgaaatt aaaagccatc ccctcagatg gcaacttcgc catgcgtgcg tctgccctgc   2040
aggaagccct ggagagagac aaagcggctg gcctgattcc tttctttatg gttgccaccc   2100
tggggaccac aacatgctgc tcctttgaca atctcttaga agtcggtcct atctgcaaca   2160
aggaagacat atggctgcac gttgatgcag cctacgcagg cagtgcattc atctgccctg   2220
agttccggca ccttctgaat ggagtggagt ttgcagattc attcaacttt aatccccaca   2280
aatggctatt ggtgaatttt gactgttctg ccatgtgggt gaaaaagaga acagacttaa   2340
cgggagcctt tagactggac cccacttacc tgaagcacag ccatcaggat tcagggctta   2400
```

tcactgacta ccggcattgg cagataccac tgggcagaag atttcgctct ttgaaaatgt 2460
ggtttgtatt taggatgtat ggagtcaaag gactgcaggc ttatatccgc aagcatgtcc 2520
agctgtccca tgagtttgag tcactggtgc gccaggatcc ccgctttgaa atctgtgtgg 2580
aagtcattct ggggcttgtc tgctttcggc taaagggttc caacaaagtg aatgaagctc 2640
ttctgcaaag aataaacagt gccaaaaaaa tccacttggt tccatgtcac ctcagggaca 2700
agtttgtcct gcgctttgcc atctgttctc gcacggtgga atctgcccat gtgcagcggg 2760
cctgggaaca catcaaagag ctggcggccg acgtgctgcg agcagagagg gagtaggagt 2820
gaagccagct gcaggaatca aaaattgaag agagatatat ctgaaaactg gaataagaag 2880
caaataaata tcatcctgcc ttcatggaac tcagctgtct gtggcttccc atgtctttct 2940
ccaaagttat ccagagggtt gtgattttgt ctgcttagta tctcatcaac aaagaaatat 3000
tatttgctaa ttaaaaagtt aatcttcatg gccatagctt ttattcatta gctgtgattt 3060
ttgttgatta aaacattata gattttcatg ttcttgcagt catcagaagt ggtaggaaag 3120
cctcactgat atattttcca gggcaatcaa tgttcacgca acttgaaatt atatctgtgg 3180
tcttcaaatt gtcttttgtc atgtggctaa atgcctaata agctgctcga gagatctacg 3240
ggtggcatcc ctgtgacccc tccccagtgc ctctcctggc cctggaagtt gccactccag 3300
tgcccaccag ccttgtccta ataaaattaa gttgcatcat tttgtctgac taggtgtcct 3360
tctataatat tatggggtgg aggggggtgg tatggagcaa ggggcaagtt gggaagacaa 3420
cctgtagggc ctgcggggtc tattgggaac caagctggag tgcagtggca caatcttggc 3480
tcactgcaat ctccgcctcc tgggttcaag cgattctcct gcctcagcct cccgagttgt 3540
tgggattcca ggcatgcatg accaggctca gctaattttt gtttttttgg tagagacggg 3600
gtttcaccat attggccagg ctggtctcca actcctaatc tcaggtgatc tacccacctt 3660
ggcctcccaa attgctggga ttacaggcgt gaaccactgc tcccttccct gtccttctga 3720
ttttgtaggt aaccgtaacc ccggaccacg tgcggaccga gcggccgctc tagagcatgg 3780
ctacgtagat aagtagcatg gcgggttaat cattaactac aaggaacccc tagtgatgga 3840
gttggccact ccctctctgc gcgctcgctc gctcactgag gccgggcgac caaaggtcgc 3900
ccgacgcccg ggcggcctca gtgagcgagc gagcgcgcag 3940

<210> SEQ ID NO 9
<211> LENGTH: 4079
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
agagcggccg caacgcgtaa acttcgtcga cgatctgcgg ccgcacgcgt ggagctagtt 240
attaatagta atcaattacg gggtcattag ttcatagccc atatatggag ttccgcgtta 300
cataacttac ggtaaatggc ccgcctggct gaccgcccaa cgacccccgc ccattgacgt 360
caataatgac gtatgttccc atagtaacgt caatagggac tttccattga cgtcaatggg 420
tggagtattt acggtaaact gcccacttgg cagtacatca agtgtatcat atgccaagta 480

```
cgccccctat tgacgtcaat gacggtaaat ggcccgcctg gcattatgcc cagtacatga    540
ccttatggga ctttcctact tggcagtaca tctacgtatt agtcatcgct attaccatgg    600
tgatgcggtt ttggcagtac atcaatgggc gtggatagcg gtttgactca cggggatttc    660
caagtctcca ccccattgac gtcaatggga gtttgttttg caccaaaatc aacgggactt    720
tccaaaatgt cgtaacaact ccgccccatt gacgcaaatg ggcggtaggc gtgtacggtg    780
ggaggtctat ataagcagag ctcgtttagt gaaccgtcag atcgcctgga gacgccatcc    840
acgctgtttt gacctccata gaagacaccg ggaccgatcc agcctccgcg gattcgaatc    900
ccggccggga acggtgcatt ggaacgcgga ttccccgtgc caagagtgac gtaagtaccg    960
cctatagagt ctataggccc acaaaaaatg ctttcttctt ttaatatact tttttgttta   1020
tcttatttct aatactttcc ctaatctctt tctttcaggg caataatgat acaatgtatc   1080
atgcctcttt gcaccattct aaagaataac agtgataatt tctgggttaa ggcaatagca   1140
atatttctgc atataaatat ttctgcatat aaattgtaac tgatgtaaga ggtttcatat   1200
tgctaatagc agctacaatc cagctaccat tctgctttta ttttatggtt gggataaggc   1260
tggattattc tgagtccaag ctaggccctt ttgctaatca tgttcatacc tcttatcttc   1320
ctcccacagc tcctgggcaa cgtgctggtc tgtgtgctgg cccatcactt tggcaaagaa   1380
ttgggattcg aacatcgaat tcgggcacga gggaggacag agagcaagtc actcccggct   1440
gcctttttca cctctgacag agcccagaca ccatgaacgc aagtgaattc cgaaggagag   1500
ggaaggagat ggtggattac gtggccaact acatggaagg cattgaggga cgccaggtct   1560
accctgacgt ggagcccggg tacctgcggc cgctgatccc tgccgctgcc cctcaggagc   1620
cagacacgtt tgaggacatc atcaacgacg ttgagaagat aatcatgcct ggggtgacgc   1680
actggcacag cccctacttc ttcgcctact tccccactgc cagctcgtac ccggccatgc   1740
ttgcggacat gctgtgcggg gccattggct gcatcggctt ctcctgggcg gcaagcccag   1800
catgcacaga gctggagact gtgatgatgg actggctcgg gaagatgctg gaactaccaa   1860
aggcattttt gaatgagaaa gctggagaag gggggaggagt gatccaggga agtgccagtg   1920
aagccaccct ggtggccctg ctggccgctc ggaccaaagt gatccatcgg ctgcaggcag   1980
cgtccccaga gctcacacag gccgctatca tggagaagct ggtggcttac tcatccgatc   2040
aggcacactc ctcagtggaa agagctgggt taattggtgg agtgaaatta aaagccatcc   2100
cctcagatgg caacttcgcc atgcgtgcgt ctgccctgca ggaagccctg gagagagaca   2160
aagcggctgg cctgattcct ttctttatgg ttgccaccct ggggaccaca acatgctgct   2220
cctttgacaa tctcttagaa gtcggtccta tctgcaacaa ggaagacata tggctgcacg   2280
ttgatgcagc ctacgcaggc agtgcattca tctgccctga gttccggcac cttctgaatg   2340
gagtggagtt tgcagattca ttcaacttta atccccacaa atggctattg gtgaattttg   2400
actgttctgc catgtgggtg aaaaagagaa cagacttaac gggagccttt agactggacc   2460
ccacttacct gaagcacagc catcaggatt cagggcttat cactgactac cggcattggc   2520
agataccact gggcagaaga tttcgctctt tgaaaatgtg gtttgtattt aggatgtatg   2580
gagtcaaagg actgcaggct tatatccgca agcatgtcca gctgtcccat gagtttgagt   2640
cactggtgcg ccaggatccc cgctttgaaa tctgtgtgga agtcattctg ggcttgtct   2700
gctttcggct aaagggttcc aacaaagtga atgaagctct tctgcaaaga ataaacagtg   2760
ccaaaaaaat ccacttggtt ccatgtcacc tcagggacaa gtttgtcctg cgctttgcca   2820
```

-continued

```
tctgttctcg cacggtggaa tctgcccatg tgcagcgggc ctgggaacac atcaaagagc   2880

tggcggccga cgtgctgcga gcagagaggg agtaggagtg aagccagctg caggaatcaa   2940

aaattgaaga gagatatatc tgaaaactgg aataagaagc aaataaatat catcctgcct   3000

tcatggaact cagctgtctg tggcttccca tgtctttctc caaagttatc cagagggttg   3060

tgattttgtc tgcttagtat ctcatcaaca aagaaatatt atttgctaat taaaaagtta   3120

atcttcatgg ccatagcttt tattcattag ctgtgatttt tgttgattaa aacattatag   3180

attttcatgt tcttgcagtc atcagaagtg gtaggaaagc ctcactgata tattttccag   3240

ggcaatcaat gttcacgcaa cttgaaatta tatctgtggt cttcaaattg tcttttgtca   3300

tgtggctaaa tgcctaataa acaattcaag tgaaatacta aaaaaaaaaa aaaaaaaaaa   3360

agctgctcga gagatctacg ggtggcatcc ctgtgacccc tccccagtgc ctctcctggc   3420

cctggaagtt gccactccag tgcccaccag ccttgtccta ataaaattaa gttgcatcat   3480

tttgtctgac taggtgtcct tctataatat tatggggtgg aggggggtgg tatggagcaa   3540

ggggcaagtt gggaagacaa cctgtagggc ctgcggggtc tattgggaac caagctggag   3600

tgcagtggca caatcttggc tcactgcaat ctccgcctcc tgggttcaag cgattctcct   3660

gcctcagcct cccgagttgt tgggattcca ggcatgcatg accaggctca gctaattttt   3720

gtttttttgg tagagacggg gtttcaccat attggccagg ctggtctcca actcctaatc   3780

tcaggtgatc tacccacctt ggcctcccaa attgctggga ttacaggcgt gaaccactgc   3840

tcccttccct gtccttctga ttttgtaggt aacgtaaccc cggaccacgt gcggaccgag   3900

cggccgctct agagcatggc tacgtagata agtagcatgg cgggttaatc attaactaca   3960

aggaacccct agtgatggag ttggccactc cctctctgcg cgctcgctcg ctcactgagg   4020

ccgggcgacc aaaggtcgcc cgacgcccgg gcggcctcag tgagcgagcg agcgcgcag    4079
```

```
<210> SEQ ID NO 10
<211> LENGTH: 9266
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

gagaggcggt ttgcgtattg ggcgctcttc cgcttcctcg ctcactgact cgctgcgctc     60

ggtcgttcgg ctgcggcgag cggtatcagc tcactcaaag gcggtaatac ggttatccac    120

agaatcaggg gataacgcag gaaagaacat gtgagcaaaa ggccagcaaa aggccaggaa    180

ccgtaaaaag gccgcgttgc tggcgttttg agatcctttt tttctgcgcg taatctgctg    240

cttgcaaaca aaaaaaccac cgctaccagc ggtggtttgt ttgccggatc aagagctacc    300

aactcttttt ccgaaggtaa ctggcttcag cagagcgcag ataccaaata ctgttcttct    360

agtgtagccg tagttaggcc accacttcaa gaactctgta gcaccgccta catacctcgc    420

tctgctaatc ctgttaccag tggctgctgc cagtggcgat aagtcgtgtc ttaccgggtt    480

ggactcaaga cgatagttac cggataaggc gcagcggtcg ggctgaacgg ggggttcgtg    540

cacacagccc agcttggagc gaacgaccta caccgaactg agatacctac agcgtgagct    600

atgagaaagc gccacgcttc ccgaagggag aaaggcggac aggtatccgg taagcggcag    660

ggtcggaaca ggagagcgca cgagggagct tccaggggga aacgcctggt atctttatag    720

tcctgtcggg tttcgccacc tctgacttga gcgtcgattt ttgtgatgct cgtcaggggg    780
```

-continued

```
gcggagccta tggaaagaag atcctttgat cttttctacg gggtctgacg ctcagtggaa    840
cgaaaactca cgttaaggga ttttggtcat gagattatca aaaaggatct tcacctagat    900
ccttttaaat taaaaatgaa gttttaaatc aagcccaatc tgaataatgt tacaaccaat    960
taaccaattc tgaaaacgcg cgatgcagct ctggcccgtg tctcaaaatc tctgatgtta   1020
cattgcacaa gataaaaata tatcatcatg aacaataaaa ctgtctgctt acataaacag   1080
taatacaagg ggtgttatga gccatattca acgggaaacg tcgaggccgc gattaaattc   1140
caacatggat gctgatttat atgggtataa atgggctcgc gataatgtcg ggcaatcagg   1200
tgcgacaatc tatcgcttgt atgggaagcc cgatgcgcca gagttgtttc tgaaacatgg   1260
caaaggtagc gttgccaatg atgttacaga tgagatggtc agactaaact ggctgacgga   1320
atttatgcct cttccgacca tcaagcattt tatccgtact cctgatgatg catggttact   1380
caccactgcg atccccggaa aaacagcatt ccaggtatta gaagaatatc ctgattcagg   1440
tgaaaatatt gttgatgcgc tggcagtgtt cctgcgccgg ttgcattcga ttcctgtttg   1500
taattgtcct tttaacagcg atcgcgtatt tcgtctcgct caggcgcaat cacgaatgaa   1560
taacggtttg gttgatgcga gtgattttga tgacgagcgt aatggctggc ctgttgaaca   1620
agtctggaaa gaaatgcata aacttttgcc attctcaccg gattcagtcg tcactcatgg   1680
tgatttctca cttgataacc ttatttttga cgaggggaaa ttaataggtt gtattgatgt   1740
tggacgagtc ggaatcgcag accgatacca ggatcttgcc atcctatgga actgcctcgg   1800
tgagttttct ccttcattac agaaacggct ttttcaaaaa tatggtattg ataatcctga   1860
tatgaataaa ttgcagtttc atttgatgct cgatgagttt ttctaatcag aattggttaa   1920
ttggttgtaa cattattcag attgggcttg atttaaaact tcatttttaa tttaaaagga   1980
tctaggtgaa gatccttttt gataatctca tgaccaaaat cccttaacgt gagttttcgt   2040
tccactgagc gtcagacccc gtagaaaaga tcaaaggatc ttcaacaccc cttgtattac   2100
tgtttatgta agcagacagt tttattgttc atgatgatat atttttatct tgtgcaatgt   2160
aacatcagag attttgagac acgggccaga gctgcatcgc gcgtttcggt gatgacggtg   2220
aaaacctctg acacatgcag ctcccgtatc tggaggctat aaatgattac gatacttcga   2280
aaacatcctt atcctggaaa actccccgtt catttcccac tctcctgcca ttcgacactc   2340
gtgcgtccat tcaagtctgt gctaatttct acgcatttcc ctctgccatt gactttgctt   2400
gcgtgggata ataactatta agccaacttg attcaactca ggcattcaaa aggcattttg   2460
attagtcgaa aagtggcacg gctgacgagt ggagctgcca tttcacgttt atttcgaact   2520
tttgattaca tggtatattt agtaatacac atatttttta gccagcaggt taatacttca   2580
aagttgtttc gattttcaac gaataaaagg aatttggcat ggtgtttttt ctggtctttg   2640
gtattgacaa atcagggata tacaatatgt attaacaaaa ttggattgct acatatattt   2700
aatgattttc attattagaa tgggtggaat aaagttttaa attacattat taatttcatt   2760
agggttggct gattgattac tatttcctca ttgaattgca ttcgatatta gcagtattta   2820
tctggcccat tttggaagtt acttaaattt cgaaccttaa gtcattatta gagctaatat   2880
acaacagagt tgtcaacttg gtttgatcag cattgaaatt aaactgattt cttgttcgtt   2940
cttatttcgt ttggttttgt atctcgtatt ttatatgcag gagggcatat attggcacaa   3000
gacaaataat cacagcaccc attctcaact ttgtcctgtt tctcagttta gtgtaaatag   3060
aatgttgcaa aaaattgaat ataagcatta tcatagtgtc aaattcgaga ggatgagttt   3120
gctgtgggtc ttcgaggttc tttccctgtg tttgccacgg ttcgttgcac gttgccactg   3180
```

```
attggacaca tgtccgcagt gaaaaatcta cggtcaggta ccacccaact aaaccggaag   3240
gcggcacgtg tgtgggcgtt gagcggtgtg ggcgtggcag ccatataatg agacatttat   3300
ttaaaaagaa cattcgaaca tttttgatgg gccatatctt ggcttgtcaa gctccagggc   3360
agacattttc ctcgactcca ccgccttttt catttgaatg gaggaggtgt agggcacaaa   3420
aaacgtttcc tgccttttta agcagcacaa aggatatgag ccattaaatt agttaatttc   3480
gagtgcattt cattttaaat aagtgttgga aagggaataa aaaagcgact gatagaaaag   3540
ttgcagacac caagagaatg ttaaatattt taataatagc tacatttttc tatctctgtg   3600
acaaggcctg tgtactttaa tgttatatta cttctttgtg tttgatttct gttaaaagtt   3660
tatgattttg gcatgtacaa atcttacaac ccttttttgt catcatgaca aaatcaaaat   3720
cgtgcaatat ttccattctc atcttttagc cgattcataa cattcgtaga aattaatatg   3780
aaatcaatca tgtataattt tcatgcacgt tatgccgatt tggtatcgtc gatttgccgg   3840
ctcatcgtcg ccattgtgtt aatggaaaag ttatgctttt cgcaggaaaa aagagttgaa   3900
aattccaatt tttgtcatgc tcatcaaaat gttatacatt cggtaatttg agctggccaa   3960
acgttaaccc cttatcgccc cgcgcaagca ttcattaact gcccccagag cgtaattaat   4020
ctctttctcg cagaatttcc ttcacagcca cgtcttgggt aaaagtcacc cctcaaagtg   4080
gcagttgcat gttgtaaatt agattttcgt ccgtcatgac aaccctcgtg cgagggttgc   4140
tgcagcattt gaatgcaaaa ctgcttttgg tcattaacct gtctgaggca ctttgctgca   4200
aaacttctat tagaattcgg tttggactcg aattcggatt tcttccccca aaatgcgatg   4260
gctacagcaa aatgctttca gcttccgaag ttttgcaacc ccaaagtcca gagtttccac   4320
gctgtcacga ttccaaagcg gcgccatttt tggctcacgc aaaacttatt aatgaacttt   4380
aagcagacta cgaggaaagg gctataatgg ccacacaaaa gggttaagca agtgttaagg   4440
gctggtggga gggaaaaatc atcaatcata ttttctgcat agctgaatca tttgcgccga   4500
tcagttgggg ttacttaatg ggtttatttc aagaagaaaa ctgtgggaaa ctaactgact   4560
ctaaacttaa tcagattaaa tgtaacctgg agatgatttt caaaatatta aaagagtttt   4620
atggaggtaa ttttaaagaa aactgaaaaa ctttgaagaa gtctataata gatccagtct   4680
taatcgtagc actgattatt tgtttttaaa ttggaaaaaa ttaaatgata catcatgctt   4740
aaatgcgatg tccaacaaat cccaagacgg taatttccgt gcgttccaaa ctcatctgaa   4800
gaatcttaca aatacatttc gtgtatcccc aggctcagcg tgcaaataaa tcttttggat   4860
ctttgcaaat gcgaaatgct tatttttatg cgttttcaat gccaattcga tggcaaaacc   4920
aacaaaatca catggaaata atggaaaagc aatttccatt tctacaaggg aggcagtgag   4980
acacaagagc agcgtataca attccccagc agcgatttga ccattaaaat tatacccaca   5040
ggacgagcag gcataaaaag cagaggatgc gaggtgttca ggggactgtc tatatctcca   5100
acttgaatat atgaaatcgt ttggaaatag ccaagcgacc aaattggcat ttggaaaatt   5160
gcacaacgac agaagaagat gtttgaaaag agaaattgaa ataataaacc aagatatatg   5220
taaacggttg gtcacatttg ggttctgaga cggtcacagc ttgtctgtaa gcggatgccg   5280
ggagcagaca agcccgtcag ggcgcgtcag cgggtgttgg cgggtgtcgg ggctggctta   5340
actatgcggc atcagagcag attgtactga gagtgcacca tatgcggtgt gaaataccgc   5400
acagatgcgt aaggagaaaa taccgcatca ggcgccattc gccattcagg ctgcgcaact   5460
gttgggaagg gcgatcggtg cgggcctctt cgctattacg ccagctggcg aaagggggat   5520
```

-continued

```
gtgctgcaag gcgattaagt tgggtaacgc cagggttttc ccagtcacga cgttgtaaaa   5580
cgacggccag tgaattcgag ctcggtacca tttaaatcgt cttggccact ccctctctgc   5640
gcgctcgctc gctcactgag gccgcccggg caaagcccgg gcgtcgggcg acctttggtc   5700
gcccggcctc agtgagcgag cgagcgcgca gagagggagt ggccaactcc atcactaggg   5760
gttccttcgc gagcttaatt aactgcggcc gctcggtccg cacgtggtta cctacaaaat   5820
cagaaggaca gggaagggag cagtggttca cgcctgtaat cccagcaatt tgggaggcca   5880
aggtgggtag atcacctgag attaggagtt ggagaccagc ctggccaata tggtgaaacc   5940
ccgtctctac caaaaaaaca aaaattagct gagcctggtc atgcatgcct ggaatcccaa   6000
caactcggga ggctgaggca ggagaatcgc ttgaacccag gaggcggaga ttgcagtgag   6060
ccaagattgt gccactgcac tccagcttgg ttcccaatag accccgcagg ccctacaggt   6120
tgtcttccca acttgcccct tgctccatac cacccccctc caccccataa tattatagaa   6180
ggacacctag tcagacaaaa tgatgcaact taattttatt aggacaaggc tggtgggcac   6240
tggagtggca acttccaggg ccaggagagg cactggggag ggtcacaggg gatgccaccc   6300
gtagatctct cgagcagctc actcctactc cctctctgct cgcagcacgt cggccgccag   6360
ctctttgatg tgttcccagg cccgctgcac atgggcagat tccaccgtgc gagaacagat   6420
ggcaaagcgc aggacaaact tgtccctgag gtgacatgga accaagtgga tttttttggc   6480
actgtttatt ctttgcagaa gagcttcatt cactttgttg gaacccttta gccgaaagca   6540
gacaagcccc agaatgactt ccacacagat ttcaaagcgg ggatcctggc gcaccagtga   6600
ctcaaactca tgggacagct ggacatgctt gcggatataa gcctgcagtc ctttgactcc   6660
atacatccta aatacaaacc acattttcaa agagcgaaat cttctgccca gtggtatctg   6720
ccaatgccgg tagtcagtga taagccctga atcctgatgg ctgtgcttca ggtaagtggg   6780
gtccagtcta aaggctcccg ttaagtctgt tctctttttc acccacatgg cagaacagtc   6840
aaaattcacc aatagccatt tgtggggatt aaagttgaat gaatctgcaa actccactcc   6900
attcagaagg tgccggaact cagggcagat gaatgcactg cctgcgtagg ctgcatcaac   6960
gtgcagccat atgtcttcct tgttgcagat aggaccgact tctaagagat tgtcaaagga   7020
gcagcatgtt gtggtcccca gggtggcaac cataaagaaa ggaatcaggc cagccgcttt   7080
gtctctctcc agggcttcct gcagggcaga cgcacgcatg gcgaagttgc catctgaggg   7140
gatggctttt aatttcactc caccaattaa cccagctctt tccactgagg agtgtgcctg   7200
atcggatgag taagccacca gcttctccat gatagcggcc tgtgtgagct ctggggacgc   7260
tgcctgcagc cgatggatca ctttggtccg agcggccagc agggccacca gggtggcttc   7320
actggcactt ccctggatca ctcctccccc ttctccagct ttctcattca aaaatgcctt   7380
tggtagttcc agcatcttcc cgagccagtc catcatcaca gtctccagct ctgtgcatgc   7440
tgggcttgcc gcccaggaga agccgatgca gccaatggcc ccgcacagca tgtccgcaag   7500
catggccggg tacgagctgg cagtggggaa gtaggcgaag aagtaggggc tgtgccagtg   7560
cgtcacccca ggcatgatta tcttctcaac gtcgttgatg atgtcctcaa acgtgtctgg   7620
ctcctgaggg gcagcggcag ggatcagcgg ccgcaggtac ccgggctcca cgtcagggta   7680
gacctggcgt ccctcaatgc cttccatgta gttggccacg taatccacca tctccttccc   7740
tctccttcgg aattcacttg cgttcatggt ggcggccgat gttcgaatcc caattctttg   7800
ccaaagtgat gggccagcac acagaccagc acgttgccca ggagctgtgg gaggaagata   7860
agaggtatga acatgattag caaaagggcc tagcttggac tcagaataat ccagccttat   7920
```

cccaaccata aaataaaagc agaatggtag ctggattgta gctgctatta gcaatatgaa 7980
acctcttaca tcagttacaa tttatatgca gaaatattta tatgcagaaa tattgctatt 8040
gccttaaccc agaaattatc actgttattc tttagaatgg tgcaaagagg catgatacat 8100
tgtatcatta ttgccctgaa agaaagagat tagggaaagt attagaaata agataaacaa 8160
aaaagtatat taaaagaaga aagcattttt tgtgggccta tagactctat aggcggtact 8220
tacgtcactc ttggcacggg gaatccgcgt tccaatgcac cgttcccggc cgggattcga 8280
atccgcggag gctggatcgg tcccggtgtc ttctatggag gtcaaaacag cgtggatggc 8340
gtctccaggc gatctgacgg ttcactaaac gagctctgct tatatagacc tcccaccgta 8400
cacgcctacc gcccatttgc gtcaatgggg cggagttgtt acgacatttt ggaaagtccc 8460
gttgattttg gtgcaaaaca aactcccatt gacgtcaatg gggtggagac ttggaaatcc 8520
ccgtgagtca aaccgctatc cacgcccatt gatgtactgc caaaaccgca tcaccatggt 8580
aatagcgatg actaatacgt agatgtactg ccaagtagga aagtcccata aggtcatgta 8640
ctgggcataa tgccaggcgg gccatttacc gtcattgacg tcaatagggg gcgtacttgg 8700
catatgatac acttgatgta ctgccaagtg ggcagtttac cgtaaatact ccacccattg 8760
acgtcaatgg aaagtcccta ttgacgttac tatgggaaca tacgtcatta ttgacgtcaa 8820
tgggcggggg tcgttgggcg gtcagccagg cgggccattt accgtaagtt atgtaacgcg 8880
gaactccata tatgggctat gaactaatga ccccgtaatt gattactatt aataactagc 8940
tccacgcgtg cggccgcaga tcgtcgacga agtttaaact caggaacccc tagtgatgga 9000
gttggccact ccctctctgc gcgctcgctc gctcactgag gccgcccggg caaagcccgg 9060
gcgtcgggcg acctttggtc gcccggcctc agtgagcgag cgagcgcgca gagagggagt 9120
ggccaacgtc atttaaatgc atgcaagctt ggcgtaatca tggtcatagc tgtttcctgt 9180
gtgaaaattg cgttgcgctc actgcccgct ttccagtcgg gaaacctgtc gtgccagctg 9240
cattaatgaa tcggccaacg cgcggg 9266

<210> SEQ ID NO 11
<211> LENGTH: 9236
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
cccgcgcgtt ggccgattca ttaatgcagc tggcacgaca ggtttcccga ctggaaagcg 60
ggcagtgagc gcaacgcaat tttcacacag gaaacagcta tgaccatgat tacgccaagc 120
ttgcatgcat ttaaatgacg cagctgcgcg ctcgctcgct cactgaggcc gcccgggcaa 180
agcccgggcg tcgggcgacc tttggtcgcc cggcctcagt gagcgagcga gcgcgcagag 240
agggagtggc caactccatc actaggggtt gagtttaaac ttcgtcgacg atctgcggcc 300
gcacgcgtgg agctagttat taatagtaat caattacggg gtcattagtt catagcccat 360
atatggagtt ccgcgttaca taacttacgg taaatggccc gcctggctga ccgcccaacg 420
acccccgccc attgacgtca ataatgacgt atgttcccat agtaacgtca atagggactt 480
tccattgacg tcaatgggtg gagtatttac ggtaaactgc ccacttggca gtacatcaag 540
tgtatcatat gccaagtacg ccccctattg acgtcaatga cggtaaatgg cccgcctggc 600
attatgccca gtacatgacc ttatgggact ttcctacttg gcagtacatc tacgtattag 660

```
tcatcgctat taccatggtg atgcggtttt ggcagtacat caatgggcgt ggatagcggt    720
ttgactcacg gggatttcca agtctccacc ccattgacgt caatgggagt ttgttttgca    780
ccaaaatcaa cgggactttc caaaatgtcg taacaactcc gccccattga cgcaaatggg    840
cggtaggcgt gtacggtggg aggtctatat aagcagagct cgtttagtga accgtcagat    900
cgcctggaga cgccatccac gctgttttga cctccataga agacaccggg accgatccag    960
cctccgcgga ttcgaatccc ggccgggaac ggtgcattgg aacgcggatt ccccgtgcca   1020
agagtgacgt aagtaccgcc tatagagtct ataggcccac aaaaaatgct ttcttctttt   1080
aatatacttt tttgtttatc ttatttctaa tactttccct aatctctttc tttcagggca   1140
ataatgatac aatgtatcat gcctctttgc accattctaa agaataacag tgataatttc   1200
tgggttaagg caatagcaat atttctgcat ataaatattt ctgcatataa attgtaactg   1260
atgtaagagg tttcatattg ctaatagcag ctacaatcca gctaccattc tgcttttatt   1320
ttatggttgg gataaggctg gattattctg agtccaagct aggccctttt gctaatcatg   1380
ttcatacctc ttatcttcct cccacagctc ctgggcaacg tgctggtctg tgtgctggcc   1440
catcactttg gcaaagaatt gggattcgaa catcggccgc caccatgaac gcaagtgaat   1500
tccgaaggag agggaaggag atggtggatt acgtggccaa ctacatggaa ggcattgagg   1560
gacgccaggt ctaccctgac gtggagcccg ggtacctgcg gccgctgatc cctgccgctg   1620
cccctcagga gccagacacg tttgaggaca tcatcaacga cgttgagaag ataatcatgc   1680
ctggggtgac gcactggcac agcccctact tcttcgccta cttccccact gccagctcgt   1740
acccggccat gcttgcggac atgctgtgcg gggccattgg ctgcatcggc ttctcctggg   1800
cggcaagccc agcatgcaca gagctggaga ctgtgatgat ggactggctc gggaagatgc   1860
tggaactacc aaaggcattt ttgaatgaga aagctggaga agggggagga gtgatccagg   1920
gaagtgccag tgaagccacc ctggtggccc tgctggccgc tcggaccaaa gtgatccatc   1980
ggctgcaggc agcgtcccca gagctcacac aggccgctat catggagaag ctggtggctt   2040
actcatccga tcaggcacac tcctcagtgg aaagagctgg gttaattggt ggagtgaaat   2100
taaaagccat cccctcagat ggcaacttcg ccatgcgtgc gtctgccctg caggaagccc   2160
tggagagaga caaagcggct ggcctgattc ctttctttat ggttgccacc ctggggacca   2220
caacatgctg ctcctttgac aatctcttag aagtcggtcc tatctgcaac aaggaagaca   2280
tatggctgca cgttgatgca gcctacgcag gcagtgcatt catctgccct gagttccggc   2340
accttctgaa tggagtggag tttgcagatt cattcaactt taatccccac aaatggctat   2400
tggtgaattt tgactgttct gccatgtggg tgaaaaagag aacagactta acgggagcct   2460
ttagactgga ccccacttac ctgaagcaca gccatcagga ttcagggctt atcactgact   2520
accggcattg gcagatacca ctgggcagaa gatttcgctc tttgaaaatg tggtttgtat   2580
ttaggatgta tggagtcaaa ggactgcagg cttatatccg caagcatgtc cagctgtccc   2640
atgagtttga gtcactggtg cgccaggatc cccgctttga aatctgtgtg gaagtcattc   2700
tggggcttgt ctgctttcgg ctaaagggtt ccaacaaagt gaatgaagct cttctgcaaa   2760
gaataaacag tgccaaaaaa atccacttgg ttccatgtca cctcagggac aagtttgtcc   2820
tgcgctttgc catctgttct cgcacggtgg aatctgccca tgtgcagcgg gcctgggaac   2880
acatcaaaga gctggcggcc gacgtgctgc gagcagagag ggagtaggag tgagctgctc   2940
gagagatcta cgggtggcat ccctgtgacc cctccccagt gcctctcctg gccctggaag   3000
```

-continued

```
ttgccactcc agtgcccacc agccttgtcc taataaaatt aagttgcatc attttgtctg   3060
actaggtgtc cttctataat attatggggt ggaggggggt ggtatggagc aaggggcaag   3120
ttgggaagac aacctgtagg gcctgcgggg tctattggga accaagctgg agtgcagtgg   3180
cacaatcttg gctcactgca atctccgcct cctgggttca agcgattctc ctgcctcagc   3240
ctcccgagtt gttgggattc caggcatgca tgaccaggct cagctaattt ttgttttttt   3300
ggtagagacg gggtttcacc atattggcca ggctggtctc caactcctaa tctcaggtga   3360
tctacccacc ttggcctccc aaattgctgg gattacaggc gtgaaccact gctcccttcc   3420
ctgtccttct gattttgtag gtaaccacgt gcggaccgag cggccgcagt taattaagct   3480
cgcgaaaccc ctagtgatgg agttggccac tccctctctg cgcgctcgct cgctcactga   3540
ggccgggcga ccaaaggtcg cccgacgccc gggctttgcc cgggcggcct cagtgagcga   3600
gcgagcgcgc agctggacga tttaaatggt accgagctcg aattcactgg ccgtcgtttt   3660
acaacgtcgt gactgggaaa accctggcgt tacccaactt aatcgccttg cagcacatcc   3720
ccctttcgcc agctggcgta atagcgaaga ggcccgcacc gatcgccctt cccaacagtt   3780
gcgcagcctg aatggcgaat ggcgcctgat gcggtatttt ctccttacgc atctgtgcgg   3840
tatttcacac cgcatatggt gcactctcag tacaatctgc tctgatgccg catagttaag   3900
ccagccccga cacccgccaa cacccgctga cgcgccctga cgggcttgtc tgctcccggc   3960
atccgcttac agacaagctg tgaccgtctc agaacccaaa tgtgaccaac cgtttacata   4020
tatcttggtt tattatttca atttctcttt tcaaacatct tcttctgtcg ttgtgcaatt   4080
ttccaaatgc caatttggtc gcttggctat ttccaaacga tttcatatat tcaagttgga   4140
gatatagaca gtcccctgaa cacctcgcat cctctgcttt ttatgcctgc tcgtcctgtg   4200
ggtataattt taatggtcaa atcgctgctg gggaattgta tacgctgctc ttgtgtctca   4260
ctgcctccct tgtagaaatg gaaattgctt ttccattatt tccatgtgat tttgttggtt   4320
ttgccatcga attggcattg aaaacgcata aaaataagca tttcgcattt gcaaagatcc   4380
aaaagattta tttgcacgct gagcctgggg atacacgaaa tgtatttgta agattcttca   4440
gatgagtttg gaacgcacgg aaattaccgt cttgggattt gttggacatc gcatttaagc   4500
atgatgtatc atttaatttt ttccaattta aaaacaaata atcagtgcta cgattaagac   4560
tggatctatt atagacttct tcaaagtttt tcagttttct ttaaaattac ctccataaaa   4620
ctcttttaat attttgaaaa tcatctccag gttacattta atctgattaa gtttagagtc   4680
agttagtttc ccacagtttt cttcttgaaa taaacccatt aagtaacccc aactgatcgg   4740
cgcaaatgat tcagctatgc agaaaatatg attgatgatt tttccctccc accagccctt   4800
aacacttgct taaccctttt gtgtggccat tatagccctt tcctcgtagt ctgcttaaag   4860
ttcattaata agttttgcgt gagccaaaaa tggcgccgct ttggaatcgt gacagcgtgg   4920
aaactctgga ctttggggtt gcaaaacttc ggaagctgaa agcattttgc tgtagccatc   4980
gcattttggg ggaagaaatc cgaattcgag tccaaaccga attctaatag aagttttgca   5040
gcaaagtgcc tcagacaggt taatgaccaa aagcagtttt gcattcaaat gctgcagcaa   5100
ccctcgcacg agggttgtca tgacggacga aaatctaatt tacaacatgc aactgccact   5160
ttgaggggtg acttttaccc aagacgtggc tgtgaaggaa attctgcgag aaagagatta   5220
attacgctct gggggcagtt aatgaatgct tgcgcggggc gataaggggt taacgtttgg   5280
ccagctcaaa ttaccgaatg tataacattt tgatgagcat gacaaaaatt ggaattttca   5340
actctttttt cctgcgaaaa gcataacttt tccattaaca caatggcgac gatgagccgg   5400
```

```
caaatcgacg ataccaaatc ggcataacgt gcatgaaaat tatacatgat tgatttcata   5460
ttaatttcta cgaatgttat gaatcggcta aaagatgaga atggaaatat tgcacgattt   5520
tgattttgtc atgatgacaa aaaagggttg taagatttgt acatgccaaa atcataaact   5580
tttaacagaa atcaaacaca aagaagtaat ataacattaa agtacacagg ccttgtcaca   5640
gagatagaaa aatgtagcta ttattaaaat atttaacatt ctcttggtgt ctgcaacttt   5700
tctatcagtc gctttttat tccctttcca acacttattt aaaatgaaat gcactcgaaa   5760
ttaactaatt taatggctca tatcctttgt gctgcttaaa aaggcaggaa acgtttttg   5820
tgccctacac ctcctccatt caaatgaaaa aggcggtgga gtcgaggaaa atgtctgccc   5880
tggagcttga caagccaaga tatggcccat caaaaatgtt cgaatgttct ttttaaataa   5940
atgtctcatt atatggctgc cacgcccaca ccgctcaacg cccacacacg tgccgccttc   6000
cggtttagtt gggtggtacc tgaccgtaga tttttcactg cggacatgtg tccaatcagt   6060
ggcaacgtgc aacgaaccgt ggcaaacaca gggaaagaac ctcgaagacc cacagcaaac   6120
tcatcctctc gaatttgaca ctatgataat gcttatattc aatttttgc aacattctat   6180
ttacactaaa ctgagaaaca ggacaaagtt gagaatgggt gctgtgatta tttgtcttgt   6240
gccaatatat gccctcctgc atataaaata cgagatacaa aaccaaacga aataagaacg   6300
aacaagaaat cagtttaatt tcaatgctga tcaaaccaag ttgacaactc tgttgtatat   6360
tagctctaat aatgacttaa ggttcgaaat ttaagtaact tccaaaatgg gccagataaa   6420
tactgctaat atcgaatgca attcaatgag gaaatagtaa tcaatcagcc aaccctaatg   6480
aaattaataa tgtaatttaa aactttattc cacccattct aataatgaaa atcattaaat   6540
atatgtagca atccaatttt gttaatacat attgtatatc cctgatttgt caataccaaa   6600
gaccagaaaa aacaccatgc caaattcctt ttattcgttg aaaatcgaaa caactttgaa   6660
gtattaacct gctggctaaa aaatatgtgt attactaaat ataccatgta atcaaaagtt   6720
cgaaataaac gtgaaatggc agctccactc gtcagccgtg ccacttttcg actaatcaaa   6780
atgccttttg aatgcctgag ttgaatcaag ttggcttaat agttattatc ccacgcaagc   6840
aaagtcaatg gcagagggaa atgcgtagaa attagcacag acttgaatgg acgcacgagt   6900
gtcgaatggc aggagagtgg gaaatgaacg gggagttttc caggataagg atgttttcga   6960
agtatcgtaa tcatttatag cctccagata cgggagctgc atgtgtcaga ggttttcacc   7020
gtcatcaccg aaacgcgcga tgcagctctg gcccgtgtct caaaatctct gatgttacat   7080
tgcacaagat aaaaatatat catcatgaac aataaaactg tctgcttaca taaacagtaa   7140
tacaaggggt gttgaagatc ctttgatctt ttctacgggg tctgacgctc agtggaacga   7200
aaactcacgt taagggattt tggtcatgag attatcaaaa aggatcttca cctagatcct   7260
tttaaattaa aaatgaagtt ttaaatcaag cccaatctga ataatgttac aaccaattaa   7320
ccaattctga ttagaaaaac tcatcgagca tcaaatgaaa ctgcaattta ttcatatcag   7380
gattatcaat accatatttt tgaaaaagcc gtttctgtaa tgaaggagaa aactcaccga   7440
ggcagttcca taggatggca agatcctggt atcggtctgc gattccgact cgtccaacat   7500
caatacaacc tattaatttc ccctcgtcaa aaataaggtt atcaagtgag aaatcaccat   7560
gagtgacgac tgaatccggt gagaatggca aaagtttatg catttctttc cagacttgtt   7620
caacaggcca gccattacgc tcgtcatcaa aatcactcgc atcaaccaaa ccgttattca   7680
ttcgtgattg cgcctgagcg agacgaaata cgcgatcgct gttaaaagga caattacaaa   7740
```

-continued

```
caggaatcga atgcaaccgg cgcaggaaca ctgccagcgc atcaacaata ttttcacctg   7800

aatcaggata ttcttctaat acctggaatg ctgtttttcc ggggatcgca gtggtgagta   7860

accatgcatc atcaggagta cggataaaat gcttgatggt cggaagaggc ataaattccg   7920

tcagccagtt tagtctgacc atctcatctg taacatcatt ggcaacgcta cctttgccat   7980

gtttcagaaa caactctggc gcatcgggct tcccatacaa gcgatagatt gtcgcacctg   8040

attgcccgac attatcgcga gcccatttat acccatataa atcagcatcc atgttggaat   8100

ttaatcgcgg cctcgacgtt tcccgttgaa tatggctcat aacacccctt gtattactgt   8160

ttatgtaagc agacagtttt attgttcatg atgatatatt tttatcttgt gcaatgtaac   8220

atcagagatt ttgagacacg ggccagagct gcatcgcgcg ttttcagaat tggttaattg   8280

gttgtaacat tattcagatt gggcttgatt taaaacttca tttttaattt aaaaggatct   8340

aggtgaagat cctttttgat aatctcatga ccaaaatccc ttaacgtgag ttttcgttcc   8400

actgagcgtc agaccccgta gaaaagatca aaggatcttc tttccatagg ctccgccccc   8460

ctgacgagca tcacaaaaat cgacgctcaa gtcagaggtg gcgaaacccg acaggactat   8520

aaagatacca ggcgtttccc cctggaagct ccctcgtgcg ctctcctgtt ccgaccctgc   8580

cgcttaccgg atacctgtcc gcctttctcc cttcgggaag cgtggcgctt tctcatagct   8640

cacgctgtag gtatctcagt tcggtgtagg tcgttcgctc caagctgggc tgtgtgcacg   8700

aaccccccgt tcagcccgac cgctgcgcct tatccggtaa ctatcgtctt gagtccaacc   8760

cggtaagaca cgacttatcg ccactggcag cagccactgg taacaggatt agcagagcga   8820

ggtatgtagg cggtgctaca gagttcttga agtggtggcc taactacggc tacactagaa   8880

gaacagtatt tggtatctgc gctctgctga agccagttac cttcggaaaa agagttggta   8940

gctcttgatc cggcaaacaa accaccgctg gtagcggtgg tttttttgtt tgcaagcagc   9000

agattacgcg cagaaaaaaa ggatctcaaa acgccagcaa cgcggccttt ttacggttcc   9060

tggccttttg ctggcctttt gctcacatgt tctttcctgc gttatcccct gattctgtgg   9120

ataaccgtat taccgccttt gagtgagctg ataccgctcg ccgcagccga acgaccgagc   9180

gcagcgagtc agtgagcgag gaagcggaag agcgcccaat acgcaaaccg cctctc       9236
```

<210> SEQ ID NO 12
<211> LENGTH: 6260
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
cccgcgcgtt ggccgattca ttaatgcagc tggcacgaca ggtttcccga ctggaaagcg     60

ggcagtgagc gcaacgcaat tttcacacag gaaacagcta tgaccatgat tacgccaagc    120

ttgcatgcat ttaaatgacg ttggccactc cctctctgcg cgctcgctcg ctcactgagg    180

ccgggcgacc aaaggtcgcc cgacgcccgg gctttgcccg ggcggcctca gtgagcgagc    240

gagcgcgcag agagggagtg gccaactcca tcactagggg ttcctgagtt taaacttcgt    300

cgacgatctg cggccgcacg cgtggagcta gttattaata gtaatcaatt acggggtcat    360

tagttcatag cccatatatg gagttccgcg ttacataact tacggtaaat ggcccgcctg    420

gctgaccgcc caacgacccc cgcccattga cgtcaataat gacgtatgtt cccatagtaa    480

cgtcaatagg gactttccat tgacgtcaat gggtggagta tttacggtaa actgcccact    540
```

-continued

```
tggcagtaca tcaagtgtat catatgccaa gtacgccccc tattgacgtc aatgacggta    600
aatggcccgc ctggcattat gcccagtaca tgaccttatg ggactttcct acttggcagt    660
acatctacgt attagtcatc gctattacca tggtgatgcg gttttggcag tacatcaatg    720
ggcgtggata gcggtttgac tcacggggat ttccaagtct ccaccccatt gacgtcaatg    780
ggagtttgtt ttgcaccaaa atcaacggga ctttccaaaa tgtcgtaaca actccgcccc    840
attgacgcaa atgggcggta ggcgtgtacg gtgggaggtc tatataagca gagctcgttt    900
agtgaaccgt cagatcgcct ggagacgcca tccacgctgt tttgacctcc atagaagaca    960
ccgggaccga tccagcctcc gcggattcga atcccggccg ggaacggtgc attggaacgc   1020
ggattccccg tgccaagagt gacgtaagta ccgcctatag agtctatagg cccacaaaaa   1080
atgctttctt cttttaatat actttttttgt ttatcttatt tctaatactt tccctaatct   1140
ctttctttca gggcaataat gatacaatgt atcatgcctc tttgcaccat tctaaagaat   1200
aacagtgata atttctgggt taaggcaata gcaatatttc tgcatataaa tatttctgca   1260
tataaattgt aactgatgta agaggtttca tattgctaat agcagctaca atccagctac   1320
cattctgctt ttattttatg gttgggataa ggctggatta ttctgagtcc aagctaggcc   1380
cttttgctaa tcatgttcat acctcttatc ttcctcccac agctcctggg caacgtgctg   1440
gtctgtgtgc tggcccatca ctttggcaaa gaattgggat tcgaacatcg gccgccacca   1500
tgaacgccag cgagttcagg aggaggggca aggagatggt ggactacgtg gccaactaca   1560
tggagggcat cgagggcagg caggtgtacc ccgacgtgga gcccggctac ctgaggcccc   1620
tgatccccgc cgccgccccc caggagcccg acaccttcga ggacatcatc aacgacgtgg   1680
agaagatcat catgcccggc gtgacccact ggcacagccc ctacttcttc gcctacttcc   1740
ccaccgccag cagctacccc gccatgctgg ccgacatgct gtgcggcgcc atcggctgca   1800
tcggcttcag ctgggccgcc agccccgcct gcaccgagct ggagaccgtg atgatggact   1860
ggctgggcaa gatgctggag ctgcccaagg ccttcctgaa cgagaaggcc ggcgagggcg   1920
gcggcgtgat ccagggcagc gccagcgagg ccaccctggt ggccctgctg gccgccagga   1980
ccaaggtgat ccacaggctg caggccgcca gccccgagct gacccaggcc gccatcatgg   2040
agaagctggt ggcctacagc agcgaccagg cccacagcag cgtggagagg gccggcctga   2100
tcggcggcgt gaagctgaag gccatcccca gcgacggcaa cttcgccatg agggccagcg   2160
ccctgcagga ggccctggag agggacaagg ccgccggcct gatccccttc ttcatggtgg   2220
ccaccctggg caccaccacc tgctgcagct tcgacaacct gctggaggtg ggccccatct   2280
gcaacaagga ggacatctgg ctgcacgtgg acgccgccta cgccggcagc gccttcatct   2340
gccccgagtt caggcacctg ctgaacggcg tggagttcgc cgacagcttc aacttcaacc   2400
cccacaagtg gctgctggtg aacttcgact gcagcgccat gtgggtgaag aagaggaccg   2460
acctgaccgg cgccttcagg ctggacccca cctacctgaa gcacagccac caggacagcg   2520
gcctgatcac cgactacagg cactggcaga tccccctggg caggaggttc aggagcctga   2580
agatgtggtt cgtgttcagg atgtacggcg tgaagggcct gcaggcctac atcaggaagc   2640
acgtgcagct gagccacgag ttcgagagcc tggtgaggca ggaccccagg ttcgagatct   2700
gcgtggaggt gatcctgggc ctggtgtgct tcaggctgaa gggcagcaac aaggtgaacg   2760
aggccctgct gcagaggatc aacagcgcca agaagatcca cctggtgccc tgccacctga   2820
gggacaagtt cgtgctgagg ttcgccatct gcagcaggac cgtggagagc gcccacgtgc   2880
agagggcctg ggagcacatc aaggagctgg ccgccgacgt gctgagggcc gagagggagt   2940
```

```
gagctgctcg agagatctac gggtggcatc cctgtgaccc ctccccagtg cctctcctgg   3000
ccctggaagt tgccactcca gtgcccacca gccttgtcct aataaaatta agttgcatca   3060
ttttgtctga ctaggtgtcc ttctataata ttatggggtg gaggggggtg gtatggagca   3120
aggggcaagt tgggaagaca acctgtaggg cctgcggggt ctattgggaa ccaagctgga   3180
gtgcagtggc acaatcttgg ctcactgcaa tctccgcctc ctgggttcaa gcgattctcc   3240
tgcctcagcc tcccgagttg ttgggattcc aggcatgcat gaccaggctc agctaatttt   3300
tgtttttttg gtagagacgg ggtttcacca tattggccag gctggtctcc aactcctaat   3360
ctcaggtgat ctacccacct tggcctccca aattgctggg attacaggcg tgaaccactg   3420
ctcccttccc tgtccttctg attttgtagg taaccacgtg cggaccgagc ggccgcagtt   3480
aattaagctc gcgaaggaac ccctagtgat ggagttggcc actccctctc tgcgcgctcg   3540
ctcgctcact gaggccgggc gaccaaaggt cgcccgacgc ccgggctttg cccgggcggc   3600
ctcagtgagc gagcgagcgc gcagagaggg agtggccaag acgatttaaa tggtaccgag   3660
ctcgaattca ctggccgtcg ttttacaacg tcgtgactgg gaaaaccctg gcgttaccca   3720
acttaatcgc cttgcagcac atcccccttt cgccagctgg cgtaatagcg aagaggcccg   3780
caccgatcgc ccttcccaac agttgcgcag cctgaatggc gaatggcgcc tgatgcggta   3840
ttttctcctt acgcatctgt gcggtatttc acaccgcata tggtgcactc tcagtacaat   3900
ctgctctgat gccgcatagt taagccagcc ccgacacccg ccaacacccg ctgacgcgcc   3960
ctgacgggct tgtctgctcc cggcatccgc ttacagacaa gctgtgaccg tctccgggag   4020
ctgcatgtgt cagaggtttt caccgtcatc accgaaacgc gcgatgcagc tctggcccgt   4080
gtctcaaaat ctctgatgtt acattgcaca agataaaaat atatcatcat gaacaataaa   4140
actgtctgct tacataaaca gtaatacaag gggtgttgaa gatcctttga tcttttctac   4200
ggggtctgac gctcagtgga acgaaaactc acgttaaggg attttggtca tgagattatc   4260
aaaaaggatc ttcacctaga tccttttaaa ttaaaaatga agttttaaat caagcccaat   4320
ctgaataatg ttacaaccaa ttaaccaatt ctgattagaa aaactcatcg agcatcaaat   4380
gaaactgcaa tttattcata tcaggattat caataccata tttttgaaaa agccgtttct   4440
gtaatgaagg agaaaactca ccgaggcagt tccataggat ggcaagatcc tggtatcggt   4500
ctgcgattcc gactcgtcca acatcaatac aacctattaa tttcccctcg tcaaaaataa   4560
ggttatcaag tgagaaatca ccatgagtga cgactgaatc cggtgagaat ggcaaaagtt   4620
tatgcatttc tttccagact tgttcaacag gccagccatt acgctcgtca tcaaaatcac   4680
tcgcatcaac caaaccgtta ttcattcgtg attgcgcctg agcgagacga aatacgcgat   4740
cgctgttaaa aggacaatta caaacaggaa tcgaatgcaa ccggcgcagg aacactgcca   4800
gcgcatcaac aatattttca cctgaatcag gatattcttc taatacctgg aatgctgttt   4860
ttccggggat cgcagtggtg agtaaccatg catcatcagg agtacggata aaatgcttga   4920
tggtcggaag aggcataaat tccgtcagcc agtttagtct gaccatctca tctgtaacat   4980
cattggcaac gctacctttg ccatgtttca gaaacaactc tggcgcatcg ggcttcccat   5040
acaagcgata gattgtcgca cctgattgcc cgacattatc gcgagcccat ttatacccat   5100
ataaatcagc atccatgttg gaatttaatc gcggcctcga cgtttcccgt tgaatatggc   5160
tcataacacc ccttgtatta ctgtttatgt aagcagacag ttttattgtt catgatgata   5220
tatttttatc ttgtgcaatg taacatcaga gattttgaga cacgggccag agctgcatcg   5280
```

-continued cgcgttttca gaattggtta attggttgta acattattca gattgggctt gatttaaaac 5340
ttcattttta atttaaaagg atctaggtga agatcctttt tgataatctc atgaccaaaa 5400
tcccttaacg tgagttttcg ttccactgag cgtcagaccc cgtagaaaag atcaaaggat 5460
cttctttcca taggctccgc ccccctgacg agcatcacaa aaatcgacgc tcaagtcaga 5520
ggtggcgaaa cccgacagga ctataaagat accaggcgtt tccccctgga agctccctcg 5580
tgcgctctcc tgttccgacc ctgccgctta ccggatacct gtccgccttt ctcccttcgg 5640
gaagcgtggc gctttctcat agctcacgct gtaggtatct cagttcggtg taggtcgttc 5700
gctccaagct gggctgtgtg cacgaacccc ccgttcagcc cgaccgctgc gccttatccg 5760
gtaactatcg tcttgagtcc aacccggtaa gacacgactt atcgccactg gcagcagcca 5820
ctggtaacag gattagcaga gcgaggtatg taggcggtgc tacagagttc ttgaagtggt 5880
ggcctaacta cggctacact agaagaacag tatttggtat ctgcgctctg ctgaagccag 5940
ttaccttcgg aaaaagagtt ggtagctctt gatccggcaa acaaaccacc gctggtagcg 6000
gtggtttttt tgtttgcaag cagcagatta cgcgcagaaa aaaaggatct caaaacgcca 6060
gcaacgcggc ctttttacgg ttcctggcct tttgctggcc ttttgctcac atgttctttc 6120
ctgcgttatc ccctgattct gtggataacc gtattaccgc ctttgagtga gctgataccg 6180
ctcgccgcag ccgaacgacc gagcgcagcg agtcagtgag cgaggaagcg gaagagcgcc 6240
caatacgcaa accgcctctc 6260

<210> SEQ ID NO 13
<211> LENGTH: 6442
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
cccgcgcgtt ggccgattca ttaatgcagc tggcacgaca ggtttcccga ctggaaagcg 60
ggcagtgagc gcaacgcaat ttcacacag gaaacagcta tgaccatgat tacgccaagc 120
ttgcatgcat ttaaatgacg cagctgcgcg ctcgctcgct cactgaggcc gcccgggcaa 180
agcccgggcg tcgggcgacc tttggtcgcc cggcctcagt gagcgagcga gcgcgcagag 240
agggagtggc caactccatc actaggggtt gagtttaaac ttcgtcgacg atctgcggcc 300
gcacgcgtgg agctagttat taatagtaat caattacggg gtcattagtt catagcccat 360
atatggagtt ccgcgttaca taacttacgg taaatggccc gcctggctga ccgcccaacg 420
acccccgccc attgacgtca ataatgacgt atgttcccat agtaacgtca atagggactt 480
tccattgacg tcaatgggtg gagtatttac ggtaaactgc ccacttggca gtacatcaag 540
tgtatcatat gccaagtacg ccccctattg acgtcaatga cggtaaatgg cccgcctggc 600
attatgccca gtacatgacc ttatgggact ttcctacttg gcagtacatc tacgtattag 660
tcatcgctat taccatggtg atgcggtttt ggcagtacat caatgggcgt ggatagcggt 720
ttgactcacg gggatttcca agtctccacc ccattgacgt caatgggagt ttgttttgca 780
ccaaaatcaa cgggactttc caaaatgtcg taacaactcc gccccattga cgcaaatggg 840
cggtaggcgt gtacggtggg aggtctatat aagcagagct cgtttagtga accgtcagat 900
cgcctggaga cgccatccac gctgttttga cctccataga agacaccggg accgatccag 960
cctccgcgga ttcgaatccc ggccgggaac ggtgcattgg aacgcggatt ccccgtgcca 1020

-continued agagtgacgt aagtaccgcc tatagagtct ataggcccac aaaaaatgct ttcttctttt 1080
aatatacttt tttgtttatc ttatttctaa tactttccct aatctctttc tttcagggca 1140
ataatgatac aatgtatcat gcctctttgc accattctaa agaataacag tgataatttc 1200
tgggttaagg caatagcaat atttctgcat ataaatattt ctgcatataa attgtaactg 1260
atgtaagagg tttcatattg ctaatagcag ctacaatcca gctaccattc tgcttttatt 1320
ttatggttgg gataaggctg gattattctg agtccaagct aggccctttt gctaatcatg 1380
ttcatacctc ttatcttcct cccacagctc ctgggcaacg tgctggtctg tgtgctggcc 1440
catcactttg gcaaagaatt gggattcgaa catcgaattc gggcacgagg gaggacagag 1500
agcaagtcac tcccggctgc ctttttcacc tctgacagag cccagacacc atgaacgcaa 1560
gtgaattccg aaggagaggg aaggagatgg tggattacgt ggccaactac atggaaggca 1620
ttgagggacg ccaggtctac cctgacgtgg agcccgggta cctgcggccg ctgatccctg 1680
ccgctgcccc tcaggagcca gacacgtttg aggacatcat caacgacgtt gagaagataa 1740
tcatgcctgg ggtgacgcac tggcacagcc cctacttctt cgcctacttc cccactgcca 1800
gctcgtaccc ggccatgctt gcggacatgc tgtgcggggc cattggctgc atcggcttct 1860
cctgggcggc aagcccagca tgcacagagc tggagactgt gatgatggac tggctcggga 1920
agatgctgga actaccaaag gcatttttga atgagaaagc tggagaaggg ggaggagtga 1980
tccagggaag tgccagtgaa gccaccctgg tggccctgct ggccgctcgg accaaagtga 2040
tccatcggct gcaggcagcg tccccagagc tcacacaggc cgctatcatg gagaagctgg 2100
tggcttactc atccgatcag gcacactcct cagtggaaag agctgggtta attggtggag 2160
tgaaattaaa agccatcccc tcagatggca acttcgccat gcgtgcgtct gccctgcagg 2220
aagccctgga gagagacaaa gcggctggcc tgattccttt ctttatggtt gccaccctgg 2280
ggaccacaac atgctgctcc tttgacaatc tcttagaagt cggtcctatc tgcaacaagg 2340
aagacatatg gctgcacgtt gatgcagcct acgcaggcag tgcattcatc tgccctgagt 2400
tccggcacct tctgaatgga gtggagtttg cagattcatt caactttaat ccccacaaat 2460
ggctattggt gaattttgac tgttctgcca tgtgggtgaa aaagagaaca gacttaacgg 2520
gagcctttag actggacccc acttacctga agcacagcca tcaggattca gggcttatca 2580
ctgactaccg gcattggcag ataccactgg gcagaagatt tcgctctttg aaaatgtggt 2640
ttgtatttag gatgtatgga gtcaaaggac tgcaggctta tatccgcaag catgtccagc 2700
tgtcccatga gtttgagtca ctggtgcgcc aggatccccg ctttgaaatc tgtgtggaag 2760
tcattctggg gcttgtctgc tttcggctaa agggttccaa caaagtgaat gaagctcttc 2820
tgcaaagaat aaacagtgcc aaaaaaatcc acttggttcc atgtcacctc agggacaagt 2880
ttgtcctgcg ctttgccatc tgttctcgca cggtggaatc tgcccatgtg cagcgggcct 2940
gggaacacat caaagagctg gcggccgacg tgctgcgagc agagagggag taggagtgaa 3000
gccagctgca ggaatcaaaa attgaagaga gatatatctg aaaactggaa taagaagcaa 3060
ataaatatca tcctgccttc atggaactca gctgtctgtg gcttcccatg tctttctcca 3120
aagttatcca gagggttgtg attttgtctg cttagtatct catcaacaaa gaaatattat 3180
ttgctaatta aaaagttaat cttcatggcc atagctttta ttcattagct gtgatttttg 3240
ttgattaaaa cattatagat tttcatgttc ttgcagtcat cagaagtggt aggaaagcct 3300
cactgatata ttttccaggg caatcaatgt tcacgcaact tgaaattata tctgtggtct 3360
tcaaattgtc ttttgtcatg tggctaaatg cctaataaac aattcaagtg aaatactaaa 3420

```
aaaaaaaaaa aaaaaaaaag ctgctcgaga gatctacggg tggcatccct gtgacccctc   3480
cccagtgcct ctcctggccc tggaagttgc cactccagtg cccaccagcc ttgtcctaat   3540
aaaattaagt tgcatcattt tgtctgacta ggtgtccttc tataatatta tggggtggag   3600
gggggtggta tggagcaagg ggcaagttgg gaagacaacc tgtagggcct gcggggtcta   3660
ttgggaacca agctggagtg cagtggcaca atcttggctc actgcaatct ccgcctcctg   3720
ggttcaagcg attctcctgc ctcagcctcc cgagttgttg ggattccagg catgcatgac   3780
caggctcagc taatttttgt ttttttggta gagacggggt ttcaccatat tggccaggct   3840
ggtctccaac tcctaatctc aggtgatcta cccaccttgg cctcccaaat tgctgggatt   3900
acaggcgtga accactgctc ccttccctgt ccttctgatt ttgtaggtaa ccacgtgcgg   3960
accgagcggc cgcagttaat taagctcgcg aaacccctag tgatggagtt ggccactccc   4020
tctctgcgcg ctcgctcgct cactgaggcc gggcgaccaa aggtcgcccg acgcccgggc   4080
tttgcccggg cggcctcagt gagcgagcga gcgcgcagct ggacgattta aatggtaccg   4140
agctcgaatt cactggccgt cgttttacaa cgtcgtgact gggaaaaccc tggcgttacc   4200
caacttaatc gccttgcagc acatccccct ttcgccagct ggcgtaatag cgaagaggcc   4260
cgcaccgatc gcccttccca acagttgcgc agcctgaatg gcgaatggcg cctgatgcgg   4320
tattttctcc ttacgcatct gtgcggtatt tcacaccgca tatggtgcac tctcagtaca   4380
atctgctctg atgccgcata gttaagccag ccccgacacc cgccaacacc cgctgacgcg   4440
ccctgacggg cttgtctgct cccggcatcc gcttacagac aagctgtgac cgtctccggg   4500
agctgcatgt gtcagaggtt ttcaccgtca tcaccgaaac gcgcgatgca gctctggccc   4560
gtgtctcaaa atctctgatg ttacattgca caagataaaa atatatcatc atgaacaata   4620
aaactgtctg cttacataaa cagtaataca aggggtgtta tgagccatat tcaacgggaa   4680
acgtcgaggc cgcgattaaa ttccaacatg gatgctgatt tatatgggta taaatgggct   4740
cgcgataatg tcgggcaatc aggtgcgaca atctatcgct tgtatgggaa gcccgatgcg   4800
ccagagttgt ttctgaaaca tggcaaaggt agcgttgcca atgatgttac agatgagatg   4860
gtcagactaa actggctgac ggaatttatg cctcttccga ccatcaagca ttttatccgt   4920
actcctgatg atgcatggtt actcaccact gcgatccccg gaaaaacagc attccaggta   4980
ttagaagaat atcctgattc aggtgaaaat attgttgatg cgctggcagt gttcctgcgc   5040
cggttgcatt cgattcctgt ttgtaattgt ccttttaaca gcgatcgcgt atttcgtctc   5100
gctcaggcgc aatcacgaat gaataacggt ttggttgatg cgagtgattt tgatgacgag   5160
cgtaatggct ggcctgttga acaagtctgg aaagaaatgc ataaactttt gccattctca   5220
ccggattcag tcgtcactca tggtgatttc tcacttgata accttatttt tgacgagggg   5280
aaattaatag gttgtattga tgttggacga gtcggaatcg cagaccgata ccaggatctt   5340
gccatcctat ggaactgcct cggtgagttt tctccttcat tacagaaacg gctttttcaa   5400
aaatatggta ttgataatcc tgatatgaat aaattgcagt ttcatttgat gctcgatgag   5460
tttttctaat cagaattggt taattggttg taacattatt cagattgggc ttgatttaaa   5520
acttcatttt taatttaaaa ggatctaggt gaagatcctt tttgataatc tcatgaccaa   5580
aatcccttaa cgtgagtttt cgttccactg agcgtcagac cccgtagaaa agatcaaagg   5640
atcttcttga gatccttttt ttctgcgcgt aatctgctgc ttgcaaacaa aaaaaccacc   5700
gctaccagcg gtggtttgtt tgccggatca agagctacca actctttttc cgaaggtaac   5760
```

```
tggcttcagc agagcgcaga taccaaatac tgttcttcta gtgtagccgt agttaggcca   5820

ccacttcaag aactctgtag caccgcctac atacctcgct ctgctaatcc tgttaccagt   5880

ggctgctgcc agtggcgata agtcgtgtct taccgggttg gactcaagac gatagttacc   5940

ggataaggcg cagcggtcgg gctgaacggg gggttcgtgc acacagccca gcttggagcg   6000

aacgacctac accgaactga gatacctaca gcgtgagcta tgagaaagcg ccacgcttcc   6060

cgaagggaga aaggcggaca ggtatccggt aagcggcagg gtcggaacag gagagcgcac   6120

gagggagctt ccagggggaa acgcctggta tctttatagt cctgtcgggt ttcgccacct   6180

ctgacttgag cgtcgatttt tgtgatgctc gtcagggggg cggagcctat ggaaaaacgc   6240

cagcaacgcg gcctttttac ggttcctggc cttttgctgg ccttttgctc acatgttctt   6300

tcctgcgtta tcccctgatt ctgtggataa ccgtattacc gcctttgagt gagctgatac   6360

cgctcgccgc agccgaacga ccgagcgcag cgagtcagtg agcgaggaag cggaagagcg   6420

cccaatacgc aaaccgcctc tc                                             6442
```

```
<210> SEQ ID NO 14
<211> LENGTH: 9260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
```

```
cccgcgcgtt ggccgattca ttaatgcagc tggcacgaca ggtttcccga ctggaaagcg     60

ggcagtgagc gcaacgcaat ttcacacag gaaacagcta tgaccatgat tacgccaagc    120

ttgcatgcat ttaaatgacg ttggccactc cctctctgcg cgctcgctcg ctcactgagg    180

ccgggcgacc aaaggtcgcc cgacgcccgg gctttgcccg ggcggcctca gtgagcgagc    240

gagcgcgcag agagggagtg gccaactcca tcactagggg ttcctgagtt taaacttcgt    300

cgacgatctg cggccgcacg cgtggagcta gttattaata gtaatcaatt acggggtcat    360

tagttcatag cccatatatg gagttccgcg ttacataact tacggtaaat ggcccgcctg    420

gctgaccgcc caacgacccc cgcccattga cgtcaataat gacgtatgtt cccatagtaa    480

cgtcaatagg gactttccat tgacgtcaat gggtggagta tttacggtaa actgcccact    540

tggcagtaca tcaagtgtat catatgccaa gtacgccccc tattgacgtc aatgacggta    600

aatggcccgc ctggcattat gcccagtaca tgaccttatg ggactttcct acttggcagt    660

acatctacgt attagtcatc gctattacca tggtgatgcg gttttggcag tacatcaatg    720

ggcgtggata gcggtttgac tcacggggat ttccaagtct ccaccccatt gacgtcaatg    780

ggagtttgtt ttgcaccaaa atcaacggga ctttccaaaa tgtcgtaaca actccgcccc    840

attgacgcaa atgggcggta ggcgtgtacg gtgggaggtc tatataagca gagctcgttt    900

agtgaaccgt cagatcgcct ggagacgcca tccacgctgt tttgacctcc atagaagaca    960

ccgggaccga tccagcctcc gcggattcga atcccggccg ggaacggtgc attggaacgc   1020

ggattccccg tgccaagagt gacgtaagta ccgcctatag agtctatagg ccccacaaaaa  1080

atgctttctt cttttaatat actttttgt ttatcttatt tctaatactt tccctaatct   1140

ctttctttca gggcaataat gatacaatgt atcatgcctc tttgcaccat tctaaagaat   1200

aacagtgata atttctgggt taaggcaata gcaatatttc tgcatataaa tatttctgca   1260

tataaattgt aactgatgta agaggtttca tattgctaat agcagctaca atccagctac   1320
```

-continued cattctgctt ttattttatg gttgggataa ggctggatta ttctgagtcc aagctaggcc 1380
cttttgctaa tcatgttcat acctcttatc ttcctcccac agctcctggg caacgtgctg 1440
gtctgtgtgc tggcccatca ctttggcaaa gaattgggat tcgaacatcg gccgccacca 1500
tgaacgccag cgagttcagg aggaggggca aggagatggt ggactacgtg gccaactaca 1560
tggagggcat cgagggcagg caggtgtacc ccgacgtgga gcccggctac ctgaggcccc 1620
tgatccccgc cgccgccccc caggagcccg acaccttcga ggacatcatc aacgacgtgg 1680
agaagatcat catgcccggc gtgacccact ggcacagccc ctacttcttc gcctacttcc 1740
ccaccgccag cagctacccc gccatgctgg ccgacatgct gtgcggcgcc atcggctgca 1800
tcggcttcag ctgggccgcc agccccgcct gcaccgagct ggagaccgtg atgatggact 1860
ggctgggcaa gatgctggag ctgcccaagg ccttcctgaa cgagaaggcc ggcgagggcg 1920
gcggcgtgat ccagggcagc gccagcgagg ccaccctggt ggccctgctg gccgccagga 1980
ccaaggtgat ccacaggctg caggccgcca gccccgagct gacccaggcc gccatcatgg 2040
agaagctggt ggcctacagc agcgaccagg cccacagcag cgtggagagg gccggcctga 2100
tcggcggcgt gaagctgaag gccatcccca gcgacggcaa cttcgccatg agggccagcg 2160
ccctgcagga ggccctggag agggacaagg ccgccggcct gatccccttc ttcatggtgg 2220
ccaccctggg caccaccacc tgctgcagct tcgacaacct gctggaggtg ggccccatct 2280
gcaacaagga ggacatctgg ctgcacgtgg acgccgccta cgccggcagc gccttcatct 2340
gccccgagtt caggcacctg ctgaacggcg tggagttcgc cgacagcttc aacttcaacc 2400
cccacaagtg gctgctggtg aacttcgact gcagcgccat gtgggtgaag aagaggaccg 2460
acctgaccgg cgccttcagg ctggacccca cctacctgaa gcacagccac caggacagcg 2520
gcctgatcac cgactacagg cactggcaga tcccccctggg caggaggttc aggagcctga 2580
agatgtggtt cgtgttcagg atgtacggcg tgaagggcct gcaggcctac atcaggaagc 2640
acgtgcagct gagccacgag ttcgagagcc tggtgaggca ggaccccagg ttcgagatct 2700
gcgtggaggt gatcctgggc ctggtgtgct tcaggctgaa gggcagcaac aaggtgaacg 2760
aggccctgct gcagaggatc aacagcgcca agaagatcca cctggtgccc tgccacctga 2820
gggacaagtt cgtgctgagg ttcgccatct gcagcaggac cgtggagagc gcccacgtgc 2880
agagggcctg ggagcacatc aaggagctgg ccgccgacgt gctgagggcc gagagggagt 2940
gagctgctcg agagatctac gggtggcatc cctgtgaccc ctccccagtg cctctcctgg 3000
ccctggaagt tgccactcca gtgcccacca gccttgtcct aataaaatta agttgcatca 3060
ttttgtctga ctaggtgtcc ttctataata ttatggggtg gaggggggtg gtatggagca 3120
aggggcaagt tgggaagaca acctgtaggg cctgcggggt ctattgggaa ccaagctgga 3180
gtgcagtggc acaatcttgg ctcactgcaa tctccgcctc ctgggttcaa gcgattctcc 3240
tgcctcagcc tcccgagttg ttgggattcc aggcatgcat gaccaggctc agctaatttt 3300 tgttttttttg gtagagacgg ggtttcacca tattggccag gctggtctcc aactcctaat 3360
ctcaggtgat ctacccacct tggcctccca aattgctggg attacaggcg tgaaccactg 3420
ctcccttccc tgtccttctg attttgtagg taaccacgtg cggaccgagc ggccgcagtt 3480
aattaagctc gcgaaggaac ccctagtgat ggagttggcc actccctctc tgcgcgctcg 3540
ctcgctcact gaggccgggc gaccaaaggt cgcccgacgc ccgggctttg cccgggcggc 3600
ctcagtgagc gagcgagcgc gcagagaggg agtggccaag acgatttaaa tggtaccgag 3660
ctcgaattca ctggccgtcg ttttacaacg tcgtgactgg gaaaaccctg gcgttaccca 3720
acttaatcgc cttgcagcac atcccccttt cgccagctgg cgtaatagcg aagaggcccg 3780
caccgatcgc ccttcccaac agttgcgcag cctgaatggc gaatggcgcc tgatgcggta 3840
ttttctcctt acgcatctgt gcggtatttc acaccgcata tggtgcactc tcagtacaat 3900
ctgctctgat gccgcatagt taagccagcc ccgacacccg ccaacacccg ctgacgcgcc 3960
ctgacgggct tgtctgctcc cggcatccgc ttacagacaa gctgtgaccg tctcagaacc 4020
caaatgtgac caaccgttta catatatctt ggtttattat ttcaatttct cttttcaaac 4080
atcttcttct gtcgttgtgc aattttccaa atgccaattt ggtcgcttgg ctatttccaa 4140
acgatttcat atattcaagt tggagatata gacagtcccc tgaacacctc gcatcctctg 4200
ctttttatgc ctgctcgtcc tgtgggtata attttaatgg tcaaatcgct gctggggaat 4260
tgtatacgct gctcttgtgt ctcactgcct cccttgtaga aatggaaatt gcttttccat 4320
tatttccatg tgattttgtt ggttttgcca tcgaattggc attgaaaacg cataaaaata 4380
agcatttcgc atttgcaaag atccaaaaga tttatttgca cgctgagcct ggggatacac 4440
gaaatgtatt tgtaagattc ttcagatgag tttggaacgc acggaaatta ccgtcttggg 4500
atttgttgga catcgcattt aagcatgatg tatcatttaa ttttttccaa tttaaaaaca 4560
aataatcagt gctacgatta agactggatc tattatagac ttcttcaaag tttttcagtt 4620
ttctttaaaa ttacctccat aaaactcttt taatattttg aaaatcatct ccaggttaca 4680
tttaatctga ttaagtttag agtcagttag tttcccacag ttttcttctt gaaataaacc 4740
cattaagtaa ccccaactga tcggcgcaaa tgattcagct atgcagaaaa tatgattgat 4800
gattttttccc tcccaccagc ccttaacact tgcttaaccc ttttgtgtgg ccattatagc 4860
cctttcctcg tagtctgctt aaagttcatt aataagtttt gcgtgagcca aaaatggcgc 4920
cgctttggaa tcgtgacagc gtggaaactc tggactttgg ggttgcaaaa cttcggaagc 4980
tgaaagcatt ttgctgtagc catcgcattt tgggggaaga aatccgaatt cgagtccaaa 5040
ccgaattcta atagaagttt tgcagcaaag tgcctcagac aggttaatga ccaaaagcag 5100
ttttgcattc aaatgctgca gcaaccctcg cacgagggtt gtcatgacgg acgaaaatct 5160
aatttacaac atgcaactgc cactttgagg ggtgactttt acccaagacg tggctgtgaa 5220
ggaaattctg cgagaaagag attaattacg ctctgggggc agttaatgaa tgcttgcgcg 5280
gggcgataag ggttaacgt ttggccagct caaattaccg aatgtataac attttgatga 5340
gcatgacaaa aattggaatt ttcaactctt ttttcctgcg aaaagcataa cttttccatt 5400
aacacaatgg cgacgatgag ccggcaaatc gacgatacca aatcggcata acgtgcatga 5460
aaattataca tgattgattt catattaatt tctacgaatg ttatgaatcg gctaaaagat 5520
gagaatggaa atattgcacg attttgattt tgtcatgatg acaaaaaagg gttgtaagat 5580
ttgtacatgc caaaatcata aacttttaac agaaatcaaa cacaaagaag taatataaca 5640
ttaaagtaca caggccttgt cacagagata gaaaaatgta gctattatta aaatatttaa 5700
cattctcttg gtgtctgcaa cttttctatc agtcgctttt ttattccctt tccaacactt 5760
atttaaaatg aaatgcactc gaaattaact aatttaatgg ctcatatcct ttgtgctgct 5820
taaaaaggca ggaaacgttt tttgtgccct acacctcctc cattcaaatg aaaaaggcgg 5880
tggagtcgag gaaaatgtct gccctggagc ttgacaagcc aagatatggc ccatcaaaaa 5940
tgttcgaatg ttctttttaa ataaatgtct cattatatgg ctgccacgcc cacaccgctc 6000
aacgcccaca cacgtgccgc cttccggttt agttgggtgg tacctgaccg tagatttttc 6060

-continued actgcggaca tgtgtccaat cagtggcaac gtgcaacgaa ccgtggcaaa cacagggaaa 6120
gaacctcgaa gacccacagc aaactcatcc tctcgaattt gacactatga taatgcttat 6180
attcaatttt ttgcaacatt ctatttacac taaactgaga aacaggacaa agttgagaat 6240
gggtgctgtg attatttgtc ttgtgccaat atatgccctc ctgcatataa aatacgagat 6300
acaaaaccaa acgaaataag aacgaacaag aaatcagttt aatttcaatg ctgatcaaac 6360
caagttgaca actctgttgt atattagctc taataatgac ttaaggttcg aaatttaagt 6420
aacttccaaa atgggccaga taaatactgc taatatcgaa tgcaattcaa tgaggaaata 6480
gtaatcaatc agccaaccct aatgaaatta ataatgtaat ttaaaacttt attccaccca 6540
ttctaataat gaaaatcatt aaatatatgt agcaatccaa ttttgttaat acatattgta 6600
tatccctgat ttgtcaatac caaagaccag aaaaaacacc atgccaaatt ccttttattc 6660
gttgaaaatc gaaacaactt tgaagtatta acctgctggc taaaaaatat gtgtattact 6720
aaatatacca tgtaatcaaa agttcgaaat aaacgtgaaa tggcagctcc actcgtcagc 6780
cgtgccactt ttcgactaat caaaatgcct tttgaatgcc tgagttgaat caagttggct 6840
taatagttat tatcccacgc aagcaaagtc aatggcagag ggaaatgcgt agaaattagc 6900
acagacttga atggacgcac gagtgtcgaa tggcaggaga gtgggaaatg aacggggagt 6960
tttccaggat aaggatgttt tcgaagtatc gtaatcattt atagcctcca gatacgggag 7020
ctgcatgtgt cagaggtttt caccgtcatc accgaaacgc gcgatgcagc tctggcccgt 7080
gtctcaaaat ctctgatgtt acattgcaca agataaaaat atatcatcat gaacaataaa 7140
actgtctgct tacataaaca gtaatacaag gggtgttgaa gatcctttga tcttttctac 7200
ggggtctgac gctcagtgga acgaaaactc acgttaaggg attttggtca tgagattatc 7260
aaaaaggatc ttcacctaga tccttttaaa ttaaaaatga agttttaaat caagcccaat 7320
ctgaataatg ttacaaccaa ttaaccaatt ctgattagaa aaactcatcg agcatcaaat 7380
gaaactgcaa tttattcata tcaggattat caataccata tttttgaaaa agccgtttct 7440
gtaatgaagg agaaaactca ccgaggcagt tccataggat ggcaagatcc tggtatcggt 7500
ctgcgattcc gactcgtcca acatcaatac aacctattaa tttcccctcg tcaaaaataa 7560
ggttatcaag tgagaaatca ccatgagtga cgactgaatc cggtgagaat ggcaaaagtt 7620
tatgcatttc tttccagact tgttcaacag gccagccatt acgctcgtca tcaaaatcac 7680
tcgcatcaac caaaccgtta ttcattcgtg attgcgcctg agcgagacga aatacgcgat 7740
cgctgttaaa aggacaatta caaacaggaa tcgaatgcaa ccggcgcagg aacactgcca 7800
gcgcatcaac aatattttca cctgaatcag gatattcttc taatacctgg aatgctgttt 7860
ttccggggat cgcagtggtg agtaaccatg catcatcagg agtacggata aaatgcttga 7920
tggtcggaag aggcataaat tccgtcagcc agtttagtct gaccatctca tctgtaacat 7980
cattggcaac gctacctttg ccatgtttca gaaacaactc tggcgcatcg ggcttcccat 8040
acaagcgata gattgtcgca cctgattgcc cgacattatc gcgagcccat ttatacccat 8100
ataaatcagc atccatgttg gaatttaatc gcggcctcga cgtttcccgt tgaatatggc 8160
tcataacacc ccttgtatta ctgtttatgt aagcagacag ttttattgtt catgatgata 8220
tatttttatc ttgtgcaatg taacatcaga gattttgaga cacgggccag agctgcatcg 8280
cgcgttttca gaattggtta attggttgta acattattca gattgggctt gatttaaaac 8340
ttcattttta atttaaaagg atctaggtga agatcctttt tgataatctc atgaccaaaa 8400
tcccttaacg tgagttttcg ttccactgag cgtcagaccc cgtagaaaag atcaaaggat 8460
cttctttcca taggctccgc ccccctgacg agcatcacaa aaatcgacgc tcaagtcaga 8520
ggtggcgaaa cccgacagga ctataaagat accaggcgtt tccccctgga agctccctcg 8580
tgcgctctcc tgttccgacc ctgccgctta ccggatacct gtccgccttt ctcccttcgg 8640
gaagcgtggc gctttctcat agctcacgct gtaggtatct cagttcggtg taggtcgttc 8700
gctccaagct gggctgtgtg cacgaacccc ccgttcagcc cgaccgctgc gccttatccg 8760
gtaactatcg tcttgagtcc aacccggtaa gacacgactt atcgccactg gcagcagcca 8820
ctggtaacag gattagcaga gcgaggtatg taggcggtgc tacagagttc ttgaagtggt 8880
ggcctaacta cggctacact agaagaacag tatttggtat ctgcgctctg ctgaagccag 8940
ttaccttcgg aaaaagagtt ggtagctctt gatccggcaa acaaaccacc gctggtagcg 9000
gtggtttttt tgtttgcaag cagcagatta cgcgcagaaa aaaaggatct caaaacgcca 9060
gcaacgcggc ctttttacgg ttcctggcct tttgctggcc ttttgctcac atgttctttc 9120
ctgcgttatc ccctgattct gtggataacc gtattaccgc ctttgagtga gctgataccg 9180
ctcgccgcag ccgaacgacc gagcgcagcg agtcagtgag cgaggaagcg gaagagcgcc 9240
caatacgcaa accgcctctc 9260

<210> SEQ ID NO 15
<211> LENGTH: 9665
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
cccgcgcgtt ggccgattca ttaatgcagc tggcacgaca ggtttcccga ctggaaagcg 60
ggcagtgagc gcaacgcaat tttcacacag gaaacagcta tgaccatgat tacgccaagc 120
ttgcatgcat ttaaatgacg ttggccactc cctctctgcg cgctcgctcg ctcactgagg 180
ccgggcgacc aaaggtcgcc cgacgcccgg gctttgcccg ggcggcctca gtgagcgagc 240
gagcgcgcag agagggagtg gccaactcca tcactagggg ttcctgagtt taaacttcgt 300
cgacgatctg cggccgcacg cgtggagcta gttattaata gtaatcaatt acggggtcat 360
tagttcatag cccatatatg gagttccgcg ttacataact tacggtaaat ggcccgcctg 420
gctgaccgcc caacgacccc cgcccattga cgtcaataat gacgtatgtt cccatagtaa 480
cgtcaatagg gactttccat tgacgtcaat gggtggagta tttacggtaa actgcccact 540
tggcagtaca tcaagtgtat catatgccaa gtacgccccc tattgacgtc aatgacggta 600
aatggcccgc ctggcattat gcccagtaca tgaccttatg ggactttcct acttggcagt 660
acatctacgt attagtcatc gctattacca tggtgatgcg gttttggcag tacatcaatg 720
ggcgtggata gcggtttgac tcacggggat ttccaagtct ccaccccatt gacgtcaatg 780
ggagtttgtt ttgcaccaaa atcaacggga ctttccaaaa tgtcgtaaca actccgcccc 840
attgacgcaa atgggcggta ggcgtgtacg gtgggaggtc tatataagca gagctcgttt 900
agtgaaccgt cagatcgcct ggagacgcca tccacgctgt tttgacctcc atagaagaca 960
ccgggaccga tccagcctcc gcggattcga atcccggccg ggaacggtgc attggaacgc 1020
ggattccccg tgccaagagt gacgtaagta ccgcctatag agtctatagg ccccacaaaaa 1080 atgctttctt cttttaatat actttttttgt ttatcttatt tctaatactt tccctaatct 1140
ctttctttca gggcaataat gatacaatgt atcatgcctc tttgcaccat tctaaagaat 1200

-continued

```
aacagtgata atttctgggt taaggcaata gcaatatttc tgcatataaa tatttctgca   1260
tataaattgt aactgatgta agaggtttca tattgctaat agcagctaca atccagctac   1320
cattctgctt ttattttatg gttgggataa ggctggatta ttctgagtcc aagctaggcc   1380
cttttgctaa tcatgttcat acctcttatc ttcctcccac agctcctggg caacgtgctg   1440
gtctgtgtgc tggcccatca ctttggcaaa gaattgggat tcgaacatcg gccgccacca   1500
tgaacgcaag tgaattccga aggagaggga aggagatggt ggattacgtg gccaactaca   1560
tggaaggcat tgagggacgc caggtctacc ctgacgtgga gcccgggtac ctgcggccgc   1620
tgatccctgc cgctgcccct caggagccag acacgtttga ggacatcatc aacgacgttg   1680
agaagataat catgcctggg gtgacgcact ggcacagccc ctacttcttc gcctacttcc   1740
ccactgccag ctcgtacccg gccatgcttg cggacatgct gtgcggggcc attggctgca   1800
tcggcttctc ctgggcggca agcccagcat gcacagagct ggagactgtg atgatggact   1860
ggctcgggaa gatgctggaa ctaccaaagg catttttgaa tgagaaagct ggagaagggg   1920
gaggagtgat ccagggaagt gccagtgaag ccaccctggt ggccctgctg gccgctcgga   1980
ccaaagtgat ccatcggctg caggcagcgt ccccagagct cacacaggcc gctatcatgg   2040
agaagctggt ggcttactca tccgatcagg cacactcctc agtggaaaga gctgggttaa   2100
ttggtggagt gaaattaaaa gccatcccct cagatggcaa cttcgccatg cgtgcgtctg   2160
ccctgcagga agccctggag agagacaaag cggctggcct gattcctttc tttatggttg   2220
ccaccctggg gaccacaaca tgctgctcct ttgacaatct cttagaagtc ggtcctatct   2280
gcaacaagga agacatatgg ctgcacgttg atgcagccta cgcaggcagt gcattcatct   2340
gccctgagtt ccggcacctt ctgaatggag tggagtttgc agattcattc aactttaatc   2400
cccacaaatg gctattggtg aattttgact gttctgccat gtgggtgaaa aagagaacag   2460
acttaacggg agcctttaga ctggacccca cttacctgaa gcacagccat caggattcag   2520
ggcttatcac tgactaccgg cattggcaga taccactggg cagaagattt cgctctttga   2580
aaatgtggtt tgtatttagg atgtatggag tcaaaggact gcaggcttat atccgcaagc   2640
atgtccagct gtcccatgag tttgagtcac tggtgcgcca ggatccccgc tttgaaatct   2700
gtgtggaagt cattctgggg cttgtctgct ttcggctaaa gggttccaac aaagtgaatg   2760
aagctcttct gcaaagaata aacagtgcca aaaaaatcca cttggttcca tgtcacctca   2820
gggacaagtt tgtcctgcgc tttgccatct gttctcgcac ggtggaatct gcccatgtgc   2880
agcgggcctg ggaacacatc aaagagctgg cggccgacgt gctgcgagca gagagggagt   2940
aggagtgaag ccagctgcag gaatcaaaaa ttgaagagag atatatctga aaactggaat   3000
aagaagcaaa taaatatcat cctgccttca tggaactcag ctgtctgtgg cttcccatgt   3060
ctttctccaa agttatccag agggttgtga ttttgtctgc ttagtatctc atcaacaaag   3120
aaatattatt tgctaattaa aaagttaatc ttcatggcca tagcttttat tcattagctg   3180
tgatttttgt tgattaaaac attatagatt ttcatgttct tgcagtcatc agaagtggta   3240
ggaaagcctc actgatatat tttccagggc aatcaatgtt cacgcaactt gaaattatat   3300
ctgtggtctt caaattgtct tttgtcatgt ggctaaatgc ctaataagct gctcgagaga   3360
tctacgggtg gcatccctgt gacccctccc cagtgcctct cctggccctg gaagttgcca   3420
ctccagtgcc caccagcctt gtcctaataa aattaagttg catcattttg tctgactagg   3480
tgtccttcta taatattatg gggtggaggg gggtggtatg gagcaagggg caagttggga   3540
```

-continued

```
agacaacctg tagggcctgc ggggtctatt gggaaccaag ctggagtgca gtggcacaat   3600
cttggctcac tgcaatctcc gcctcctggg ttcaagcgat tctcctgcct cagcctcccg   3660
agttgttggg attccaggca tgcatgacca ggctcagcta atttttgttt ttttggtaga   3720
gacggggttt caccatattg gccaggctgg tctccaactc ctaatctcag gtgatctacc   3780
caccttggcc tcccaaattg ctgggattac aggcgtgaac cactgctccc ttccctgtcc   3840
ttctgatttt gtaggtaacc acgtgcggac cgagcggccg cagttaatta agctcgcgaa   3900
ggaaccccta gtgatggagt tggccactcc ctctctgcgc gctcgctcgc tcactgaggc   3960
cgggcgacca aaggtcgccc gacgcccggg ctttgcccgg gcggcctcag tgagcgagcg   4020
agcgcgcaga gagggagtgg ccaagacgat ttaaatggta ccgagctcga attcactggc   4080
cgtcgtttta caacgtcgtg actgggaaaa ccctggcgtt acccaactta atcgccttgc   4140
agcacatccc cctttcgcca gctggcgtaa tagcgaagag gcccgcaccg atcgcccttc   4200
ccaacagttg cgcagcctga atggcgaatg gcgcctgatg cggtattttc tccttacgca   4260
tctgtgcggt atttcacacc gcatatggtg cactctcagt acaatctgct ctgatgccgc   4320
atagttaagc cagccccgac acccgccaac acccgctgac gcgccctgac gggcttgtct   4380
gctcccggca tccgcttaca gacaagctgt gaccgtctca gaacccaaat gtgaccaacc   4440
gtttacatat atcttggttt attatttcaa tttctctttt caaacatctt cttctgtcgt   4500
tgtgcaattt tccaaatgcc aatttggtcg cttggctatt tccaaacgat ttcatatatt   4560
caagttggag atatagacag tcccctgaac acctcgcatc ctctgctttt tatgcctgct   4620
cgtcctgtgg gtataatttt aatggtcaaa tcgctgctgg ggaattgtat acgctgctct   4680
tgtgtctcac tgcctcccct gtagaaatgg aaattgcttt tccattattt ccatgtgatt   4740
ttgttggttt tgccatcgaa ttggcattga aaacgcataa aaataagcat ttcgcatttg   4800
caaagatcca aaagatttat ttgcacgctg agcctgggga tacacgaaat gtatttgtaa   4860
gattcttcag atgagtttgg aacgcacgga aattaccgtc ttgggatttg ttggacatcg   4920
catttaagca tgatgtatca tttaattttt tccaatttaa aaacaaataa tcagtgctac   4980
gattaagact ggatctatta tagacttctt caaagttttt cagttttctt taaaattacc   5040
tccataaaac tcttttaata ttttgaaaat catctccagg ttacatttaa tctgattaag   5100
tttagagtca gttagtttcc cacagttttc ttcttgaaat aaacccatta agtaacccca   5160
actgatcggc gcaaatgatt cagctatgca gaaaatatga ttgatgattt ttccctccca   5220
ccagccctta acacttgctt aacccttttg tgtggccatt atagcccttt cctcgtagtc   5280
tgcttaaagt tcattaataa gttttgcgtg agccaaaaat ggcgccgctt tggaatcgtg   5340
acagcgtgga aactctggac tttggggttg caaaacttcg gaagctgaaa gcattttgct   5400
gtagccatcg cattttgggg gaagaaatcc gaattcgagt ccaaaccgaa ttctaataga   5460
agttttgcag caaagtgcct cagacaggtt aatgaccaaa agcagttttg cattcaaatg   5520
ctgcagcaac cctcgcacga gggttgtcat gacggacgaa aatctaattt acaacatgca   5580
actgccactt tgaggggtga cttttaccca agacgtggct gtgaaggaaa ttctgcgaga   5640
aagagattaa ttacgctctg gggcagtta atgaatgctt gcgcggggcg ataaggggtt   5700
aacgtttggc cagctcaaat taccgaatgt ataacatttt gatgagcatg acaaaaattg   5760
gaattttcaa ctctttttc ctgcgaaaag cataactttt ccattaacac aatggcgacg   5820
atgagccggc aaatcgacga taccaaatcg gcataacgtg catgaaaatt atacatgatt   5880
gatttcatat taatttctac gaatgttatg aatcggctaa aagatgagaa tggaaatatt   5940
```

```
gcacgatttt gattttgtca tgatgacaaa aaagggttgt aagatttgta catgccaaaa    6000

tcataaactt ttaacagaaa tcaaacacaa agaagtaata taacattaaa gtacacaggc    6060

cttgtcacag agatagaaaa atgtagctat tattaaaata tttaacattc tcttggtgtc    6120

tgcaactttt ctatcagtcg cttttttatt cccttttccaa cacttattta aaatgaaatg    6180

cactcgaaat taactaattt aatggctcat atcctttgtg ctgcttaaaa aggcaggaaa    6240

cgttttttgt gccctacacc tcctccattc aaatgaaaaa ggcggtggag tcgaggaaaa    6300

tgtctgccct ggagcttgac aagccaagat atggcccatc aaaaatgttc gaatgttctt    6360

tttaaataaa tgtctcatta tatggctgcc acgcccacac cgctcaacgc ccacacacgt    6420

gccgccttcc ggtttagttg ggtggtacct gaccgtagat ttttcactgc ggacatgtgt    6480

ccaatcagtg gcaacgtgca acgaaccgtg gcaaacacag ggaaagaacc tcgaagaccc    6540

acagcaaact catcctctcg aatttgacac tatgataatg cttatattca attttttgca    6600

acattctatt tacactaaac tgagaaacag gacaaagttg agaatgggtg ctgtgattat    6660

ttgtcttgtg ccaatatatg ccctcctgca tataaaatac gagatacaaa accaaacgaa    6720

ataagaacga acaagaaatc agtttaattt caatgctgat caaaccaagt tgacaactct    6780

gttgtatatt agctctaata atgacttaag gttcgaaatt taagtaactt ccaaaatggg    6840

ccagataaat actgctaata tcgaatgcaa ttcaatgagg aaatagtaat caatcagcca    6900

accctaatga aattaataat gtaatttaaa actttattcc acccattcta ataatgaaaa    6960

tcattaaata tatgtagcaa tccaattttg ttaatacata ttgtatatcc ctgatttgtc    7020

aataccaaag accagaaaaa acaccatgcc aaattccttt tattcgttga aaatcgaaac    7080

aactttgaag tattaacctg ctggctaaaa aatatgtgta ttactaaata taccatgtaa    7140

tcaaaagttc gaaataaacg tgaaatggca gctccactcg tcagccgtgc cacttttcga    7200

ctaatcaaaa tgccttttga atgcctgagt tgaatcaagt tggcttaata gttattatcc    7260

cacgcaagca aagtcaatgg cagagggaaa tgcgtagaaa ttagcacaga cttgaatgga    7320

cgcacgagtg tcgaatggca ggagagtggg aaatgaacgg ggagttttcc aggataagga    7380

tgttttcgaa gtatcgtaat catttatagc ctccagatac gggagctgca tgtgtcagag    7440

gttttcaccg tcatcaccga aacgcgcgat gcagctctgg cccgtgtctc aaaatctctg    7500

atgttacatt gcacaagata aaaatatatc atcatgaaca ataaaactgt ctgcttacat    7560

aaacagtaat acaaggggtg ttgaagatcc tttgatcttt tctacggggt ctgacgctca    7620

gtggaacgaa aactcacgtt aagggatttt ggtcatgaga ttatcaaaaa ggatcttcac    7680

ctagatcctt ttaaattaaa aatgaagttt taaatcaagc ccaatctgaa taatgttaca    7740

accaattaac caattctgat tagaaaaact catcgagcat caaatgaaac tgcaatttat    7800

tcatatcagg attatcaata ccatattttt gaaaaagccg tttctgtaat gaaggagaaa    7860

actcaccgag gcagttccat aggatggcaa gatcctggta tcggtctgcg attccgactc    7920

gtccaacatc aatacaacct attaatttcc cctcgtcaaa aataaggtta tcaagtgaga    7980

aatcaccatg agtgacgact gaatccggtg agaatggcaa aagtttatgc atttctttcc    8040

agacttgttc aacaggccag ccattacgct cgtcatcaaa atcactcgca tcaaccaaac    8100

cgttattcat tcgtgattgc gcctgagcga gacgaaatac gcgatcgctg ttaaaaggac    8160

aattacaaac aggaatcgaa tgcaaccggc gcaggaacac tgccagcgca tcaacaatat    8220

tttcacctga atcaggatat tcttctaata cctggaatgc tgttttttccg gggatcgcag    8280
```

tggtgagtaa ccatgcatca tcaggagtac ggataaaatg cttgatggtc ggaagaggca 8340
taaattccgt cagccagttt agtctgacca tctcatctgt aacatcattg gcaacgctac 8400
ctttgccatg tttcagaaac aactctggcg catcgggctt cccatacaag cgatagattg 8460
tcgcacctga ttgcccgaca ttatcgcgag cccatttata cccatataaa tcagcatcca 8520
tgttggaatt taatcgcggc ctcgacgttt cccgttgaat atggctcata acaccccttg 8580
tattactgtt tatgtaagca gacagtttta ttgttcatga tgatatattt ttatcttgtg 8640
caatgtaaca tcagagattt tgagacacgg gccagagctg catcgcgcgt tttcagaatt 8700
ggttaattgg ttgtaacatt attcagattg ggcttgattt aaaacttcat ttttaattta 8760
aaaggatcta ggtgaagatc ctttttgata atctcatgac caaaatccct taacgtgagt 8820
tttcgttcca ctgagcgtca gaccccgtag aaaagatcaa aggatcttct ttccataggc 8880
tccgcccccc tgacgagcat cacaaaaatc gacgctcaag tcagaggtgg cgaaacccga 8940
caggactata aagataccag gcgtttcccc ctggaagctc cctcgtgcgc tctcctgttc 9000
cgaccctgcc gcttaccgga tacctgtccg cctttctccc ttcgggaagc gtggcgcttt 9060
ctcatagctc acgctgtagg tatctcagtt cggtgtaggt cgttcgctcc aagctgggct 9120
gtgtgcacga accccccgtt cagcccgacc gctgcgcctt atccggtaac tatcgtcttg 9180
agtccaaccc ggtaagacac gacttatcgc cactggcagc agccactggt aacaggatta 9240
gcagagcgag gtatgtaggc ggtgctacag agttcttgaa gtggtggcct aactacggct 9300
acactagaag aacagtattt ggtatctgcg ctctgctgaa gccagttacc ttcggaaaaa 9360
gagttggtag ctcttgatcc ggcaaacaaa ccaccgctgg tagcggtggt ttttttgttt 9420
gcaagcagca gattacgcgc agaaaaaaag gatctcaaaa cgccagcaac gcggcctttt 9480
tacggttcct ggccttttgc tggccttttg ctcacatgtt ctttcctgcg ttatcccctg 9540
attctgtgga taaccgtatt accgcctttg agtgagctga taccgctcgc cgcagccgaa 9600
cgaccgagcg cagcgagtca gtgagcgagg aagcggaaga gcgcccaata cgcaaaccgc 9660
ctctc 9665

<210> SEQ ID NO 16
<211> LENGTH: 6236
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
cccgcgcgtt ggccgattca ttaatgcagc tggcacgaca ggtttcccga ctggaaagcg 60
ggcagtgagc gcaacgcaat ttcacacag gaaacagcta tgaccatgat tacgccaagc 120
ttgcatgcat ttaaatgacg cagctgcgcg ctcgctcgct cactgaggcc gcccgggcaa 180
agcccgggcg tcgggcgacc tttggtcgcc cggcctcagt gagcgagcga gcgcgcagag 240
agggagtggc caactccatc actaggggtt gagtttaaac ttcgtcgacg atctgcggcc 300
gcacgcgtgg agctagttat taatagtaat caattacggg gtcattagtt catagcccat 360
atatggagtt ccgcgttaca taacttacgg taaatggccc gcctggctga ccgcccaacg 420
acccccgccc attgacgtca ataatgacgt atgttcccat agtaacgtca atagggactt 480
tccattgacg tcaatgggtg gagtatttac ggtaaactgc ccacttggca gtacatcaag 540
tgtatcatat gccaagtacg ccccctattg acgtcaatga cggtaaatgg cccgcctggc 600

-continued

```
attatgccca gtacatgacc ttatgggact ttcctacttg gcagtacatc tacgtattag    660
tcatcgctat taccatggtg atgcggtttt ggcagtacat caatgggcgt ggatagcggt    720
ttgactcacg gggatttcca agtctccacc ccattgacgt caatgggagt ttgttttgca    780
ccaaaatcaa cgggactttc caaaatgtcg taacaactcc gccccattga cgcaaatggg    840
cggtaggcgt gtacggtggg aggtctatat aagcagagct cgtttagtga accgtcagat    900
cgcctggaga cgccatccac gctgttttga cctccataga agacaccggg accgatccag    960
cctccgcgga ttcgaatccc ggccgggaac ggtgcattgg aacgcggatt ccccgtgcca   1020
agagtgacgt aagtaccgcc tatagagtct ataggcccac aaaaaatgct ttcttctttt   1080
aatatacttt tttgtttatc ttatttctaa tactttccct aatctctttc tttcagggca   1140
ataatgatac aatgtatcat gcctctttgc accattctaa agaataacag tgataatttc   1200
tgggttaagg caatagcaat atttctgcat ataaatattt ctgcatataa attgtaactg   1260
atgtaagagg tttcatattg ctaatagcag ctacaatcca gctaccattc tgcttttatt   1320
ttatggttgg gataaggctg gattattctg agtccaagct aggccctttt gctaatcatg   1380
ttcatacctc ttatcttcct cccacagctc ctgggcaacg tgctggtctg tgtgctggcc   1440
catcactttg gcaaagaatt gggattcgaa catcggccgc caccatgaac gcaagtgaat   1500
tccgaaggag agggaaggag atggtggatt acgtggccaa ctacatggaa ggcattgagg   1560
gacgccaggt ctaccctgac gtggagcccg ggtacctgcg gccgctgatc cctgccgctg   1620
cccctcagga gccagacacg tttgaggaca tcatcaacga cgttgagaag ataatcatgc   1680
ctggggtgac gcactggcac agcccctact tcttcgccta cttccccact gccagctcgt   1740
acccggccat gcttgcggac atgctgtgcg gggccattgg ctgcatcggc ttctcctggg   1800
cggcaagccc agcatgcaca gagctggaga ctgtgatgat ggactggctc gggaagatgc   1860
tggaactacc aaaggcattt ttgaatgaga aagctggaga agggggagga gtgatccagg   1920
gaagtgccag tgaagccacc ctggtggccc tgctggccgc tcggaccaaa gtgatccatc   1980
ggctgcaggc agcgtcccca gagctcacac aggccgctat catggagaag ctggtggctt   2040
actcatccga tcaggcacac tcctcagtgg aaagagctgg gttaattggt ggagtgaaat   2100
taaaagccat cccctcagat ggcaacttcg ccatgcgtgc gtctgccctg caggaagccc   2160
tggagagaga caaagcggct ggcctgattc ctttctttat ggttgccacc ctggggacca   2220
caacatgctg ctcctttgac aatctcttag aagtcggtcc tatctgcaac aaggaagaca   2280
tatggctgca cgttgatgca gcctacgcag gcagtgcatt catctgccct gagttccggc   2340
accttctgaa tggagtggag tttgcagatt cattcaactt taatccccac aaatggctat   2400
tggtgaattt tgactgttct gccatgtggg tgaaaaagag aacagactta acgggagcct   2460
ttagactgga ccccacttac ctgaagcaca gccatcagga ttcagggctt atcactgact   2520
accggcattg gcagatacca ctgggcagaa gatttcgctc tttgaaaatg tggtttgtat   2580
ttaggatgta tggagtcaaa ggactgcagg cttatatccg caagcatgtc cagctgtccc   2640
atgagtttga gtcactggtg cgccaggatc cccgctttga aatctgtgtg gaagtcattc   2700
tggggcttgt ctgctttcgg ctaaagggtt ccaacaaagt gaatgaagct cttctgcaaa   2760
gaataaacag tgccaaaaaa atccacttgg ttccatgtca cctcagggac aagtttgtcc   2820
tgcgctttgc catctgttct cgcacggtgg aatctgccca tgtgcagcgg gcctgggaac   2880
acatcaaaga gctggcggcc gacgtgctgc gagcagagag ggagtaggag tgagctgctc   2940
gagagatcta cgggtggcat ccctgtgacc cctccccagt gcctctcctg gccctggaag   3000
```

ttgccactcc agtgcccacc agccttgtcc taataaaatt aagttgcatc attttgtctg 3060
actaggtgtc cttctataat attatggggt ggaggggggt ggtatggagc aaggggcaag 3120
ttgggaagac aacctgtagg gcctgcgggg tctattggga accaagctgg agtgcagtgg 3180
cacaatcttg gctcactgca atctccgcct cctgggttca agcgattctc ctgcctcagc 3240
ctcccgagtt gttgggattc caggcatgca tgaccaggct cagctaattt ttgttttttt 3300
ggtagagacg gggtttcacc atattggcca ggctggtctc caactcctaa tctcaggtga 3360
tctacccacc ttggcctccc aaattgctgg gattacaggc gtgaaccact gctcccttcc 3420
ctgtccttct gattttgtag gtaaccacgt gcggaccgag cggccgcagt taattaagct 3480
cgcgaaaccc ctagtgatgg agttggccac tccctctctg cgcgctcgct cgctcactga 3540
ggccgggcga ccaaaggtcg cccgacgccc gggctttgcc cgggcggcct cagtgagcga 3600
gcgagcgcgc agctggacga tttaaatggt accgagctcg aattcactgg ccgtcgtttt 3660
acaacgtcgt gactgggaaa accctggcgt tacccaactt aatcgccttg cagcacatcc 3720
ccctttcgcc agctggcgta atagcgaaga ggcccgcacc gatcgccctt cccaacagtt 3780
gcgcagcctg aatggcgaat ggcgcctgat gcggtatttt ctccttacgc atctgtgcgg 3840
tatttcacac cgcatatggt gcactctcag tacaatctgc tctgatgccg catagttaag 3900
ccagccccga cacccgccaa cacccgctga cgcgccctga cgggcttgtc tgctcccggc 3960
atccgcttac agacaagctg tgaccgtctc cgggagctgc atgtgtcaga ggttttcacc 4020
gtcatcaccg aaacgcgcga tgcagctctg gcccgtgtct caaaatctct gatgttacat 4080
tgcacaagat aaaaatatat catcatgaac aataaaactg tctgcttaca taaacagtaa 4140
tacaaggggt gttgaagatc ctttgatctt ttctacgggg tctgacgctc agtggaacga 4200
aaactcacgt taagggattt tggtcatgag attatcaaaa aggatcttca cctagatcct 4260
tttaaattaa aaatgaagtt ttaaatcaag cccaatctga ataatgttac aaccaattaa 4320
ccaattctga ttagaaaaac tcatcgagca tcaaatgaaa ctgcaattta ttcatatcag 4380
gattatcaat accatatttt tgaaaaagcc gtttctgtaa tgaaggagaa aactcaccga 4440
ggcagttcca taggatggca agatcctggt atcggtctgc gattccgact cgtccaacat 4500
caatacaacc tattaatttc ccctcgtcaa aaataaggtt atcaagtgag aaatcaccat 4560
gagtgacgac tgaatccggt gagaatggca aaagtttatg catttctttc cagacttgtt 4620
caacaggcca gccattacgc tcgtcatcaa aatcactcgc atcaaccaaa ccgttattca 4680
ttcgtgattg cgcctgagcg agacgaaata cgcgatcgct gttaaaagga caattacaaa 4740
caggaatcga atgcaaccgg cgcaggaaca ctgccagcgc atcaacaata ttttcacctg 4800
aatcaggata ttcttctaat acctggaatg ctgtttttcc ggggatcgca gtggtgagta 4860
accatgcatc atcaggagta cggataaaat gcttgatggt cggaagaggc ataaattccg 4920
tcagccagtt tagtctgacc atctcatctg taacatcatt ggcaacgcta cctttgccat 4980
gtttcagaaa caactctggc gcatcgggct tcccatacaa gcgatagatt gtcgcacctg 5040
attgcccgac attatcgcga gcccatttat acccatataa atcagcatcc atgttggaat 5100
ttaatcgcgg cctcgacgtt tcccgttgaa tatggctcat aacacccctt gtattactgt 5160
ttatgtaagc agacagtttt attgttcatg atgatatatt tttatcttgt gcaatgtaac 5220
atcagagatt ttgagacacg ggccagagct gcatcgcgcg ttttcagaat tggttaattg 5280
gttgtaacat tattcagatt gggcttgatt taaaacttca tttttaattt aaaaggatct 5340

```
aggtgaagat cctttttgat aatctcatga ccaaaatccc ttaacgtgag ttttcgttcc   5400

actgagcgtc agaccccgta gaaaagatca aaggatcttc tttccatagg ctccgccccc   5460

ctgacgagca tcacaaaaat cgacgctcaa gtcagaggtg gcgaaacccg acaggactat   5520

aaagatacca ggcgtttccc cctggaagct ccctcgtgcg ctctcctgtt ccgaccctgc   5580

cgcttaccgg atacctgtcc gcctttctcc cttcgggaag cgtggcgctt tctcatagct   5640

cacgctgtag gtatctcagt tcggtgtagg tcgttcgctc caagctgggc tgtgtgcacg   5700

aaccccccgt tcagcccgac cgctgcgcct tatccggtaa ctatcgtctt gagtccaacc   5760

cggtaagaca cgacttatcg ccactggcag cagccactgg taacaggatt agcagagcga   5820

ggtatgtagg cggtgctaca gagttcttga agtggtggcc taactacggc tacactagaa   5880

gaacagtatt tggtatctgc gctctgctga agccagttac cttcggaaaa agagttggta   5940

gctcttgatc cggcaaacaa accaccgctg gtagcggtgg tttttttgtt tgcaagcagc   6000

agattacgcg cagaaaaaaa ggatctcaaa acgccagcaa cgcggccttt ttacggttcc   6060

tggccttttg ctggcctttt gctcacatgt tctttcctgc gttatcccct gattctgtgg   6120

ataaccgtat taccgccttt gagtgagctg ataccgctcg ccgcagccga acgaccgagc   6180

gcagcgagtc agtgagcgag gaagcggaag agcgcccaat acgcaaaccg cctctc       6236
```

```
<210> SEQ ID NO 17
<211> LENGTH: 3497
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgagtttaaa cttcgtcgac gatctgcggc cgcacgcgtg    180

gagctagtta ttaatagtaa tcaattacgg ggtcattagt tcatagccca tatatggagt    240

tccgcgttac ataacttacg gtaaatggcc cgcctggctg accgcccaac gacccccgcc    300

cattgacgtc aataatgacg tatgttccca tagtaacgtc aatagggact ttccattgac    360

gtcaatgggt ggagtattta cggtaaactg cccacttggc agtacatcaa gtgtatcata    420

tgccaagtac gccccctatt gacgtcaatg acggtaaatg gcccgcctgg cattatgccc    480

agtacatgac cttatgggac tttcctactt ggcagtacat ctacgtatta gtcatcgcta    540

ttaccatggt gatgcggttt tggcagtaca tcaatgggcg tggatagcgg tttgactcac    600

ggggatttcc aagtctccac cccattgacg tcaatgggag tttgttttgc accaaaatca    660

acgggacttt ccaaaatgtc gtaacaactc cgccccattg acgcaaatgg gcggtaggcg    720

tgtacggtgg gaggtctata taagcagagc tcgtttagtg aaccgtcaga tcgcctggag    780

acgccatcca cgctgttttg acctccatag aagacaccgg gaccgatcca gcctccgcgg    840

attcgaatcc cggccgggaa cggtgcattg gaacgcggat tccccgtgcc aagagtgacg    900

taagtaccgc ctatagagtc tataggccca caaaaaatgc tttcttcttt taatatactt    960

ttttgtttat cttatttcta atactttccc taatctcttt ctttcagggc aataatgata   1020

caatgtatca tgcctctttg caccattcta aagaataaca gtgataattt ctgggttaag   1080

gcaatagcaa tatttctgca tataaatatt tctgcatata aattgtaact gatgtaagag   1140
```

-continued

```
gtttcatatt gctaatagca gctacaatcc agctaccatt ctgcttttat tttatggttg   1200
ggataaggct ggattattct gagtccaagc taggcccttt tgctaatcat gttcatacct   1260
cttatcttcc tcccacagct cctgggcaac gtgctggtct gtgtgctggc ccatcacttt   1320
ggcaaagaat tgggattcga acatcggccg ccaccatgaa cgcaagtgaa ttccgaagga   1380
gagggaagga gatggtggat tacgtggcca actacatgga aggcattgag ggacgccagg   1440
tctaccctga cgtggagccc gggtacctgc ggccgctgat ccctgccgct gcccctcagg   1500
agccagacac gtttgaggac atcatcaacg acgttgagaa gataatcatg cctggggtga   1560
cgcactggca cagcccctac ttcttcgcct acttccccac tgccagctcg tacccggcca   1620
tgcttgcgga catgctgtgc ggggccattg gctgcatcgg cttctcctgg gcggcaagcc   1680
cagcatgcac agagctggag actgtgatga tggactggct cgggaagatg ctggaactac   1740
caaaggcatt tttgaatgag aaagctggag aagggggagg agtgatccag ggaagtgcca   1800
gtgaagccac cctggtggcc ctgctggccg ctcggaccaa agtgatccat cggctgcagg   1860
cagcgtcccc agagctcaca caggccgcta tcatggagaa gctggtggct tactcatccg   1920
atcaggcaca ctcctcagtg gaaagagctg ggttaattgg tggagtgaaa ttaaaagcca   1980
tcccctcaga tggcaacttc gccatgcgtg cgtctgccct gcaggaagcc ctggagagag   2040
acaaagcggc tggcctgatt cctttcttta tggttgccac cctggggacc acaacatgct   2100
gctcctttga caatctctta gaagtcggtc ctatctgcaa caaggaagac atatggctgc   2160
acgttgatgc agcctacgca ggcagtgcat tcatctgccc tgagttccgg caccttctga   2220
atggagtgga gtttgcagat tcattcaact ttaatcccca caaatggcta ttggtgaatt   2280
ttgactgttc tgccatgtgg gtgaaaaaga gaacagactt aacgggagcc tttagactgg   2340
accccactta cctgaagcac agccatcagg attcagggct tatcactgac taccggcatt   2400
ggcagatacc actgggcaga agatttcgct ctttgaaaat gtggtttgta tttaggatgt   2460
atggagtcaa aggactgcag gcttatatcc gcaagcatgt ccagctgtcc catgagtttg   2520
agtcactggt gcgccaggat ccccgctttg aaatctgtgt ggaagtcatt ctggggcttg   2580
tctgctttcg gctaaagggt tccaacaaag tgaatgaagc tcttctgcaa agaataaaca   2640
gtgccaaaaa aatccacttg gttccatgtc acctcaggga caagtttgtc ctgcgctttg   2700
ccatctgttc tcgcacggtg gaatctgccc atgtgcagcg ggcctgggaa cacatcaaag   2760
agctggcggc cgacgtgctg cgagcagaga gggagtagga gtgagctgct cgagagatct   2820
acgggtggca tccctgtgac ccctccccag tgcctctcct ggccctggaa gttgccactc   2880
cagtgcccac cagccttgtc ctaataaaat taagttgcat cattttgtct gactaggtgt   2940
ccttctataa tattatgggg tggagggggg tggtatggag caaggggcaa gttgggaaga   3000
caacctgtag ggcctgcggg gtctattggg aaccaagctg gagtgcagtg gcacaatctt   3060
ggctcactgc aatctccgcc tcctgggttc aagcgattct cctgcctcag cctcccgagt   3120
tgttgggatt ccaggcatgc atgaccaggc tcagctaatt tttgtttttt tggtagagac   3180
ggggtttcac catattggcc aggctggtct ccaactccta atctcaggtg atctacccac   3240
cttggcctcc caaattgctg ggattacagg cgtgaaccac tgctcccttc cctgtccttc   3300
tgattttgta ggtaaccacg tgcggaccga gcggccgcag ttaattaagc tcgcgaagga   3360
acccctagtg atggagttgg ccactccctc tctgcgcgct cgctcgctca ctgaggccgg   3420
gcgaccaaag gtcgcccgac gcccgggctt tgcccgggcg gcctcagtga gcgagcgagc   3480
gcgcagctgc ctgcagg                                                  3497
```

<210> SEQ ID NO 18
<211> LENGTH: 3497
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgagtttaaa cttcgtcgac gatctgcggc cgcacgcgtg 180
gagctagtta ttaatagtaa tcaattacgg ggtcattagt tcatagccca tatatggagt 240
tccgcgttac ataacttacg gtaaatggcc cgcctggctg accgcccaac gacccccgcc 300
cattgacgtc aataatgacg tatgttccca tagtaacgtc aatagggact ttccattgac 360
gtcaatgggt ggagtattta cggtaaactg cccacttggc agtacatcaa gtgtatcata 420
tgccaagtac gccccctatt gacgtcaatg acggtaaatg gcccgcctgg cattatgccc 480
agtacatgac cttatgggac tttcctactt ggcagtacat ctacgtatta gtcatcgcta 540
ttaccatggt gatgcggttt tggcagtaca tcaatgggcg tggatagcgg tttgactcac 600
ggggatttcc aagtctccac cccattgacg tcaatgggag tttgttttgc accaaaatca 660
acgggacttt ccaaaatgtc gtaacaactc cgccccattg acgcaaatgg gcggtaggcg 720
tgtacggtgg gaggtctata taagcagagc tcgtttagtg aaccgtcaga tcgcctggag 780
acgccatcca cgctgttttg acctccatag aagacaccgg gaccgatcca gcctccgcgg 840
attcgaatcc cggccgggaa cggtgcattg gaacgcggat tccccgtgcc aagagtgacg 900
taagtaccgc ctatagagtc tataggccca caaaaaatgc tttcttcttt taatatactt 960
ttttgtttat cttatttcta atactttccc taatctcttt ctttcagggc aataatgata 1020
caatgtatca tgcctctttg caccattcta aagaataaca gtgataattt ctgggttaag 1080
gcaatagcaa tatttctgca tataaatatt tctgcatata aattgtaact gatgtaagag 1140
gtttcatatt gctaatagca gctacaatcc agctaccatt ctgcttttat tttatggttg 1200
ggataaggct ggattattct gagtccaagc taggcccttt tgctaatcat gttcatacct 1260
cttatcttcc tcccacagct cctgggcaac gtgctggtct gtgtgctggc ccatcacttt 1320
ggcaaagaat tgggattcga acatcggccg ccaccatgaa cgcaagtgaa ttccgaagga 1380
gagggaagga gatggtggat tacgtggcca actacatgga aggcattgag ggacgccagg 1440
tctaccctga cgtggagccc gggtacctgc ggccgctgat ccctgccgct gcccctcagg 1500
agccagacac gtttgaggac atcatcaacg acgttgagaa gataatcatg cctggggtga 1560
cgcactggca cagcccctac ttcttcgcct acttccccac tgccagctcg tacccggcca 1620
tgcttgcgga catgctgtgc ggggccattg gctgcatcgg cttctcctgg gcggcaagcc 1680
cagcatgcac agagctggag actgtgatga tggactggct cgggaagatg ctggaactac 1740
caaaggcatt tttgaatgag aaagctggag aagggggagg agtgatccag ggaagtgcca 1800
gtgaagccac cctggtggcc ctgctggccg ctcggaccaa agtgatccat cggctgcagg 1860
cagcgtcccc agagctcaca caggccgcta tcatggagaa gctggtggct tactcatccg 1920
atcaggcaca ctcctcagtg gaaagagctg ggttaattgg tggagtgaaa ttaaaagcca 1980
tcccctcaga tggcaacttc gccatgcgtg cgtctgccct gcaggaagcc ctggagagag 2040

-continued acaaagcggc tggcctgatt cctttcttta tggttgccac cctggggacc acaacatgct 2100
gctcctttga caatctctta gaagtcggtc ctatctgcaa caaggaagac atatggctgc 2160
acgttgatgc agcctacgca ggcagtgcat tcatctgccc tgagttccgg caccttctga 2220
atggagtgga gtttgcagat tcattcaact ttaatcccca caaatggcta ttggtgaatt 2280
ttgactgttc tgccatgtgg gtgaaaaaga gaacagactt aacgggagcc tttagactgg 2340
accccactta cctgaagcac agccatcagg attcagggct tatcactgac taccggcatt 2400
ggcagatacc actgggcaga agatttcgct ctttgaaaat gtggtttgta tttaggatgt 2460
atggagtcaa aggactgcag gcttatatcc gcaagcatgt ccagctgtcc catgagtttg 2520
agtcactggt gcgccaggat ccccgctttg aaatctgtgt ggaagtcatt ctggggcttg 2580
tctgctttcg gctaaagggt tccaacaaag tgaatgaagc tcttctgcaa agaataaaca 2640
gtgccaaaaa aatccacttg gttccatgtc acctcaggga caagtttgtc ctgcgctttg 2700
ccatctgttc tcgcacggtg gaatctgccc atgtgcagcg ggcctgggaa cacatcaaag 2760
agctggcggc cgacgtgctg cgagcagaga gggagtagga gtgagctgct cgagagatct 2820
acgggtggca tccctgtgac ccctccccag tgcctctcct ggccctggaa gttgccactc 2880
cagtgcccac cagccttgtc ctaataaaat taagttgcat cattttgtct gactaggtgt 2940
ccttctataa tattatgggg tggagggggg tggtatggag caaggggcaa gttgggaaga 3000
caacctgtag ggcctgcggg gtctattggg aaccaagctg gagtgcagtg gcacaatctt 3060
ggctcactgc aatctccgcc tcctgggttc aagcgattct cctgcctcag cctcccgagt 3120
tgttgggatt ccaggcatgc atgaccaggc tcagctaatt tttgtttttt tggtagagac 3180
ggggtttcac catattggcc aggctggtct ccaactccta atctcaggtg atctacccac 3240
cttggcctcc caaattgctg ggattacagg cgtgaaccac tgctcccttc cctgtccttc 3300
tgattttgta ggtaaccacg tgcggaccga gcggccgcag ttaattaagc tcgcgaagga 3360
acccctagtg atggagttgg ccactccctc tctgcgcgct cgctcgctca ctgaggccgg 3420
gcgaccaaag gtcgcccgac gcccgggctt tgcccgggcg gcctcagtga gcgagcgagc 3480
gcgcagctgc ctgcagg 3497

<210> SEQ ID NO 19
<211> LENGTH: 3491
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 19
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgagtttaaa cttcgtcgac gatctgcggc cgcacgcgtg 180
gagctagtta ttaatagtaa tcaattacgg ggtcattagt tcatagccca tatatggagt 240
tccgcgttac ataacttacg gtaaatggcc cgcctggctg accgcccaac gacccccgcc 300
cattgacgtc aataatgacg tatgttccca tagtaacgtc aatagggact ttccattgac 360
gtcaatgggt ggagtattta cggtaaactg cccacttggc agtacatcaa gtgtatcata 420
tgccaagtac gccccctatt gacgtcaatg acggtaaatg gcccgcctgg cattatgccc 480
agtacatgac cttatgggac tttcctactt ggcagtacat ctacgtatta gtcatcgcta 540

-continued

```
ttaccatggt gatgcggttt tggcagtaca tcaatgggcg tggatagcgg tttgactcac    600
ggggatttcc aagtctccac cccattgacg tcaatgggag tttgttttgc accaaaatca    660
acgggacttt ccaaaatgtc gtaacaactc cgccccattg acgcaaatgg gcggtaggcg    720
tgtacggtgg gaggtctata taagcagagc tcgtttagtg aaccgtcaga tcgcctggag    780
acgccatcca cgctgttttg acctccatag aagacaccgg gaccgatcca gcctccgcgg    840
attcgaatcc cggccgggaa cggtgcattg gaacgcggat tccccgtgcc aagagtgacg    900
taagtaccgc ctatagagtc tataggccca caaaaaatgc tttcttcttt taatatactt    960
ttttgtttat cttatttcta atactttccc taatctcttt ctttcagggc aataatgata   1020
caatgtatca tgcctctttg caccattcta aagaataaca gtgataattt ctgggttaag   1080
gcaatagcaa tatttctgca tataaatatt tctgcatata aattgtaact gatgtaagag   1140
gtttcatatt gctaatagca gctacaatcc agctaccatt ctgcttttat tttatggttg   1200
ggataaggct ggattattct gagtccaagc taggcccttt tgctaatcat gttcatacct   1260
cttatcttcc tcccacagct cctgggcaac gtgctggtct gtgtgctggc ccatcacttt   1320
ggcaaagaat tgggattcga acatcggccg ccaccatgaa cgccagcgag ttcaggagga   1380
ggggcaagga gatggtggac tacgtggcca actacatgga gggcatcgag ggcaggcagg   1440
tgtaccccga cgtggagccc ggctacctga ggcccctgat ccccgccgcc gccccccagg   1500
agcccgacac cttcgaggac atcatcaacg acgtggagaa gatcatcatg cccggcgtga   1560
cccactggca cagcccctac ttcttcgcct acttccccac cgccagcagc taccccgcca   1620
tgctggccga catgctgtgc ggcgccatcg gctgcatcgg cttcagctgg gccgccagcc   1680
ccgcctgcac cgagctggag accgtgatga tggactggct gggcaagatg ctggagctgc   1740
ccaaggcctt cctgaacgag aaggccggcg agggcggcgg cgtgatccag ggcagcgcca   1800
gcgaggccac cctggtggcc ctgctggccg ccaggaccaa ggtgatccac aggctgcagg   1860
ccgccagccc cgagctgacc caggccgcca tcatggagaa gctggtggcc tacagcagcg   1920
accaggccca cagcagcgtg gagagggccg gcctgatcgg cggcgtgaag ctgaaggcca   1980
tccccagcga cggcaacttc gccatgaggg ccagcgccct gcaggaggcc ctggagaggg   2040
acaaggccgc cggcctgatc cccttcttca tggtggccac cctgggcacc accacctgct   2100
gcagcttcga caacctgctg gaggtgggcc ccatctgcaa caaggaggac atctggctgc   2160
acgtggacgc cgcctacgcc ggcagcgcct tcatctgccc cgagttcagg cacctgctga   2220
acggcgtgga gttcgccgac agcttcaact tcaacccca caagtggctg ctggtgaact   2280
tcgactgcag cgccatgtgg gtgaagaaga ggaccgacct gaccggcgcc ttcaggctgg   2340
accccaccta cctgaagcac agccaccagg acagcggcct gatcaccgac tacaggcact   2400
ggcagatccc cctgggcagg aggttcagga gcctgaagat gtggttcgtg ttcaggatgt   2460
acggcgtgaa gggcctgcag gcctacatca ggaagcacgt gcagctgagc cacgagttcg   2520
agagcctggt gaggcaggac cccaggttcg agatctgcgt ggaggtgatc ctgggcctgg   2580
tgtgcttcag gctgaagggc agcaacaagg tgaacgaggc cctgctgcag aggatcaaca   2640
gcgccaagaa gatccacctg gtgccctgcc acctgaggga caagttcgtg ctgaggttcg   2700
ccatctgcag caggaccgtg gagagcgccc acgtgcagag ggcctgggag cacatcaagg   2760
agctggccgc cgacgtgctg agggccgaga gggagtgagc tgctcgagag atctacgggt   2820
ggcatccctg tgacccctcc ccagtgcctc tcctggccct ggaagttgcc actccagtgc   2880
```

-continued

```
ccaccagcct tgtcctaata aaattaagtt gcatcatttt gtctgactag gtgtccttct   2940
ataatattat ggggtggagg ggggtggtat ggagcaaggg gcaagttggg aagacaacct   3000
gtagggcctg cggggtctat tgggaaccaa gctggagtgc agtggcacaa tcttggctca   3060
ctgcaatctc cgcctcctgg gttcaagcga ttctcctgcc tcagcctccc gagttgttgg   3120
gattccaggc atgcatgacc aggctcagct aatttttgtt tttttggtag agacggggtt   3180
tcaccatatt ggccaggctg gtctccaact cctaatctca ggtgatctac ccaccttggc   3240
ctcccaaatt gctgggatta caggcgtgaa ccactgctcc cttccctgtc cttctgattt   3300
tgtaggtaac cacgtgcgga ccgagcggcc gcagttaatt aagctcgcga aggaacccct   3360
agtgatggag ttggccactc cctctctgcg cgctcgctcg ctcactgagg ccgggcgacc   3420
aaaggtcgcc cgacgcccgg gctttgcccg ggcggcctca gtgagcgagc gagcgcgcag   3480
ctgcctgcag g                                                        3491
```

<210> SEQ ID NO 20
<211> LENGTH: 4003
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgagtttaaa cttcgtcgac gatctgcggc cgcacgcgtg    180
gagctagtta ttaatagtaa tcaattacgg ggtcattagt tcatagccca tatatggagt    240
tccgcgttac ataacttacg gtaaatggcc cgcctggctg accgcccaac gacccccgcc    300
cattgacgtc aataatgacg tatgttccca tagtaacgtc aatagggact ttccattgac    360
gtcaatgggt ggagtattta cggtaaactg cccacttggc agtacatcaa gtgtatcata    420
tgccaagtac gccccctatt gacgtcaatg acggtaaatg gcccgcctgg cattatgccc    480
agtacatgac cttatgggac tttcctactt ggcagtacat ctacgtatta gtcatcgcta    540
ttaccatggt gatgcggttt tggcagtaca tcaatgggcg tggatagcgg tttgactcac    600
ggggatttcc aagtctccac cccattgacg tcaatgggag tttgttttgc accaaaatca    660
acgggacttt ccaaaatgtc gtaacaactc cgccccattg acgcaaatgg gcggtaggcg    720
tgtacggtgg gaggtctata taagcagagc tcgtttagtg aaccgtcaga tcgcctggag    780
acgccatcca cgctgttttg acctccatag aagacaccgg gaccgatcca gcctccgcgg    840
attcgaatcc cggccgggaa cggtgcattg gaacgcggat tccccgtgcc aagagtgacg    900
taagtaccgc ctatagagtc tataggccca caaaaaatgc tttcttcttt taatatactt    960
ttttgtttat cttatttcta atactttccc taatctcttt ctttcagggc aataatgata   1020
caatgtatca tgcctctttg caccattcta aagaataaca gtgataattt ctgggttaag   1080
gcaatagcaa tatttctgca tataaatatt tctgcatata aattgtaact gatgtaagag   1140
gtttcatatt gctaatagca gctacaatcc agctaccatt ctgcttttat tttatggttg   1200
ggataaggct ggattattct gagtccaagc taggcccttt tgctaatcat gttcatacct   1260
cttatcttcc tcccacagct cctgggcaac gtgctggtct gtgtgctggc ccatcacttt   1320
ggcaaagaat tgggattcga acatcgaatt cgggcacgag ggaggacaga gagcaagtca   1380
```

-continued

```
ctcccggctg cctttttcac ctctgacaga gcccagacac catgaacgca agtgaattcc   1440
gaaggagagg gaaggagatg gtggattacg tggccaacta catggaaggc attgagggac   1500
gccaggtcta ccctgacgtg gagcccgggt acctgcggcc gctgatccct gccgctgccc   1560
ctcaggagcc agacacgttt gaggacatca tcaacgacgt tgagaagata atcatgcctg   1620
gggtgacgca ctggcacagc ccctacttct tcgcctactt ccccactgcc agctcgtacc   1680
cggccatgct tgcggacatg ctgtgcgggg ccattggctg catcggcttc tcctgggcgg   1740
caagcccagc atgcacagag ctggagactg tgatgatgga ctggctcggg aagatgctgg   1800
aactaccaaa ggcatttttg aatgagaaag ctggagaagg gggaggagtg atccagggaa   1860
gtgccagtga agccaccctg gtggccctgc tggccgctcg gaccaaagtg atccatcggc   1920
tgcaggcagc gtccccagag ctcacacagg ccgctatcat ggagaagctg gtggcttact   1980
catccgatca ggcacactcc tcagtggaaa gagctgggtt aattggtgga gtgaaattaa   2040
aagccatccc ctcagatggc aacttcgcca tgcgtgcgtc tgccctgcag gaagccctgg   2100
agagagacaa agcggctggc ctgattcctt tctttatggt tgccaccctg ggaccacaa    2160
catgctgctc ctttgacaat ctcttagaag tcggtcctat ctgcaacaag gaagacatat   2220
ggctgcacgt tgatgcagcc tacgcaggca gtgcattcat ctgccctgag ttccggcacc   2280
ttctgaatgg agtggagttt gcagattcat tcaactttaa tccccacaaa tggctattgg   2340
tgaattttga ctgttctgcc atgtgggtga aaaagagaac agacttaacg ggagccttta   2400
gactggaccc cacttacctg aagcacagcc atcaggattc agggcttatc actgactacc   2460
ggcattggca gataccactg ggcagaagat ttcgctcttt gaaaatgtgg tttgtattta   2520
ggatgtatgg agtcaaagga ctgcaggctt atatccgcaa gcatgtccag ctgtcccatg   2580
agtttgagtc actggtgcgc caggatcccc gctttgaaat ctgtgtggaa gtcattctgg   2640
ggcttgtctg ctttcggcta aagggttcca acaaagtgaa tgaagctctt ctgcaaagaa   2700
taaacagtgc caaaaaaatc cacttggttc catgtcacct cagggacaag tttgtcctgc   2760
gctttgccat ctgttctcgc acggtggaat ctgcccatgt gcagcgggcc tgggaacaca   2820
tcaaagagct ggcggccgac gtgctgcgag cagagaggga gtaggagtga agccagctgc   2880
aggaatcaaa aattgaagag agatatatct gaaaactgga ataagaagca aataaatatc   2940
atcctgcctt catggaactc agctgtctgt ggcttcccat gtctttctcc aaagttatcc   3000
agagggttgt gattttgtct gcttagtatc tcatcaacaa agaaatatta tttgctaatt   3060
aaaaagttaa tcttcatggc catagctttt attcattagc tgtgattttt gttgattaaa   3120
acattataga ttttcatgtt cttgcagtca tcagaagtgg taggaaagcc tcactgatat   3180
attttccagg gcaatcaatg ttcacgcaac ttgaaattat atctgtggtc ttcaaattgt   3240
cttttgtcat gtggctaaat gcctaataaa caattcaagt gaaatactaa aaaaaaaaaa   3300
aaaaaaaaaa gctgctcgag agatctacgg gtggcatccc tgtgacccct ccccagtgcc   3360
tctcctggcc ctggaagttg ccactccagt gcccaccagc cttgtcctaa taaaattaag   3420
ttgcatcatt ttgtctgact aggtgtcctt ctataatatt atggggtgga ggggggtggt   3480
atggagcaag gggcaagttg ggaagacaac ctgtagggcc tgcggggtct attgggaacc   3540
aagctggagt gcagtggcac aatcttggct cactgcaatc tccgcctcct gggttcaagc   3600
gattctcctg cctcagcctc ccgagttgtt gggattccag gcatgcatga ccaggctcag   3660
ctaatttttg tttttttggt agagacgggg tttcaccata ttggccaggc tggtctccaa   3720
ctcctaatct caggtgatct acccaccttg gcctcccaaa ttgctgggat tacaggcgtg   3780
```

aaccactgct cccttccctg tccttctgat tttgtaggta accacgtgcg gaccgagcgg 3840
ccgcagttaa ttaagctcgc gaaggaaccc ctagtgatgg agttggccac tccctctctg 3900
cgcgctcgct cgctcactga ggccgggcga ccaaaggtcg cccgacgccc gggctttgcc 3960
cgggcggcct cagtgagcga gcgagcgcgc agctgcctgc agg 4003

<210> SEQ ID NO 21
<211> LENGTH: 3499
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgagtt taaacttcgt cgacgatctg cggccgcacg 180
cgtggagcta gttattaata gtaatcaatt acggggtcat tagttcatag cccatatatg 240
gagttccgcg ttacataact tacggtaaat ggcccgcctg gctgaccgcc caacgacccc 300
cgcccattga cgtcaataat gacgtatgtt cccatagtaa cgtcaatagg gactttccat 360
tgacgtcaat gggtggagta tttacggtaa actgcccact tggcagtaca tcaagtgtat 420
catatgccaa gtacgccccc tattgacgtc aatgacggta aatggcccgc ctggcattat 480
gcccagtaca tgaccttatg ggactttcct acttggcagt acatctacgt attagtcatc 540
gctattacca tggtgatgcg gttttggcag tacatcaatg ggcgtggata gcggtttgac 600
tcacggggat ttccaagtct ccaccccatt gacgtcaatg ggagtttgtt ttgcaccaaa 660
atcaacggga ctttccaaaa tgtcgtaaca actccgcccc attgacgcaa atgggcggta 720
ggcgtgtacg gtgggaggtc tatataagca gagctcgttt agtgaaccgt cagatcgcct 780
ggagacgcca tccacgctgt tttgacctcc atagaagaca ccgggaccga tccagcctcc 840
gcggattcga atcccggccg ggaacggtgc attggaacgc ggattccccg tgccaagagt 900
gacgtaagta ccgcctatag agtctatagg cccacaaaaa atgctttctt cttttaatat 960
acttttttgt ttatcttatt tctaatactt tccctaatct ctttctttca gggcaataat 1020
gatacaatgt atcatgcctc tttgcaccat tctaaagaat aacagtgata atttctgggt 1080
taaggcaata gcaatatttc tgcatataaa tatttctgca tataaattgt aactgatgta 1140
agaggtttca tattgctaat agcagctaca atccagctac cattctgctt ttattttatg 1200
gttgggataa ggctggatta ttctgagtcc aagctaggcc cttttgctaa tcatgttcat 1260
acctcttatc ttcctcccac agctcctggg caacgtgctg gtctgtgtgc tggcccatca 1320
ctttggcaaa gaattgggat tcgaacatcg gccgccacca tgaacgccag cgagttcagg 1380
aggaggggca aggagatggt ggactacgtg gccaactaca tggagggcat cgagggcagg 1440
caggtgtacc ccgacgtgga gcccggctac ctgaggcccc tgatccccgc cgccgccccc 1500
caggagcccg acaccttcga ggacatcatc aacgacgtgg agaagatcat catgcccggc 1560
gtgacccact ggcacagccc ctacttcttc gcctacttcc ccaccgccag cagctacccc 1620
gccatgctgg ccgacatgct gtgcggcgcc atcggctgca tcggcttcag ctgggccgcc 1680
agccccgcct gcaccgagct ggagaccgtg atgatggact ggctgggcaa gatgctggag 1740
ctgcccaagg ccttcctgaa cgagaaggcc ggcgagggcg gcggcgtgat ccagggcagc 1800
gccagcgagg ccaccctggt ggccctgctg gccgccagga ccaaggtgat ccacaggctg 1860
caggccgcca gccccgagct gacccaggcc gccatcatgg agaagctggt ggcctacagc 1920
agcgaccagg cccacagcag cgtggagagg gccggcctga tcggcggcgt gaagctgaag 1980
gccatcccca gcgacggcaa cttcgccatg agggccagcg ccctgcagga ggccctggag 2040
agggacaagg ccgccggcct gatccccttc ttcatggtgg ccaccctggg caccaccacc 2100
tgctgcagct tcgacaacct gctggaggtg ggccccatct gcaacaagga ggacatctgg 2160
ctgcacgtgg acgccgccta cgccggcagc gccttcatct gccccgagtt caggcacctg 2220
ctgaacggcg tggagttcgc cgacagcttc aacttcaacc cccacaagtg gctgctggtg 2280
aacttcgact gcagcgccat gtgggtgaag aagaggaccg acctgaccgg cgccttcagg 2340
ctggacccca cctacctgaa gcacagccac caggacagcg gcctgatcac cgactacagg 2400
cactggcaga tccccctggg caggaggttc aggagcctga agatgtggtt cgtgttcagg 2460
atgtacggcg tgaagggcct gcaggcctac atcaggaagc acgtgcagct gagccacgag 2520
ttcgagagcc tggtgaggca ggaccccagg ttcgagatct gcgtggaggt gatcctgggc 2580
ctggtgtgct tcaggctgaa gggcagcaac aaggtgaacg aggccctgct gcagaggatc 2640
aacagcgcca agaagatcca cctggtgccc tgccacctga gggacaagtt cgtgctgagg 2700
ttcgccatct gcagcaggac cgtggagagc gcccacgtgc agagggcctg ggagcacatc 2760
aaggagctgg ccgccgacgt gctgagggcc gagagggagt gagctgctcg agagatctac 2820
gggtggcatc cctgtgaccc ctccccagtg cctctcctgg ccctggaagt tgccactcca 2880
gtgcccacca gccttgtcct aataaaatta agttgcatca ttttgtctga ctaggtgtcc 2940
ttctataata ttatggggtg gaggggggtg gtatggagca aggggcaagt tgggaagaca 3000
acctgtaggg cctgcggggt ctattgggaa ccaagctgga gtgcagtggc acaatcttgg 3060
ctcactgcaa tctccgcctc ctgggttcaa gcgattctcc tgcctcagcc tcccgagttg 3120
ttgggattcc aggcatgcat gaccaggctc agctaatttt tgttttttttg gtagagacgg 3180
ggtttcacca tattggccag gctggtctcc aactcctaat ctcaggtgat ctacccacct 3240
tggcctccca aattgctggg attacaggcg tgaaccactg ctcccttccc tgtccttctg 3300
attttgtagg taaccacgtg cggaccgagc ggccgcagtt aattaagctc gcgaaggaac 3360
ccctagtgat ggagttggcc actccctctc tgcgcgctcg ctcgctcact gaggccgggc 3420
gaccaaaggt cgcccgacgc ccgggctttg cccgggcggc ctcagtgagc gagcgagcgc 3480
gcagagaggg agtggccaa 3499

<210> SEQ ID NO 22
<211> LENGTH: 3896
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgagtttaaa cttcgtcgac gatctgcggc cgcacgcgtg 180
gagctagtta ttaatagtaa tcaattacgg ggtcattagt tcatagccca tatatggagt 240
tccgcgttac ataacttacg gtaaatggcc cgcctggctg accgcccaac gacccccgcc 300

-continued

```
cattgacgtc aataatgacg tatgttccca tagtaacgtc aatagggact ttccattgac    360
gtcaatgggt ggagtattta cggtaaactg cccacttggc agtacatcaa gtgtatcata    420
tgccaagtac gccccctatt gacgtcaatg acggtaaatg gcccgcctgg cattatgccc    480
agtacatgac cttatgggac tttcctactt ggcagtacat ctacgtatta gtcatcgcta    540
ttaccatggt gatgcggttt tggcagtaca tcaatgggcg tggatagcgg tttgactcac    600
ggggatttcc aagtctccac cccattgacg tcaatgggag tttgttttgc accaaaatca    660
acgggacttt ccaaaatgtc gtaacaactc cgccccattg acgcaaatgg gcggtaggcg    720
tgtacggtgg gaggtctata taagcagagc tcgtttagtg aaccgtcaga tcgcctggag    780
acgccatcca cgctgttttg acctccatag aagacaccgg gaccgatcca gcctccgcgg    840
attcgaatcc cggccgggaa cggtgcattg gaacgcggat tccccgtgcc aagagtgacg    900
taagtaccgc ctatagagtc tataggccca caaaaaatgc tttcttcttt taatatactt    960
ttttgtttat cttatttcta atactttccc taatctcttt ctttcagggc aataatgata   1020
caatgtatca tgcctctttg caccattcta aagaataaca gtgataattt ctgggttaag   1080
gcaatagcaa tatttctgca tataaatatt tctgcatata aattgtaact gatgtaagag   1140
gtttcatatt gctaatagca gctacaatcc agctaccatt ctgcttttat tttatggttg   1200
ggataaggct ggattattct gagtccaagc taggcccttt tgctaatcat gttcatacct   1260
cttatcttcc tcccacagct cctgggcaac gtgctggtct gtgtgctggc ccatcacttt   1320
ggcaaagaat tgggattcga acatcggccg ccaccatgaa cgcaagtgaa ttccgaagga   1380
gagggaagga gatggtggat tacgtggcca actacatgga aggcattgag ggacgccagg   1440
tctaccctga cgtggagccc gggtacctgc ggccgctgat ccctgccgct gcccctcagg   1500
agccagacac gtttgaggac atcatcaacg acgttgagaa gataatcatg cctggggtga   1560
cgcactggca cagcccctac ttcttcgcct acttccccac tgccagctcg tacccggcca   1620
tgcttgcgga catgctgtgc ggggccattg gctgcatcgg cttctcctgg gcggcaagcc   1680
cagcatgcac agagctggag actgtgatga tggactggct cgggaagatg ctggaactac   1740
caaaggcatt tttgaatgag aaagctggag aagggggagg agtgatccag ggaagtgcca   1800
gtgaagccac cctggtggcc ctgctggccg ctcggaccaa agtgatccat cggctgcagg   1860
cagcgtcccc agagctcaca caggccgcta tcatggagaa gctggtggct tactcatccg   1920
atcaggcaca ctcctcagtg gaaagagctg ggttaattgg tggagtgaaa ttaaaagcca   1980
tcccctcaga tggcaacttc gccatgcgtg cgtctgccct gcaggaagcc ctggagagag   2040
acaaagcggc tggcctgatt cctttcttta tggttgccac cctggggacc acaacatgct   2100
gctcctttga caatctctta gaagtcggtc ctatctgcaa caaggaagac atatggctgc   2160
acgttgatgc agcctacgca ggcagtgcat tcatctgccc tgagttccgg caccttctga   2220
atggagtgga gtttgcagat tcattcaact ttaatcccca caaatggcta ttggtgaatt   2280
ttgactgttc tgccatgtgg gtgaaaaaga gaacagactt aacgggagcc tttagactgg   2340
accccactta cctgaagcac agccatcagg attcagggct tatcactgac taccggcatt   2400
ggcagatacc actgggcaga agatttcgct ctttgaaaat gtggtttgta tttaggatgt   2460
atggagtcaa aggactgcag gcttatatcc gcaagcatgt ccagctgtcc catgagtttg   2520
agtcactggt gcgccaggat ccccgctttg aaatctgtgt ggaagtcatt ctggggcttg   2580
tctgctttcg gctaaagggt tccaacaaag tgaatgaagc tcttctgcaa agaataaaca   2640
```

-continued gtgccaaaaa aatccacttg gttccatgtc acctcaggga caagtttgtc ctgcgctttg 2700
ccatctgttc tcgcacggtg gaatctgccc atgtgcagcg ggcctgggaa cacatcaaag 2760
agctggcggc cgacgtgctg cgagcagaga gggagtagga gtgaagccag ctgcaggaat 2820
caaaaattga agagagatat atctgaaaac tggaataaga agcaaataaa tatcatcctg 2880
ccttcatgga actcagctgt ctgtggcttc ccatgtcttt ctccaaagtt atccagaggg 2940
ttgtgatttt gtctgcttag tatctcatca acaaagaaat attatttgct aattaaaaag 3000
ttaatcttca tggccatagc ttttattcat tagctgtgat tttgttgat taaaacatta 3060 tagattttca tgttcttgca gtcatcagaa gtggtaggaa agcctcactg atatattttc 3120
cagggcaatc aatgttcacg caacttgaaa ttatatctgt ggtcttcaaa ttgtcttttg 3180
tcatgtggct aaatgcctaa taagctgctc gagagatcta cgggtggcat ccctgtgacc 3240
cctccccagt gcctctcctg gccctggaag ttgccactcc agtgcccacc agccttgtcc 3300
taataaaatt aagttgcatc attttgtctg actaggtgtc cttctataat attatggggt 3360
ggaggggggt ggtatggagc aaggggcaag ttgggaagac aacctgtagg gcctgcgggg 3420
tctattggga accaagctgg agtgcagtgg cacaatcttg gctcactgca atctccgcct 3480
cctgggttca agcgattctc ctgcctcagc ctcccgagtt gttgggattc caggcatgca 3540
tgaccaggct cagctaattt ttgttttttt ggtagagacg gggtttcacc atattggcca 3600
ggctggtctc caactcctaa tctcaggtga tctacccacc ttggcctccc aaattgctgg 3660
gattacaggc gtgaaccact gctcccttcc ctgtccttct gattttgtag gtaaccacgt 3720
gcggaccgag cggccgcagt taattaagct cgcgaaggaa cccctagtga tggagttggc 3780
cactccctct ctgcgcgctc gctcgctcac tgaggccggg cgaccaaagg tcgcccgacg 3840
cccgggcttt gcccgggcgg cctcagtgag cgagcgagcg cgcagctgcc tgcagg 3896

<210> SEQ ID NO 23
<211> LENGTH: 3475
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 23
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt gagtttaaac ttcgtcgacg atctgcggcc gcacgcgtgg agctagttat 180
taatagtaat caattacggg gtcattagtt catagcccat atatggagtt ccgcgttaca 240
taacttacgg taaatggccc gcctggctga ccgcccaacg acccccgccc attgacgtca 300
ataatgacgt atgttcccat agtaacgtca atagggactt tccattgacg tcaatgggtg 360
gagtatttac ggtaaactgc ccacttggca gtacatcaag tgtatcatat gccaagtacg 420
ccccctattg acgtcaatga cggtaaatgg cccgcctggc attatgccca gtacatgacc 480
ttatgggact ttcctacttg gcagtacatc tacgtattag tcatcgctat taccatggtg 540
atgcggtttt ggcagtacat caatgggcgt ggatagcggt ttgactcacg gggatttcca 600
agtctccacc ccattgacgt caatgggagt ttgttttgca ccaaaatcaa cgggactttc 660
caaaatgtcg taacaactcc gccccattga cgcaaatggg cggtaggcgt gtacggtggg 720
aggtctatat aagcagagct cgtttagtga accgtcagat cgcctggaga cgccatccac 780

-continued

```
gctgttttga cctccataga agacaccggg accgatccag cctccgcgga ttcgaatccc    840
ggccgggaac ggtgcattgg aacgcggatt ccccgtgcca agagtgacgt aagtaccgcc    900
tatagagtct ataggcccac aaaaaatgct ttcttctttt aatatacttt tttgtttatc    960
ttatttctaa tactttccct aatctctttc tttcagggca ataatgatac aatgtatcat   1020
gcctctttgc accattctaa agaataacag tgataatttc tgggttaagg caatagcaat   1080
atttctgcat ataaatattt ctgcatataa attgtaactg atgtaagagg tttcatattg   1140
ctaatagcag ctacaatcca gctaccattc tgcttttatt ttatggttgg gataaggctg   1200
gattattctg agtccaagct aggccctttt gctaatcatg ttcatacctc ttatcttcct   1260
cccacagctc ctgggcaacg tgctggtctg tgtgctggcc catcactttg gcaaagaatt   1320
gggattcgaa catcggccgc caccatgaac gcaagtgaat tccgaaggag agggaaggag   1380
atggtggatt acgtggccaa ctacatggaa ggcattgagg gacgccaggt ctaccctgac   1440
gtggagcccg ggtacctgcg gccgctgatc cctgccgctg cccctcagga gccagacacg   1500
tttgaggaca tcatcaacga cgttgagaag ataatcatgc ctggggtgac gcactggcac   1560
agcccctact tcttcgccta cttccccact gccagctcgt acccggccat gcttgcggac   1620
atgctgtgcg gggccattgg ctgcatcggc ttctcctggg cggcaagccc agcatgcaca   1680
gagctggaga ctgtgatgat ggactggctc gggaagatgc tggaactacc aaaggcattt   1740
ttgaatgaga aagctggaga agggggagga gtgatccagg gaagtgccag tgaagccacc   1800
ctggtggccc tgctggccgc tcggaccaaa gtgatccatc ggctgcaggc agcgtcccca   1860
gagctcacac aggccgctat catggagaag ctggtggctt actcatccga tcaggcacac   1920
tcctcagtgg aaagagctgg gttaattggt ggagtgaaat taaaagccat cccctcagat   1980
ggcaacttcg ccatgcgtgc gtctgccctg caggaagccc tggagagaga caaagcggct   2040
ggcctgattc ctttctttat ggttgccacc ctggggacca caacatgctg ctcctttgac   2100
aatctcttag aagtcggtcc tatctgcaac aaggaagaca tatggctgca cgttgatgca   2160
gcctacgcag gcagtgcatt catctgccct gagttccggc accttctgaa tggagtggag   2220
tttgcagatt cattcaactt taatccccac aaatggctat tggtgaattt tgactgttct   2280
gccatgtggg tgaaaaagag aacagactta acgggagcct ttagactgga ccccacttac   2340
ctgaagcaca gccatcagga ttcagggctt atcactgact accggcattg gcagatacca   2400
ctgggcagaa gatttcgctc tttgaaaatg tggtttgtat ttaggatgta tggagtcaaa   2460
ggactgcagg cttatatccg caagcatgtc cagctgtccc atgagtttga gtcactggtg   2520
cgccaggatc cccgctttga aatctgtgtg gaagtcattc tggggcttgt ctgctttcgg   2580
ctaaagggtt ccaacaaagt gaatgaagct cttctgcaaa gaataaacag tgccaaaaaa   2640
atccacttgg ttccatgtca cctcagggac aagtttgtcc tgcgctttgc catctgttct   2700
cgcacggtgg aatctgccca tgtgcagcgg gcctgggaac acatcaaaga gctggcggcc   2760
gacgtgctgc gagcagagag ggagtaggag tgagctgctc gagagatcta cgggtggcat   2820
ccctgtgacc cctccccagt gcctctcctg gccctggaag ttgccactcc agtgcccacc   2880
agccttgtcc taataaaatt aagttgcatc attttgtctg actaggtgtc cttctataat   2940
attatggggt ggaggggggt ggtatggagc aaggggcaag ttgggaagac aacctgtagg   3000
gcctgcgggg tctattggga accaagctgg agtgcagtgg cacaatcttg gctcactgca   3060
atctccgcct cctgggttca agcgattctc ctgcctcagc ctcccgagtt gttgggattc   3120
caggcatgca tgaccaggct cagctaattt ttgttttttt ggtagagacg ggtttcacc    3180
```

-continued

```
atattggcca ggctggtctc caactcctaa tctcaggtga tctacccacc ttggcctccc   3240

aaattgctgg gattacaggc gtgaaccact gctcccttcc ctgtccttct gattttgtag   3300

gtaaccacgt gcggaccgag cggccgcagt taattaagct cgcgaaaccc ctagtgatgg   3360

agttggccac tccctctctg cgcgctcgct cgctcactga ggccgggcga ccaaaggtcg   3420

cccgacgccc gggctttgcc cgggcggcct cagtgagcga gcgagcgcgc agctg        3475
```

AADC POLYNUCLEOTIDES FOR THE TREATMENT OF PARKINSON'S DISEASE

CROSS REFERENCE TO RELATED APPLICATIONS

This application is a continuation application which claims the benefit of U.S. patent application Ser. No. 16/136,926 filed Sep. 20, 2018, entitled AADC Polynucleotides for the Treatment of Parkinson's Disease; which is a continuation application which claims the benefit of U.S. patent application Ser. No. 15/524,986 filed May 5, 2017, and entitled AADC Polynucleotides for the Treatment of Parkinson's Disease; which is a national stage filing under 35 U.S.C. § 371 of International Application No. PCT/US2015/059201 filed Nov. 5, 2015, and entitled AADC Polynucleotides for the Treatment of Parkinson's Disease; which claims priority to U.S. Provisional Patent Application No. 62/075,298 filed Nov. 5, 2014, entitled AADC Polynucleotides for the Treatment of Parkinson's Disease, and U.S. Provisional Patent Application No. 62/155,692 filed May 1, 2015, entitled AADC Polynucleotides for the Treatment of Parkinson's Disease, and U.S. Provisional Patent Application No. 62/199,578 filed Jul. 31, 2015, entitled AADC Polynucleotides for the Treatment of Parkinson's Disease, and U.S. Provisional Patent Application No. 62/243,537 filed Oct. 19, 2015, entitled AADC Polynucleotides for the Treatment of Parkinson's Disease; the contents of each of which is herein incorporated by reference in its entirety.

REFERENCE TO SEQUENCE LISTING

The present application includes a Sequence Listing which is filed in electronic format. The Sequence Listing file, entitled 20571010USCON4_SL.txt, was created on Aug. 14, 2019 and is 178,299 bytes in size. The information in electronic format of the Sequence Listing is incorporated herein by reference in its entirety.

FIELD OF THE DISCLOSURE

The invention relates to compositions, particularly nucleic acid molecules, e.g., polynucleotides encoding AADC, for use in the treatment of Parkinson's disease. In some embodiments such AADC polynucleotides may be encoded by or within recombinant adeno-associated viruses (AAVs).

BACKGROUND

Aromatic L-amino acid decarboxylase (AADC) is a homodimeric pyridoxal phosphate-dependent enzyme responsible for the synthesis of dopamine and serotonin. The encoded protein catalyzes the decarboxylation of L-3,4-dihydroxyphenylalanine (L-DOPA or levodopa) to dopamine; L-5-hydroxytryptophan to serotonin; and L-tryptophan to tryptamine. Detects in this gene are the cause of aromatic L-amino-acid decarboxylase deficiency (AADCD), which is an inborn error in neurotransmitter metabolism leading to combined serotonin and catecholamine deficiency that results in severe motor and autonomic dysfunctions.

Parkinson's Disease (PD) is a progressive neurodegenerative disease of the central nervous system (CNS) producing sensory and motor symptoms. Dopamine replacement (i.e., levodopa) has been the standard pharmacotherapy for motor impairment in PD. However, the benefit of dopamine therapy becomes less marked over time, due, in part, to the progressive death of dopamine-generating cells and corresponding loss of AADC activity. Furthermore, systemic administration of high-dose dopamine is complicated by side effects, such as fluctuations in motor performance, dyskinesias, and hallucinations, resulting from dopaminergic stimulation of the mesolimbic system. One strategy to restore dopaminergic function and minimize side effects is the use of gene therapy to deliver AADC directly to a targeted region of the CNS.

The adeno-associated virus (AAV) has emerged as an attractive vector for gene therapy due to its long-term gene expression, the inability to autonomously replicate without a helper virus, the ability to transduce dividing and non-diving cells, and the lack of pathogenicity from wild-type infections (See e.g., Hadaczek et al. Mol. Ther. 18(8), 1458-1461, August 2010). AAV is a helper-dependent DNA parvovirus which belongs to the genus *Dependovirus*.

The present invention provides such improved nucleic acid constructs, e.g., polynucleotides, for use with AAV-derived vectors comprising dopa carboxylase ("DDC") gene sequence which encodes a full-length AADC protein for the purpose of gene therapy in the treatment of Parkinson's Disease.

The nucleic acid constructs described herein comprise at least a 5'-ITR and a 3'-ITR, each or both of which may be derived from an AAV, positioned about a DDC gene sequence, as well as additional components required for gene expression and clone selection.

SUMMARY

Described herein are compositions, methods, processes, kits and devices for the design, preparation, manufacture and/or formulation of AADC polynucleotides.

In some embodiments such AADC polynucleotides may be encoded by or contained within plasmids or vectors or recombinant adeno-associated viruses (AAV).

The details of various embodiments of the invention are set forth in the description below. Other features, objects, and advantages of the invention will be apparent from the description and from the claims.

DETAILED DESCRIPTION

Compositions

According to the present invention, AADC polynucleotides are provided which function alone or in combination with additional nucleic acid sequence(s) to encode the AADC protein. As used herein an "AADC polynucleotide" is any nucleic acid polymer which encodes an AADC protein and when present in a vector, plasmid or translatable construct, expresses such AADC protein in a cell, tissue, organ or organism.

AADC polynucleotides include precursor molecules which are processed inside the cell. AADC polynucleotides or the processed forms thereof may be encoded in a plasmid, vector, genome or other nucleic acid expression vector for delivery to a cell.

In some embodiments AADC polynucleotides are designed as components of AAV viral genomes and packaged in AAV viral particles which are processed within the cell to produce the wild type AADC protein.

As used herein, the wild type AADC protein may be any of the naturally occurring isoforms or variants from the DDC gene. Multiple alternatively spliced transcript variants encoding different isoforms of AADC have been identified. Specifically, the DDC gene produces seven transcript variants that encode six distinct isoforms. DDC transcript variants 1 and 2 both encode AADC isoform 1. In some embodiments, the AADC polynucleotides encode DDC transcript variant 2, thereby encoding a native AADC isoform 1 (NCBI Reference Sequence: NP_000781.0. This sequence is given here:

```
                                    (SEQ ID NO: 1)
MNASEFRRRGKEMVDYVANYMEGIEGRQVYPDVEPGYLRPLIPAAAPQEP

DTFEDIINDVEKIIMPGVTHWHSPYFFAYFPTASSYPAMLADMLCGAIGC

IGFSWAASPACTELETVMMDWLGKMLELPKAFLNEKAGEGGGVIQGSASE

ATLVALLAARTKVIHRLQAASPELTQAAIMEKLVAYSSDQAHSSVERAGL

IGGVKLKAIPSDGNFAMRASALQEALERDKAAGLIPFFMVATLGTTTCCS

FDNLLEVGPICNKEDIWLHVDAAYAGSAFICPEFRHLLNGVEFADSFNFN

PHKWLLVNFDCSAMWVKKRTDLTGAFRLDPTYTKHSHQDSGLITDYRHWQ

IPLGRRFRSLKMWFVFRMYGVKGLQAYIRKHVQLSHEFESLVRQDPRFEI

CVEVILGLVCFRLKGSNKVNEALLQRINSAKKIHLVPCHLRDKFVLRFAI

CSRTVESAHVQRAWEHIKELAADVLRAERE
```

The AADC polynucleotides of the invention, may be engineered to contain modular elements and/or sequence motifs assembled to create AADC polynucleotide constructs.

AADC Polynucleotide Constructs

According to the present invention, AADC polynucleotides are provided. Such polynucleotides comprise nucleic acid polymers which comprise a region of linked nucleosides encoding one or more isoforms or variants of the AADC protein.

In some embodiments, the AADC polynucleotide comprises a codon optimized transcript encoding an AADC protein.

In some embodiments, the AADC polynucleotide comprises a sequence region encoding one or more wild type isoforms or variants of an AADC protein. Such polynucleotides may also comprise a sequence region encoding any one or more of the following: a 5' ITR, a cytomegalovirus (CMV) Enhancer, a CMV Promoter, an ie1 exon 1, an ie1 intron1, an hbBglobin intron2, an hBglobin exon 3, a 5' UTR, a 3' UTR, an hGH poly(A) signal, and/or a 3' ITR. Such sequence regions are taught herein or may be any of those known in the art.

In some embodiments, the AADC polynucleotide comprises a sequence of any of SEQ ID NOs. 2-23.

In one embodiment, the AADC polynucleotide comprises a sequence which has a percent identity to any of SEQ ID NOs: 2-23. The AADC polynucleotide may have 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% identity to any of SEQ ID NOs: 2-23. The AADC polynucleotide may have 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% to any of SEQ ID NOs: 2-23. As a non-limiting example, the AADC polynucleotide comprises a sequence which as 80% identity to any of SEQ ID NOs 6, 7, 8, 9, 17, 18, 19, 20, 21, 22, and 23. As another non-limiting example, the AADC polynucleotide comprises a sequence which as 85% identity to any of SEQ ID NOs 6, 7, 8, 9, 17, 18, 19, 20, 21, 22, and 23. As another non-limiting example, the AADC polynucleotide comprises a sequence which as 90% identity to any of SEQ ID NOs 6, 7, 8, 9, 17, 18, 19, 20, 21, 22, and 23. As another non-limiting example, the AADC polynucleotide comprises a sequence which as 95% identity to any of SEQ ID NOs 6, 7, 8, 9, 17, 18, 19, 20, 21, 22, and 23. As another non-limiting example, the AADC polynucleotide comprises a sequence which as 99% identity to any of SEQ ID NOs 6, 7, 8, 9, 17, 18, 19, 20, 21, 22, and 23.

In some embodiments the AADC coding region is 1440 nucleotides in length. Such an AADC polynucleotide may be codon optimized over all or a portion of the polynucleotide.

In some embodiments the AADC coding region is 1443 nucleotides in length. In such case, an additional codon may be present at the 3' end of the polynucleotide.

In some embodiments the AADC coding region is 1449 nucleotides in length. In such case, additional codons may be present at the 3' end of the polynucleotide.

In some embodiments, the AADC polynucleotide comprises any of SEQ ID NOs 6-9, 17-23 but lacking the 5' and/or 3' ITRs. Such a polynucleotide may be incorporated into a plasmid or vector and utilized to express the encoded AADC protein.

In one embodiment, the AADC polynucleotides may be produced in insect cells (e.g., Sf9 cells).

In one embodiment, the AADC polynucleotides may be produced using triple transfection.

In one embodiment, the AADC polynucleotide may comprise a codon optimized open reading frame of an AADC mRNA, at least one 5'ITR and at least one 3'UTR where the one or more of the 5'ITRs may be located at the 5' end of the promoter region and one or more 3' ITRs may be located at the 3' end of the poly(A) signal. The AADC mRNA may comprise a promoter region, a 5' untranslated region (UTR), a 3'UTR and a poly(A) signal. The promoter region may include, but is not limited to, enhancer element, a promoter element, a first exon region, a first intron region, a second intron region and a second exon region. As a non-limiting example, the enhancer element and the promoter element are derived from CMV. As another non-limiting example, the first exon region is ie1 exon 1 or fragments thereof, the first intron region is ie1 intron 1 or fragments thereof, the second intron region is hbBglobin intron 2 or fragments thereof and the second exon region is hbBglobin exon 3 or fragments thereof. As yet another non-limiting example, the poly(A) signal is derived from human growth hormone.

In one embodiment, the AADC polynucleotide is encoded in a plasmid or vector, which may be derived from an adeno-associated virus (AAV). The AAV may be a recombinant AAV virus and may comprise a capsid serotype such as, but not limited to, of AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ, and AAV-DJ8. As a non-limiting example, the capsid of the recombinant AAV virus is AAV2. As a non-limiting example, the capsid of the recombinant AAV virus is AAVrh10. As a non-limiting example, the capsid of the recombinant AAV virus is AAV9(hu14). As a non-limiting example, the capsid of the recombinant AAV virus is AAV-DJ. As a non-limiting example, the capsid of the recombinant AAV virus is AAV9.47. As a non-limiting example, the capsid of the recombinant AAV virus is AAV-DJ8.

Promoters

A person skilled in the art may recognize that a target cell may require a specific promoter including but not limited to a promoter that is species specific, inducible, tissue-specific, or cell cycle-specific Parr et al., *Nat, Med.* 3:1145-9 (1997); the contents of which are herein incorporated by reference in its entirety).

In one embodiment, the promoter is a promoter deemed to be efficient for the AADC polynucleotide.

In one embodiment, the promoter is a promoter deemed to be efficient for the cell being targeted.

In one embodiment, the promoter is a weak promoter which provides expression of a payload for a period of time in targeted tissues such as, but not limited to, nervous system tissues. Expression may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years. As a non-limiting example, the promoter is a weak promoter for sustained expression of a payload in nervous tissues. As another non-limiting example, the promoter is a weak promoter for sustained frataxin expression in nervous system tissue such as, but not limited to, neuronal tissue and glial tissue.

In one embodiment, the FRDA promoter is used with the AADC polynuelleotides described herein.

In one embodiment, there is a region located approximately ~5 kb upstream of the first exon of the payload. As a non-limiting example, there is a 17 bp region located approximately 4.9 kb upstream of the first exon of the frataxin gene in order to allow for expression with the FRDA promoter (See e.g., Puspasari et al. *Long Range Regulation of Human FXN Gene Expression*, PLOS ONE, 2011; the contents of which is herein incorporated by reference in its entirety).

In one embodiment, the promoter may be a promoter which is less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800.

In one embodiment, the promoter may be a combination of two or more components such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. As a non-limiting example, the promoter is a combination of a 382 nucleotide CMV-enhancer sequence and a 260 nucleotide CBA-promoter sequence.

In one embodiment, at least one element may be used with the AADC polynucleotides described herein to enhance the transgene target specificity and expression (See e.g., Powell et al. *Viral Expression Cassette Elements to Enhance Transgene Target Specificity and Expression in Gene Therapy,* 2015; the contents of which are herein incorporated by reference in its entirety). Non-limiting examples of elements to enhance the transgene target specificity and expression include promoters, endogenous miRNAs, post-transcriptional regulatory elements (PREs), polyadenylation (PolyA) signal sequences and upstream enhancers (USEs), CMV enhancers and introns.

In one embodiment, at least one element may be used with the AADC polynucleotides described herein to enhance the transgene target specificity and expression (See e.g., Powell et al. *Viral Expression Cassette Elements to Enhance Transgene Target Specificity and Expression in Gene Therapy,* 2015; the contents of which are herein incorporated by reference in its entirety) such as promoters. Promoters for which promote expression in most tissues include, but are not limited to, human elongation factor 1α-subunit (EP1α), immediate-early cytomegalovirus (CMV), chicken β-actin (CBA) and its derivative CAG, the β glucuronidase (GUSB), or ubiquitin C (UBC). Tissue-specific expression elements can be used to restrict expression to certain cell types such as, but not limited to, nervous system promoters which can be used to restrict expression to neurons, astrocytes, or oligodendrocytes. Non-limiting example of tissue-specific expression elements for neurons include neuron-specific enolase (NSE), platelet-derived growth factor (PDGF), platelet-derived growth factor B-chain (PDGF-β), the synapsin (Syn), the methyl-CpG binding protein 2 (MeCP2), CaMKII, mGluR2, NFL, NFH, nβ2, PPE, Enk and EAAT2 promoters. A non-limiting example of a tissue-specific expression elements for astrocytes include the glial fibrillary acidic protein (GFAP) and EAAT2 promoters. A non-limiting example of a tissue-specific expression element for oligodendrocytes include the myelin basic protein (MBP) promoter.

In one embodiment, a ubiquitous promoter may be used with the AADC polynucleotides described herein. Non-limiting examples of ubiquitous promoters include CMV, CBA (including derivatives CAG, CBh, etc.), EF-1α, PGK, UBC, GUSB (hGBp), and UCOE (promoter of HNRPA2B1-CBX3) Yu et al. (Molecular Pain 2011, 7:63; the contents of which are herein incorporated by reference in its entirety) evaluated the expression of eGFP under the CAG, EFIα, PGK and LBC promoters in rat DRG cells and primary DRG cells using lentiviral vectors and found that UBC showed weaker expression than the other 3 promoters and there was only 10-12% glia expression seen for all promoters. Soderblom et al. (E. Neuro 2015; the contents of which are herein incorporated by reference in its entirety) the expression of eGFP in AAV8 with CMV and UBC promoters and AAV2 with the CMV promoter after injection in the motor cortex. Intranasal administration of a plasmid containing a UBC or EFIα promoter showed a sustained airway expression greater than the expression with the CMV promoter (See e.g., Gill et al., Gene Therapy 2001, Vol. 8, 1539-1546; the contents of which are herein incorporated by reference in its entirety) Husain et al. (Gene Therapy 2009; the contents of which are herein incorporated by reference in its entirety) evaluated a HβH construct with a hGUSB promoter, a HSV-ILAT promoter and a NSE promoter and found that the HβH construct showed weaker expression than NSE in mice brain. Passini and Wolfe (J. Virol. 2001, 12382-12392, the contents of which are herein incorporated by reference in its entirety) evaluated the long term effects of the HβH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in its entirety) when NF-L and NF-H promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650 nucleotide promoter and NFH is a 920 nucleotide promoter which are both absent in the liver but NFH is abundant in the sensory proprioceptive neurons, brain and spinal cord and NFH is present in the heart. Scn8a is a 470 nucleotide promoter which expresses throughout the DRG, spinal cord and brain with particularly high expression seen in the hippocampal neurons and cerebellar Purkinje cells, cortex, thalamus and hypothalamus (See e.g., Drews et al. 2007 and Raymond et al, 2004; the contents of each of which are herein incorporated by reference in their entireties).

In one embodiment, an UBC promoter may be used with the AADC polynucleotides described herein. The UBC promoter may have a size of 300-350 nucleotides. As a non-limiting example, the UBC promoter is 332 nucleotides.

In one embodiment, a GUSB promoter may be used with the AADC polynucleotides described herein. The GUSB promoter may have a size of 350-400 nucleotides. As a non-limiting example, the GUSB promoter is 378 nucleotides. As a non-limiting example, the construct may be AAV-promoter-CMV/globin intron-hFXN-RBG, where the AAV may be self-complementary and the AAV may be the DJ serotype.

In one embodiment, a NFL promoter may be used with the AADC polynucleotides described herein. The NTL promoter may have a size of 600-700 nucleotides. As a non-limiting example, the NFL promoter is 650 nucleotides. As a non-limiting example, the construct may be AAV-promoter-CMV/globin intron-hFXN-RBG, where the AAV may be self-complementary and the AAV may be the DJ serotype.

In one embodiment, a NFH promoter may be used with the AADC polynucleotides described herein. The NFH promoter may have a size of 900-950 nucleotides. As a non-limiting example, the NFH promoter is 920 nucleotides. As a non-limiting example, the construct may be AAV-promoter-CMV/globin intron-hFXN-RBG, where the AAV may be self-complementary and the AAV may be the DJ serotype.

In one embodiment, a scn8a promoter may be used with the AADC polynucleotides described herein. The scn8a promoter may have a size of 450-500 nucleotides. As a non-limiting example, the scn8a promoter is 470 nucleotides. As a non-limiting example, the construct may be AAV-promoter-CMV/globin intron-hFXN-RBG, where the AAV may be self-complementary and the AAV may be the DJ serotype.

In one embodiment, a FXN promoter may be used with the ADC polynucleotides described herein.

In one embodiment, a PGK promoter may be used with the AADC polynucleotides described herein.

In one embodiment, a CBA promote may be used with the AADC polynucleotides described herein.

In one embodiment, a CMV promoter may be used with the AADC polynucleotides described herein.

In one embodiment, a liver or a skeletal muscle promoter may be used with the AADC polynucleotides described herein. Non-limiting examples of liver promoters include hAAT and TBG. Non-limiting examples of skeletal muscle promoters include Desmin, MCK and C5-12.

In one embodiment, an enhancer element, a promoter and/or a 5'UTR intron may be used with the AADC polynucleotides described herein. The enhancer may be, but is not limited to, a CMV enhancer, the promoter may be, but is not limited to, a CMV, CBA, UBC, GUSB, NSE, Sunapsin, MeCP2, and GFAP promoter and the 5'UTR/intron may be, but is not limited to, SV40, and CBA-MVM. As a non-limiting example, the enhancer, promoter and/or intron used in combination may be: (1) CMV enhancer, CMV promoter, SV40 5'UTR intron, (2) CMV enhancer, CBA promoter, SV 40 5'UTR intron; (3) CMV enhancer, CBA promoter, CBA-MVM 5'UTR intron; (4) LBC promoter; (5) GUSB promoter; (6) NSE promoter; (7) Synapsin promoter; (8) MeCP2 promoter and (9) GFAP promoter.

In one embodiment, an engineered promoter may be used with the AADC polynucleotides described herein.

Introns

In one embodiment, at least one element may be used with the AADC polynucleotides described herein to enhance the transgene target specificity and expression (See e.g., Powell et al. *Viral Expression Cassette Elements to Enhance Transgene Target Specificity and Expression in Gene Therapy*, 2015; the contents of which are herein incorporated by reference in its entirety) such as an intron. Non-limiting examples of introns include, MVM (67-97 bps), FIX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The intron may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500.

Introduction into Cells

The AADC polynucleotides of the invention can be introduced into host cells using any of a variety of approaches. Infection with a viral vector comprising the AADC polynucleotide can be effected. Examples of suitable viral vectors include replication defective retroviral vectors, adenoviral vectors, adeno-associated vectors and lentiviral vectors.

According to the present invention, viral vectors for use in therapeutics and/or diagnostics comprise a virus that has been distilled or reduced to the minimum components necessary for transduction of a nucleic acid payload or cargo of interest.

In this manner, viral vectors are engineered as vehicles for specific delivery while lacking the deleterious replication and/or integration features found in wild-type virus.

As used herein, a "vector" is any molecule or moiety which transports, transduces or otherwise acts as a carrier of a heterologous molecule such as the polynucleotides of the invention. A "viral vector" is a vector which comprises one or more polynucleotide regions encoding or comprising payload molecule of interest, e.g., a transgene, a polynucleotide encoding a polypeptide or multi-polypeptide. Viral vectors of the present invention may be produced recombinantly and may be based on adeno-associated virus (AAV) parent or reference sequence. Serotypes which may be useful in the present invention include any of those arising from AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ, and AAV-DJ18.

In one embodiment, the serotype which may be useful in the present invention may be AAV-DJ8. The amino acid sequence of AAV-DJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in its entirety, may comprise two mutations: (1) R587Q where arginine (R; arg) at amino acid 587 is changed to glutamine (Q; gin) and (2) R590T where arginine (R; arg) at amino acid 590 is changed to threonine (T; thr). As another non-limiting example, may comprise three mutations: (1) K406R where lysine (K; lys) at amino acid 406 is changed to arginine (R; arg), (2) R587Q where arginine (R; arg) at amino acid 587 is changed to glutamine (Q; gin) and (3) R590T where arginine (R; arg) at amino acid 590 is changed to threonine (T; thr).

AAV vectors may also comprise self-complementary AAV vectors (scAAVs). scAAV vectors contain both DNA strands which anneal together to form double stranded DNA. By skipping second strand synthesis, scAAVs allow for rapid expression in the cell.

Pharmaceutical Compositions

Although the descriptions of pharmaceutical compositions, e.g., those polynucleotides (including the encoding plasmids or expression vectors, such as viruses, e.g., AAV) comprising a payload, e.g., AADC encoding sequences, to be delivered, provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

In some embodiments, compositions are administered to humans, human patients or subjects. For the purposes of the present disclosure, the phrase "active ingredient" generally refers either to the viral vector carrying the payload or to the polynucleotide payload molecule delivered by a viral vector as described herein.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered.

In one embodiment, the pharmaceutical composition comprises a recombinant adeno-associated virus (AAV) vector comprising an AAV capsid and an AAV vector genome. The AAV vector genome may comprise at least one AADC polynucleotide described herein, such as, but not limited to, SEQ ID NOs 6, 7, 8, 9, 17, 18, 19, 20, 21, 22, and 23 or variants having at least 95% identity thereto. The recombinant AAV vectors in the pharmaceutical composition may have at least 70% which contain an AAV vector genome.

Formulation

The AADC polynucleotides or viral vectors encoding them can be formulated using one or more excipients to: (1) increase stability; (2) increase cell transfection or transduction; (3) permit the sustained or delayed release; or (4) alter the biodistribution (e.g., target the viral vector to specific tissues or cell types).

Formulations of the present invention can include, without limitation, saline, lipidoids, liposomes, lipid nanoparticles, polymers, lipoplexes, core-shell nanoparticles, peptides, proteins, cells transfected with viral vectors (e.g., for transplantation into a subject), nanoparticle mimics and combinations thereof. Further, the viral vectors of the present invention may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the formulations described herein may contain at least one payload molecule, e.g., an AADC polynucleotide. As a non-limiting example, the formulations may contain 1, 2, 3, 4 or 5 AADC polynucleotide payload molecules.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

In one embodiment, the AADC polynucleotides may be formulated in a hydrogel prior to administration. Hydrogels have a degree of flexibility which is similar to natural tissue as a result of their significant water content.

In another embodiment, a hydrogel may be administered to a subject prior to the administration of an AADC polynucleotide formulation. As a non-limiting example, the site of administration of the hydrogel may be within 3 inches within 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1 or less than 0.1 inches) of the site of administration of the AADC polynucleotide formulation.

In one embodiment, the AADC polynucleotides may be administered in saline. As a non-limiting example, the formulation may be phosphate buffered saline (PBS) with 0.001% Pluronic acid (F-68). Additionally the formulation may be sterilized.

Inactive Ingredients

In some embodiments, AADC polynucleotide formulations may comprise at least one excipient which is an inactive ingredient. As used herein, the term "inactive ingredient" refers to one or more inactive agents included in formulations. In some embodiments, all, none or some of the inactive ingredients which may be used in the formulations of the present invention may be approved by the US Food and Drug Administration (FDA).

Formulations of viral vectors carrying AADC polynucleotides disclosed herein may include cations or anions. In one embodiment, the formulations include metal cations such as, but not limited to, Zn2+, Ca2+, Cu2+, Mg+ and combinations thereof. As a non-limiting example, formulations may include polymers and AADC polynucleotides complexed with a metal cation (See e.g., U.S. Pat. Nos. 6,265,389 and 6,555,525, each of which is herein incorporated by reference in its entirety)

Administration

The viral vectors comprising AADC polynucleotides of the present invention may be administered by any route which results in a therapeutically effective outcome. These include, but are not limited to epidural (into the dura matter), oral (by way of the mouth), transdermal, peridural, intracerebral (into the cerebrum), intracerebroventricular (into the cerebral ventricles), subcutaneous (under the skin), nasal administration (through the nose), intravenous (into a vein), intravenous bolus, intravenous drip, intraarterial (into an artery), intrathecal (into the spinal canal), endocervical, intracaudal (within the cauda equine), intracisternal (within the cisterna magna cerebellomedularis), intradiscal (within a disc), intradural (within or beneath the dura), intrameningeal (within the meninges), intrapleural (within the pleura), intraspinal (within the vertebral column), intrathecal (within the cerebrospinal fluid at any level of the cerebrospinal axis), intrathoracic (within the thorax), intrastriatal (within the striatum, caudate nucleus and/or putamen), caudal block, nerve block, or spinal. In specific embodiments, compositions may be administered in a way which allows them cross the blood-brain barrier, vascular barrier, or other epithelial barrier. In one embodiment, a formulation for a route of administration may include at least one inactive ingredient.

In one embodiment, the viral vectors comprising AADC polynucleotides of the present invention may be administered to the right putamen and/or the left putamen. The administration may be at one or more sites in the putamen such as, but not limited to, 2 sites, 3 sites, 4 sites or more than 4 sites. As a non-limiting example, the viral vectors comprising AADC polynucleotides of the present invention are delivered to 2 sites in the left putamen and 2 sites in the right putamen.

In one embodiment, the administration of the formulation of the viral vectors comprising the AADC polynucleotides of the present invention to a subject provides coverage of the putamen of a subject (e.g., the left and/or tight putamen). In one aspect, the administration of the viral vectors comprising the AADC polynucleotides may provide at least 8%, 9%, 10%, 13%, 14%, 15%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more than 95% to the left and/or right putamen of a subject. As a non-limiting example, the coverage is at least 20%. As a non-limiting example, the coverage is at least 40%. In another aspect, the administration of the viral vectors comprising the AADC polynucleotides may provide at least 8%, 9%, 10%, 13%, 14%, 15%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more than 95% coverage of the surface area of the left and/or right putamen of a subject. As a non-limiting example, the total coverage is at least 20%. As a non-limiting example, the total coverage is at least 40%. In yet another aspect, the administration of the viral vectors comprising the AADC polynucleotides may provide 10-40%, 20-40%, 70-30%, 70-35%, 20-50%, 30-40%, 35-40%, 30-60%, 40-70%, 50-80% or 60-90% coverage to the left and/or right putamen of a subject or to the total surface area of the left and/or right putamen of a subject.

In one embodiment, the administration of the formulation of the viral vectors comprising the AADC polynucleotides of the present invention to a subject provides coverage of the posterior putamen of a subject (e.g., the left and/or right posterior putamen). In one aspect, the administration of the viral vectors comprising the AADC polynucleotides may provide at least 10%, 15%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more than 95% to the left and/or right posterior putamen of a subject. As a non-limiting example, the coverage is at least 20%. As a non-limiting example, the coverage is at least 40%. In another aspect, the administration of the viral vectors comprising the AADC polynucleotides may provide at least 10%, 15%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43% 44%, 45%, 46%, 47%, 48%, 49%, 50%, 51%, 52%, 53%, 54%, 55% 60%, 65%, 70%, 75%, 80%, 85%, 90%, 95% or more than 95% coverage of the surface area of the left and/or right posterior putamen of a subject. As a non-limiting example, the total coverage is at least 20%. As a non-limiting example, the total coverage is at least 40%. In yet another aspect, the administration of the viral vectors comprising the AADC polynucleotides may provide 10-40%, 20-50%, 30-60%, 40-70%, 50-80% or 60-90% coverage to the left and/or right posterior putamen of a subject or to the total surface area of the left and/or right putamen of a subject.

In one embodiment, a subject may be administered the viral-vectors comprising AADC polynucleotides of the present invention safely delivered to substantia nigra pars compacta (SNpc) and ventral tegmental area (VTA) via bilateral infusions, or alternatively, intrastriatally (into the caudate nucleus and putamen), or into the subthalamic nucleus (STN).

In one embodiment, the AADC polynucleotides described herein may be administered using acute bilateral placement of catheters into each putamen. The placement may use magnetic resonance image (MRI)-guided stereotactic neurosurgical techniques known in the art or described herein. Additionally, a contrast agent such as, but not limited to a gadolinium based contrast agent (e.g., PROHANCE®) may be used in the formulation to monitor and confirm the distribution of the formulation.

In one embodiment, a subject may be administered the viral vectors comprising AADC polynucleotides of the present invention in a bilateral stereotactic CED-assisted step infusion into the putamen (e.g., the post commissural putamen).

In one embodiment, delivery of viral vector pharmaceutical compositions in accordance with the present invention to cells of the central nervous system (e.g., parenchyma) comprises a rate of delivery defined by [VG/hour=mL/hour*VG/mL] wherein VG is viral genomes, VG/mL is composition concentration, and mL/hour is rate of prolonged infusion.

In one embodiment, delivery of viral vector pharmaceutical compositions in accordance with the present invention to cells of the central nervous system (e.g., parenchyma) comprises infusion of up to 1 mL. In one embodiment, delivery of viral vector pharmaceutical compositions in accordance with the present invention to cells of the central nervous system (e.g., parenchyma) may comprise infusion of 0.001, 0.002, 0.003, 0.004, 0.005, 0.010, 0.015, 0.020, 0.025, 0.030, 0.040, 0.050, 0.060, 0.070, 0.080, 0.090, 0.1, 0.2, 0.3, 0.4, 0.5, 0.6, 0.7, 0.8, or 0.9 mL.

In one embodiment, delivery of viral vector pharmaceutical compositions in accordance with the present invention to cells of the central nervous system (e.g., parenchyma) comprises infusion of between about 1 mL to about 120 mL. In one embodiment, delivery of viral vector pharmaceutical compositions in accordance with the present invention to cells of the central nervous system (e.g., parenchyma) may comprise infusion of 0.1, 1, 1.1, 1.2, 1.3, 1.4, 1.5, 1.6, 1.7, 1.8, 1.9, 2, 4, 5, 6, 7, 8, 9, 10, 11, 12, 13, 14, 15, 16, 17, 18, 19, 20, 21, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 mL. In one embodiment, delivery of AAV particles to cells of the central nervous system (e.g., parenchyma) comprises infusion of at least 3 mL. In one embodiment, delivery of AAV particles to cells of the central nervous system (e.g., parenchyma) consists of infusion of 3 mL. In one embodiment, delivery of AAV particles to cells of the central nervous system (e.g., parenchyma) comprises infusion of at least 10 mL. In one embodiment, delivery of AAV particles to cells of the central nervous system (e.g., parenchyma) consists of infusion of 10 mL.

In one embodiment, the volume of the viral vector pharmaceutical composition delivered to the cells of the central nervous system (e.g., parenchyma) of a subject is 50 ul, 100 ul, 200 ul, 300 ul, 400 ul, 500 ul, 600 ul, 700 ul, 800 ul, 900 ul, 1000 ul, 1100 ul, 1200 ul, 1300 ul, 1400 ul, 1500 ul, 1600 ul, 1700 ul, 1800 ul, 1900 ul, 2000 ul or more than 2000 ul.

In one embodiment, the volume of the viral vector pharmaceutical composition delivered to a region in both hemispheres of a subject brain is 50 ul, 100 ul, 200 ul, 300 ul, 400 ul, 500 ul, 600 ul, 700 ul, 800 ul, 900 ul, 1000 ul, 1100 ul, 1200 ul, 1300 ul, 1400 ul, 1500 ul, 1600 ul, 1700 ul, 1800 ul, 1900 ul, 2000 ul or more than 2000 ul. As a non-limiting example, the volume delivered to a region in both hemispheres is 200 ul. As another non-limiting example, the volume delivered to a region in both hemispheres is 900 ul. As yet another non-limiting example, the volume delivered to a region in both hemispheres is 1800 ul.

In one embodiment, the volume of the viral vector pharmaceutical composition delivered to the putamen in both hemispheres of a subject brain is 50 ul, 100 ul, 200 ul, 300 ul, 400 ul, 450 ul, 500 ul, 600 ul, 700 ul, 800 ul, 900 ul, 1000 ul, 1100 ul, 1200 ul, 1300 ul, 1400 ul, 1500 ul, 1600 ul, 1700 ul, 1800 ul, 1900 ul, 2000 ul or more than 2000 ul. As a non-limiting example, the volume delivered to the putamen in both hemispheres is 100 ul. As another non-limiting example, the volume delivered to the putamen in both hemispheres is 200 ul. As a non-limiting example, the volume delivered to the putamen in both hemispheres is 300 ul. As another non-limiting example, the volume delivered to the putamen in both hemispheres is 450 ul. As another non-limiting example, the volume delivered to the putamen in both hemispheres is 900 ul. As yet another non-limiting example, the volume delivered to the putamen both hemispheres is 1800 ul.

In one embodiment, the total volume delivered to a subject may be split between one or more administration sites e.g., 1, 2, 3, 4, 5 or more than 5 sites. As a non-limiting example, the total volume is split between administration to the left and right putamen. As another non-limiting example, the total volume is split between two sites of administration to each of the left and right putamen.

In one embodiment, the viral vector pharmaceutical composition is administered using a fenestrated needle. Non-limiting examples of fenestrated needles are described in U.S. Pat. Nos. 8,333,734, 7,135,010, 7,575,572, 7,699,852, 4,411,657, 6,890,319, 6,613,026, 6,726,659, 6,565,572, 6,520,949, 6,382,212, 5,848,996, 5,759,179, 5,674,267, 5,588,960, 5,484,401, 5,199,441, 5,012,818, 4,474,569, 3,766,907, 3,552,394, the contents of each of which are herein incorporated by reference in its entirety.

In one embodiment, a composition comprises AADC polynucleotides described herein and the AADC polynucleotides are components of an AAV viral genome packaged in an AAV viral particle. The percent (%) ratio of AAV viral particles comprising the AADC polynucleotide (also referred to herein and AADC particles) to the AAV viral particles without the AADC polynucleotide (also referred to herein as empty capsids) in the composition may be 0:100, 1:99, 0:90, 15:85, 25:75, 30:70, 50:50, 70:30, 85:15, 90:10, 99:1 or 100:0. As a non-limiting example, the percent ratio of AADC particles to empty capsids is 50:50. As another non-limiting example, the percent ratio of AADC particles to empty capsids is 70:30. As another non-limiting example, the percent ratio of AADC particles to empty capsids is 85:15. As another non-limiting example, the percent ratio of AADC particles to empty capsids is 100:0.

In one embodiment, the composition described herein comprises at least 1, 5, 10, 15, 20, 25, 30, 35, 40, 45, 50, 51, 52, 53, 54, 55, 60, 65, 70, 75, 80, 81, 82, 83, 84, 85, 86, 87, 88, 89, 90, 91, 92, 93, 94, 95, 96, 97, 98, 99 or greater than 99% AADC particles. As a non-limiting example, the composition comprises at least 50% AADC particles. As another non-limiting example, the composition comprises at least 52% AADC particles. As another non-limiting example, the composition comprises at least 58% AADC particles. As another non-limiting example, the composition comprises at least 70% AADC particles. As another non-limiting example, the composition comprises at least 83% AADC particles. As another non-limiting example, the composition comprises at least 85% AADC particles. As another non-limiting example, the composition comprises at least 99% AADC particles. As another non-limiting example, the composition comprises 100% AADC particles.

In one embodiment, the composition described herein comprises 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% AADC particles. As a non-limiting example, the composition described herein comprises 50-100% AADC particles. As another non-limiting example, the composition described herein comprises 50-60% AADC particles. As another non-limiting example, the composition described herein comprises 80-99% AADC particles. As another non-limiting example, the composition described herein comprises 80-90% AADC particles. As a non-limiting example, the composition described herein comprises 80-95% AADC particles. As a non-limiting example, the composition described herein comprises 80-85% AADC particles.

In one embodiment, the composition described herein comprises less than 1, 5, 10, 15, 20, 25, 30, 35, 40, 45, 50, 51, 52, 53, 54, 55, 60, 65, 70, 75, 80, 81, 82, 83, 84, 85, 86, 87, 88, 89, 90, 91, 92, 93, 94, 95, 96, 97, 98, 99 or 100% empty particles. As a non-limiting example, the composition comprises less than 50% empty particles. As a non-limiting example, the composition comprises less than 45% empty particles. As a non-limiting example, the composition comprises less than 40% empty particles. As a non-limiting example, the composition comprises less than 35% empty particles. As a non-limiting example, the composition comprises less than 30% empty particles. As a non-limiting example, the composition comprises less than 25% empty particles. As a non-limiting example, the composition comprises less than 20% empty particles. As a non-limiting example, the composition comprises less than 15% empty particles. As a non-limiting example, the composition comprises less than 10% empty particles. As a non-limiting example, the composition comprises less than 5% empty particles. As a non-limiting example, the composition comprises less than 1% empty particles.

In the composition described herein comprises 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% empty particles. As a non-limiting example, the composition described herein comprises 30-40% empty particles. As another non-limiting example, the composition described herein comprises 30-50% empty particles. As another non-limiting example, the composition described herein comprises 30-60% empty particles. As another non-limiting example, the composition described herein comprises 30-70% empty particles. As a non-limiting example, the composition described herein comprises 30-80% empty particles. As a non-limiting example, the composition described herein comprises 30-90% empty particles.

In one embodiment, the AADC polynucleotides described herein may be administered to a subject who is also undergoing levodopa therapy. As a non-limiting example, the subject may have a positive response to levodopa therapy and at least one symptom of PD is reduced. As another non-limiting example, the subject may have a response to levodopa therapy where the symptoms of PD experienced by the subject are stable. As yet another non-limiting example, the subject may have a negative response to levodopa therapy where the symptoms of PD experienced by the subject are increasing.

In one embodiment, the dose of levodopa administered to the subject prior to the AADC polynucleotides is 1, 2, 3, 4, 5, 6, 7, 8, 9, 10, 11, 12, 13, 14, 15, 16, 17, 18, 19, 20, 21, 22, 23, 24, 25 or more than 25 mg/kg. As a non-limiting example, the dose is 3 mg/kg. As another non-limiting example, the dose is 10 mg/kg. As yet another non-limiting example, the dose is 20 mg/kg. The subject's response (e.g., behavioral response) to levodopa may be assessed prior to administration of the AADC polynucleotides. Additionally, the subject may be administered levodopa again after the administration of the AADC polynucleotides (e.g., 1 week, 2, weeks, 3 weeks, 1 month, 2 months, 3 months, 4 months, 5 months, 6 months, 7 months, 8 months, 9 months, 10 months, 11 months, 1 year or more than 1 year after the administration of AADC polynucleotides). The behavioral response can be re-assessed and compared to the initial response to determine the effects of the AADC polynucleotides. The subject may have 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% behavioral improvement.

In one embodiment, Levodopa may be administered multiple times after the administration of the AADC polynucleotides. Levodopa may be administered on a repeating schedule (e.g., every 5 days, weekly, every 10 days, every 15 days, every 30 days, monthly, bimonthly, every 3 months, every 4 months, every 5 months, every 6 months, every 7 months, every 8 months, every 9 months, every 10 months, every 11 months or yearly) or as symptoms arise. As a non-limiting example, 3 years post administration of AADC polynucleotides a subject may have 1-10%, 5-15%, 10-20%, 15-30%, 20-40%, 25-50%, 30-50%, 40-50%, 40-60%, 50-70%, 50-80%, 60-70%, 60-75%, 60-80%, 60-90%, 70-80%, 70-90%, 75-90%, 80-90%, 90-100% of the striatal neurons within the infused region of the putamen to be AADC-immunoreactive. As a non-limiting example, 6 years post administration of AADC polynucleotides a subject may have 1-10%, 5-15%, 10-20%, 15-30%, 20-40%, 25-50%, 30-50%, 40-50%, 40-60%, 50-70%, 50-80%, 60-70%, 60-75%, 60-80%, 60-90%, 70-80%, 70-90%, 75-90%, 80-90%, 90-100% of the striatal neurons within the infused region of the putamen to be AADC-immunoreactive. As a non-limiting example, 9 years post administration of AADC polynucleotides a subject may have 1-10%, 5-15%, 10-20%, 15-30%, 20-40%, 25-50%, 30-50%, 40-50%, 40-60%, 50-70%, 50-80%, 60-70%, 60-75%, 60-80%, 60-90%, 70-80%, 70-90%, 75-90%, 80-90%, 90-100% of the striatal neurons within the infused region of the putamen to be AADC-immunoreactive.

In one embodiment, a subject who may be administered the AADC polynucleotides described herein have a documented response to levodopa therapy but have medically refractory fluctuations and are considered good surgical candidates. The determination if a subject is a good surgical candidate may be made by the physician treating the subject for PD or the physician administering the AADC polynucleotides who takes into consideration the overall risk to benefit ratio for the patient for the surgical intervention required for delivery of the AADC polynucleotides.

In one embodiment, the ratio of distribution volume in the parenchyma of an area of a subject to the infusion volume of an area of a subject may be 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0 or more than 6.0. As a non-limiting example, the ratio of distribution volume in the parenchyma to infusion volume was 1.6 in the caudate nucleus. As a non-limiting example, the ratio of distribution volume in the parenchyma to infusion volume was 3.1 in the putamen. As a non-limiting example, the distribution of the AADC polynucleotides in the putamen may be 2-3 times the volume infused.

Dosing

The present invention provides methods comprising administering viral vectors and their AADC polynucleotide payload or complexes in accordance with the invention to a subject in need thereof. Viral vector pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the invention are typically formulated in unit dosage form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific polynucleotide payload employed; the duration of the treatment; drugs used in combination or coincidental with the specific compound employed; and like factors well known in the medical arts.

In certain embodiments, viral vector pharmaceutical compositions in accordance with the present invention may be administered at AADC polynucleotide dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired AADC polynucleotide dosage may be delivered three times in a single day, two times in a single day, once in a single day or in a period of 24 hours the dosage may be delivered once, twice, three times or more than three times. In certain embodiments, the desired AADC polynucleotide dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of single unit dose or total dose into two or more doses, e.g., two or more administrations of the single unit dose. As used herein, a "single unit dose" is a dose of any polynucleotide therapeutic administered in one dose/at one time/single route/single point of contact, i.e., single administration event. As used herein, a "total daily dose" is an amount given or prescribed in 24 hr period. It may be administered as a single unit dose. In one embodiment, the viral vectors comprising the AADC polynucleotides of the present invention are administered to a subject in split doses. They may be formulated in buffer only or in a formulation described herein.

In one embodiment, delivery of viral vector pharmaceutical compositions in accordance with the present invention to cells of the central nervous system (e.g., parenchyma) may comprise a total concentration between about $1\times10^6$ VG/mL and about $1\times10^{10}$ VG/mL. In some embodiments, delivery may comprise a composition concentration of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^5$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $1.8\times10^{11}$, $2\times10^{11}$, $3\times10^{11}$, $4\times10^{11}$, $5\times10^{11}$, $5.5\times10^{11}$, $6\times10^{11}$, $7\times10^{11}$, $8\times10^{11}$, $9\times10^{11}$, $0.8\times10^{12}$, $0.83\times10^{12}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{12}$, $2.4\times10^{12}$, $2.5\times10^{12}$, $2.6\times10^{12}$, $2.7\times10^{12}$, $2.8\times10^{12}$, $2.9\times10^{12}$, $3\times10^{12}$, $3.1\times10^{12}$, $3.2\times10^{12}$, $3.3\times10^{12}$, $3.4\times10^{12}$, $3.5\times10^{12}$, $3.6\times10^{12}$, $3.7\times10^{12}$, $3.8\times10^{12}$, $3.9\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/mL. In one embodiment, the concentration of the viral vector in the composition is $1\times10^{13}$ VG/mL. In one embodiment, the concentration of the viral vector in the composition is $3\times10^{12}$ VG/mL. In one embodiment, the concentration of the viral vector in the composition is $1.1\times10^{12}$ VG/mL. In one embodiment, the concentration of the viral vector in the composition is $3.7\times10^{12}$ VG/mL. In one embodiment, the concentration of the viral vector in the composition is $8\times10^{11}$ VG/mL. In one embodiment, the concentration of the viral vector in the composition is $2.6\times10^{12}$ VG/mL. In one embodiment, the concentration of the viral vector in the composition is $4.9\times10^{12}$ VG/mL. In one embodiment, the concentration of the viral vector in the composition is $0.8\times10^{12}$ VG/mL. In one embodiment, the concentration of the viral vector in the composition is $0.83\times10^{12}$ VG/mL. In one embodiment, the concentration of the viral vector in the composition is the maximum final dose which can be contained in a vial.

In one embodiment, delivery of viral vector pharmaceutical compositions in accordance with the present invention to cells of the central nervous system (e.g., parenchyma) may comprise a total concentration per subject between about $1\times10^{6}$ VG and about $1\times10^{16}$ VG. In some embodiments, delivery may comprise a composition concentration of about $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $1.5\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $1.3\times10^{11}$, $2\times10^{11}$, $2.1\times10^{11}$, $2.2\times10^{11}$, $2.3\times10^{11}$, $2.4\times10^{11}$, $2.5\times10^{11}$, $2.6\times10^{11}$, $2.7\times10^{10}$, $2.8\times10^{11}$, $2.9\times10^{11}$, $3\times10^{11}$, $4\times10^{11}$, $5\times10^{11}$, $5.4\times10^{11}$, $6\times10^{11}$, $7\times10^{11}$, $7.1\times10^{11}$, $7.2\times10^{11}$, $7.3\times10^{11}$, $7.4\times10^{11}$, $7.5\times10^{11}$, $7.6\times10^{11}$, $7.7\times10^{11}$, $7.8\times10^{11}$, $7.9\times10^{11}$, $8\times10^{11}$, $9\times10^{11}$, $9.4\times10^{11}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.3\times10^{12}$, $2.4\times10^{12}$, $3\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $7\times10^{12}$, $8\times10^{12}$, $8.1\times10^{12}$, $8.2\times10^{12}$, $8.3\times10^{12}$, $8.4\times10^{12}$, $8.5\times10^{12}$, $8.6\times10^{12}$, $8.7\times10^{12}$, $8.8\times10^{12}$, $8.9\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/subject. In one embodiment, the concentration of the viral vector in the composition is $1\times10^{13}$ VG/subject. In one embodiment, the concentration of the viral vector in the composition is $3\times10^{12}$ VG/subject. As a non-limiting example, the composition administered to the subject has a concentration of about $3\times10^{11}$ VG/subject. As a non-limiting example, the composition administered to the subject has a concentration of about $9\times10^{11}$ VG/subject. In one embodiment, the concentration of the viral vector in the composition is $2.3\times10^{11}$ VG/subject. In one embodiment, the concentration of the viral vector in the composition is $7.2\times10^{11}$ VG/subject. In one embodiment, the concentration of the viral vector in the composition is $7.5\times10^{11}$ VG/subject. In one embodiment, the concentration of the viral vector in the composition is $1.4\times10^{12}$ VG/subject. In one embodiment, the concentration of the viral vector in the composition is $4.8\times10^{12}$ VG/subject. In one embodiment, the concentration of the viral vector in the composition is $8.8\times10^{12}$ VG/subject. In one embodiment, the concentration of the viral vector in the composition is $2.3\times10^{12}$ VG/subject.

In one embodiment, the effectiveness of the dose, route of administration and/or volume of administration may be evaluated using various methods described herein such as, but not limited to, PET imaging, L-DOPA challenge test (e.g., see Forsayeth et al. 2006, Mol. Ther. 14(4): 571-577), UPDRS scores and patient diaries. As a non-limiting example, a subject may have decreased dyskinesia or periods of decreased dyskinesia after administration of the AADC polynucleotide composition. As another non-limiting example, a subject may have a decrease in Parkinson's Disease related symptoms including limited mobility and dyskinesia. As yet another non-limiting example, a subject may show improvement in off time and motor fluctuations. The improvement may be at least 10%, at least 20%, at least 30%, at least 40%, at least 50%, at least 60%, at least 70%, at least 80%, at least 90% or greater than 90%. The improvement may last for minutes (e.g., 1, 2, 3, 4, 5, 6, 7, 8, 9, 10, 15, 20, 25, 30, 35, 40, 45, 50, 55 or more than 55), hours (e.g., 1, 2, 3, 4, 5, 6, 7, 8, 9, 10, 11, 12, 13, 14, 15, 16, 17, 18, 19, 20, 21, 22, 23 or more than 24), days (e.g., 1, 2, 3, 4, 5, 6 or more than 7), weeks (1, 2, 3, 4, 5, 6, 7 or more than, months (1, 2, 3, 4, 5, 6, 7, 8, 9, 10, 11 or more than 11) or years (e.g., 1, 2, 3, 4, 5, 6, 7, 8, 9 or more than 9).

In one embodiment, the selection of subjects for administration of the viral vectors described herein and/or the effectiveness of the dose, route of administration and/or volume of administration may be evaluated using imaging of the perivascular spaces (PVS) which are also known as Virchow-Robin spaces. PVS surround the arterioles and venules as they perforate brain parenchyma and are filled with cerebrospinal fluid (CSF)/interstitial fluid. PVS are common in the midbrain, BG, and centrum semiovale. While not wishing to be bound by theory, PVS may play a role in the normal clearance of metabolites and have been associated with worse cognition and several disease states including Parkinson's disease. PVS are usually normal in size but they can increase in size in a number of disease states. Potter et al. (Cerebrovasc Dis. 2015 January; 39(4): 224-231; the contents of which are herein incorporated by reference in its entirety) developed a grading method where they studied a full range of PVS and rated basal ganglia, centrum semiovale and midbrain PVS. They used the frequency and range of PVS used by Mac and Lullich et al. (J Neurol Neurosurg Psychiatry. 2004 November; 75(11): 1519-23; the contents of which are herein incorporated by reference in its entirety) and Potter et al. gave 5 ratings to basal ganglia and centrum semiovale PVS: 0 (none), 1 (1-10), 2 (11-20), 3 (21-40) and 4 (>40) and 2 ratings to midbrain PVS: 0 (non visible) or 1 (visible). The user guide for the rating system by Potter et al. can be found at: www.sbirc.ed.ac.uk/documents/epvs-rating-scale-user-guide.pdf.

In one embodiment, the selection of subjects for administration of the viral vectors described herein and/or the effectiveness of the dose, route of administration and/or volume of administration may be evaluated using positron emission tomography (PET) measurements of neuroimaging biomarkers such as, but not limited to [$^{18}$F]FDOPA. Neuroimaging biomarkers such as [$^{18}$F]FDOPA may be used to identify affected individuals and/or may be used to detect a nigrostriatal defect prior to the onset of clinical manifestations. Further, PET-based criteria may be used to categorize subjects based on their nigrostriatal neuronal integrity (e.g., abnormal, normal or uncertain nigrostriatal neuronal integrity) (Rachette et al. Am J Med Genet B Neuropsychiatr Genet. 2006 Apr. 5; 141B (3): 245-249; the contents of which are herein incorporated by reference in its entirety).

In one embodiment, a subject who may be administered a dose of the AADC polynucleotides described herein may have advanced PD and still respond to levodopa therapy but the subject also experiences medically refractory motor complications (e.g., sever motor fluctuations and/or dyskinesias that occur during levodopa and other dopaminergic therapies despite adjustments in and optimization of medication). The subject may be healthy enough to undergo a neurosurgical procedure which may be determined by methods known in the art. As a non-limiting example, the subject may meet the selection criteria for deep brain stimulation (DBS). The subject may have idiopathic PD, younger than 69 years of age, have pronounced responses to levodopa, have medication-refractory symptoms (e.g., motor fluctuation and/or dyskinesia) and/or have little or no cognitive dysfunction.

In one embodiment, a subject who may be administered a dose of the AADC polynucleotides described herein may also suffer from dementia or cognitive impairment.

In one embodiment, a subject who may be administered a dose of the AADC polynucleotides described herein may have been previously treated with the same or similar therapeutic. In another embodiment, a subject may have been treated with a therapeutic which has been shown to reduce the symptoms of Parkinson's Disease.

In one embodiment, a subject who may be administered a dose of the AADC polynucleotides described herein may have failed to derive adequate benefit from standard medical therapy. As a non-limiting example, the subject may not have responded to treatment. As another non-limiting example, a subject may have residual disability despite treatment.

In one embodiment, a subject who may be administered a dose of the AADC polynucleotides described herein may undergo testing to evaluate the levels of neurotransmitter analytes to determine the effectiveness of the dose. As a non-limiting example, CSF neurotransmitters, plasma AADC activity and/or urine VLA may be analyzed.

In one embodiment, a subject who may be administered a dose of the AADC polynucleotide described herein may be videotaped or recorded in order to monitor the progress of the subject during the course of treatment.

Combinations

The viral vectors comprising the AADC polynucleotide may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, inhibit their excretion, and/or modify their distribution within the body.

Delivery

In one embodiment, the viral vector comprising an AADC polynucleotide may be administered or delivered using the methods for the delivery of AAV virions described in European Patent Application No. EP1857552, the contents of which are herein incorporated by reference in its entirety.

In one embodiment, the viral vector comprising an AADC polynucleotide may be administered or delivered using the methods for delivering proteins using AAV vectors described in European Patent Application No. EP2678433, the contents of which are herein incorporated by reference in its entirety.

In one embodiment, the viral vector comprising an AADC polynucleotide may be administered or delivered using the methods for delivering DNA molecules using AAV vectors described in U.S. Pat. No. 5,858,351, the contents of which are herein incorporated by reference in its entirety.

In one embodiment, the viral vector comprising an AADC polynucleotide may be administered or delivered using the methods for delivering DNA to the bloodstream described in U.S. Pat. No. 6,211,163, the contents of which are herein incorporated by reference in its entirety.

In one embodiment, the viral vector comprising an AADC polynucleotide may be administered or delivered using the methods for delivering AAV virions described in U.S. Pat. No. 6,325,998, the contents of which are herein incorporated by reference in its entirety.

In one embodiment, the viral vector comprising an AADC polynucleotide may be administered or delivered using the methods for delivering a payload to the central nervous system described in U.S. Pat. No. 7,588,757, the contents of which are herein incorporated by reference in its entirety.

In one embodiment, the viral vector comprising an AADC polynucleotide may be administered or delivered using the methods for delivering a payload described in U.S. Pat. No. 8,283,151, the contents of which are herein incorporated by reference in its entirety.

In one embodiment, the viral vector comprising an AADC polynucleotide may be administered or delivered using the methods for delivering a payload using a glutamic acid decarboxylase (GAD) delivery vector described in International Patent Publication No. WO2001089583, the contents of which are herein incorporated by reference in its entirety.

In one embodiment, the viral vector comprising an AADC polynucleotide may be administered or delivered using the methods for delivering a payload to neural cells described in International Patent Publication No. WO2012057363, the contents of which are herein incorporated by reference in its entirety.

The pharmaceutical compositions of viral vectors described herein may be characterized by one or more of bioavailability, therapeutic window and/or volume of distribution.

Bioavailability

Viral vectors comprising an AADC polynucleotide of the present invention, when formulated into compositions with delivery/formulation agents or vehicles as described herein, may exhibit increased bioavailability as compared to compositions lacking delivery agents as described herein. As used herein, the term "bioavailability" refers to the systemic availability of a given amount of a particular agent administered to a subject. Bioavailability may be assessed by measuring the area under the curve (AUC) or the maximum serum or plasma concentration ($C_{max}$) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound may be calculated using methods known to those of ordinary skill in the art and as described in G. S. Banker, Modern Pharmaceutics, Drugs and the Pharmaceutical Sciences, v. 72, Marcel Dekker, New York, Inc., 1996, the contents of which are herein incorporated by reference in their entirety.

$C_{max}$ values are maximum concentrations of compounds achieved in serum or plasma of a subject following administration of compounds to the subject. $C_{max}$ values of particular compounds may be measured using methods known to those of ordinary skill in the art. As used herein, the phrases "increasing bioavailability" or "improving the pharmacokinetics," refer to actions that may increase the systemic availability of a viral vector of the present invention (as measured by AUC, $C_{max}$, or $C_{min}$) in a subject. In some embodiments, such actions may comprise co-administration with one or more delivery agents as described herein. In some embodiments, the bioavailability of viral vectors may increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or about 100%.

Therapeutic Window

Viral vectors comprising an AADC polynucleotide of the present invention, when formulated with one or more delivery agents as described herein, may exhibit increases in the therapeutic window of compound and/or composition administration as compared to the therapeutic window of viral vectors administered without one or more delivery agents as described herein. As used herein, the term "therapeutic window" refers to the range of plasma concentrations, or the range of levels of therapeutically active substance at the site of action, with a high probability of eliciting a therapeutic effect. In some embodiments, therapeutic windows of viral vectors when administered in a formulation may increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or about 100%.

Volume of Distribution

Viral vectors comprising an AADC polynucleotide of the present invention, when formulated with one or more delivery agents as described herein, may exhibit an improved volume of distribution ($V_{dist}$), e.g., reduced or targeted, relative to formulations lacking one or more delivery agents as described herein. $V_{dist}$ relates the amount of an agent in the body to the concentration of the same agent in the blood or plasma. As used herein, the term "volume of distribution" refers to the fluid volume that would be required to contain the total amount of an agent in the body at the same concentration as in the blood or plasma: $V_{dist}$ equals the amount of an agent in the body/concentration of the agent in blood or plasma. For example, for a 10 mg dose of a given agent and a plasma concentration of 10 mg/L, the volume of distribution would be 1 liter. The volume of distribution reflects the extent to which an agent is present in the extravascular tissue. Large volumes of distribution reflect the tendency of agents to bind to the tissue components as compared with plasma proteins. In clinical settings, $V_{dist}$ may be used to determine loading doses to achieve steady state concentrations. In some embodiments, volumes of distribution of viral vector compositions of the present invention when co-administered with one or more delivery agents as described herein may decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

Kits and Devices

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

Any of the AADC vectors, AADC constructs, AADC polynucleotides, or AADC polypeptides of the present invention may be comprised in a kit. In some embodiments, kits may further include reagents and/or instructions for creating and/or synthesizing compounds and/or compositions of the present invention. In some embodiments, kits may also include one or more buffers. In some embodiments, kits of the invention may include components for making protein or nucleic acid arrays or libraries and thus, may include, for example, solid supports.

In some embodiments, kit components may be packaged either in aqueous media or in lyophilized form. The container means of the kits will generally include at least one vial, test tube, flask, bottle, syringe or other container means, into which a component may be placed, and preferably, suitably ali quoted. Where there are more than one kit component, (labeling reagent and label may be packaged together), kits may also generally contain second, third or other additional containers into which additional components may be separately placed. In some embodiments, kits may also comprise second container means for containing sterile, pharmaceutically acceptable buffers and/or other diluents. In some embodiments, various combinations of components may be comprised in one or more vial. Kits of the present invention may also typically include means for containing compounds and/or compositions of the present invention, e.g., proteins, nucleic acids, and any other reagent containers in close confinement for commercial sale. Such containers may include injection or blow-molded plastic containers into which desired vials are retained.

In some embodiments, kit components are provided in one and/or more liquid solutions. In some embodiments, liquid solutions are aqueous solutions, with sterile aqueous solutions being particularly preferred. In some embodiments, kit components may be provided as dried powder(s). When reagents and/or components are provided as dry powders, such powders may be reconstituted by the addition of suitable volumes of solvent. In some embodiments, it is envisioned that solvents may also be provided in another container means. In some embodiments, labeling dyes are provided as dried powders. In some embodiments, it is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 micrograms or at least or at most those amounts of dried dye are provided in kits of the invention. In such embodiments, dye may then be resuspended in any suitable solvent, such as DMSO.

In some embodiments, kits may include instructions for employing kit components as well the use of any other reagent not included in the kit. Instructions may include variations that may be implemented.

Devices

In some embodiments, AADC compounds and/or AADC compositions of the present invention may be combined with, coated onto or embedded in a device. Devices may include, but are not limited to stents, pumps, and/or other implantable therapeutic device. Additionally AADC compounds and/or AADC compositions may be delivered to a subject while the subject is using a compression device such as, but not limited to, a compression device to reduce the chances of deep vein thrombosis (DVT) in a subject.

The present invention provides for devices which may incorporate viral vectors that encode one or more AADC polynucleotide payload molecules. These devices contain in a stable formulation the viral vectors which may be immediately delivered to a subject in need thereof, such as a human patient.

Devices for administration may be employed to deliver the viral vectors comprising an AADC polynucleotide of the present invention according to single, multi- or split-dosing regimens taught herein.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

In some embodiments, AADC compounds and/or AADC compositions of the present invention may be delivered using a device such as, but not limited to, a stent, a tube, a catheter, a pipe, a straw, needle and/or a duct. Methods of using these devices are described herein and are known in the art.

In one embodiment, the AADC polynucleotides of the present invention may be administered to a subject using delivery systems which integrate image guided therapy and integrate imaging such as, but not limited to, laser, MRgFUS, endoscopic and robotic surgery devices.

In one embodiment, the AADC polynucleotides of the present invention may be administered to a subject using the CLEARPOINT® neuro intervention system by MRI Interventions, Inc. The CLEARPOINT® neuro intervention system may be used alone or in combination with any of the other administration methods and devices described herein. The CLEARPOINT® neuro intervention system helps to provide stereotactic guidance in the placement and operation of instruments or devices during the planning and operation of neurological procedures.

In one embodiment, the AADC polynucleotides of the present invention may be administered to a subject using the NEUROMATE® stereotactic robot system by Renishaw PLC. The NEUROMATE® system may be used alone or in combination with any of the other administration methods and devices described herein. As a non-limiting example, the NEUROMATE® system may be used with head holders, CT image localizers, frame attachments, remote controls and software.

In one embodiment, the AADC polynucleotides of the present invention may be administered to a subject using the Elekta MICRODRIVE™ device by Elekta AB. The MICRODRIVE™ device may be used alone or in combination with any of the other administration methods and devices described herein. As a non-limiting example, the MICRODRIVE™ device may be used to position electrodes (e.g., for micro electrode recording (MER), macro stimulation and deep brain stimulation (DBS) electrode implantation), implantation of catheters, tubes or DBS electrodes using cross-hair and A-P holders to verify position, biopsies, injections and aspirations, brain lesioning, endoscope guidance and GAMMA KNIFE® radiosurgery.

In one embodiment, the AADC polynucleotides of the present invention may be administered to a subject using the AXIIIS® stereotactic miniframe by MONTERIS® Medical, Inc. The AXIIIS® stereotactic miniframe may be used alone or in combination with any of the other administration methods and devices described herein. The AXIIIS® stereotactic miniframe is a trajectory alignment device which may be used for laser coagulation, biopsies, catheter placement, electrode implant, endoscopy, and clot evacuation. The miniframe allows for 360 degree interface and provides access to multiple intracranial targets with a simple adjustment. Further, the miniframe is compatible with MRI.

In one embodiment, the AADC polynucleotides of the present invention may be administered to a subject using the INTEGRA™ CRW® system by Integra LifeSciences Corporation. The INTEGRA™ CRW® system may be used alone or in combination with any of the other administration methods and devices described herein. The CRW® system may be used for various applications such as, but not limited to, stereotactic surgery, microsurgery, catheterization and biopsy. The CRW® system is designed to provide accuracy to those who use the system (e.g., thumb lock screws, Vernier scaling, double bolt fixation, and a solid frame).

In one embodiment, the AADC polynucleotides of the present invention may be administered to a subject using the EPOCH® solution system by Stereotaxis, Inc. which may include the NIOBE® ES magnetic navigation system, the VDRIVE® robotic navigation system and/or the ODYSSEY® information solution (all by Stereotaxis, Inc.). The EPOCH® solution system may be used alone or in combination with any of the other administration methods and devices described herein. As a non-limiting example, the NIOBE® ES magnetic navigation system may be used to accurately contact a subject. As another non-limiting example the NIOBE® ES magnetic system may be used with the VDRIVE® robotic navigation system to provide precise movement and stability.

In one embodiment, the AADC polynucleotides of the present invention may be administered to a subject using a NeuroStation workstation which uses frameless stereotactic methods to provide image-guidance for applications such as, but not limited to, surgical planning, biopsies, craniotomies, endoscopy, intra-operative ultrasound and radiation therapy.

In one embodiment, the AADC polynucleotides of the present invention may be administered to a subject using a robotic stereotaxis system such as, but not limited to the device described in U.S. Pat. No. 5,078,140, the contents of which are herein incorporated by reference in its entirety. The robotic arm of the device may be used to precisely orient the surgical tools or other implements used to conduct a procedure.

In one embodiment, the AADC polynucleotides of the present invention may be administered to a subject using an automatic delivery system such as, but not limited to the device described in U.S. Pat. No. 5,865,744, the contents of which are herein incorporated by reference in its entirety. Based on the images gathered by the delivery system, the computer adjusts the administration of the needle to be the appropriate depth for the particular subject.

In one embodiment, the AADC polynucleotides of the present invention may be administered to a subject who is simultaneously using during administration, and/or uses for a period of time before and/or after administration a compression device such as, but not limited to, a compression device which reduces the chances of deep vein thrombosis (DVT) in a subject. The compression device may be used for at least 5 minutes, 15 minutes, 30 minutes, 45 minutes, 1 hour, 2 hours, 3 hours, 4 hours, 5 hours, 6 hours, 7 hours, 8 hours, or more than 8 hours before a subject is administered the AADC polynucleotides. The compression device may be used for at least 5 minutes, 15 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 2.2 hours, 23 hours, 1 day, 2 days, 3 days, 4 days, 5 days, 6 days, 1 week, 2 weeks, 3 weeks or a month after the AADC polynucleotides are administered. As a non-limiting example, the compression device is used simultaneously during the procedure of the delivery of the AADC polynucleotides. As another non-limiting example, the compression device is used before the administration of the AADC polynucleotides. As another non-limiting example, the compression device is used after administration of the AADC polynucleotides. As another non-limiting example, the compression device is used before, during and after administration of the AADC polynucleotides.

Non-limiting examples, of compression devices include ActiveCare +S.F.T. intermittent compression device, ActiveCare +S.F.T pneumatic compression device, DVTlite's Venowave, KCI system compression pump, Aircast VenaFlow system, SCD Express Compression System or Bio Compression Systems, Inc. pneumatic compression therapy equipment (e.g., the pump may be selected from Model SC-2004, Model SC-2004-FC, Model SC-3004, Model SC-3004-FC, Model SC-2008, Model SC-2008-DL, Model SC-3008-T, the BioCryo system, Model IC-BAP-DL or multi-flo DVT combo IC_1545-DL and the garment used with the pump may be a 4 chamber, 8 chamber, BioCryo, Multi-Flo or BioArterial garment).

CNS Diseases

The polynucleotides of the present invention may be used in the treatment, prophylaxis or amelioration of any disease or disorder characterized by aberrant or undesired target expression. In one embodiment, the invention relates to compositions, particularly nucleic acid molecules, e.g., polynucleotides encoding AADC, for use in the treatment of Parkinson's disease.

In some embodiments, the polynucleotides of the invention may be used in the treatment, prophylaxis or amelioration of any disease or disorder characterized by aberrant or undesired target expression wherein the payload, i.e. AADC, is swapped for an alternate payload.

The present disclosure provides a method for treating a disease, disorder and/or condition in a mammalian subject, including a human subject, comprising administering to the subject any of the viral particles e.g., AAV, AAV polynucleotides or AAV genomes described herein (i.e., viral genomes or "VG") or administering to the subject a particle comprising said AAV polynucleotide or AAV genome, or administering to the subject any of the described compositions, including pharmaceutical compositions.

In one embodiment, the disease, disorder and/or condition is a neurological disease, disorder and/or condition. The CNS diseases may be diseases that affect any component of the brain (including the cerebral hemispheres, diencephalon, brain stem, and cerebellum) or the spinal cord.

In some embodiments, viral particles of the present invention, through delivery of a functional payload that is a therapeutic product that can modulate the level or function of a gene product in the CNS, may be used to treat a neurodegenerative diseases and/or diseases or disorders that are characteristic with neurodegeneration, neuromuscular diseases, lysosomal diseases, trauma, bone marrow injuries, pain (including neuropathic pain), cancers of the nervous system, demyelinating diseases, autoimmune diseases of the nervous system, neurotoxic syndromes, sleeping disorders, genetic brain disorders and developmental CNS disorders. A functional payload may alleviate or reduce symptoms that result from abnormal level and/or function of a gene product (e.g., an absence or defect in a protein) in a subject in need thereof or that otherwise confers a benefit to a CNS disorder in a subject in need thereof.

As non-limiting examples, therapeutic products delivered by viral particles of the present invention may include, but are not limited to, growth and trophic factors, cytokines, hormones, neurotransmitters, enzymes, anti-apoptotic factors, angiogenic factors, and any protein known to be mutated in pathological disorders such as the "survival of motor neuron" protein (SMN); antisense RNA or RNAi targeting messenger RNAs coding for proteins having a therapeutic interest in any of CNS diseases discussed herein; or microRNAs that function in gene silencing and post-transcriptionally regulation of gene expression in the CNS (e.g., brain specific Mir-128a, See Adlakha and Saini, Molecular cancer, 2014, 13:33). For example, an RNAi targeting the superoxide dismutase enzyme may be packaged by viral particles of the present invention, for the treatment of ALS.

The growth and trophic factors may include, but are not limited to brain-derived growth factor (BDNF), epidermal growth factor (EGF), basic Fibroblast growth factor (bFGF), Ciliary neurotrophic factor (CNTF), corticotropin-releasing factor (CRF), Glial cell line derived growth factor (GDNF), Insulin-like growth factor-1 (IGF-1), nerve growth factor (NGF), neurotrophin-3 (NT-3), neurotrophin-4 (NT-4), and vascular endothelial growth factor (VEGF). Cytokines may include interleukin-10 (IL-10), interleukin-6, Interleukin-8, chemokine CXCL12 (SDF-1), TGF-beta, and Growth and differentiation factor (GDF-1/10).

In some embodiments, the neurological disorders may be neurodegenerative disorders including, but not limited to, Alzheimer's Diseases (AD); Amyotrophic lateral sclerosis (ALS); Creutzfeldt-jakob Disease (CJD); Huntingtin's disease (HD); Friedreich's ataxia (FA); Parkinson Disease (PD); Multiple System Atrophy (MSA); Spinal Muscular Atrophy (SMA), Multiple Sclerosis (MS); Primary progressive aphasia; Progressive supranuclear palsy (PSP); Dementia; Brain Cancer, Degenerative Nerve Diseases, Encephalitis, Epilepsy, Genetic Brain Disorders that cause neurodegeneration, Retinitis pigmentosa (RP), Head and Brain Malformations, Hydrocephalus, Stroke, Prion disease, Infantile neuronal ceroid lipofuscinosis (INCL) (a neurodegenerative disease of children caused by a deficiency in the lysosomal enzyme palmitoyl protein thioesterase-1 (PPT1)), and others.

In some embodiments, viral particles of the present invention may be used to treat diseases that are associated with impairments of the growth and development of the CNS, i.e., neurodevelopmental disorders. In some aspects, such neurodevelopmental disorders may be caused by genetic mutations, including but not limited to, Fragile X syndrome (caused by mutations in FMR1 gene), Down syndrome (caused by trisomy of chromosome 21), Rett syndrome, Williams syndrome, Angelman syndrome, Smith-Magenis syndrome, ATR-X syndrome, Barth syndrome, Immune dysfunction and/or infectious diseases during infancy such as Sydenham's chorea, Schizophrenia Congenital toxoplasmosis, Congenital rubella syndrome, Metabolic disorders such as diabetes mellitus and phenylketonuria; nutritional defects and/or brain trauma, Autism and autism spectrum.

In some embodiments, viral particles of the present invention, may be used to treat a tumor in the CNS, including but not limited to, acoustic neuroma, Astrocytoma (Grades I, II, III and IV), Chordoma, CNS Lymphoma, Craniopharyngioma, Gliomas (e.g., brain stem glioma, ependymoma, optical nerve glioma, subependymoma), Medulloblastoma, Meningioma, Metastatic brain tumors, Oligodendroglioma, Pituitary Tumors, Primitive neuroectodermal (PNET), and Schwannoma.

In some embodiments, the neurological disorders may be functional neurological disorders with motor and/or sensory symptoms which have neurological origin in the CNS. As non-limiting examples, functional neurological disorders may be chronic pain, seizures, speech problems, involuntary movements, and sleep disturbances.

In some embodiments, the neurological disorders may be white matter disorders (a group of diseases that affects nerve fibers in the CNS) including but not limited to, Pelizaeus-Merzbacher disease, Hypomyelination with atrophy of basal ganglia and cerebellum, Aicardi-Goutières syndrome, Megalencephalic leukoencephalopathy with subcortical cysts, Congenital muscular dystrophies, Myotonic dystrophy, Wilson disease, Lowe syndrome, Sjögren-Larsson syndrome, PIBD or Tay syndrome, Cockayne's disease, erebrotendinous xanthomatosis, Zellweger syndrome, Neonatal adrenoleukodystrophy, Infantile Refsum disease, Zellweger-like syndrome, Pseudo-Zellweger syndrome, Pseudo-neonatal adrenoleukodystrophy, Bifunctional protein deficiency, X-linked adrenoleukodystrophy and adrenomyeloneuropathy and Refsum disease.

In some embodiments, the neurological disorders may be lysosomal storage disorders (LSDs) caused by the inability of cells in the CNS to break down metabolic end products, including but not limited to Niemann-Pick disease (a LSD resulting from inherited deficiency in acid sphingomyelinase (ASM); Metachromatic leukodystrophy (MLD) (a LSD characterized by accumulation of sulfatides in glial cells and neurons, the result of an inherited deficiency of arylsulfatase A (ARSA)); Globoid-cell leukodystrophy (GLD) (a LSD caused by mutations in galactosylceratnidase); Fabry disease (a LSD caused by mutations in the alpha-galactosidase A (GLA) gene); Gaucher disease (caused by mutations in the beta-glucocerebrosidase (GBA) gene); GM1/GM2 gangliosidosis; Mucopolysaccharidoses disorder; Pompe disease; and Neuronal ceroid lipofuscinosis.

In one embodiment, the neurological disease, disorder and/or condition is Parkinson's disease. In one embodiment the polynucleotide used to treat Parkinson's disease comprises any one of SEQ ID NOs 2-23, such as, but not limited to SEQ ID NOs: 6-9 and 17-23, wherein the payload is replaced by AADC or any other payload known in the art for treating Parkinson's disease. As a non-limiting example, the condition is early stage Parkinson's disease. As another non-limiting example, the condition is late stage Parkinson's disease.

In one embodiment, the subject is a human patient who has a minimum motor score of about 30 to a maximum score of about 100, about 10 to a maximum score of about 100, about 20 to a maximum score of about 100 in the Unified Parkinson's Disease Rating Scale.

In one embodiment, the subject has been diagnosed with Parkinson's disease within the past 5 years prior to treatment with the compositions described herein. As a non-limiting example, the subject may have been diagnosed with Parkinson's disease within a week, 2 weeks, 3 weeks, 4 weeks, 5 weeks, 6 weeks, 7 weeks, 8 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 1 year, 2 years, 3 years, 4 years or less than 5 years prior to treatment with the compositions described herein.

In one embodiment, the subject has been diagnosed with Parkinson's disease between 5 and 10 years prior to treatment with the compositions described herein. As a non-limiting example, the subject may have been diagnosed with Parkinson's disease 5, 5.5, 6, 6.5, 7, 7.5, 8, 8.5, 9, 9.5 or 10 years prior to treatment with the compositions described herein.

In one embodiment, the subject has been diagnosed with Parkinson's disease more than 10 years prior to treatment with the compositions described herein. As a non-limiting example, the subject may have been diagnosed with Parkinson's disease 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24 or more than 24 years prior to treatment with the compositions described herein.

In one embodiment, a subject has seen a change in motor symptoms such as tremors and movements prior to administration of the composition described herein. Non-limiting examples of tremors include, unilateral or bilateral mild tremors, bilateral or midline moderate tremors or intractable tremors. Non-limiting examples of movements include mild bradykinesia, moderate bradykinesia, severe bradykinesia and morning akinesia.

In one embodiment, a subject may have changes in balance such as, but not limited to, impaired balance, impaired righting reflexes, significant balance disorder or falling.

In one embodiment, a subject may have a reduced quality of life. As a non-limiting example, the subject may have a moderate impact on their quality of life such as experiencing some limitations to activities of daily living. As another non-limiting example, the subject may have a quality of life which has been diminished by illness.

In one embodiment, a subject has seen a change in non-motor symptoms prior to administration of the composition described herein. As a non-limiting example, the subject may have mild to moderate cognitive impairment prior to administration to the composition described herein. As another non-limiting example, the subject may have significant cognitive impairment such as dementia which may also include behavioral disturbances such as hallucinations.

In one embodiment, a subject may have a satisfactory response with limited fluctuations on one or more dopaminergic medications prior to administration of the compositions described herein.

In one embodiment, a subject may have motor fluctuations causing mild to moderate disability on one or more dopaminergic medications prior to administration of the compositions described herein.

In one embodiment, a subject may have medically refractory motor fluctuations consisting of "wearing off" and/or levodopa-induced dyskinesias causing significant disability prior to administration of the compositions described herein.

In one embodiment, a subject may have mild symptoms associated with Parkinson's disease such as, but not limited to, no cognitive impairment, diagnosed within the past 5 years, satisfactory response with limited fluctuations on one or more dopaminergic medications, unilateral or bilateral mild tremors, little to no impact on the quality of life, and/or no balance impairment.

In one embodiment, a subject may have moderate symptoms associated with Parkinson's disease such as, but not limited to, mild to moderate cognitive impairment, first signs of impaired balance and righting reflexes, motor fluctuations causing mild-moderate disability on one or more dopaminergic medications, diagnosed within the past 5 to 10 years, bilateral or midline moderate tremors, moderate bradykinesia and/or subject experiencing some limitations to activities of daily living.

In one embodiment, a subject may have advanced symptoms associated with Parkinson's disease such as, but not limited to, being diagnosed with Parkinson's more than 10 years, medium refractory motor fluctuations wearing off and/or levodopa-induced dyskinesia causing significant disability, intractable tremors, significant balance disorder and/or falling, significant cognitive impairment (such as dementia with or without behavioral disturbances), sever bradykinesia, quality of life markedly diminished by illness and/or morning akinesia.

In one embodiment, a subject has been referred to a movement disorder specialist (MDS) but has not undergone deep brain stimulation.

In one embodiment, a subject is using DUOPA™ in combination with the compositions described herein. As a non-limiting example, the subject may have success with using DUOPA™ alone. As a non-limiting example, the subject may not have any success or limited success using DUOPA™ alone.

In another embodiment, the neurological disease, disorder and/or condition is Friedreich's Ataxia. In one embodiment the polynucleotide used to treat Friedreich's Ataxia comprises any one of SEQ ID NOs 2-23, such as, but not limited to SEQ ID NOs: 6-9 and 17-23, wherein the payload is replaced by Frataxin or any other payload known in the art for treating Friedreich's Ataxia.

In another embodiment, the neurological disease, disorder and/or condition is Amyotrophic lateral sclerosis (ALS). In one embodiment the polynucleotide used to treat ALS comprises any one of SEQ ID NOs 2-23, such as, but not limited to SEQ ID NOs: 6-9 and 17-23, wherein the payload is replaced by an shRNA, miRNA, siRNA, RNAi for SOD1 or any other payload known in the art for treating ALS.

In another embodiment, the neurological disease, disorder and/or condition is Huntington's disease. In one embodiment the polynucleotide used to treat Huntington's disease comprises any one of SEQ ID NOs 2-23, such as, but not limited to SEQ ID NOs: 6-9 and 17-23, wherein the payload is replaced by an shRNA, miRNA, siRNA, RNAi for Htt or any other payload known in the art for treating Huntington's disease.

In another embodiment, the neurological disease, disorder or condition is spinal muscular atrophy (SMA). In one embodiment the polynucleotide used to treat SMA comprises any one of SEQ ID NOs 2-23, such as, but not limited to SEQ ID NOs: 6-9 and 17-23, wherein the payload is replaced by SMN or any other payload known in the art for treating SMA.

Circadian Rhythm and Sleep-Wake Cycles

Circadian rhythms are physical, mental and behavioral changes that tend to follow a 24 hour cycle, Circadian rhythms can influence sleep-wake cycles, hormone release, body temperature and other bodily functions. Changes in the circadian rhythm can cause conditions and/or disorder such as, but not limited to sleep disorders (e.g., insomnia), depression, bipolar disorder, seasonal affective disorder, obesity and diabetes.

In one embodiment, the AADC polynucleotides described herein may be used to treat insomnia.

The sleep-wake cycle comprises periods of sleep and periods of wake. Generally, in a 24 hour period the total hours of sleep are less than the total hours of wakefulness. As a non-limiting example, the sleep-wake cycle comprises 7-9 hours of sleep and 15-17 hours of wakefulness. As a non-limiting example, the sleep-wake cycle comprises 8 hours of sleep and 16 hours of wakefulness. As a non-limiting example, the sleep-wake cycle comprises 8-10 hours of sleep and 14-16 hours of wakefulness.

In one embodiment, the sleep-wake cycle of a subject is improved by administered to the subject the AADC polynucleotides described herein.

In one embodiment, the sleep-wake cycle of a subject is regulated by administering to the subject the AADC polynucleotides described herein. As a non-limiting example, the regulation may be the correction of more periods of sleep occurring at night and less periods of sleep occurring In one embodiment, the sleep-wake cycle of a subject administered the AADC polynucleotides described herein improves as compared to the sleep-wake cycle of the subject prior to administration of the AADC polynucleotides. As a non-limiting example, the subject has an increased period of sleep and a decreased period of wakefulness. As another non-limiting example, the subject has a decreased period of sleep and an increased period of wakefulness.

In one embodiment, the sleep-wake cycle of a subject administered the AADC polynucleotides described herein is regulated as compared to the sleep-wake cycle of the subject prior to administration of the AADC polynucleotides. As a non-limiting example, the length of the periods of sleep and the periods of wakefulness may be about the same (e.g., +/−1 hour) for at least 2 days. As another non-limiting example, the length of the periods of sleep and the periods of wakefulness if a 24 hours period may be within 10 minutes, 15 minutes, 20 minutes, 25 minutes, 30 minutes, 35 minutes, 40 minutes, 45 minutes, 50 minutes, 55 minutes, 1 hour, 1.5 hours, or 2 hours of the previous 24 hour period.

In one embodiment, the amount of rapid eye movement (REM) sleep a subject experiences in a 24 hour period is altered after the subject is administered the AADC polynucleotides described herein. REM sleep is generally considered an active period of sleep marked by intense brain activity where brain waves are fast and desynchronized. An adult, on average, spends about 20-25% of their total daily sleep period in REM sleep. As a non-limiting example, the amount of REM sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of REM sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. As a non-limiting example, the amount of REM sleep is increased by 1%, 2%, 3%, 4%, 5%, 6%, 7%, 8%, 9%, 10%, 11%, 12%, 13%, 14%, 15%, 20%, 25%, 30% 35%, 40%, 45%, 50%, 55%, 60%, 65% or more than 65%. As a non-limiting example, the amount of REM sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In one embodiment, the amount of non-REM (NREM) sleep a subject experiences in a 24 hour period is altered after the subject is administered the AADC polynucleotides described herein. NREM sleep is generally characterized by a reduction in physiological activity since as the brain waves, measured by EEG, get slower and have greater amplitude. NREM has four stages: Stage 1 is the time of drowsiness or transition from being awake to falling asleep where the brain waves and muscle activity begin to slow; Stage 2 is a period of light sleep during which eye movements stop and brain waves become slower with occasional bursts of rapid waves (sometimes called sleep spindles); Stage 3 and Stage 4 (collectively referred to as slow wave sleep) are characterized by the presence of slow brain waves (delta waves) interspersed with smaller faster waves where there are no eye movements. An adult, on average, spends about 75-80% of their total daily sleep period in NREM sleep with about half of their total daily sleep time in NREM stage 2 sleep.

In one embodiment, the amount of NREM sleep a subject experiences is altered after the subject is administered the AADC polynucleotides described herein. As a non-limiting example, the amount of NREM sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. As a non-limiting example, the amount of NREM sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In one embodiment, the amount of NREM Stage 1 sleep a subject experiences is altered after the subject is administered the AADC polynucleotides described herein. As a non-limiting example, the amount of NREM Stage 1 sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM Stage 1 sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. As a non-limiting example, the amount of NREM Stage 1 sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55% 60%, 65% or more than 65%. As a non-limiting example, the amount of NREM Stage 1 sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In one embodiment, the amount of NREM Stage 2 sleep a subject experiences is altered after the subject is administered the AADC polynucleotides described herein. As a non-limiting example, the amount of NREM Stage 2 sleep is decreased by 1%, 2%, 3%, 4%, 5%, 6%, 7%, 8%, 9% 10%, 11%, 12%, 13%, 14%, 15%, 20%, 25%, 30%, 35% 40%, 45%, 50%, 55% 60%, 65% or more than 65. As a non-limiting example, the amount of NREM Stage 2 sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. As a non-limiting example, the amount of NREM Stage 2 sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM Stage 2 sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In one embodiment, the amount of NREM Stage 3 and 4 sleep a subject experiences is altered after the subject is administered the AADC polynucleotides described herein. As a non-limiting example, the amount of NREM Stage 3 and 4 sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM Stage 3 and 4 sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. As a non-limiting example, the amount of NREM Stage 3 and 4 sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. As a non-limiting example, the amount of NREM Stage 3 and 4 sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In one embodiment, periods of NREM and REM cycles are more consistent n a subject after the subject is administered the AADC polynucleotides described herein. Generally NREM and REM cycles alternate every 90 to 110 minutes four to six times per night.

Definitions

At various places in the present specification, substituents of compounds of the present disclosure are disclosed in groups or in ranges. It is specifically intended that the present disclosure include each and every individual subcombination of the members of such groups and ranges.

About: As used herein, the term "about" means +/−10% of the recited value.

Activity: As used herein, the term "activity" refers to the condition in which things are happening or being done. Compositions described herein may have activity and this activity may involve one or more biological events.

Adeno-associated virus: The term "adeno-associated virus" or "AAV" as used herein refers to members of the *dependovirus* genus comprising any particle, sequence, gene, protein, or component derived therefrom. The term "AAV particle" as used herein comprises a capsid and a polynucleotide. The AAV particle may be derived from any serotype, described herein or known in the art, including combinations of serotypes (i.e., "pseudotyped" AAV) or from various genomes (e.g., single stranded or self-complementary). In addition, the AAV particle may be replication defective and/or targeted.

Administered in combination: As used herein, the term "administered in combination" or "combined administration" means that two or more agents (e.g., AAV) are administered to a subject at the same time or within an interval such that there may be an overlap of an effect of each agent on the patient and/or the subject is at some point in time simultaneously exposed to both. In some embodiments, they are administered within about 60, 30, 15, 10, 5, or 1 minutes of one another or within about 24 hours, 12 hours, 6 hours, 3 hours of at least one dose of one or more other agents. In some embodiments, administration occurs in overlapping dosage regimens. As used herein, the term "dosage regimen" refers to a plurality of doses spaced apart in time. Such doses may occur at regular intervals or may include one or more hiatus in administration. In some embodiments, the administrations of the agents are spaced sufficiently closely together such that a combinatorial (e.g., a synergistic) effect is achieved.

Amelioration: As used herein, the term "amelioration" or "ameliorating" refers to a lessening of severity of at least one indicator of a condition or disease. For example, in the context of neurodegeneration disorder, amelioration includes the reduction of neuron loss.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antisense strand: As used herein, the term "the antisense strand" or "the first strand" or "the guide strand" of a siRNA molecule refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may affect the same outcome or a different outcome. The structure that produces the function may be the same or different.

Biologically active: As used herein, the phrase "biologically active" refers to a characteristic of any substance (e.g., AAV) that has activity in a biological system and/or organism. For instance, a substance that, when administered to an organism, has a biological effect on that organism, is considered to be biologically active. In particular embodiments, a polynucleotide of the present invention may be considered biologically active if even a portion of the polynucleotides is biologically active or mimics an activity considered biologically relevant.

Biological system: As used herein, the term "biological system" refers to a group of organs, tissues, cells, intracellular components, proteins, nucleic acids, molecules (including, but not limited to biomolecules) that function together to perform a certain biological task within cellular membranes, cellular compartments, cells, tissues, organs, organ systems, multicellular organisms, or any biological entity. In some embodiments, biological systems are cell signaling pathways comprising intracellular and/or extracellular cell signaling biomolecules. In some embodiments, biological systems comprise growth factor signaling events within the extracellular/cellular matrix and/or cellular niches.

Biomolecule: As used herein, the term "biomolecule" is any natural molecule which is amino acid-based, nucleic acid-based, carbohydrate-based or lipid-based, and the like.

Complementary and substantially complementary: As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pairs in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100% complementarity refers to the situation in which each nucleotide unit of one polynucleotide strand can form a hydrogen bond with a nucleotide unit of a second polynucleotide strand. Less than perfect complementarity refers to the situation in which some, but not all, nucleotide units of two strands can form hydrogen bonds with each other. For example, for two 20-mers, if only two base pairs on each strand can form hydrogen bonds with each other, the polynucleotide strands exhibit 10% complementarity. In the same example, if 18 base pairs on each strand can form hydrogen bonds with each other, the polynucleotide strands exhibit 90% complementarity. As used herein, the term "substantially complementary" means that the siRNA has a sequence (e.g., in the antisense strand) which is sufficient to bind the desired target mRNA, and to trigger the RNA silencing of the target mRNA.

Compound: As used herein, the term "compound," refers to a distinct chemical entity. In some embodiments, a particular compound may exist in one or more isomeric or isotopic forms (including, but not limited to stereoisomers, geometric isomers and isotopes). In some embodiments, a compound is provided or utilized in only a single such form. In some embodiments, a compound is provided or utilized as a mixture of two or more such forms (including, but not limited to a racemic mixture of stereoisomers). Those of skill in the art appreciate that some compounds exist in different such forms, show different properties and/or activities (including, but not limited to biological activities). In such cases it is within the ordinary skill of those in the art to select or avoid particular forms of the compound for use in accordance with the present invention. For example, compounds that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide, a polynucleotide or polypeptide or may apply to a portion, region or feature thereof.

In one embodiment, conserved sequences are not contiguous. Those skilled in the art are able to appreciate how to achieve alignment when gaps in contiguous alignment are present between sequences, and to align corresponding residues not withstanding insertions or deletions present.

In one embodiment, conserved sequences are not contiguous. Those skilled in the art are able to appreciate how to achieve alignment when gaps in contiguous alignment are present between sequences, and to align corresponding residues not withstanding insertions or deletions present.

Delivery: As used herein, "delivery" refers to the act or manner of delivering a compound such as a parvovirus, e.g. an AAV and/or AAV compound, substance, entity, moiety, cargo or payload to a target. Such target may be a cell, tissue, organ, organism, or system (whether biological or production).

Delivery Agent: As used herein, "delivery agent" refers to any agent or substance which facilitates, at least in part, the in vivo and/or in vitro delivery of a polynucleotide and/or one or more substances (including, but not limited to a compounds and/or compositions of the present invention, e.g., viral particles or expression vectors) to targeted cells.

Destabilized: As used herein, the term "destable," "destabilize," or "destabilizing region" means a region or molecule that is less stable than a starting, reference, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance immunological detection, and the like. Detectable labels may include radioisotopes, fluorophores, chromophores, enzymes, dyes, metal ions, ligands such as biotin, avidin, streptavidin and haptens, quantum dots, and the like. Detectable labels may be located at any position in the entity with which they are attached, incorporated or associated. For example, when attached, incorporated in or associated with a peptide or protein, they may be within the amino acids, the peptides, or proteins, or located at the N- or C-termini.

Dosing regimen: As used herein, a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, upon single or multiple dose administration to a subject cell, in curing, alleviating, relieving or improving one or more symptoms of a disorder, clinical results, and, as such, an "effective amount" depends upon the context in which it is being applied. For example, in the context of administering an agent that treats Parkinson's Disease, an effective amount of an agent is, for example, an amount sufficient to achieve treatment, as defined herein, of Parkinson's Disease, as compared to the response obtained without administration of the agent.

Encapsulate: As used herein, the term "encapsulate" means to enclose, surround or encase.

Engineered: As used herein, embodiments are "engineered" when they are designed to have a feature or property, whether structural or chemical, that varies from a starting point, wild-type or native molecule. Thus, engineered agents or entities are those whose design and/or production include an act of the hand of man.

Epitope: As used herein, an "epitope" refers to a surface or region on a molecule that is capable of interacting with a biomolecule. For example a protein may contain one or more amino acids, e.g., an epitope, which interacts with an antibody, e.g., a biomolecule. In some embodiments, when referring to a protein or protein module, an epitope may comprise a linear stretch of amino acids or a three dimensional structure formed by folded amino acid chains.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; (4) folding of a polypeptide or protein; and (5) post-translational modification of a polypeptide or protein.

Feature: As used herein, a "feature" refers to a characteristic, a property, or a distinctive element.

Formulation: As used herein, a "formulation" includes at least one polynucleotide and/or compound and/or composition of the present disclosure (e.g., a vector, AAV particle, etc.) and a delivery agent.

Fragment: A "fragment," as used herein, refers to a contiguous portion of a whole. For example, fragments of proteins may comprise polypeptides obtained by digesting full-length protein isolated from cultured cells. In some embodiments, a fragment of a protein includes at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250 or more amino acids. In some embodiments, fragments of an antibody include portions of an antibody subjected to enzymatic digestion or synthesized as such.

Functional: As used herein, a "functional" biological molecule is a biological molecule and/or entity with a structure and in a form in which it exhibits a property and/or activity by which it is characterized.

Gene expression: The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is typically determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids. In many embodiments, homologous protein may show a large overall degree of homology and a high degree of homology over at least one short stretch of at least 3, 4, 5, 6, 7, 8, 9, 10, 11, 12, 13, 14, 15, 16, 17, 18, 19, 20, 25, 30, 35, 40, 45, 50 or more amino acids. In many embodiments, homologous proteins share one or more characteristic sequence elements. As used herein, the term "characteristic sequence element" refers to a motif present in related proteins. In some embodiments, the presence of such motifs correlates with a particular activity (such as biological activity).

Identity: As used herein, the term "identity" refers to the overall relatedness between polymeric molecules, e.g., between oligonucleotide and/or polynucleotide molecules (e.g. DNA molecules and/or RNA molecules) and/or between polypeptide molecules. Calculation of the percent identity of two polynucleotide sequences, for example, may be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference in its entirety. For example, the percent identity between two nucleotide sequences can be determined, for example using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference in its entirety. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product may be RNA transcribed from the gene (e.g. mRNA) or a polypeptide translated from mRNA transcribed from the gene. Typically a reduction in the level of mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" is synonymous with "separated", but carries with it the inference separation was carried out by the hand of man. In one embodiment, an isolated substance or entity is one that has been separated from at least some of the components with which it was previously associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art. In some embodiments, isolation of a substance or entity includes disruption of chemical associations and/or bonds. In some embodiments, isolation includes only the separation from components with which the isolated substance or entity was previously combined and does not include such disruption.

Modified: As used herein, the term "modified" refers to a changed state or structure of a molecule or entity of the invention as compared with a parent or reference molecule or entity. Molecules may be modified in many ways including chemically, structurally, and functionally. In some embodiments, compounds and/or compositions of the present disclosure are modified by the introduction of non-natural amino acids, or non-natural nucleotides.

Mutation: As used herein, the term "mutation" refers to a change and/or alteration. In some embodiments, mutations may be changes and/or alterations to proteins (including peptides and polypeptides) and/or nucleic acids (including polynucleic acids). In some embodiments, mutations comprise changes and/or alterations to a protein and/or nucleic acid sequence. Such changes and/or alterations may comprise the addition, substitution and or deletion of one or more amino acids (in the case of proteins and/or peptides) and/or nucleotides (in the case of nucleic acids and or polynucleic acids). In embodiments wherein mutations comprise the addition and/or substitution of amino acids and/or nucleotides, such additions and/or substitutions may comprise 1 or more amino acid and/or nucleotide residues and may include modified amino acids and/or nucleotides.

Naturally occurring: As used herein, "naturally occurring" means existing in nature without artificial aid or involvement of the hand of man Non-human vertebrate: As used herein, a "non-human vertebrate" includes all vertebrates except Homo sapiens, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid: As used herein, the term "nucleic acid", "polynucleotide" and "oligonucleotide" refer to any nucleic acid polymers composed of either polydeoxyribonucleotides (containing 2-deoxy-D-ribose), or polyribonucleotides (containing D-ribose), or any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA.

Off-target: As used herein, "off target" refers to any unintended effect on any one or more target, gene and/or cellular transcript.

Open reading, frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Particle: As used herein, a "particle" is a virus comprised of at least two components, a protein capsid and a polynucleotide sequence enclosed within the capsid.

Patient: As used herein, "patient" refers to a subject who may seek or be in need of treatment, requires treatment, is receiving treatment, will receive treatment, or a subject who is under care by a trained professional for a particular disease or condition, such as for example Parkinson's Disease.

Payload: As used herein, "payload" refers to one or more polynucleotides or polynucleotide regions encoded by or within a viral genome or an expression product of such polynucleotide or polynucleotide region, e.g., a transgene, a polynucleotide encoding a polypeptide or multi-polypeptide or a modulatory nucleic acid or regulatory nucleic acid.

Payload construct: As used herein, "payload construct" is one or more polynucleotide regions encoding or comprising a payload that is flanked on one or both sides by an inverted terminal repeat (ITR) sequence. The payload construct is a template that is replicated in a viral production cell to produce a viral genome.

Payload construct vector: As used herein, "payload construct vector" is a vector encoding or comprising a payload construct, and regulatory regions for replication and expression in bacterial cells.

Payload construct expression vector: As used herein, a "payload construct expression vector" is a vector encoding or comprising a payload construct and which further comprises one or more polynucleotide regions encoding or comprising components for viral expression in a viral replication cell.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers to any ingredient other than the compounds and/or active agents (e.g. as described herein) present in pharmaceutical compositions and having the properties of being substantially nontoxic and non-inflammatory in a subject such as a patient. In some embodiments, pharmaceutically acceptable excipients are vehicles capable of suspending and/or dissolving active agents. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspension or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystal line cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: Pharmaceutically acceptable salts of the compounds described herein. As used herein, "pharmaceutically acceptable salts" refers to derivatives or forms of the disclosed compounds wherein the parent compound is modified by converting an existing acid or base moiety to its salt form (e.g., as generated by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. In some embodiments a pharmaceutically acceptable salt of the present disclosure can be synthesized salt prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

Pharmaceutically acceptable solvate: The term "pharmaceutically acceptable solvate," as used herein, refers to a crystalline form of a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate." In some embodiments, the solvent incorporated into a solvate is of a type or at a level that is physiologically tolerable to an organism to which the solvate is administered (e.g., in a unit dosage form of a pharmaceutical composition).

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition, such as for example Parkinson's Disease.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand, replicate or increase or cause to grow, expand, replicate or increase. "Proliferative" means having the ability to proliferate. "Anti-proliferative" means having properties counter to or in opposition to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease.

Protein of interest: As used herein, the terms "proteins of interest" or "desired proteins" include those provided herein and fragments, mutants, variants, and alterations thereof.

Purified: As used herein, "purify," "purified," "purification" means to make substantially pure or clear from unwanted components, material defilement, admixture or imperfection.

"Purified" refers to the state of being pure. "Purification" refers to the process of making pure.

Region: As used herein, the term "region" refers to a zone or general area. In some embodiments, when referring to a protein or protein module, a region may comprise a linear sequence of amino acids along the protein or protein module or may comprise a three dimensional area, an epitope and/or a cluster of epitopes. In some embodiments, regions comprise terminal regions. As used herein, the term "terminal region" refers to regions located at the ends or termini of a given agent. When referring to proteins, terminal regions may comprise N- and/or C-termini. N-termini refer to the end of a protein comprising an amino acid with a free amino group. C-termini refer to the end of a protein comprising an amino acid with a free carboxyl group. N- and/or C-terminal regions may therefore comprise the N- and/or C-termini as well as surrounding amino acids. In some embodiments, N- and/or C-terminal regions comprise from about 3 amino acid to about 30 amino acids, from about 5 amino acids to about 40 amino acids, from about 10 amino acids to about 50 amino acids, from about 20 amino acids to about 100 amino acids and/or at least 100 amino acids. In some embodiments, N-terminal regions may comprise any length of amino acids that includes the N-terminus, but does not include the C-terminus. In some embodiments, C-terminal regions may comprise any length of amino acids, which include the C-terminus, but do not comprise the N-terminus.

In some embodiments, when referring to a polynucleotide, a region may comprise a linear sequence of nucleic acids along the polynucleotide or may comprise a three dimensional area, secondary structure, or tertiary structure. In some embodiments, regions comprise terminal regions. As used herein, the term "terminal region" refers to regions located at the ends or termini of a given agent. When referring to polynucleotides, terminal regions may comprise 5' and 3' termini. 5' termini refer to the end of a polynucleotide comprising a nucleic acid with a free phosphate group. 3' termini refer to the end of a polynucleotide comprising a nucleic acid with a free hydroxyl group. 5' and 3' regions may therefore comprise the 5' and 3' termini as well as surrounding nucleic acids. In some embodiments, 5' and 3' terminal regions comprise from about 9 nucleic acids to about 90 nucleic acids, from about 15 nucleic acids to about 120 nucleic acids, from about 30 nucleic acids to about 150 nucleic acids, from about 60 nucleic acids to about 300 nucleic acids and/or at least 300 nucleic acids. In some embodiments, 5' regions may comprise any length of nucleic acids that includes the 5' terminus, but does not include the 3' terminus. In some embodiments, 3' regions may comprise any length of nucleic acids, which include the 3' terminus, but does not comprise the 5' terminus.

RNA or RNA molecule: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

RNA interference: As used herein, the term "RNA interference" or "RNAi" refers to a sequence specific regulatory mechanism mediated by RNA molecules which results in the inhibition or interference or "silencing" of the expression of a corresponding protein-coding gene.

Sample: As used herein, the term "sample" refers to an aliquot, subset or portion taken from a source and/or provided for analysis or processing. In some embodiments, a sample is from a biological source such as a tissue, cell or component part (e.g. a body fluid, including but not limited to blood, mucus, lymphatic fluid, synovial fluid, cerebrospinal fluid, saliva, amniotic fluid, amniotic cord blood, urine, vaginal fluid and semen). In some embodiments, a sample may be or comprise a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, or organs. In some embodiments, a sample is or comprises a medium, such as a nutrient broth or gel, which may contain cellular components, such as proteins or nucleic acid molecule. In some embodiments, a "primary" sample is an aliquot of the source. In some embodiments, a primary sample is subjected to one or more processing (e.g., separation, purification, etc.) steps to prepare a sample for analysis or other use.

Self-complementary viral particle: As used herein, a "self-complementary viral particle" is a particle comprised of at least two components, a protein capsid and a polynucleotide sequence encoding a self-complementary genome enclosed within the capsid.

Sense strand: As used herein, the term "the sense strand" or "the second strand" or "the passenger strand" of a siRNA molecule refers to a strand that is complementary to the anti sense strand or first strand. The antisense and sense strands of a siRNA molecule are hybridized to form a duplex structure. As used herein, a "siRNA duplex" includes a siRNA strand having sufficient complementarity to a section of about 10-50 nucleotides of the mRNA of the gene targeted for silencing and a siRNA strand having sufficient complementarily to form a duplex with the siRNA strand.

Signal Sequences: As used herein, the phrase "signal sequences" refers to a sequence which can direct the transport or localization.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc.).

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Small/short interfering RNA: As used herein, the term "small/short interfering RNA" or "siRNA" refers to an RNA molecule (or RNA analog) comprising between about 5-60 nucleotides (or nucleotide analogs) which is capable of directing or mediating RNAi. Preferably, a siRNA molecule comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising 5-23 nucleotides, preferably 21 nucleotides (or nucleotide analogs), for example, 19, 20, 21 or 22 nucleotides. The term "long" siRNA refers to a siRNA comprising 24-60 nucleotides, preferably about 24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA. siRNAs can be single stranded RNA molecules (ss-siRNAs) or double stranded RNA molecules (ds-siRNAs) comprising a sense strand and an anti sense strand which hybridized to form a duplex structure called siRNA duplex.

Split dose: As used herein, a "split dose" is the division of single unit dose or total daily dose into two or more doses.

Stable: As used herein "stable" refers to a compound or entity that is sufficiently robust survive isolation to a useful degree of purity from a reaction mixture, and preferably capable of formulation into an efficacious therapeutic agent.

Stabilized: As used herein, the term "stabilize", "stabilized," "stabilized region" means to make or become stable. In some embodiments, stability is measured relative to an absolute value. In some embodiments, stability is measured relative to a reference compound or entity.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants. In some embodiments, the subject may be an infant, neonate, or a child under the age of 12 years old. In some embodiments, the subject may be in utero.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to e differences between doses, the term means plus/minus 2%.

Substantially simultaneously: As used herein and as it relates to plurality of doses, the term typically means within about 2 seconds.

Suffering from: An individual who is "suffering from" a disease, disorder, and/or condition has been diagnosed with or displays one or more symptoms of a disease, disorder, and/or condition such as for example Parkinson's Disease.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or polypeptides or other molecules of the present invention may be chemical or enzymatic.

Targeting: As used herein, "targeting" means the process of design and selection of nucleic acid sequence that will hybridize to a target nucleic acid and induce a desired effect.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition such as for example Parkinson's Disease. In some embodiments, a therapeutically effective amount is provided in a single dose. In some embodiments, a therapeutically effective amount is administered in a dosage regimen comprising a plurality of doses. Those skilled in the art will appreciate that in some embodiments, a unit dosage form may be considered to comprise a therapeutically effective amount of a particular agent or entity if it comprises an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Transfection: As used herein, the term "transfection" refers to methods to introduce exogenous nucleic acids into a cell. Methods of transfection include, but are not limited to, chemical methods, physical treatments and cationic lipids or mixtures.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition such as for example Parkinson's Disease.

Unmodified: As used herein, "unmodified" refers to any substance, compound or molecule prior to being changed in any way. Unmodified may, but does not always, refer to the wild type or native form of a biomolecule or entity. Molecules or entities may undergo a series of modifications whereby each modified substance, compound, molecule or entity may serve as the "unmodified" starting molecule for a subsequent modification.

Vector: As used herein, a "vector" is any molecule or moiety which transports, transduces or otherwise acts as a carrier of a heterologous molecule. Vectors of the present disclosure may be produced recombinantly and may be based on and/or may comprise adeno-associated virus (AAV) parent or reference sequence. Such parent or reference AAV sequences may serve as an original, second, third or subsequent sequence for engineering vectors. In non-limiting examples, such parent or reference AAV sequences may comprise any one or more of the following sequences: a polynucleotide sequence encoding a polypeptide or multi-polypeptide, which sequence may be wild-type or modified from wild-type and which sequence may encode full-length or partial sequence of a protein, protein domain, or one or more subunits of a protein; a polynucleotide comprising a modulatory or regulatory nucleic acid which sequence may be wild-type or modified from wild-type; and a transgene that may or may not be modified from wild-type sequence. These AAV sequences may serve as either the "donor" sequence of one or more codons (at the nucleic acid level) or amino acids (at the polypeptide level) or "acceptor" sequences of one or more codons (at the nucleic acid level) or amino acids (at the polypeptide level).

Viral construct vector: As used herein, a "viral construct vector" is a vector which comprises one or more polynucleotide regions encoding or comprising Rep and or Cap protein.

Viral construct expression vector: As used herein, a "viral construct expression vector" is a vector which comprises one or more polynucleotide regions encoding or comprising Rep and or Cap that further comprises one or more polynucleotide regions encoding or comprising components for viral expression in a viral replication cell.

Viral genome: As used herein, a "viral genome" is a polynucleotide encoding at least one inverted terminal repeat (ITR), at least one regulatory sequence, and at least one payload. The viral genome is derived by replication of a payload construct from the payload construct expression vector. A viral genome encodes at least one copy of the payload construct.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1

Design of AADC Polynucleotides

AADC polynucleotides are designed to comprise at a minimum a nucleic acid sequence encoding an AADC protein.

Once designed, the sequence is engineered or synthesized or inserted in a plasmid or vector and administered to a cell or organism. Suitable plasmids or vectors are any which transduce or transfect the target cell.

Adeno-associated viral vectors (AAV), viral particles or entire viruses may be used.

Administration results in the processing of the AADC polynucleotide to generate the AADC protein which alters the etiology of the disease, in this case Parkinson's Disease.

In one non-limiting example, plasmids containing an AADC polynucleotide of the invention are given in Table 1. These AADC polynucleotides in the table are contained in a Fastback plasmid and have a CMV promoter and encode AADC. In some embodiments the open reading frame of the AADC protein mRNA is codon optimized (e.g., codop).

TABLE 1

AADC polynucleotide-containing plasmids/vectors.

| Construct | SEQ ID NO |
|---|---|
| pFB CMV hAADC-1 | 2 |
| pFB CMV hAADC-2 | 3 |
| pFB CMV hAADC-3 | 4 |
| pFB CMV hAADC-4 | 5 |

Example 2

AADC Polynucleotides: ITR to ITR

AADC polynucleotides suitable for use in an AAV viral vector include those in Table 2.

Given in Table 2 are the ITR to ITR sequences from Table 1.

TABLE 2

ITR to ITR AADC polynucleotides

| Construct | SEQ ID NO |
|---|---|
| pFB CMV hAADC-1 (ITR to ITR) | 6 |
| pFB CMV hAADC-2 (ITR to ITR) | 7 |
| pFB CMV hAADC-3 (ITR to ITR) | 8 |
| pFB CMV hAADC-4 (ITR to ITR) | 9 |

Example 3

Relative to the ITR to ITR Parent Sequence

AADC polynucleotides are designed according to Table 3 and Table 4, The start and stop positions given are relative to the ITR to ITR AADC polynucleotides described in Table 2.

TABLE 3

Component modules or sequence regions of AADC polynucleotides

| | pFB CMV hAADC-1 (ITR to ITR) | | pFB CMV hAADC-2 (ITR to ITR) | | pFB CMV hAADC-3 (ITR to ITR) | | pFB CMV hAADC-4 (ITR to ITR) | |
|---|---|---|---|---|---|---|---|---|
| | Start | Stop | Start | Stop | Start | Stop | Start | Stop |
| 5' ITR | 1 | 130 | 1 | 130 | 1 | 130 | 1 | 130 |
| CMV Enhancer | 263 | 566 | 263 | 566 | 263 | 566 | 296 | 599 |
| CMV Promoter | 567 | 769 | 567 | 769 | 567 | 769 | 600 | 802 |
| ie1 exon 1 | 784 | 917 | 784 | 917 | 784 | 917 | 817 | 950 |
| ie1 intron1 | 918 | 949 | 918 | 949 | 918 | 949 | 951 | 982 |
| hBglobin intron2 | 950 | 1296 | 950 | 1296 | 950 | 1296 | 983 | 1329 |
| hBglobin exon 3 | 1297 | 1349 | 1297 | 1349 | 1297 | 1349 | 1330 | 1382 |
| 5' UTR | — | — | — | — | — | — | 1398 | 1468 |
| hAADC | 1374 | 2822 | — | — | 1374 | 2822 | 1473 | 2921 |
| hAADC codop | — | — | 1374 | 2816 | — | — | — | — |
| 3' UTR | — | — | — | — | 2823 | 3221 | 2922 | 3361 |
| hGH poly(A) signal | 2841 | 3317 | 2835 | 3311 | 3240 | 3716 | 3380 | 3856 |
| 3' ITR | 3417 | 3535 | 3416 | 3534 | 3822 | 3940 | 3961 | 4079 |

TABLE 4

| Component modules or sequence regions of AADC polynucleotides | hAADC_1k | | hAADC_2k | | hAADC_3k | | hAADC_4 | |
|---|---|---|---|---|---|---|---|---|
| | Start | Stop | Start | Stop | Start | Stop | Start | Stop |
| 5' ITR | 1 | 141 | 1 | 141 | 1 | 141 | 1 | 141 |
| CMV Enhancer | 245 | 548 | 245 | 548 | 245 | 548 | 245 | 548 |
| CMV Promoter | 549 | 751 | 549 | 751 | 549 | 751 | 549 | 751 |
| ie1 exon 1 | 766 | 899 | 766 | 899 | 766 | 899 | 766 | 899 |
| ie1 intron1 | 900 | 931 | 900 | 931 | 900 | 931 | 900 | 931 |
| hBglobin intron2 | 932 | 1278 | 932 | 1278 | 932 | 1278 | 932 | 1278 |
| hBglobin exon 3 | 1279 | 1331 | 1279 | 1331 | 1279 | 1331 | 1279 | 1331 |
| 5' UTR | — | — | — | — | — | — | 1347 | 3310 |
| hAADC | 1356 | 2804 | 1356 | 2804 | — | — | 1422 | 2864 |
| hAADC codop | — | — | — | — | 1356 | 2798 | — | — |
| 3' UTR | — | — | — | — | — | — | 2865 | 3310 |
| hGH poly(A) signal | 2823 | 3299 | 2823 | 3299 | 2817 | 3293 | 3329 | 3805 |
| 3' ITR | 3357 | 3497 | 3357 | 3497 | 3351 | 3491 | 3863 | 4003 |

TABLE 5

| Component modules or sequence regions of AADC polynucleotides | hAADC_5k | | hAADC_6k | | hAADC_9k | |
|---|---|---|---|---|---|---|
| | Start | Stop | Start | Stop | Start | Stop |
| 5' ITR | 1 | 145 | 1 | 141 | 1 | 130 |
| CMV Enhancer | 249 | 552 | 245 | 548 | 234 | 537 |
| CMV Promoter | 553 | 755 | 549 | 751 | 538 | 740 |
| ie1 exon 1 | 770 | 903 | 766 | 899 | 755 | 888 |
| ie1 intron1 | 904 | 935 | 900 | 931 | 889 | 920 |
| hBglobin intron2 | 936 | 1282 | 932 | 1278 | 921 | 1267 |
| hBglobin exon 3 | 1283 | 1335 | 1279 | 1331 | 1268 | 1320 |
| 5' UTR | — | — | — | — | — | — |
| hAADC | | | 1356 | 2798 | 1345 | 2793 |
| hAADC codop | 1360 | 2802 | — | — | — | — |
| 3' UTR | — | — | 2799 | 3203 | — | — |
| hGH poly(A) signal | 2821 | 3297 | 3222 | 3698 | 2812 | 3288 |
| 3' ITR | 3355 | 3499 | 3756 | 3896 | 3346 | 3475 |

Example 4

Design of AADC Polynucleotides

AADC polynucleotides are designed to comprise at a minimum a nucleic acid sequence encoding an AADC protein.

Once designed, the sequence is engineered or synthesized or inserted in a plasmid or vector and administered to a cell or organism. Suitable plasmids or vectors are any which transduce or transfect the target cell.

Adeno-associated viral vectors (AAV), viral particles or entire viruses may be used.

Administration results in the processing of the AADC polynucleotide to generate the AADC protein which alters the etiology of the disease, in this case Parkinson's Disease.

In one non-limiting example, plasmids containing an AADC polynucleotide of the invention are given in Table 6. These AADC polynucleotides in the table are contained in a Fastback plasmid and have a CMV promoter and encode AADC. In some embodiments the open reading frame of the AADC protein mRNA is codon optimized (e.g., codop).

TABLE 6

| AADC polynucleotide-containing plasmids/vectors. | |
|---|---|
| Construct | SEQ ID NO |
| phAADC_1k | 10 |
| phAADC_2k | 11 |
| phAADC_3k | 12 |
| phAADC_4 | 13 |
| phAADC_5k | 14 |
| phAADC_6k | 15 |
| phAADC_9k | 16 |

Given in Table 7 are the ITR to ITR sequences from Table 6.

TABLE 7

| ITR to ITR AADC polynucleotides | |
|---|---|
| Construct | SEQ ID NO |
| phAADC_1k (ITR to ITR) | 17 |
| phAADC_2k (ITR to ITR) | 18 |
| phAADC_3k (ITR to ITR) | 19 |
| phAADC_4 (ITR to ITR) | 20 |
| phAADC_5k (ITR to ITR) | 21 |
| phAADC_6k (ITR to ITR) | 22 |
| phAADC_9k (ITR to ITR) | 23 |

Example 5

Administration of AADC Polynucleotide Compositions to Patients for Gene Therapy AADC polynucleotide-containing recombinant AAV vector compositions are infused into the substantia nigra, and in particular, the substantia nigra pars compacta (SNpc) and ventral tegmental area (VTA) of patients having Parkinson's Disease and identified as qualified for treatment according to methods known in the art.

One method of administration contemplated for use in the methods described herein is real-time convection-enhanced delivery (RCD) of AADC polynucleotide-containing AAV vector compositions by co-infusion of gadoteridol (a magnetic resonance (MR) contrast agent) and T1 or T2 magnetic resonance imaging (MRI), which can predict areas of subsequent AADC gene expression. As described in Richardson, et al., 2011, the accuracy of cannula placement and initial infusate distribution may be safely determined by saline infusion without significantly altering the subsequent distribution of the tracer agent (Richardson, et al., 2011, Neurosurgery, 69(1):154-163). T2 RCD provides detection of intraparenchymal convection-enhanced delivery in the uninjured brain and may predict subsequent distribution of a transgene after viral vector infusion. Subjects undergo saline infusion/T2 acquisition, immediately followed by gadoteridol infusion/T1 acquisition in the putamen and brainstem. Distribution volumes and spatial patterns are analyzed. Gadoteridol and AAV-encoded AADC are co-infused under alternating T2/T1 acquisition in the thalamus, and hyperintense areas are compared with areas of subsequent transgene expression. Ratios of distribution volume to infusion volume are expected to be similar between saline and gadoteridol RCD. Spatial overlap should correlate well between T2 and T1 images. The second infusate will follow a spatiotemporal pattern similar to that of the first, filling the target area before developing extra-target distribution. Areas of AADC expression should correlate well with areas of both T1 and T2 hyperintensity observed during RCD (Richardson, et al., 2011, Neurosurgery, 69(1):154-163).

Convection-enhanced delivery (CED) of macromolecules directly into the brain parenchyma has been known for over two decades. CED is a term that denotes the use of a pressure gradient to generate bulk flow within the brain parenchyma, i.e. convection of macromolecules within the interstitial fluid driven by infusing a solution through a cannula placed directly in the targeted structure. This method allows therapeutic agents to be homogenously distributed through large volumes of brain tissue by bypassing the blood brain barrier and surpassing simple diffusion (Richardson, et al., 2011, Stereotact. Funct. Neurosurg. 89:141-151).

Salegio, et al. recently demonstrated the distribution of nanoparticles of different sizes, including micelles (~15 nm in size), AAV (~20-25 nm) and liposomes (~65 nm), within the CNS of rodents and NHPs (Salegio et al., 2014, Frontiers in Neuroanatomy, vol. 8, article 9: pp. 1-8). Simple injections cannot engage the perivascular system, and specialized infusion cannulae are required, enabling constant pressures to be exerted at the tip of the cannula such that the interstitial hydrostatic pressure is exceeded and infusate can flow out into the tissue. Simple needles generate significant reflux; thus, reflux-resistant cannulas have been developed to counter this tendency. The advent of platforms for MRI-guided convection-enhanced infusions further refined understanding of the mechanics of perivascular flow, and it was demonstrated that perivascular distribution of liposomes was linear with respect to time, the slope of the curve was increased in myelinated regions, and cessation of infusion prevented further expansion in the volume of distribution. (Richardson, et al., 2011, Stereotact. Funct. Neurosurg. 89:141-151; Salegio et al., 2014, Frontiers in Neuroanatomy, vol. 8, article 9: pp. 1-8).

Intraparenchymal rAAV injections are known to result in robust but relatively local transduction. Such local delivery methods are advantageous when attempting gene therapy for neurological disorders that result from neuropathology that is localized to a specific anatomical region or anatomical circuitry such as in the case of Parkinson's disease. However, in treatments requiring more widespread CNS transduction, intraparenchymal injections are impractical. Treatment of neurological disorders attributable to inborn errors of metabolism and/or single-gene defects, or those that affect motor neurons of the spinal cord can require transduction of large proportions of the brain or spinal cord, respectively. Development of less invasive trans-BBB delivery methods for vectors is an extremely important endeavor. Numerous attempts to use molecules that are known to interact with various active transport mechanisms (probably receptor-mediated) to convey proteins across the BBB have been reported with varying results. Given the large number of AAV serotypes available, one or more serotypes may bind a cell-entry receptor capable of transporting the AAV capsid across the BBB (Manfredsson, et al., 2009, "AAV9: a potential blood brain barrier buster." Molecular Therapy 17(3):403-405).

Vector and Stereotaxic Infusion

A stereotactic approach may be used to surgically deliver the AADC polynucleotides. Although individuals with AADC deficiency lack epinephrine and norepinephrine these patients should maintain stable blood pressure and heart rates during the surgery. There should be no notable intracerebral hemorrhages in the postoperative computed tomography (CT) or MRI scans. The needle tracts, as shown on the MRI scans, should show accurate injection into the substantia nigra pars compacta (SNpc) and ventral tegmental area (VTA). The patients will be discharged from the hospital about one week after the surgery (Hwu, W. L., et al., 2012. Gene therapy for aromatic L-amino acid decarboxylase deficiency. *Sci. Transl. Med. Vol.* 4, 134ra61).

Subjects of treatment receive the AAV-vector composition vector, safely delivered to substantia nigra pars compacta (SNpc) and ventral tegmental area (VTA) via bilateral infusions, or alternatively, intrastriatally (into the caudate nucleus and putamen), or into the subthalamic nucleus (STN), for example optionally using the FDA-approved SMARTFLOW® neuroventricular cannula (SurgiVision, Inc.) specifically designed for clinical application, with or without the aid of the CLEARPOINT® system to help the treating neurosurgeon(s) target and observe the delivery of the therapeutic agent in the brain (See, for example, San Sebastian, et al., 2014, *Mol. Ther. Methods Clin. Dev.* 3: 14049; See, for example, Feng and Maguire-Zeiss, 2010, *CNS Drugs* 24(3):177-192).

For example, during the surgery, two target points are determined in the substantia nigra pars compacta (SNpc) and ventral tegmental area (VIA) that are sufficiently separated from each other in dorsolateral directions and identified on a magnetic resonance image. One burr hole is trepanned in each side of the cranial bone, through which the vector is injected into the two target points via the two-track insertion route. The AAV-vector-containing solution is prepared to a concentration of $1.5\times10^{12}$ vector genome/ml, and 50 μl per point of the solution is injected at 1 μl/min; each patient receives $3\times10^{11}$ vector genome of the AAV-vector construct.

Neutralizing antibody titers against AAV2 are determined by measuring β-galactosidase activities in HEK293 cells transduced with $5\times10^{3}$ vector genome/cell of AAV2 vectors expressing β-galactosidase in various dilutions of sera.

PET

The AADC expression level in the substantia nigra are assessed on PET imaging with FMT six days before surgery and at one- and six-months after gene transfer. All patients cease taking dopaminergic medications 18 hours before PET and take 2.5 mg/kg of carbidopa orally one hour before FMT injection. Subsequently, 0.12 mCi/kg of FMT in saline is infused into an antecubital vein, and a 90-minute dynamic acquisition sequence is obtained. The PET and magnetic resonance imaging data are co-registered with a fusion processing program (Syntegra; Philips, Amsterdam, The Netherlands) to produce the fusion images. Radioactivities within volumes of interest drawn in the nigrostriatal pathway are calculated between 80 and 90 minutes after tracer injection. A change in nigrostriatal pathway FMT uptake from baseline to 24 weeks is assessed using the substantia nigra to striatal ratio of radioactivities.

Statistical Analysis

Values at baseline and 6 months after gene transfer are compared using Student's t-test (paired analyses). A two-sided P value $<0.05$ is taken to indicate significant differences. Two-way analysis of variance with Bonferroni correction of P values is used for the short-duration response to levodopa. (See, for example, Muramatsu, et al., 2010, "A phase I study of aromatic L-amino acid decarboxylase gene therapy for Parkinson's disease." *Mol. Ther.* 18:1731-1735).

Safety and tolerability of bilateral administration of AAV-vector compositions using real-time image-guided infusion into the brains of Parkinson's Disease subjects may be monitored for up to or after 9 months post-surgery. Broad coverage of targeted areas (substantia nigra pars compacta (SNpc) and ventral tegmental area (VTA)) and widespread AADC protein distribution in the striatum should be achieved without inducing any adverse effects.

Changes in growth and motor skills: The patients should gain weight and exhibit improvement in their motor scores after gene transfer, within a year, post-treatment. Weight will be measured at 3 to 6 months after gene transfer. All patients initially should have raw scores of zero on the Alberta Infant Motor Scale (AIMS) and very low raw scores for the Peabody Developmental Motor Scale, Second Edition (PDMS-II). After the gene transfer, all of the patients should show continuous increases in their raw scores on these two scales, which indicates that their motor functions have improved. The Comprehensive Developmental Inventory for Infants and Toddlers (CDIIT) covers both cognition and motor development. All of the patients should show low raw CDIIT scores before gene transfer, and the subsequent increase in scores demonstrate improvement in both motor and cognitive functions.

Subjective Improvements after Gene Transfer

To document the symptoms that are more difficult to quantify, spouses, guardians or caretakers of the patients are asked to fill out a questionnaire at the end of the study. The symptoms of the oculogyric crises should lessen, and eye deviations and sleep disruptions, for example, are some mild symptoms of the oculogyric crises that may remain after gene therapy. Subjects may experience increased emotional stability, and/or some improvements in sweating and hyperthermia (a common manifestation of body temperature instability in hot weather). There should be no detectable abnormality in heart rate variability as assessed by 24-hour Holter monitoring either before or after gene transfer. Before gene therapy, patients that were bedridden and showed little spontaneous movement may exhibit less severe ptosis (drooping of the upper eyelid) one to two weeks after the gene transfer. According to previous studies, dyskinesia may occur one month after gene transfer, but upon observation of a decrease in dyskinesia, motor development should start (Hwu, W. L. et at, 2012. Gene therapy for aromatic L-amino acid decarboxylase deficiency. *Sci. Transl. Med.* Vol. 4, 134ra61). Subjects may exhibit increased head control after three months, sitting with support after six to nine months, sitting up from the prone position after thirteen months, and holding toys and standing with support sixteen months after the gene transfer, for example. Anti-AAV2 antibodies should be negative in the patients before gene therapy, and the titers may increase slightly after gene transfer.

PET Scans and CSF Analyses

PET scans and CSF analyses are completed for the treated patients. Six months after gene transfer, PET scans should reveal that uptake of 6-[18F] fluorodopa (FDOPA) increase from baseline in the combined (right and left) treatment sites. The CSF analysis should reveal increases in the levels of homovanillic acid (HVA, a metabolite of dopamine) and 5-hydroxyindoleacetic acid (HIAA, a metabolite of serotonin). However, the levels of L-DOPA and 3-O-methyldopa may remain elevated (Hwu, W. L., et al., 2012. Gene therapy for aromatic L-amino acid decarboxylase deficiency. *Sci. Transl. Med.* Vol. 4, 134ra61).

Example 6

Administration of AADC Pol Nucleotides

AADC polynucleotide-containing recombinant AAV vector compositions are infused into the putamen of patients having Parkinson's Disease using the administration methods described in Example 5. The dose, number of patients and volume are outlined in Table 8.

TABLE 8

| Study Design | | | |
|---|---|---|---|
| Study No. | Number of Patients | Dose | Volume |
| 1 | 6 | $3 \times 10^{11}$ vg | 100 ul per putamen |
| 2 | 6 | $9 \times 10^{11}$ vg | 300 ul per putamen |
| 3 | 10 | $2.3 \times 10^{11}$ vg | 100 ul per putanten |
| 4 | 10 | $7.5 \times 10^{11}$ vg | 100 ul per putamen |
| 5 | 5 | $7.5 \times 10^{11}$ vg | 450 ul per putamen |
| 6 | Up to 20 | $1.4 \times 10^{12}$ vg | Up to 900 ul per putamen |
| 7 | Up to 20 | $4.8 \times 10^{12}$ vg | Up to 900 ul per putamen |
| 8 | Up to 20 | $8.8 \times 10^{12}$ vg | Up to 900 ul per putamen |

During the course of the study the safety and tolerability of the infusion of the AADC polynucleotide-containing recombinant adeno-associated virus (AAV) vector compositions in human patients diagnosed with Parkinson's Disease is evaluated. Patients are evaluated preoperatively and monthly postoperatively for six months, using multiple measures, including the Global Systonia Scale (GDS) (see Cornelia, et at, 2003, *Movement Disorders,* 18(3):303-312), L-DOPA challenge test, UPDRS scores, motor state diaries, and laboratory tests. Using diaries that separate the day into half-hour segments, the caregivers of the patients will record their mobility during the four days before admission and for another four days at six months after admission to the study site. The patient caregivers are trained to rate subject's condition as sleeping, immobile, mobile without troublesome dyskinesias, or mobile with troublesome dyskinesias. The total number of hours spent in each of these categories is calculated, and the differences between the baseline and the six-month scores are compared between the groups. The short-duration response to levodopa is evaluated at baseline and 6 months after gene transfer; subjects take 100 mg of levodopa orally with 25 mg benserazide after 20 hours without dopaminergic medication. Motor symptoms based on GDS and plasma levodopa concentrations are assessed at baseline and 30 minutes, 1, 2, 3, and 4 hours after levodopa intake (See, for example, Muramatsu, et al, 2010, "A phase I study of aromatic L-amino acid decarboxylase gene therapy for Parkinson's disease," *Mol. Ther.* 18:1731-1735).

Example 7

In Viva Administration of AADC Polynucleotides

Two AADC polynucleotide-containing recombinant AAV vector compositions (plasmid SEQ ID NO: 10 and 12; ITR to ITR SEQ ID NO: 17 and 19), a control and a standard were administered to rats (n=5) by bilateral intrastriation (10 ul/side) at a dose level of $2\times10^{12}$ Vg/ml. The expression of AADC in rat striatum was determined by ELISA after 4 and 8 weeks. Variation was seen between the animals and the hemispheres due to variable delivery between the infusion sites. Both constructs expressed AADC, but the phAADC_3k construct (plasmid SEQ ID NO: 12; ITR to ITR SEQ ID NO: 19) showed up to 200% increase of expression as compared to the standard construct.

Example 8

Dose Response Study of AADC Polynucleotides

Compositions of AADC polynucleotide-containing recombinant AAV vectors (plasmid SEQ ID NO: 10; ITR to ITR SEQ ID NO: 17) at five different dose levels ranging from $1\times10^{11}$ vg/ml to $1\times10^{13}$ vg/ml and a control are administered to 6-OHDA lesioned rats. The behavioral response to low-dose levodopa administration is quantified before and after (week 3 and 4) delivery of the composition. 5 weeks after dosing, necropsy is conducted and the AADC enzymatic activity is measured in ex vivo striatal tissue assay and the distribution of AADC in the brain is determined by immunohistochemical (MC) staining.

Example 9

Effect of Empty Particles on Intrastriatal Transduction

Adult rats (n=6) were administered varying ratios of full:empty vector particles at: 0% full, 50% full, 85% full or 99% full. AADC polynucleotide-containing recombinant AAV vector (plasmid SEQ ID NO: 10; ITR to ITR SEQ ID NO: 17) at a constant dose and volume (5 ul and 1×10 vg) was administered intrastriatally. The rats were evaluated 4 weeks after administration. The low vector dose resulted in limited. AADC vector expression. The volume of distribution for the particles is shown in Table 9 (ELISA) and the striatal levels of AADC expression is shown in Table 10 (Histology).

TABLE 9

| Volume of Distribution | |
|---|---|
| % Ratio of full AAV2-AADC particle to empty capsids | Approximate Volume of Distribution ($mm^3$) |
| 50:50 | 2 |
| 70:30 | 2.4 |
| 85:15 | 2.5 |
| 100:0 | 3 |

TABLE 10

| Striatal Levels | |
|---|---|
| % full of AAV2-AADC particles | AADC pg/ug protein |
| 0 | 0.4 |
| 52 | 1.1 |
| 58 | 1.7 |
| 83 | 2 |
| >99 | 2.1 |

Distribution was comparable for all groups. Relatively low vector dose resulted in limited AADC expression. There was also a trend to lower AADC expression levels with >30% empty particles.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

We claim:

1. A polynucleotide comprising:

a) a 5' inverted terminal repeat (ITR), wherein said 5' ITR is 141 nucleotides in length, b) a cytomegalovirus (CMV) sequence region comprising from 5' to 3' a CMV enhancer or a fragment thereof comprising at least 250 nucleotides, and a CMV promoter or a fragment thereof comprising at least 150 nucleotides, c) an immediate early 1 (IE1) sequence region comprising an IE1 exon1 or a fragment thereof of at least 50 nucleotides, and an IE1 intron 1 or a fragment thereof of at least 20 nucleotides, d) a human beta globin (HB) sequence region comprising an HB intron 2 or a fragment thereof of at least 250 nucleotides, and an HB exon 3 or a fragment thereof of at least 40 nucleotides, e) a polynucleotide sequence encoding Aromatic L-Amino Acid Decarboxylase (AADC) or an isoform thereof, f) a poly(A) signal sequence region comprising a human growth hormone (hGH) poly(A) signal or a fragment thereof of at least 200 nucleotides, and g) a 3' ITR, wherein said 3' ITR is 141 nucleotides in length;

wherein the polynucleotide comprises a nucleotide sequence at least 95% identical to SEQ ID NO: 17.

2. The polynucleotide of claim 1, wherein the 5' ITR and the 3' ITR are derived from AAV2.

3. The polynucleotide of claim 1, wherein the CMV sequence region is 507 nucleotides in length.

4. The polynucleotide of claim 1, wherein the IE1 sequence region is 166 nucleotides in length.

5. The polynucleotide of claim 1, wherein the HB sequence region is 400 nucleotides in length.

6. The polynucleotide of claim 1, wherein the polynucleotide sequence encoding AADC or an isoform thereof is 1440, 1443, or 1449 nucleotides in length.

7. The polynucleotide of claim 1, wherein the polynucleotide sequence encoding AADC or an isoform thereof is 1440 nucleotides in length.

8. The polynucleotide of claim 1, wherein the poly(A) signal sequence region is 477 nucleotides in length.

9. The polynucleotide of claim 1, wherein the CMV sequence region is 507 nucleotides in length, the IE1 sequence region is 166 nucleotides in length, the HB sequence region is 400 nucleotides in length, the polynucleotide sequence encoding AADC or a variant or isoform thereof is 1440 nucleotides in length, and the poly(A) signal region is 477 nucleotides in length.

10. The polynucleotide of claim 1, wherein the 5' ITR consists of nucleotides 1-141 of SEQ ID NO: 17.

11. The polynucleotide of claim 1, wherein the 3' ITR consists of nucleotides 3357-3497 of SEQ ID NO: 17.

12. The polynucleotide of claim 9, wherein the 5' ITR consists of nucleotides 1-141 of SEQ ID NO: 17, the 3' ITR consists of nucleotides 3357-3497 of SEQ ID NO: 17, or the 5' ITR consists of nucleotides 1-141 of SEQ ID NO: 17 and the 3' ITR consists of nucleotides 3357-3497 of SEQ ID NO: 17.

13. A recombinant adeno-associated virus (rAAV) comprising an adeno-associated virus (AAV) vector genome and an AAV capsid, wherein the AAV vector genome comprises the polynucleotide of claim 1.

14. A recombinant adeno-associated virus (rAAV) comprising an adeno-associated virus (AAV) vector genome and an AAV capsid, wherein the AAV vector genome comprises the polynucleotide of claim 12.

15. The rAAV of claim 13, wherein the AAV capsid is AAV2, AAV1, AAV3, AAV4, AAV5, AAV6, AAV7, AAV8, AAV9, AAV9.47, AAV9(hu14), AAV10, AAV11, AAV12, AAVrh8, AAVrh10, AAV-DJ or AAV-DJ8.

16. The rAAV of claim 14, wherein the AAV capsid is AAV2, AAV1, AAV3, AAV4, AAV5, AAV6, AAV7, AAV8, AAV9, AAV9.47, AAV9(hu14), AAV10, AAV11, AAV12, AAVrh8, AAVrh10, AAV-DJ or AAV-DJ8.

17. The rAAV of claim 15, wherein the AAV capsid is AAV2.

18. The rAAV of claim 16, wherein the AAV capsid is AAV2.

19. A pharmaceutical composition comprising the rAAV of claim 17 and a pharmaceutically acceptable excipient.

20. A pharmaceutical composition comprising the rAAV of claim 18 and a pharmaceutically acceptable excipient.

21. The pharmaceutical composition of claim 19, wherein at least 70% of the rAAV vectors contain an AAV vector genome.

22. The pharmaceutical composition of claim 20, wherein at least 70% of the rAAV vectors contain an AAV vector genome.

23. A method of increasing the level of Aromatic L-Amino Acid Decarboxylase (AADC) protein in a subject comprising administering an effective amount of the pharmaceutical composition of claim 19.

24. The method of claim 23, wherein the subject has Parkinson's Disease.

25. A method of increasing the level of Aromatic L-Amino Acid Decarboxylase (AADC) protein in a subject comprising administering an effective amount of the pharmaceutical composition of claim 20.

26. The method of claim 25, wherein the subject has Parkinson's Disease.

* * * * *